United States Patent
Ting et al.

(10) Patent No.: US 9,598,480 B2
(45) Date of Patent: *Mar. 21, 2017

(54) RECOMBINANT NEL-LIKE (NELL) PROTEIN PRODUCTION

(71) Applicant: The Regents of the University of California, Oakland, CA (US)

(72) Inventors: Kang Ting, Beverly Hills, CA (US); Chia Soo, Beverly Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/769,222

(22) Filed: Feb. 15, 2013

(65) Prior Publication Data

US 2014/0336367 A1    Nov. 13, 2014

Related U.S. Application Data

(60) Continuation of application No. 13/121,394, filed as application No. PCT/US2009/059893 on Oct. 7, 2009, now abandoned, application No. 13/769,222, which is a continuation-in-part of application No. 13/253,859, filed on Oct. 5, 2011, now abandoned, which is a division of application No. 12/700,630, filed on Feb. 4, 2010, now Pat. No. 8,053,412, which is a division of application No. 11/601,529, filed on Nov. 17, 2006, now Pat. No. 7,691,607, which is a continuation-in-part of application No. 10/544,553, filed on May 15, 2006, now Pat. No. 7,544,486, which is a continuation-in-part of application No. PCT/US2006/005473, filed as application No. PCT/US2004/003808 on Feb. 9, 2004.

(60) Provisional application No. 61/103,534, filed on Oct. 7, 2008.

(51) Int. Cl.

| | |
|---|---|
| C12N 15/06 | (2006.01) |
| C12N 15/07 | (2006.01) |
| C12N 15/12 | (2006.01) |
| C12N 15/19 | (2006.01) |
| C12N 15/63 | (2006.01) |
| C12N 15/85 | (2006.01) |
| C07K 14/475 | (2006.01) |
| C07K 14/51 | (2006.01) |
| C12N 15/62 | (2006.01) |

(52) U.S. Cl.
CPC ............ *C07K 14/475* (2013.01); *C07K 14/51* (2013.01); *C12N 15/625* (2013.01); *C07K 2319/02* (2013.01); *C07K 2319/036* (2013.01)

(58) Field of Classification Search
None
See application file for complete search history.

(56) References Cited

U.S. PATENT DOCUMENTS

| | | | |
|---|---|---|---|
| 5,831,058 A | * | 11/1998 | Fujiwara et al. ............ 536/23.5 |
| 6,780,327 B1 | | 8/2004 | Wu et al. |
| 2007/0128697 A1 | | 6/2007 | Ting et al. |

FOREIGN PATENT DOCUMENTS

| | | | |
|---|---|---|---|
| WO | WO 01/24821 | * | 4/2001 |
| WO | WO 2004/072100 | | 8/2004 |

OTHER PUBLICATIONS

Zhang et al., 2002, J. Clin. Invest. 110 :861-870.*
Ting et al., 1999, J. Bone Miner. Res. 14:80-89.*
Tara Aghaloo et al., "A Study of the Role of Nell-1 Gene Modified Goat Bone Marrow Stromal Cells in Promoting New Bone Formation", Mol. Therapy vol. 15 (10) pp. 1872-1880 (2007).
Tara Aghaloo et al., "Nell-1 Induced Bone Regeneration in Calvarial Defects" The Am. J. of Pathology vol. 169 (3) pp. 903-915 (2006).
Zhang et al., "Craniosynostosis in Transgenic Mice Overexpressing Nell-1" The J. of Clinical Investigation vol. 110 (6) pp. 861-870 (2002).

* cited by examiner

*Primary Examiner* — Elizabeth C Kemmerer
(74) *Attorney, Agent, or Firm* — Duane Morris LLP

(57) ABSTRACT

The present invention provides a method and system for producing a NELL protein. The method and system comprise a CELL encoding a NELL protein or peptide and a non-insect secretory signal peptide.

14 Claims, 38 Drawing Sheets

```
atg aaa ttc tta gtc aac gtt gca cta gtt ttt atg gtc gtg tac att     48   SEQ ID NO:609
Met Lys Phe Leu Val Asn Val Ala Leu Val Phe Met Val Val Tyr Ile          SEQ ID NO:610
1               5                   10                  15 tct tac atc tat gcg atg ccg atg gat gtg att tta gtt ttg tgg ttc     96
Ser Tyr Ile Tyr Ala Met Pro Met Asp Val Ile Leu Val Leu Trp Phe
                20                  25                  30 tgt gta tgc acc gcc agg aca gtg ttg ggc ttt ggg atg gac cct gac    144
Cys Val Cys Thr Ala Arg Thr Val Leu Gly Phe Gly Met Asp Pro Asp
            35                  40                  45 ctt cag ctg gac atc atc tca gag ctc gac ctg gtg aac acc acc ctg    192
Leu Gln Leu Asp Ile Ile Ser Glu Leu Asp Leu Val Asn Thr Thr Leu
        50                  55                  60 gga gtc acg cag gtg gct gga ctg cac aac gcc agt aaa gca ttt cta    240
Gly Val Thr Gln Val Ala Gly Leu His Asn Ala Ser Lys Ala Phe Leu
65              70                  75                  80 ttt caa gat gta cag aga gag atc cat tcg gcc cct cac gtg agt gag    288
Phe Gln Asp Val Gln Arg Glu Ile His Ser Ala Pro His Val Ser Glu
                85                  90                  95 aag ctg atc cag cta ttc cgg aat aag agc gag ttc acc ttt ttg gct    336
Lys Leu Ile Gln Leu Phe Arg Asn Lys Ser Glu Phe Thr Phe Leu Ala
                100                 105                 110 aca gtg cag cag aaa cca tcc acc tca ggg gtg ata ctg tcc atc cgg    384
Thr Val Gln Gln Lys Pro Ser Thr Ser Gly Val Ile Leu Ser Ile Arg
            115                 120                 125 gag ctg gag cac agc tat ttt gaa ctg gag agc agt ggc cca aga gaa    432
Glu Leu Glu His Ser Tyr Phe Glu Leu Glu Ser Ser Gly Pro Arg Glu
        130                 135                 140 gag ata cgc tac cat tac ata cat ggt gga aag ccc agg act gag gcc    480
Glu Ile Arg Tyr His Tyr Ile His Gly Gly Lys Pro Arg Thr Glu Ala
145                 150                 155                 160 ctt ccc tac cgc atg gca gac gga caa tgg cac aag gtc gcg ctg tca    528
Leu Pro Tyr Arg Met Ala Asp Gly Gln Trp His Lys Val Ala Leu Ser
                165                 170                 175 gtg agc gcc tct cac ctc ctg ctc cac atc gac tgc aat agg att tac    576
Val Ser Ala Ser His Leu Leu Leu His Ile Asp Cys Asn Arg Ile Tyr
                180                 185                 190 gag cgt gtg ata gac cct ccg gag acc aac ctt cct cca gga agc aat    624
Glu Arg Val Ile Asp Pro Pro Glu Thr Asn Leu Pro Pro Gly Ser Asn
            195                 200                 205
```

Figure 1A

```
ctg tgg ctt ggg caa cgt aac caa aag cat ggc ttt ttc aaa gga atc     672   SEQ ID NO:609
Leu Trp Leu Gly Gln Arg Asn Gln Lys His Gly Phe Phe Lys Gly Ile           SEQ ID NO:610
    210                 215                 220 atc caa gat ggt aag atc atc ttc atg ccg aat ggt ttc atc aca cag     720
Ile Gln Asp Gly Lys Ile Ile Phe Met Pro Asn Gly Phe Ile Thr Gln
225                 230                 235                 240 tgt ccc aac ctc aat cgc act tgc cca aca tgc agt gac ttc ctg agc     768
Cys Pro Asn Leu Asn Arg Thr Cys Pro Thr Cys Ser Asp Phe Leu Ser
                245                 250                 255 ctg gtt caa gga ata atg gat ttg caa gag ctt ttg gcc aag atg act     816
Leu Val Gln Gly Ile Met Asp Leu Gln Glu Leu Leu Ala Lys Met Thr
            260                 265                 270 gca aaa ctg aat tat gca gag acg aga ctt ggt caa ctg gaa aat tgc     864
Ala Lys Leu Asn Tyr Ala Glu Thr Arg Leu Gly Gln Leu Glu Asn Cys
        275                 280                 285 cac tgt gag aag acc tgc caa gtg agt ggg ctc ctc tac agg gac caa     912
His Cys Glu Lys Thr Cys Gln Val Ser Gly Leu Leu Tyr Arg Asp Gln
    290                 295                 300 gac tcc tgg gtg gat ggt gac aac tgt ggg aac tgc acg tgc aaa agt     960
Asp Ser Trp Val Asp Gly Asp Asn Cys Gly Asn Cys Thr Cys Lys Ser
305                 310                 315                 320 ggt gcc gtg gag tgc cgc agg atg tcc tgt ccc ccg ctc aac tgt tcc    1008
Gly Ala Val Glu Cys Arg Arg Met Ser Cys Pro Pro Leu Asn Cys Ser
                325                 330                 335 ccg gac tca ctt cct gtg cac att tcc ggc cag tgt tgt aaa gtt tgc    1056
Pro Asp Ser Leu Pro Val His Ile Ser Gly Gln Cys Cys Lys Val Cys
            340                 345                 350 aga cca aaa tgt atc tat gga gga aaa gtt ctt gct gag ggc cag cgg    1104
Arg Pro Lys Cys Ile Tyr Gly Gly Lys Val Leu Ala Glu Gly Gln Arg
        355                 360                 365 att tta acc aag acc tgc cgg gaa tgt cga ggt gga gtc ttg gta aaa    1152
Ile Leu Thr Lys Thr Cys Arg Glu Cys Arg Gly Gly Val Leu Val Lys
    370                 375                 380 atc aca gaa gct tgc cct cct ttg aac tgc tca gca aag gat cat att    1200
Ile Thr Glu Ala Cys Pro Pro Leu Asn Cys Ser Ala Lys Asp His Ile
385                 390                 395                 400 ctt cca gag aat cag tgc tgc agg gtc tgc cca ggt cat aac ttc tgt    1248
Leu Pro Glu Asn Gln Cys Cys Arg Val Cys Pro Gly His Asn Phe Cys
                405                 410                 415
```

Figure 1B

```
gca gaa gca cct aag tgc gga gaa aac tcg gaa tgc aaa aat tgg aat  1296   SEQ ID NO:609
Ala Glu Ala Pro Lys Cys Gly Glu Asn Ser Glu Cys Lys Asn Trp Asn         SEQ ID NO:610
            420             425             430 aca aaa gca acc tgt gag tgc aag aat gga tac atc tct gtc cag ggc  1344
Thr Lys Ala Thr Cys Glu Cys Lys Asn Gly Tyr Ile Ser Val Gln Gly
            435             440             445 aac tct gca tac tgt gaa gat att gat gag tgt gca gct aaa atg cac  1392
Asn Ser Ala Tyr Cys Glu Asp Ile Asp Glu Cys Ala Ala Lys Met His
            450             455             460 tat tgt cat gcc aac acc gtg tgt gtc aac ttg ccg ggg ttg tat cgc  1440
Tyr Cys His Ala Asn Thr Val Cys Val Asn Leu Pro Gly Leu Tyr Arg
465             470             475             480 tgt gac tgc gtc cca ggg tac atc cgt gtg gat gac ttc tct tgt acg  1488
Cys Asp Cys Val Pro Gly Tyr Ile Arg Val Asp Asp Phe Ser Cys Thr
                485             490             495 gag cat gat gat tgt ggc agc gga caa cac aac tgc gac aaa aat gcc  1536
Glu His Asp Asp Cys Gly Ser Gly Gln His Asn Cys Asp Lys Asn Ala
            500             505             510 atc tgt acc aac aca gtc cag gga cac agc tgc acc tgc cag ccg ggt  1584
Ile Cys Thr Asn Thr Val Gln Gly His Ser Cys Thr Cys Gln Pro Gly
            515             520             525 tac gtg gga aat ggc acc atc tgc aaa gca ttc tgt gaa gag ggt tgc  1632
Tyr Val Gly Asn Gly Thr Ile Cys Lys Ala Phe Cys Glu Glu Gly Cys
            530             535             540 aga tac gga ggt acc tgt gtg gct cct aac aag tgt gtc tgt cct tct  1680
Arg Tyr Gly Gly Thr Cys Val Ala Pro Asn Lys Cys Val Cys Pro Ser
545             550             555             560 gga ttc acg gga agc cac tgt gag aaa gat att gat gaa tgc gca gag  1728
Gly Phe Thr Gly Ser His Cys Glu Lys Asp Ile Asp Glu Cys Ala Glu
                565             570             575 gga ttc gtt gaa tgc cac aac tac tcc cgc tgt gtt aac ctg cca ggg  1776
Gly Phe Val Glu Cys His Asn Tyr Ser Arg Cys Val Asn Leu Pro Gly
            580             585             590 tgg tac cac tgt gag tgc aga agc ggt ttc cat gac gat ggg acc tac  1824
Trp Tyr His Cys Glu Cys Arg Ser Gly Phe His Asp Asp Gly Thr Tyr
            595             600             605 tca ctg tcc ggg gag tcc tgc att gat atc gat gaa tgt gcc tta aga  1872
Ser Leu Ser Gly Glu Ser Cys Ile Asp Ile Asp Glu Cys Ala Leu Arg
610             615             620
```

Figure 1C

```
act cac act tgt tgg aat gac tct gcc tgc atc aac tta gca gga gga  1920   SEQ ID NO:609
Thr His Thr Cys Trp Asn Asp Ser Ala Cys Ile Asn Leu Ala Gly Gly         SEQ ID NO:610
625             630             635             640 ttt gac tgc ctg tgt ccc tct ggg ccc tcc tgc tct ggt gac tgt ccc  1968
Phe Asp Cys Leu Cys Pro Ser Gly Pro Ser Cys Ser Gly Asp Cys Pro
                645             650             655 cac gaa gga ggg ctg aag cat aat ggg cag gtg tgg att ctg aga gaa  2016
His Glu Gly Gly Leu Lys His Asn Gly Gln Val Trp Ile Leu Arg Glu
        660             665             670 gac agg tgt tca gtc tgt tcc tgc aag gat ggg aag ata ttc tgc cgg  2064
Asp Arg Cys Ser Val Cys Ser Cys Lys Asp Gly Lys Ile Phe Cys Arg
        675             680             685 cgg aca gct tgt gat tgc cag aat cca aat gtt gac ctt ttt tgc tgc  2112
Arg Thr Ala Cys Asp Cys Gln Asn Pro Asn Val Asp Leu Phe Cys Cys
690             695             700 cca gag tgc gat acc agg gtc acc agc caa tgt tta gat caa agt gga  2160
Pro Glu Cys Asp Thr Arg Val Thr Ser Gln Cys Leu Asp Gln Ser Gly
705             710             715             720 cag aag ctc tat cga agt gga gac aac tgg acc cac agc tgc cag cag  2208
Gln Lys Leu Tyr Arg Ser Gly Asp Asn Trp Thr His Ser Cys Gln Gln
                725             730             735 tgc cga tgt ctg gaa gga gag gca gac tgc tgg cct ctg gct tgc cct  2256
Cys Arg Cys Leu Glu Gly Glu Ala Asp Cys Trp Pro Leu Ala Cys Pro
        740             745             750 agt ttg ggc tgt gaa tac aca gcc atg ttt gaa ggg gag tgt tgt ccc  2304
Ser Leu Gly Cys Glu Tyr Thr Ala Met Phe Glu Gly Glu Cys Cys Pro
        755             760             765 cga tgt gtc agt gac ccc tgc ctg gct ggt aat att gcc tat gac atc  2352
Arg Cys Val Ser Asp Pro Cys Leu Ala Gly Asn Ile Ala Tyr Asp Ile
770             775             780 aga aaa act tgc ctg gac agc ttt ggt gtt tcg agg ctg agc gga gcc  2400
Arg Lys Thr Cys Leu Asp Ser Phe Gly Val Ser Arg Leu Ser Gly Ala
785             790             795             800 gtg tgg aca atg gct gga tct cct tgt aca acc tgc aaa tgc aag aat  2448
Val Trp Thr Met Ala Gly Ser Pro Cys Thr Thr Cys Lys Cys Lys Asn
                805             810             815 ggg aga gtc tgc tgc tct gtg gat ctg gag tgt att gag aat aac tga  2496
Gly Arg Val Cys Cys Ser Val Asp Leu Glu Cys Ile Glu Asn Asn
        820             825             830 gac tac aag gac gac gat gac aag          2520   SEQ ID NO:609
Asp Tyr Lys Asp Asp Asp Asp Lys                 SEQ ID NO:610
                835
```

Figure 1D

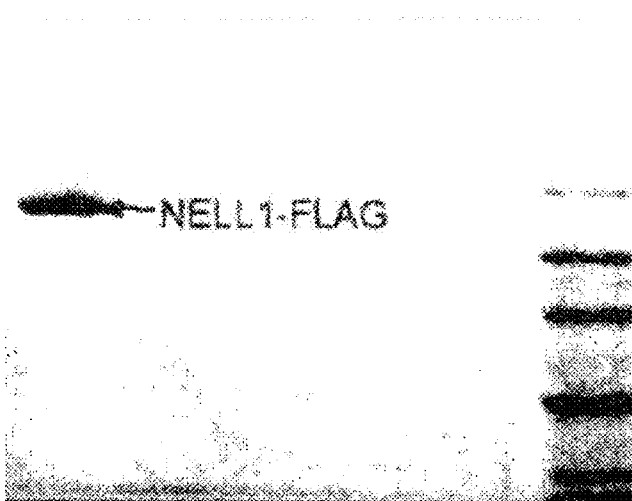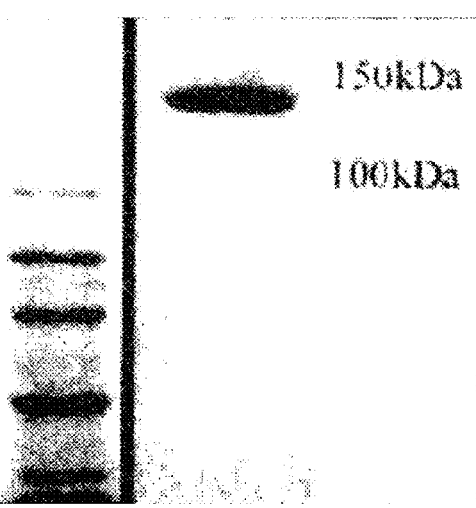
Figure 2A    Figure 2B
Purified NELL1-FLAG protein
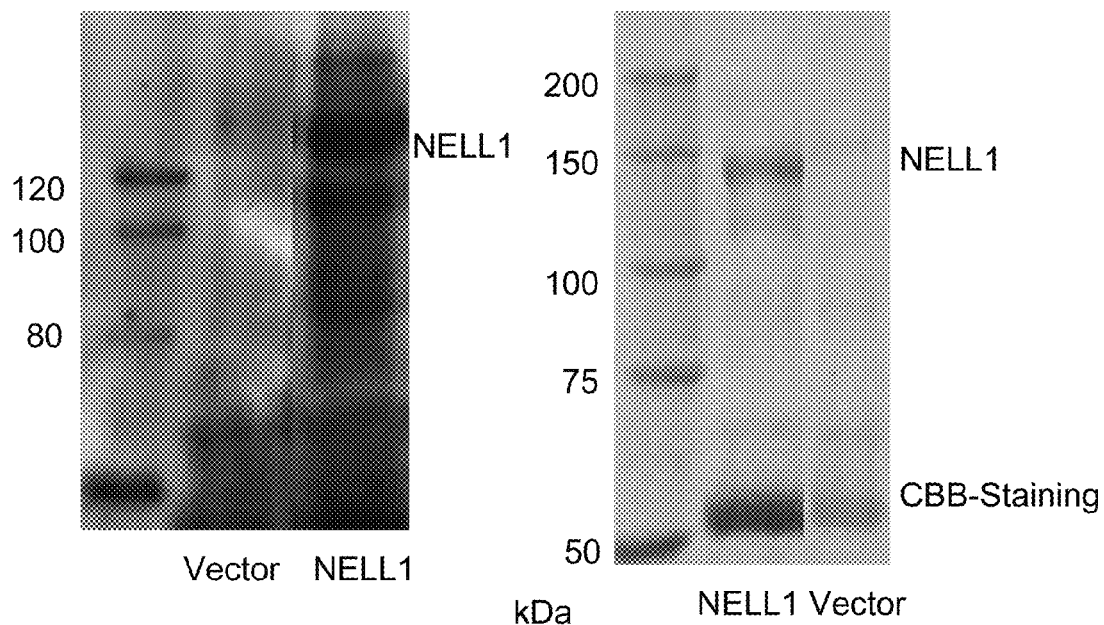
Figure 2C    Figure 2D

```
atg ccg atg gat ttg att tta gtt gtg tgg ttc tgt gtg tgc act gcc   48   SEQ ID NO:1
Met Pro Met Asp Leu Ile Leu Val Val Trp Phe Cys Val Cys Thr Ala        SEQ ID NO:2
1               5                   10                  15 agg aca gtg gtg ggc ttt ggg atg gac cct gac ctt cag atg gat atc   96
Arg Thr Val Val Gly Phe Gly Met Asp Pro Asp Leu Gln Met Asp Ile
                20                  25                  30 gtc acc gag ctt gac ctt gtg aac acc acc ctt gga gtt gct cag gtg   144
Val Thr Glu Leu Asp Leu Val Asn Thr Thr Leu Gly Val Ala Gln Val
        35                  40                  45 tct gga atg cac aat gcc agc aaa gca ttt tta ttt caa gac ata gaa   192
Ser Gly Met His Asn Ala Ser Lys Ala Phe Leu Phe Gln Asp Ile Glu
    50                  55                  60 aga gag atc cat gca gct cct cat gtg agt gag aaa tta att cag ctg   240
Arg Glu Ile His Ala Ala Pro His Val Ser Glu Lys Leu Ile Gln Leu
65                  70                  75                  80 ttc cag aac aag agt gaa ttc acc att ttg gcc act gta cag cag aag   288
Phe Gln Asn Lys Ser Glu Phe Thr Ile Leu Ala Thr Val Gln Gln Lys
                85                  90                  95 cca tcc act tca gga gtg ata ctg tcc att cga gaa ctg gag cac agc   336
Pro Ser Thr Ser Gly Val Ile Leu Ser Ile Arg Glu Leu Glu His Ser
                100                 105                 110 tat ttt gaa ctg gag agc agt ggc ctg agg gat gag att cgg tat cac   384
Tyr Phe Glu Leu Glu Ser Ser Gly Leu Arg Asp Glu Ile Arg Tyr His
        115                 120                 125 tac ata cac aat ggg aag cca agg aca gag gca ctt cct tac cgc atg   432
Tyr Ile His Asn Gly Lys Pro Arg Thr Glu Ala Leu Pro Tyr Arg Met
    130                 135                 140 gca gat gga caa tgg cac aag gtt gca ctg tca gtt agc gcc tct cat   480
Ala Asp Gly Gln Trp His Lys Val Ala Leu Ser Val Ser Ala Ser His
145                 150                 155                 160 ctc ctg ctc cat gtc gac tgt aac agg att tat gag cgt gtg ata gac   528
Leu Leu Leu His Val Asp Cys Asn Arg Ile Tyr Glu Arg Val Ile Asp
                165                 170                 175 cct cca gat acc aac ctt ccc cca gga atc aat tta tgg ctt ggc cag   576
Pro Pro Asp Thr Asn Leu Pro Pro Gly Ile Asn Leu Trp Leu Gly Gln
                180                 185                 190 cgc aac caa aag cat ggc tta ttc aaa ggg atc atc caa gat ggg aag   624
Arg Asn Gln Lys His Gly Leu Phe Lys Gly Ile Ile Gln Asp Gly Lys
        195                 200                 205
```

FIGURE 4A

```
atc atc ttt atg ccg aat gga tat ata aca cag tgt cca aat cta aat   672    SEQ ID NO:1
Ile Ile Phe Met Pro Asn Gly Tyr Ile Thr Gln Cys Pro Asn Leu Asn          SEQ ID NO:2
    210                 215                 220 cac act tgc cca acc tgc agt gat ttc tta agc ctg gtg caa gga ata          720
His Thr Cys Pro Thr Cys Ser Asp Phe Leu Ser Leu Val Gln Gly Ile
225                 230                 235                 240 atg gat tta caa gag ctt ttg gcc aag atg act gca aaa cta aat tat          768
Met Asp Leu Gln Glu Leu Leu Ala Lys Met Thr Ala Lys Leu Asn Tyr
                245                 250                 255 gca gag aca aga ctt agt caa ttg gaa aac tgt cat tgt gag aag act          816
Ala Glu Thr Arg Leu Ser Gln Leu Glu Asn Cys His Cys Glu Lys Thr
                260                 265                 270 tgt caa gtg agt gga ctg ctc tat cga gat caa gac tct tgg gta gat          864
Cys Gln Val Ser Gly Leu Leu Tyr Arg Asp Gln Asp Ser Trp Val Asp
            275                 280                 285 ggt gac cat tgc agg aac tgc act tgc aaa agt ggt gcc gtg gaa tgc          912
Gly Asp His Cys Arg Asn Cys Thr Cys Lys Ser Gly Ala Val Glu Cys
290                 295                 300 cga agg atg tcc tgt ccc cct ctc aat tgc tcc cca gac tcc ctc cca          960
Arg Arg Met Ser Cys Pro Pro Leu Asn Cys Ser Pro Asp Ser Leu Pro
305                 310                 315                 320 gta cac att gct ggc cag tgc tgt aag gtc tgc cga cca aaa tgt atc         1008
Val His Ile Ala Gly Gln Cys Cys Lys Val Cys Arg Pro Lys Cys Ile
                325                 330                 335 tat gga gga aaa gtt ctt gca gaa ggc cag cgg att tta acc aag agc         1056
Tyr Gly Gly Lys Val Leu Ala Glu Gly Gln Arg Ile Leu Thr Lys Ser
                340                 345                 350 tgt cgg gaa tgc cga ggt gga gtt tta gta aaa att aca gaa atg tgt         1104
Cys Arg Glu Cys Arg Gly Gly Val Leu Val Lys Ile Thr Glu Met Cys
            355                 360                 365 cct cct ttg aac tgc tca gaa aag gat cac att ctt cct gag aat cag         1152
Pro Pro Leu Asn Cys Ser Glu Lys Asp His Ile Leu Pro Glu Asn Gln
370                 375                 380 tgc tgc cgt gtc tgt aga ggt cat aac ttt tgt gca gaa gga cct aaa         1200
Cys Cys Arg Val Cys Arg Gly His Asn Phe Cys Ala Glu Gly Pro Lys
385                 390                 395                 400 tgt ggt gaa aac tca gag tgc aaa aac tgg aat aca aaa gct act tgt         1248
Cys Gly Glu Asn Ser Glu Cys Lys Asn Trp Asn Thr Lys Ala Thr Cys
                405                 410                 415
```

FIGURE 4B

```
gag tgc aag agt ggt tac atc tct gtc cag gga gac tct gcc tac tgt  1296   SEQ ID NO:1
Glu Cys Lys Ser Gly Tyr Ile Ser Val Gln Gly Asp Ser Ala Tyr Cys         SEQ ID NO:2
            420             425             430 gaa gat att gat gag tgt gca gct aag atg cat tac tgt cat gcc aat  1344
Glu Asp Ile Asp Glu Cys Ala Ala Lys Met His Tyr Cys His Ala Asn
            435             440             445 act gtg tgt gtc aac ctt cct ggg tta tat cgc tgt gac tgt gtc cca  1392
Thr Val Cys Val Asn Leu Pro Gly Leu Tyr Arg Cys Asp Cys Val Pro
            450             455             460 gga tac att cgt gtg gat gac ttc tct tgt aca gaa cac gat gaa tgt  1440
Gly Tyr Ile Arg Val Asp Asp Phe Ser Cys Thr Glu His Asp Glu Cys
465             470             475             480 ggc agc ggc cag cac aac tgt gat gag aat gcc atc tgc acc aac act  1488
Gly Ser Gly Gln His Asn Cys Asp Glu Asn Ala Ile Cys Thr Asn Thr
            485             490             495 gtc cag gga cac agc tgc acc tgc aaa ccg ggc tac gtg ggg aac ggg  1536
Val Gln Gly His Ser Cys Thr Cys Lys Pro Gly Tyr Val Gly Asn Gly
            500             505             510 acc atc tgc aga gct ttc tgt gaa gag ggc tgc aga tac ggt gga acg  1584
Thr Ile Cys Arg Ala Phe Cys Glu Glu Gly Cys Arg Tyr Gly Gly Thr
            515             520             525 tgt gtg gct ccc aac aaa tgt gtc tgt cca tct gga ttc aca gga agc  1632
Cys Val Ala Pro Asn Lys Cys Val Cys Pro Ser Gly Phe Thr Gly Ser
            530             535             540 cac tgc gag aaa gat att gat gaa tgt tca gag gga atc att gag tgc  1680
His Cys Glu Lys Asp Ile Asp Glu Cys Ser Glu Gly Ile Ile Glu Cys
545             550             555             560 cac aac cat tcc cgc tgc gtt aac ctg cca ggg tgg tac cac tgt gag  1728
His Asn His Ser Arg Cys Val Asn Leu Pro Gly Trp Tyr His Cys Glu
            565             570             575 tgc aga agc ggt ttc cat gac gat ggg acc tat tca ctg tcc ggg gag  1776
Cys Arg Ser Gly Phe His Asp Asp Gly Thr Tyr Ser Leu Ser Gly Glu
            580             585             590 tcc tgt att gac att gat gaa tgt gcc tta aga act cac acc tgt tgg  1824
Ser Cys Ile Asp Ile Asp Glu Cys Ala Leu Arg Thr His Thr Cys Trp
            595             600             605 aac gat tct gcc tgc atc aac ctg gca ggg ggt ttt gac tgt ctc tgc  1872
Asn Asp Ser Ala Cys Ile Asn Leu Ala Gly Gly Phe Asp Cys Leu Cys
            610             615             620
```

FIGURE 4C

```
ccc tct ggg ccc tcc tgc tct ggt gac tgt cct cat gaa ggg ggg ctg      1920
Pro Ser Gly Pro Ser Cys Ser Gly Asp Cys Pro His Glu Gly Gly Leu
625             630                 635                 640 aag cac aat ggc cag gtg tgg acc ttg aaa gaa gac agg tgt tct gtc      1968
Lys His Asn Gly Gln Val Trp Thr Leu Lys Glu Asp Arg Cys Ser Val
                645                 650                 655 tgc tcc tgc aag gat ggc aag ata ttc tgc cga cgg aca gct tgt gat      2016
Cys Ser Cys Lys Asp Gly Lys Ile Phe Cys Arg Arg Thr Ala Cys Asp
            660                 665                 670 tgc cag aat cca agt gct gac cta ttc tgt tgc cca gaa tgt gac acc      2064
Cys Gln Asn Pro Ser Ala Asp Leu Phe Cys Cys Pro Glu Cys Asp Thr
        675                 680                 685 aga gtc aca agt caa tgt tta gac caa aat ggt cac aag ctg tat cga      2112
Arg Val Thr Ser Gln Cys Leu Asp Gln Asn Gly His Lys Leu Tyr Arg
    690                 695                 700 agt gga gac aat tgg acc cat agc tgt cag cag tgt cgg tgt ctg gaa      2160
Ser Gly Asp Asn Trp Thr His Ser Cys Gln Gln Cys Arg Cys Leu Glu
705                 710                 715                 720 gga gag gta gat tgc tgg cca ctc act tgc ccc aac ttg agc tgt gag      2208
Gly Glu Val Asp Cys Trp Pro Leu Thr Cys Pro Asn Leu Ser Cys Glu
                725                 730                 735 tat aca gct atc tta gaa ggg gaa tgt tgt ccc cgc tgt gtc agt gac      2256
Tyr Thr Ala Ile Leu Glu Gly Glu Cys Cys Pro Arg Cys Val Ser Asp
            740                 745                 750 ccc tgc cta gct gat aac atc acc tat gac atc aga aaa act tgc ctg      2304
Pro Cys Leu Ala Asp Asn Ile Thr Tyr Asp Ile Arg Lys Thr Cys Leu
        755                 760                 765 gac agc tat ggt gtt tca cgg ctt agt ggc tca gtg tgg acg atg gct      2352
Asp Ser Tyr Gly Val Ser Arg Leu Ser Gly Ser Val Trp Thr Met Ala
    770                 775                 780 gga tct ccc tgc aca acc tgt aaa tgc aag aat gga aga gtc tgt tgt      2400
Gly Ser Pro Cys Thr Thr Cys Lys Cys Lys Asn Gly Arg Val Cys Cys
785                 790                 795                 800 tct gtg gat ttt gag tgt ctt caa aat aat tga    2433   SEQ ID NO:1
Ser Val Asp Phe Glu Cys Leu Gln Asn Asn                SEQ ID NO:2
                805                 810
```

FIGURE 4D

```
atg ccg atg gat gtg att tta gtt ttg tgg ttc tgt gta tgc acc gcc    48   SEQ ID NO:
Met Pro Met Asp Val Ile Leu Val Leu Trp Phe Cys Val Cys Thr Ala         SEQ ID NO:
1               5                   10                  15 agg aca gtg ttg ggc ttt ggg atg gac cct gac ctt cag ctg gac atc    96
Arg Thr Val Leu Gly Phe Gly Met Asp Pro Asp Leu Gln Leu Asp Ile
                20                  25                  30 atc tca gag ctc gac ctg gtg aac acc acc ctg gga gtc acg cag gtg   144
Ile Ser Glu Leu Asp Leu Val Asn Thr Thr Leu Gly Val Thr Gln Val
        35                  40                  45 gct gga ctg cac aac gcc agt aaa gca ttt cta ttt caa gat gta cag   192
Ala Gly Leu His Asn Ala Ser Lys Ala Phe Leu Phe Gln Asp Val Gln
    50                  55                  60 aga gag atc cat tcg gcc cct cac gtg agt gag aag ctg atc cag cta   240
Arg Glu Ile His Ser Ala Pro His Val Ser Glu Lys Leu Ile Gln Leu
65                  70                  75                  80 ttc cgg aat aag agc gag ttc acc ttt ttg gct aca gtg cag cag aaa   288
Phe Arg Asn Lys Ser Glu Phe Thr Phe Leu Ala Thr Val Gln Gln Lys
                85                  90                  95 cca tcc acc tca ggg gtg ata ctg tcc atc cgg gag ctg gag cac agc   336
Pro Ser Thr Ser Gly Val Ile Leu Ser Ile Arg Glu Leu Glu His Ser
                100                 105                 110 tat ttt gaa ctg gag agc agt ggc cca aga gaa gag ata cgc tac cat   384
Tyr Phe Glu Leu Glu Ser Ser Gly Pro Arg Glu Glu Ile Arg Tyr His
        115                 120                 125 tac ata cat ggt gga aag ccc agg act gag gcc ctt ccc tac cgc atg   432
Tyr Ile His Gly Gly Lys Pro Arg Thr Glu Ala Leu Pro Tyr Arg Met
    130                 135                 140 gca gac gga caa tgg cac aag gtc gcg ctg tca gtg agc gcc tct cac   480
Ala Asp Gly Gln Trp His Lys Val Ala Leu Ser Val Ser Ala Ser His
145                 150                 155                 160 ctc ctg ctc cac atc gac tgc aat agg att tac gag cgt gtg ata gac   528
Leu Leu Leu His Ile Asp Cys Asn Arg Ile Tyr Glu Arg Val Ile Asp
                165                 170                 175 cct ccg gag acc aac ctt cct cca gga agc aat ctg tgg ctt ggg caa   576
Pro Pro Glu Thr Asn Leu Pro Pro Gly Ser Asn Leu Trp Leu Gly Gln
                180                 185                 190 cgt aac caa aag cat ggc ttt ttc aaa gga atc atc caa gat ggt aag   624
Arg Asn Gln Lys His Gly Phe Phe Lys Gly Ile Ile Gln Asp Gly Lys
        195                 200                 205
```

FIGURE 5A

```
atc atc ttc atg ccg aat ggt ttc atc aca cag tgt ccc aac ctc aat  672   SEQ ID NO:3
Ile Ile Phe Met Pro Asn Gly Phe Ile Thr Gln Cys Pro Asn Leu Asn        SEQ ID NO:4
210             215                 220 cgc act tgc cca aca tgc agt gac ttc ctg agc ctg gtt caa gga ata        720
Arg Thr Cys Pro Thr Cys Ser Asp Phe Leu Ser Leu Val Gln Gly Ile
225             230                 235                 240 atg gat ttg caa gag ctt ttg gcc aag atg act gca aaa ctg aat tat        768
Met Asp Leu Gln Glu Leu Leu Ala Lys Met Thr Ala Lys Leu Asn Tyr
            245                 250                 255 gca gag acg aga ctt ggt caa ctg gaa aat tgc cac tgt gag aag acc        816
Ala Glu Thr Arg Leu Gly Gln Leu Glu Asn Cys His Cys Glu Lys Thr
                260                 265                 270 tgc caa gtg agt ggg ctg ctc tac agg gac caa gac tcc tgg gtg gat        864
Cys Gln Val Ser Gly Leu Leu Tyr Arg Asp Gln Asp Ser Trp Val Asp
            275                 280                 285 ggt gac aac tgt ggg aac tgc acg tgc aaa agt ggt gcc gtg gag tgc        912
Gly Asp Asn Cys Gly Asn Cys Thr Cys Lys Ser Gly Ala Val Glu Cys
            290                 295                 300 cgc agg atg tcc tgt ccc ccg ctc aac tgt tcc ccg gac tca ctt cct        960
Arg Arg Met Ser Cys Pro Pro Leu Asn Cys Ser Pro Asp Ser Leu Pro
305             310                 315                 320 gtg cac att tcc ggc cag tgt tgt aaa gtt tgc aga cca aaa tgt atc       1008
Val His Ile Ser Gly Gln Cys Cys Lys Val Cys Arg Pro Lys Cys Ile
                325                 330                 335 tat gga gga aaa gtt ctt gct gag ggc cag cgg att tta acc aag acc       1056
Tyr Gly Gly Lys Val Leu Ala Glu Gly Gln Arg Ile Leu Thr Lys Thr
            340                 345                 350 tgc cgg gaa tgt cga ggt gga gtc ttg gta aaa atc aca gaa gct tgc       1104
Cys Arg Glu Cys Arg Gly Gly Val Leu Val Lys Ile Thr Glu Ala Cys
            355                 360                 365 cct cct ttg aac tgc tca gca aag gat cat att ctt cca gag aat cag       1152
Pro Pro Leu Asn Cys Ser Ala Lys Asp His Ile Leu Pro Glu Asn Gln
            370                 375                 380 tgc tgc agg gtc tgc cca ggt cat aac ttc tgt gca gaa gca cct aag       1200
Cys Cys Arg Val Cys Pro Gly His Asn Phe Cys Ala Glu Ala Pro Lys
385             390                 395                 400 tgc gga gaa aac tcg gaa tgc aaa aat tgg aat aca aaa gca acc tgt       1248
Cys Gly Glu Asn Ser Glu Cys Lys Asn Trp Asn Thr Lys Ala Thr Cys
            405                 410                 415
```

FIGURE 5B

```
gag tgc aag aat gga tac atc tct gtc cag ggc aac tct gca tac tgt   1296   SEQ ID NO:3
Glu Cys Lys Asn Gly Tyr Ile Ser Val Gln Gly Asn Ser Ala Tyr Cys          SEQ ID NO:4
            420                 425                 430 gaa gat att gat gag tgt gca gct aaa atg cac tat tgt cat gcc aac   1344
Glu Asp Ile Asp Glu Cys Ala Ala Lys Met His Tyr Cys His Ala Asn
            435                 440                 445 acc gtg tgt gtc aac ttg ccg ggg ttg tat cgc tgt gac tgc gtc cca   1392
Thr Val Cys Val Asn Leu Pro Gly Leu Tyr Arg Cys Asp Cys Val Pro
450                 455                 460 ggg tac atc cgt gtg gat gac ttc tct tgt acg gag cat gat gat tgt   1440
Gly Tyr Ile Arg Val Asp Asp Phe Ser Cys Thr Glu His Asp Asp Cys
465                 470                 475                 480 ggc agc gga caa cac aac tgc gac aaa aat gcc atc tgt acc aac aca   1488
Gly Ser Gly Gln His Asn Cys Asp Lys Asn Ala Ile Cys Thr Asn Thr
            485                 490                 495 gtc cag gga cac agc tgc acc tgc cag ccg ggt tac gtg gga aat ggc   1536
Val Gln Gly His Ser Cys Thr Cys Gln Pro Gly Tyr Val Gly Asn Gly
            500                 505                 510 acc atc tgc aaa gca ttc tgt gaa gag ggt tgc aga tac gga ggt acc   1584
Thr Ile Cys Lys Ala Phe Cys Glu Glu Gly Cys Arg Tyr Gly Gly Thr
            515                 520                 525 tgt gtg gct cct aac aag tgt gtc tgt cct tct gga ttc acg gga agc   1632
Cys Val Ala Pro Asn Lys Cys Val Cys Pro Ser Gly Phe Thr Gly Ser
            530                 535                 540 cac tgt gag aaa gat att gat gaa tgc gca gag gga ttc gtt gaa tgc   1680
His Cys Glu Lys Asp Ile Asp Glu Cys Ala Glu Gly Phe Val Glu Cys
545                 550                 555                 560 cac aac tac tcc cgc tgt gtt aac ctg cca ggg tgg tac cac tgt gag   1728
His Asn Tyr Ser Arg Cys Val Asn Leu Pro Gly Trp Tyr His Cys Glu
            565                 570                 575 tgc aga agc ggt ttc cat gac gat ggg acc tac tca ctg tcc ggg gag   1776
Cys Arg Ser Gly Phe His Asp Asp Gly Thr Tyr Ser Leu Ser Gly Glu
            580                 585                 590 tcc tgc att gat atc gat gaa tgt gcc tta aga act cac act tgt tgg   1824
Ser Cys Ile Asp Ile Asp Glu Cys Ala Leu Arg Thr His Thr Cys Trp
            595                 600                 605 aat gac tct gcc tgc atc aac tta gca gga gga ttt gac tgc ctg tgt   1872
Asn Asp Ser Ala Cys Ile Asn Leu Ala Gly Gly Phe Asp Cys Leu Cys
610                 615                 620
```

FIGURE 5C

```
ccc tct ggg ccc tcc tgc tct ggt gac tgt ccc cac gaa gga ggg ctg      1920
Pro Ser Gly Pro Ser Cys Ser Gly Asp Cys Pro His Glu Gly Gly Leu
625             630             635             640 aag cat aat ggg cag gtg tgg att ctg aga gaa gac agg tgt tca gtc      1968
Lys His Asn Gly Gln Val Trp Ile Leu Arg Glu Asp Arg Cys Ser Val
                645             650             655 tgt tcc tgc aag gat ggg aag ata ttc tgc cgg cgg aca gct tgt gat      2016
Cys Ser Cys Lys Asp Gly Lys Ile Phe Cys Arg Arg Thr Ala Cys Asp
            660             665             670 tgc cag aat cca aat gtt gac ctt ttt tgc tgc cca gag tgc gat acc      2064
Cys Gln Asn Pro Asn Val Asp Leu Phe Cys Cys Pro Glu Cys Asp Thr
        675             680             685 agg gtc acc agc caa tgt tta gat caa agt gga cag aag ctc tat cga      2112
Arg Val Thr Ser Gln Cys Leu Asp Gln Ser Gly Gln Lys Leu Tyr Arg
    690             695             700 agt gga gac aac tgg acc cac agc tgc cag cag tgc cga tgt ctg gaa      2160
Ser Gly Asp Asn Trp Thr His Ser Cys Gln Gln Cys Arg Cys Leu Glu
705             710             715             720 gga gag gca gac tgc tgg cct ctg gct tgc cct agt ttg ggc tgt gaa      2208
Gly Glu Ala Asp Cys Trp Pro Leu Ala Cys Pro Ser Leu Gly Cys Glu
                725             730             735 tac aca gcc atg ttt gaa ggg gag tgt tgt ccc cga tgt gtc agt gac      2256
Tyr Thr Ala Met Phe Glu Gly Glu Cys Cys Pro Arg Cys Val Ser Asp
                740             745             750 ccc tgc ctg gct ggt aat att gcc tat gac atc aga aaa act tgc ctg      2304
Pro Cys Leu Ala Gly Asn Ile Ala Tyr Asp Ile Arg Lys Thr Cys Leu
            755             760             765 gac agc ttt ggt gtt tcg agg ctg agc gga gcc gtg tgg aca atg gct      2352
Asp Ser Phe Gly Val Ser Arg Leu Ser Gly Ala Val Trp Thr Met Ala
        770             775             780 gga tct cct tgt aca acc tgc aaa tgc aag aat ggg aga gtc tgc tgc      2400
Gly Ser Pro Cys Thr Thr Cys Lys Cys Lys Asn Gly Arg Val Cys Cys
785             790             795             800 tct gtg gat ctg gag tgt att gag aat aac tga    2433  SEQ ID NO:3
Ser Val Asp Leu Glu Cys Ile Glu Asn Asn                SEQ ID NO:4
                805             810
```

FIGURE 5D

```
atgccgatgg atgtgatttt agttttgtgg ttctgtgtgt gcaccgccag gacagtgctg    60  SEQ ID NO:5
ggctttggga tggaccctga ccttcagatg gacatcatca ctgaacttga ccttgtgaac   120
accaccctgg gcgtcactca ggtggctgga ctacacaatg ccagtaaggc atttctgttt   180
caagatgtac agagagagat ccactcagcc cctcatgtga gtgagaagct gatccagcta   240
ttccggaata gagtgagtt accttttg gctacagtgc agcagaagcc gtccacctca      300
ggggtgatac tgtcgatccg ggagctggaa cacagctatt ttgaactgga gagcagtggc   360
ccaagagaag agatacgcta tcattacatc catggcggca agcccaggac tgaggccctt   420
ccctaccgca tggccgatgg acagtggcac aaggtcgcgc tgtctgtgag cgcctctcac   480
ctcctactcc atgtcgactg caataggatt tatgagcgtg tgatagatcc tccggagacc   540
aaccttcctc caggaagcaa tctatggctt gggcaacgta atcaaaagca tggcttttc    600
aaaggaatca tccaagatgg caagatcatc ttcatgccga acggcttcat cacacagtgc   660
cccaacctaa atcgcacttg cccaacatgc agtgatttcc tgagcctggt tcaaggaata   720
atggatttgc aagagctttt ggccaagatg actgcaaaac tgaattatgc agagacgaga   780
cttggtcaac tggaaaattg ccactgtgag aagacctgcc aagtgagtgg gctgctctac   840
agggaccaag actcctgggt agatggtgac aactgcagga actgcacatg caaaagtggt   900
gctgtggagt gccgaaggat gtcctgtccc ccactcaact gttccccaga ctcacttcct   960
gtgcatattt ctggccaatg ttgtaaagtt tgcagaccaa aatgtatcta tggaggaaaa  1020
gttcttgctg agggccagcg gattttaacc aagacctgcc gggaatgtcg aggtggagtc  1080
ttggtaaaaa tcacagaagc ttgccctcct ttgaactgct cagagaagga tcatattctt  1140
ccggagaacc agtgctgcag ggtctgccga ggtcataact tctgtgcaga agcacctaag  1200
tgtggagaaa actcggaatg caaaaattgg aatacaaaag cgacttgtga gtgcaagaat  1260
ggatacatct ctgtccaggg caactctgca tactgtgaag atatcgatga gtgtgcagca  1320
aagatgcact actgtcatgc caacacggtg tgtgtcaact gccgggggtt atatcgctgt  1380
gactgcatcc aggatacat ccgtgtggat gacttctctt gtacggagca tgatgattgt   1440
ggcagcggac aacacaactg tgacaaaaat gccatctgta ccaacacagt ccagggacac  1500
agctgtacct gccagccagg ctacgtggga aatggtactg tctgcaaagc attctgtgaa  1560
```

FIGURE 6A

```
gagggttgca gatacggagg tacctgtgtg gcccctaaca aatgtgtctg tccttctgga    1620
ttcacaggaa gccactgtga gaaagatatt gatgaatgtg cagagggatt cgttgagtgc    1680
cacaaccact cccgctgcgt taaccttcca gggtggtacc actgtgagtg cagaagcggt    1740
ttccatgacg atgggaccta ttcactgtcc ggggagtcct gcattgatat tgatgaatgt    1800
gccttaagaa ctcacacttg ttggaatgac tctgcctgca tcaacttagc aggaggattt    1860
gactgcctgt gtccctctgg gccctcctgc tctggtgact gtcccacga agggggctg     1920 aagcataatg ggcaggtgtg gattctgaga gaagacaggt gttcagtctg ttcctgtaag    1980
gatgggaaga tattctgccg gcggacagct tgtgattgcc agaatccaaa tgttgaccTt    2040
ttctgctgcc cagagtgtga caccagggtc actagccaat gtttagatca aagcggacag    2100
aagctctatc gaagtggaga caactggacc cacagctgcc agcagtgccg atgtctggaa    2160
ggagaggcag actgctggcc tctagcttgc cctagtttga gctgtaata cacagccatc    2220 tttgaaggag agtgttgtcc ccgctgtgtc agtgacccct gcctggctga taatattgcc    2280
tatgacatca gaaaaacttg cctggacagc tctggtattt cgaggctgag cggcgcagtg    2340
tggacaatgg ctggatctcc ctgtacaacc tgtcaatgca gaatgggag agtctgctgc    2400 tctgtggatc tggtgtgtct tgagaataac tga  2433   SEQ ID NO:5
```

FIGURE 6B

```
Met Pro Met Asp Val Ile Leu Val Leu Trp Phe Cys Val Cys Thr Ala    SEQ ID NO:6
1               5                   10                  15

Arg Thr Val Leu Gly Phe Gly Met Asp Pro Asp Leu Gln Met Asp Ile
                20                  25                  30

Ile Thr Glu Leu Asp Leu Val Asn Thr Thr Leu Gly Val Thr Gln Val
            35                  40                  45

Ala Gly Leu His Asn Ala Ser Lys Ala Phe Leu Phe Gln Asp Val Gln
        50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
                100                 105                 110

Tyr Phe Glu Leu Glu Ser Ser Gly Pro Arg Glu Glu Ile Arg Tyr His
            115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205
```

FIGURE 6C

```
Ile Ile Phe Met Pro Asn Gly Phe Ile Thr Gln Cys Pro Asn Leu Asn    SEQ ID NO:6
        210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
                260                 265                 270

Cys Gln Val Ser Gly Leu Leu Tyr Arg Asp Gln Asp Ser Trp Val Asp
            275                 280                 285

Gly Asp Asn Cys Arg Asn Cys Thr Cys Lys Ser Gly Ala Val Glu Cys
        290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
                340                 345                 350

Cys Arg Glu Cys Arg Gly Gly Val Leu Val Lys Ile Thr Glu Ala Cys
            355                 360                 365

Pro Pro Leu Asn Cys Ser Glu Lys Asp His Ile Leu Pro Glu Asn Gln
            370                 375                 380

Cys Cys Arg Val Cys Arg Gly His Asn Phe Cys Ala Glu Ala Pro Lys
385                 390                 395                 400

Cys Gly Glu Asn Ser Glu Cys Lys Asn Trp Asn Thr Lys Ala Thr Cys
                405                 410                 415
```

FIGURE 6D

```
Glu Cys Lys Asn Gly Tyr Ile Ser Val Gln Gly Asn Ser Ala Tyr Cys   SEQ ID NO:6
            420                 425                 430

Glu Asp Ile Asp Glu Cys Ala Ala Lys Met His Tyr Cys His Ala Asn
            435                 440                 445

Thr Val Cys Val Asn Leu Pro Gly Leu Tyr Arg Cys Asp Cys Ile Pro
            450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
                500                 505                 510

Thr Val Cys Lys Ala Phe Cys Glu Glu Gly Cys Arg Tyr Gly Gly Thr
            515                 520                 525

Cys Val Ala Pro Asn Lys Cys Val Cys Pro Ser Gly Phe Thr Gly Ser
            530                 535                 540

His Cys Glu Lys Asp Ile Asp Glu Cys Ala Glu Gly Phe Val Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
                580                 585                 590

Ser Cys Ile Asp Ile Asp Glu Cys Ala Leu Arg Thr His Thr Cys Trp
            595                 600                 605

Asn Asp Ser Ala Cys Ile Asn Leu Ala Gly Gly Phe Asp Cys Leu Cys
            610                 615                 620
```

FIGURE 6E

```
Pro Ser Gly Pro Ser Cys Ser Gly Asp Cys Pro His Glu Gly Gly Leu    SEQ ID NO:6
625                 630                 635                 640

Lys His Asn Gly Gln Val Trp Ile Leu Arg Glu Asp Arg Cys Ser Val
            645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
        675                 680                 685

Arg Val Thr Ser Gln Cys Leu Asp Gln Ser Gly Gln Lys Leu Tyr Arg
    690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Ser Cys Glu
                725                 730                 735

Tyr Thr Ala Ile Phe Glu Gly Glu Cys Cys Pro Arg Cys Val Ser Asp
            740                 745                 750

Pro Cys Leu Ala Asp Asn Ile Ala Tyr Asp Ile Arg Lys Thr Cys Leu
        755                 760                 765

Asp Ser Ser Gly Ile Ser Arg Leu Ser Gly Ala Val Trp Thr Met Ala
    770                 775                 780

Gly Ser Pro Cys Thr Thr Cys Gln Cys Lys Asn Gly Arg Val Cys Cys
785                 790                 795                 800

Ser Val Asp Leu Val Cys Leu Glu Asn Asn
            805                 810
```

FIGURE 6F

```
atg gag tct cgg gtc tta ctg aga aca ttc tgt ttg atc ttc ggt ctc    48  SEQ ID NO:7
Met Glu Ser Arg Val Leu Leu Arg Thr Phe Cys Leu Ile Phe Gly Leu        SEQ ID NO:8
1               5                   10                  15 gga gca gtt tgg ggg ctt ggt gtg gac cct tcc cta cag att gac gtc    96
Gly Ala Val Trp Gly Leu Gly Val Asp Pro Ser Leu Gln Ile Asp Val
            20                  25                  30 tta aca gag tta gaa ctt ggg gag tcc acg acc gga gtg cgt cag gtc    144
Leu Thr Glu Leu Glu Leu Gly Glu Ser Thr Thr Gly Val Arg Gln Val
        35                  40                  45 ccg ggg ctg cat aat ggg acg aaa gcc ttt ctc ttt caa gat act ccc    192
Pro Gly Leu His Asn Gly Thr Lys Ala Phe Leu Phe Gln Asp Thr Pro
    50                  55                  60 aga agc ata aaa gca tcc act gct aca gct gaa cag ttt ttt cag aag    240
Arg Ser Ile Lys Ala Ser Thr Ala Thr Ala Glu Gln Phe Phe Gln Lys
65                  70                  75                  80 ctg aga aat aaa cat gaa ttt act att ttg gtg acc cta aaa cag acc    288
Leu Arg Asn Lys His Glu Phe Thr Ile Leu Val Thr Leu Lys Gln Thr
                85                  90                  95 cac tta aat tca gga gtt att ctc tca att cac cac ttg gat cac agg    336
His Leu Asn Ser Gly Val Ile Leu Ser Ile His His Leu Asp His Arg
            100                 105                 110 tac ctg gaa ctg gaa agt agt ggc cat cgg aat gaa gtc aga ctg cat    384
Tyr Leu Glu Leu Glu Ser Ser Gly His Arg Asn Glu Val Arg Leu His
        115                 120                 125 tac cgc tca ggc agt cac cgc cct cac aca gaa gtg ttt cct tac att    432
Tyr Arg Ser Gly Ser His Arg Pro His Thr Glu Val Phe Pro Tyr Ile
    130                 135                 140 ttg gct gat gac aag tgg cac aag ctc tcc tta gcc atc agt gct tcc    480
Leu Ala Asp Asp Lys Trp His Lys Leu Ser Leu Ala Ile Ser Ala Ser
145                 150                 155                 160 cat ttg att tta cac att gac tgc aat aaa att tat gaa agg gta gta    528
His Leu Ile Leu His Ile Asp Cys Asn Lys Ile Tyr Glu Arg Val Val
                165                 170                 175 gaa aag ccc tcc aca gac ttg cct cta ggc aca aca ttt tgg cta gga    576
Glu Lys Pro Ser Thr Asp Leu Pro Leu Gly Thr Thr Phe Trp Leu Gly
            180                 185                 190 cag aga aat aat gcg cat gga tat ttt aag ggt ata atg caa gat gtc    624
Gln Arg Asn Asn Ala His Gly Tyr Phe Lys Gly Ile Met Gln Asp Val
        195                 200                 205
```

FIGURE 7A

```
caa tta ctt gtc atg ccc cag gga ttt att gct cag tgc cca gat ctt    672    SEQ ID NO:7
Gln Leu Leu Val Met Pro Gln Gly Phe Ile Ala Gln Cys Pro Asp Leu           SEQ ID NO:8
    210             215             220 aat cgc acc tgt cca act tgc aat gac ttc cat gga ctt gtg cag aaa    720
Asn Arg Thr Cys Pro Thr Cys Asn Asp Phe His Gly Leu Val Gln Lys
225             230             235             240 atc atg gag cta cag gat att tta gcc aaa aca tca gcc aag ctg tct    768
Ile Met Glu Leu Gln Asp Ile Leu Ala Lys Thr Ser Ala Lys Leu Ser
            245             250             255 cga gct gaa cag cga atg aat aga ttg gat cag tgc tat tgt gaa agg    816
Arg Ala Glu Gln Arg Met Asn Arg Leu Asp Gln Cys Tyr Cys Glu Arg
        260             265             270 act tgc acc atg aag gga acc acc tac cga gaa ttt gag tcc tgg ata    864
Thr Cys Thr Met Lys Gly Thr Thr Tyr Arg Glu Phe Glu Ser Trp Ile
    275             280             285 gac ggc tgt aag aac tgc aca tgc ctg aat gga acc atc cag tgt gaa    912
Asp Gly Cys Lys Asn Cys Thr Cys Leu Asn Gly Thr Ile Gln Cys Glu
290             295             300 act cta atc tgc cca aat cct gac tgc cca ctt aag tcg gct ctt gcg    960
Thr Leu Ile Cys Pro Asn Pro Asp Cys Pro Leu Lys Ser Ala Leu Ala
305             310             315             320 tat gtg gat ggc aaa tgc tgt aag gaa tgc aaa tcg ata tgc caa ttt   1008
Tyr Val Asp Gly Lys Cys Cys Lys Glu Cys Lys Ser Ile Cys Gln Phe
            325             330             335 caa gga cga acc tac ttt gaa gga gaa aga aat aca gtc tat tcc tct   1056
Gln Gly Arg Thr Tyr Phe Glu Gly Glu Arg Asn Thr Val Tyr Ser Ser
        340             345             350 tct gga gta tgt gtt ctc tat gag tgc aag gac cag acc atg aaa ctt   1104
Ser Gly Val Cys Val Leu Tyr Glu Cys Lys Asp Gln Thr Met Lys Leu
    355             360             365 gtt gag agt tca ggc tgt cca gct ttg gat tgt cca gag tct cat cag   1152
Val Glu Ser Ser Gly Cys Pro Ala Leu Asp Cys Pro Glu Ser His Gln
370             375             380 ata acc ttg tct cac agc tgt tgc aaa gtt tgt aaa ggt tat gac ttt   1200
Ile Thr Leu Ser His Ser Cys Cys Lys Val Cys Lys Gly Tyr Asp Phe
385             390             395             400 tgt tct gaa agg cat aac tgc atg gag aat tcc atc tgc aga aat ctg   1248
Cys Ser Glu Arg His Asn Cys Met Glu Asn Ser Ile Cys Arg Asn Leu
            405             410             415
```

FIGURE 7B

```
aat gac agg gct gtt tgt agc tgt cga gat ggt ttt agg gct ctt cga   1296  SEQ ID NO:7
Asn Asp Arg Ala Val Cys Ser Cys Arg Asp Gly Phe Arg Ala Leu Arg         SEQ ID NO:8
            420             425             430 gag gat aat gcc tac tgt gaa gac atc gat gag tgt gct gaa ggg cgc   1344
Glu Asp Asn Ala Tyr Cys Glu Asp Ile Asp Glu Cys Ala Glu Gly Arg
            435             440             445 cat tac tgt cgt gaa aat aca atg tgt gtc aac acc ccg ggt tct ttt   1392
His Tyr Cys Arg Glu Asn Thr Met Cys Val Asn Thr Pro Gly Ser Phe
    450             455             460 atg tgc atc tgc aaa act gga tac atc aga att gat gat tat tca tgt   1440
Met Cys Ile Cys Lys Thr Gly Tyr Ile Arg Ile Asp Asp Tyr Ser Cys
465             470             475             480 aca gaa cat gat gag tgt atc aca aat cag cac aac tgt gat gaa aat   1488
Thr Glu His Asp Glu Cys Ile Thr Asn Gln His Asn Cys Asp Glu Asn
                485             490             495 gct tta tgc ttc aac act gtt gga gga cac aac tgt gtt tgc aag ccg   1536
Ala Leu Cys Phe Asn Thr Val Gly Gly His Asn Cys Val Cys Lys Pro
            500             505             510 ggc tat aca ggg aat gga acg aca tgc aaa gca ttt tgc aaa gat ggc   1584
Gly Tyr Thr Gly Asn Gly Thr Thr Cys Lys Ala Phe Cys Lys Asp Gly
        515             520             525 tgt agg aat gga gga gcc tgt att gcc gct aat gtg tgt gcc tgc cca   1632
Cys Arg Asn Gly Gly Ala Cys Ile Ala Ala Asn Val Cys Ala Cys Pro
    530             535             540 caa ggc ttc act gga ccc agc tgt gaa acg gac att gat gaa tgc tct   1680
Gln Gly Phe Thr Gly Pro Ser Cys Glu Thr Asp Ile Asp Glu Cys Ser
545             550             555             560 gat ggt ttt gtt caa tgt gac agt cgt gct aat tgc att aac ctg cct   1728
Asp Gly Phe Val Gln Cys Asp Ser Arg Ala Asn Cys Ile Asn Leu Pro
                565             570             575 gga tgg tac cac tgt gag tgc aga gat ggc tac cat gac aat ggg atg   1776
Gly Trp Tyr His Cys Glu Cys Arg Asp Gly Tyr His Asp Asn Gly Met
            580             585             590 ttt tca cca agt gga gaa tcg tgt gaa gat att gat gag tgt ggg acc   1824
Phe Ser Pro Ser Gly Glu Ser Cys Glu Asp Ile Asp Glu Cys Gly Thr
        595             600             605 ggg agg cac agc tgt gcc aat gat acc att tgc ttc aat ttg gat ggc   1872
Gly Arg His Ser Cys Ala Asn Asp Thr Ile Cys Phe Asn Leu Asp Gly
    610             615             620
```

FIGURE 7C

```
gga tat gat tgt cga tgt cct cat gga aag aat tgc aca ggg gac tgc   1920   SEQ ID NO:7
Gly Tyr Asp Cys Arg Cys Pro His Gly Lys Asn Cys Thr Gly Asp Cys          SEQ ID NO:8
625             630              635             640 atc cat gat gga aaa gtt aag cac aat ggt cag att tgg gtg ttg gaa   1968
Ile His Asp Gly Lys Val Lys His Asn Gly Gln Ile Trp Val Leu Glu
                645              650             655 aat gac agg tgc tct gtg tgc tca tgt cag aat gga ttc gtt atg tgt   2016
Asn Asp Arg Cys Ser Val Cys Ser Cys Gln Asn Gly Phe Val Met Cys
                660              665             670 cga cgg atg gtc tgt gac tgt gag aat ccc aca gtt gat ctt ttt tgc   2064
Arg Arg Met Val Cys Asp Cys Glu Asn Pro Thr Val Asp Leu Phe Cys
                675              680             685 tgc cct gaa tgt gac cca agg ctt agt agt cag tgc ctc cat caa aat   2112
Cys Pro Glu Cys Asp Pro Arg Leu Ser Ser Gln Cys Leu His Gln Asn
        690              695             700 ggg gaa act ttg tat aac agt ggt gac acc tgg gtc cag aat tgt caa   2160
Gly Glu Thr Leu Tyr Asn Ser Gly Asp Thr Trp Val Gln Asn Cys Gln
705             710              715             720 cag tgc cgc tgc ttg caa ggg gaa gtt gat tgt tgg ccc ctg cct tgc   2208
Gln Cys Arg Cys Leu Gln Gly Glu Val Asp Cys Trp Pro Leu Pro Cys
                725              730             735 cca gat gtg gag tgt gaa ttc agc att ctc cca gag aat gag tgc tgc   2256
Pro Asp Val Glu Cys Glu Phe Ser Ile Leu Pro Glu Asn Glu Cys Cys
                740              745             750 ccg cgc tgt gtc aca gac cct tgc cag gct gac acc atc cgc aat gac   2304
Pro Arg Cys Val Thr Asp Pro Cys Gln Ala Asp Thr Ile Arg Asn Asp
                755              760             765 atc acc aag act tgc ctg gac gaa atg aat gtg gtt cgc ttc acc ggg   2352
Ile Thr Lys Thr Cys Leu Asp Glu Met Asn Val Val Arg Phe Thr Gly
            770              775             780 tcc tct tgg atc aaa cat ggc act gag tgt act ctc tgc cag tgc aag   2400
Ser Ser Trp Ile Lys His Gly Thr Glu Cys Thr Leu Cys Gln Cys Lys
785             790              795             800 aat ggc cac atc tgt tgc tca gtg gat cca cag tgc ctt cag gaa ctg   2448
Asn Gly His Ile Cys Cys Ser Val Asp Pro Gln Cys Leu Gln Glu Leu
                805              810             815 tga                                                               2451
```

FIGURE 7D

```
atg gaa tcc cgg gta tta ctg aga acg ttc tgc gtg atc ctc ggg ctc    48   SEQ ID NO:9
Met Glu Ser Arg Val Leu Leu Arg Thr Phe Cys Val Ile Leu Gly Leu         SEQ ID NO:10
1               5                   10                  15 gaa gcg gtt tgg gga ctt ggt gtg gac ccc tcc cta cag att gac gtc    96
Glu Ala Val Trp Gly Leu Gly Val Asp Pro Ser Leu Gln Ile Asp Val
                20                  25                  30 tta tca gag tta gaa ctt ggg gag tcc aca gct gga gtg cgc caa gtc    144
Leu Ser Glu Leu Glu Leu Gly Glu Ser Thr Ala Gly Val Arg Gln Val
        35                  40                  45 cca gga ctg cat aat ggg acg aaa gcc ttc ctc ttc caa gat tcc ccc    192
Pro Gly Leu His Asn Gly Thr Lys Ala Phe Leu Phe Gln Asp Ser Pro
    50                  55                  60 aga agc ata aaa gca ccc att gct aca gct gag cgg ttt ttc cag aag    240
Arg Ser Ile Lys Ala Pro Ile Ala Thr Ala Glu Arg Phe Phe Gln Lys
65                  70                  75                  80 ctg agg aat aaa cac gag ttc aca att ctg gtg acc ctg aaa cag atc    288
Leu Arg Asn Lys His Glu Phe Thr Ile Leu Val Thr Leu Lys Gln Ile
                85                  90                  95 cac tta aat tcg gga gtc att ctc tcc atc cac cac ttg gat cac agg    336
His Leu Asn Ser Gly Val Ile Leu Ser Ile His His Leu Asp His Arg
                100                 105                 110 tac ctg gaa ctg gaa agc agc ggc cac cgg aat gag atc aga ctg cat    384
Tyr Leu Glu Leu Glu Ser Ser Gly His Arg Asn Glu Ile Arg Leu His
        115                 120                 125 tac cgc tct gga act cac cgc ccg cac acg gaa gtg ttt cct tat att    432
Tyr Arg Ser Gly Thr His Arg Pro His Thr Glu Val Phe Pro Tyr Ile
    130                 135                 140 ttg gct gat gcc aag tgg cac aag ctc tcc tta gcc ttc agt gcc tcc    480
Leu Ala Asp Ala Lys Trp His Lys Leu Ser Leu Ala Phe Ser Ala Ser
145                 150                 155                 160 cac tta att tta cac atc gac tgc aac aag atc tat gaa cga gtg gtg    528
His Leu Ile Leu His Ile Asp Cys Asn Lys Ile Tyr Glu Arg Val Val
                165                 170                 175 gaa atg cct tct aca gac ttg cct ctg ggc acc aca ttt tgg ttg gga    576
Glu Met Pro Ser Thr Asp Leu Pro Leu Gly Thr Thr Phe Trp Leu Gly
                180                 185                 190 cag aga aat aac gca cac ggg tat ttt aag gga ata atg caa gat gtg    624
Gln Arg Asn Asn Ala His Gly Tyr Phe Lys Gly Ile Met Gln Asp Val
        195                 200                 205
```

FIGURE 8A

```
caa tta ctt gtc atg ccc cag ggg ttc atc gct cag tgc ccg gat ctt  672  SEQ ID NO:9
Gln Leu Leu Val Met Pro Gln Gly Phe Ile Ala Gln Cys Pro Asp Leu       SEQ ID NO:10
    210                 215                 220 aat cga acc tgt cca aca tgc aac gac ttc cat ggg ctt gtg cag aaa  720
Asn Arg Thr Cys Pro Thr Cys Asn Asp Phe His Gly Leu Val Gln Lys
225                 230                 235                 240 atc atg gag ctg cag gac att tta tcg aag acg tca gcc aag ttg tct  768
Ile Met Glu Leu Gln Asp Ile Leu Ser Lys Thr Ser Ala Lys Leu Ser
                245                 250                 255 aga gct gaa caa cga atg aac agg ctg gat cag tgc tac tgt gag cgg  816
Arg Ala Glu Gln Arg Met Asn Arg Leu Asp Gln Cys Tyr Cys Glu Arg
            260                 265                 270 acg tgc acc atg aag gga gcc acc tac cgg gag ttc gag tcc tgg aca  864
Thr Cys Thr Met Lys Gly Ala Thr Tyr Arg Glu Phe Glu Ser Trp Thr
        275                 280                 285 gac ggc tgc aag aac tgc aca tgc ttg aat ggg acc atc cag tgc gag  912
Asp Gly Cys Lys Asn Cys Thr Cys Leu Asn Gly Thr Ile Gln Cys Glu
    290                 295                 300 act ctg gtc tgc cct gct ccc gac tgc ccg gct aaa tcg gct cca gcg  960
Thr Leu Val Cys Pro Ala Pro Asp Cys Pro Ala Lys Ser Ala Pro Ala
305                 310                 315                 320 tac gtg gat ggc aag tgc tgt aag gag tgc aag tcc acc tgc cag ttc  1008
Tyr Val Asp Gly Lys Cys Cys Lys Glu Cys Lys Ser Thr Cys Gln Phe
                325                 330                 335 cag ggg cgg agc tac ttt gag gga gaa agg agc aca gtc ttc tca gct  1056
Gln Gly Arg Ser Tyr Phe Glu Gly Glu Arg Ser Thr Val Phe Ser Ala
            340                 345                 350 tcc gga atg tgc gtc ttg tat gaa tgc aag gat cag acc atg aag ctt  1104
Ser Gly Met Cys Val Leu Tyr Glu Cys Lys Asp Gln Thr Met Lys Leu
        355                 360                 365 gtt gag aac gcc ggc tgc ccg gct tta gat tgc ccc gag tct cat cag  1152
Val Glu Asn Ala Gly Cys Pro Ala Leu Asp Cys Pro Glu Ser His Gln
    370                 375                 380 atc gcc ttg tct cac agc tgc tgc aag gtt tgc aaa ggt tat gac ttc  1200
Ile Ala Leu Ser His Ser Cys Cys Lys Val Cys Lys Gly Tyr Asp Phe
385                 390                 395                 400 tgt tct gag aag cat aca tgc atg gag aac tca gtc tgc agg aac ctg  1248
Cys Ser Glu Lys His Thr Cys Met Glu Asn Ser Val Cys Arg Asn Leu
                405                 410                 415
```

FIGURE 8B

```
aac gac agg gca gtg tgc agc tgc cgg gat ggt ttc cgg gcc ctc cgg  1296  SEQ ID NO:9
Asn Asp Arg Ala Val Cys Ser Cys Arg Asp Gly Phe Arg Ala Leu Arg        SEQ ID NO:10
            420             425             430 gag gac aat gcc tac tgt gaa gac att gac gag tgt gca gag ggg cgc  1344
Glu Asp Asn Ala Tyr Cys Glu Asp Ile Asp Glu Cys Ala Glu Gly Arg
            435             440             445 cat tac tgc cgt gag aac acc atg tgt gtg aac aca ccg ggc tct ttc  1392
His Tyr Cys Arg Glu Asn Thr Met Cys Val Asn Thr Pro Gly Ser Phe
    450             455             460 ctg tgt atc tgc caa aca ggg tac atc aga atc gac gat tac tcg tgt  1440
Leu Cys Ile Cys Gln Thr Gly Tyr Ile Arg Ile Asp Asp Tyr Ser Cys
465             470             475             480 acg gaa cat gac gag tgc ctc aca aac cag cac aac tgt gac gag aac  1488
Thr Glu His Asp Glu Cys Leu Thr Asn Gln His Asn Cys Asp Glu Asn
            485             490             495 gct ttg tgc ttt aac acc gtt gga ggt cac aac tgc gtc tgc aag cct  1536
Ala Leu Cys Phe Asn Thr Val Gly Gly His Asn Cys Val Cys Lys Pro
            500             505             510 ggg tac act ggg aat gga acc acg tgc aaa gct ttc tgc aaa gac ggc  1584
Gly Tyr Thr Gly Asn Gly Thr Thr Cys Lys Ala Phe Cys Lys Asp Gly
        515             520             525 tgc aaa aac gga ggt gcc tgc att gct gcc aat gtc tgt gct tgc cca  1632
Cys Lys Asn Gly Gly Ala Cys Ile Ala Ala Asn Val Cys Ala Cys Pro
        530             535             540 caa ggc ttc acc gga ccc agc tgt gag aca gac att gat gag tgc tct  1680
Gln Gly Phe Thr Gly Pro Ser Cys Glu Thr Asp Ile Asp Glu Cys Ser
545             550             555             560 gag ggc ttt gtt cag tgt gac agc cgt gcc aac tgc att aac ctg cct  1728
Glu Gly Phe Val Gln Cys Asp Ser Arg Ala Asn Cys Ile Asn Leu Pro
            565             570             575 ggg tgg tac cac tgt gag tgc aga gat ggc tac cat gac aat ggg atg  1776
Gly Trp Tyr His Cys Glu Cys Arg Asp Gly Tyr His Asp Asn Gly Met
            580             585             590 ttt gcg cca ggt gga gaa tcc tgt gaa gat att gat gaa tgt ggg act  1824
Phe Ala Pro Gly Gly Glu Ser Cys Glu Asp Ile Asp Glu Cys Gly Thr
        595             600             605 ggg agg cac agc tgt gcc aat gac acc att tgc ttc aac ttg gac ggt  1872
Gly Arg His Ser Cys Ala Asn Asp Thr Ile Cys Phe Asn Leu Asp Gly
    610             615             620
```

FIGURE 8C

```
ggc tac gat tgc cgg tgt ccc cat gga aag aac tgc aca ggg gac tgc   1920   SEQ ID NO:9
Gly Tyr Asp Cys Arg Cys Pro His Gly Lys Asn Cys Thr Gly Asp Cys          SEQ ID NO:10
625                 630                 635                 640 gtg cac gac ggg aaa gtc aaa cac aac ggc cag atc tgg gtg ctg gag   1968
Val His Asp Gly Lys Val Lys His Asn Gly Gln Ile Trp Val Leu Glu
                645                 650                 655 aac gac agg tgc tct gtg tgt tcc tgc cag act gga ttt gtt atg tgc   2016
Asn Asp Arg Cys Ser Val Cys Ser Cys Gln Thr Gly Phe Val Met Cys
                    660                 665                 670 caa cgg atg gtc tgt gac tgc gaa aac ccc aca gtt gac ctc tcc tgc   2064
Gln Arg Met Val Cys Asp Cys Glu Asn Pro Thr Val Asp Leu Ser Cys
            675                 680                 685 tgc cct gag tgc gac cca agg ctg agc agc cag tgc ctg cat caa aac   2112
Cys Pro Glu Cys Asp Pro Arg Leu Ser Ser Gln Cys Leu His Gln Asn
        690                 695                 700 ggg gaa acc gtg tac aac agc ggt gac acc tgg gcc cag gat tgc cgt   2160
Gly Glu Thr Val Tyr Asn Ser Gly Asp Thr Trp Ala Gln Asp Cys Arg
705                 710                 715                 720 cag tgc cgc tgc ttg caa gaa gaa gtt gac tgc tgg ccc ctg gct tgc   2208
Gln Cys Arg Cys Leu Gln Glu Glu Val Asp Cys Trp Pro Leu Ala Cys
                725                 730                 735 cca gag gta gag tgt gaa ttt agt gtc ctt cct gag aac gag tgc tgc   2256
Pro Glu Val Glu Cys Glu Phe Ser Val Leu Pro Glu Asn Glu Cys Cys
            740                 745                 750 cca cgc tgt gtc acc gat cct tgt cag gct gac acc atc cgc aat gac   2304
Pro Arg Cys Val Thr Asp Pro Cys Gln Ala Asp Thr Ile Arg Asn Asp
        755                 760                 765 atc acc aaa acc tgc ctg gac gag atg aac gtg gtt cgc ttc act ggg   2352
Ile Thr Lys Thr Cys Leu Asp Glu Met Asn Val Val Arg Phe Thr Gly
770                 775                 780 tct tcc tgg atc aag cac ggc acg gag tgc acc ctc tgc cag tgc aag   2400
Ser Ser Trp Ile Lys His Gly Thr Glu Cys Thr Leu Cys Gln Cys Lys
                790                 795                 800 aac ggc cac gtg tgc tgc tca gtg gac cca cag tgc ctc cag gag ctg   2448
Asn Gly His Val Cys Cys Ser Val Asp Pro Gln Cys Leu Gln Glu Leu
            805                 810                 815 tga                                                               2451
```

FIGURE 8D

```
atg cac gcc atg gaa tcc cgg gtg tta ctg aga acg ttc tgc gtg atc   48   SEQ ID NO:11
Met His Ala Met Glu Ser Arg Val Leu Leu Arg Thr Phe Cys Val Ile        SEQ ID NO:12
1               5                   10                  15 ctc ggc ctt gga gcg gtt tgg ggg ctt ggt gtg gac ccc tcc cta cag   96
Leu Gly Leu Gly Ala Val Trp Gly Leu Gly Val Asp Pro Ser Leu Gln
            20                  25                  30 att gac gtc tta aca gag tta gaa ctt ggg gag tct aca gat gga gtg   144
Ile Asp Val Leu Thr Glu Leu Glu Leu Gly Glu Ser Thr Asp Gly Val
                35                  40                  45 cgc caa gtc ccg gga ctg cat aat ggg acg aaa gcc ttc ctc ttc caa   192
Arg Gln Val Pro Gly Leu His Asn Gly Thr Lys Ala Phe Leu Phe Gln
    50                  55                  60 gag tcc ccc aga agc ata aag gca tcc act gct aca gct gag cgg ttt   240
Glu Ser Pro Arg Ser Ile Lys Ala Ser Thr Ala Thr Ala Glu Arg Phe
65                  70                  75                  80 ctc cag aag ctg aga aat aaa cac gag ttc aca atc ttg gtg acc tta   288
Leu Gln Lys Leu Arg Asn Lys His Glu Phe Thr Ile Leu Val Thr Leu
                85                  90                  95 aaa cag atc cac tta aat tcg gga gtt atc ctc tcc atc cac cac ttg   336
Lys Gln Ile His Leu Asn Ser Gly Val Ile Leu Ser Ile His His Leu
            100                 105                 110 gat cac agg tac ctg gaa ctg gaa agc agt ggc cat cgg aat gag atc   384
Asp His Arg Tyr Leu Glu Leu Glu Ser Ser Gly His Arg Asn Glu Ile
        115                 120                 125 aga ctc cac tac cgc tct ggc act cac cgc ccc cac acg gaa gtg ttt   432
Arg Leu His Tyr Arg Ser Gly Thr His Arg Pro His Thr Glu Val Phe
    130                 135                 140 cct tat att ttg gct gat gcc aag tgg cac aag ctc tcc tta gcc ttc   480
Pro Tyr Ile Leu Ala Asp Ala Lys Trp His Lys Leu Ser Leu Ala Phe
145                 150                 155                 160 agt gcc tct cac tta att tta cac atc gac tgc aat aag atc tat gaa   528
Ser Ala Ser His Leu Ile Leu His Ile Asp Cys Asn Lys Ile Tyr Glu
                165                 170                 175 cga gtg gtg gaa atg ccc ttc aca gac ttg gct ctg ggc aca aca ttt   576
Arg Val Val Glu Met Pro Phe Thr Asp Leu Ala Leu Gly Thr Thr Phe
            180                 185                 190 tgg ttg gga cag aga aat aat gca cat ggc tat ttt aag gga ata atg   624
Trp Leu Gly Gln Arg Asn Asn Ala His Gly Tyr Phe Lys Gly Ile Met
        195                 200                 205
```

FIGURE 9A

```
cag gat gtg cac gtc ctt gtc atg cct cag ggc ttc att gct cag tgc    672   SEQ ID NO:11
Gln Asp Val His Val Leu Val Met Pro Gln Gly Phe Ile Ala Gln Cys          SEQ ID NO:12
    210             215                 220 ccg gac ctt aat cga acc tgt cca aca tgc aac gac ttc cat ggg ctt    720
Pro Asp Leu Asn Arg Thr Cys Pro Thr Cys Asn Asp Phe His Gly Leu
225             230                 235                 240 gtg cag aaa atc atg gag ctg cag gac att tta tca aag acg tca gcc    768
Val Gln Lys Ile Met Glu Leu Gln Asp Ile Leu Ser Lys Thr Ser Ala
            245                 250                 255 aag ctg tcc cga gct gaa caa aga atg aac agg ctg gat cag tgc tac    816
Lys Leu Ser Arg Ala Glu Gln Arg Met Asn Arg Leu Asp Gln Cys Tyr
        260                 265                 270 tgt gag cgg aca tgc act gtg aag gga acc acc tac cga gag tct gag    864
Cys Glu Arg Thr Cys Thr Val Lys Gly Thr Thr Tyr Arg Glu Ser Glu
    275                 280                 285 tcc tgg aca gac ggc tgt aag aac tgc aca tgc ttg aac ggg acc atc    912
Ser Trp Thr Asp Gly Cys Lys Asn Cys Thr Cys Leu Asn Gly Thr Ile
290                 295                 300 cag tgc gag act ctg gtc tgc cct gct cct gac tgc cct cct aaa tcg    960
Gln Cys Glu Thr Leu Val Cys Pro Ala Pro Asp Cys Pro Pro Lys Ser
305             310                 315                 320 gcc cct gcg tat gtg gat ggc aag tgc tgt aag gag tgc aaa tca acc    1008
Ala Pro Ala Tyr Val Asp Gly Lys Cys Cys Lys Glu Cys Lys Ser Thr
            325                 330                 335 tgc cag ttc cag gga cgg agc tac ttt gag gga gaa agg aac acg gca    1056
Cys Gln Phe Gln Gly Arg Ser Tyr Phe Glu Gly Glu Arg Asn Thr Ala
        340                 345                 350 tac tca tct tct gga atg tgt gtc tta tat gaa tgc aag gat cag acc    1104
Tyr Ser Ser Ser Gly Met Cys Val Leu Tyr Glu Cys Lys Asp Gln Thr
    355                 360                 365 atg aag ctt gtt gag aac att ggc tgc cca ccc tta gat tgt ccc gag    1152
Met Lys Leu Val Glu Asn Ile Gly Cys Pro Pro Leu Asp Cys Pro Glu
370                 375                 380 tct cat cag att gcc ttg tct cac agc tgc tgc aag gtt tgt aaa ggt    1200
Ser His Gln Ile Ala Leu Ser His Ser Cys Cys Lys Val Cys Lys Gly
385             390                 395                 400 tat gac ttc tgt tct gag aag cat acc tgc atg gag aac tcg gtc tgc    1248
Tyr Asp Phe Cys Ser Glu Lys His Thr Cys Met Glu Asn Ser Val Cys
            405                 410                 415
```

FIGURE 9B

```
agg aac ctg aac gac agg gtt gtg tgc agc tgc agg gat ggt ttt cgg   1296   SEQ ID NO:11
Arg Asn Leu Asn Asp Arg Val Val Cys Ser Cys Arg Asp Gly Phe Arg          SEQ ID NO:12
            420             425             430 gct ctc cga gag gac aac gcc tac tgt gaa gac att gac gag tgt gca   1344
Ala Leu Arg Glu Asp Asn Ala Tyr Cys Glu Asp Ile Asp Glu Cys Ala
            435             440             445 gaa ggg cgc cat tac tgc cgt gag aac acc atg tgt gtg aat aca cct   1392
Glu Gly Arg His Tyr Cys Arg Glu Asn Thr Met Cys Val Asn Thr Pro
    450             455             460 ggt tct ttc atg tgt gtc tgc aaa act ggg tac atc agg atc gac gat   1440
Gly Ser Phe Met Cys Val Cys Lys Thr Gly Tyr Ile Arg Ile Asp Asp
465             470             475             480 tac tca tgt aca gaa cat gat gag tgt ctc aca acc cag cac aat tgt   1488
Tyr Ser Cys Thr Glu His Asp Glu Cys Leu Thr Thr Gln His Asn Cys
                485             490             495 gat gaa aac gct ttg tgc ttt aac act gtt gga gga cac aac tgt gtc   1536
Asp Glu Asn Ala Leu Cys Phe Asn Thr Val Gly Gly His Asn Cys Val
            500             505             510 tgc aag cct ggc tac acc ggg aat gga acc acg tgc aaa gct ttc tgc   1584
Cys Lys Pro Gly Tyr Thr Gly Asn Gly Thr Thr Cys Lys Ala Phe Cys
            515             520             525 aaa gat ggc tgt aga aac gga gga gcg tgc att gct gcc aat gtg tgt   1632
Lys Asp Gly Cys Arg Asn Gly Gly Ala Cys Ile Ala Ala Asn Val Cys
    530             535             540 gcc tgc cca caa ggc ttc acg gga ccc agc tgt gag aca gac att gac   1680
Ala Cys Pro Gln Gly Phe Thr Gly Pro Ser Cys Glu Thr Asp Ile Asp
545             550             555             560 gag tgc tct gag ggc ttt gtt cag tgt gac agc cgt gcc aac tgc atc   1728
Glu Cys Ser Glu Gly Phe Val Gln Cys Asp Ser Arg Ala Asn Cys Ile
                565             570             575 aac ctg cct ggg tgg tat cac tgt gag tgc aga gac ggc tac cat gac   1776
Asn Leu Pro Gly Trp Tyr His Cys Glu Cys Arg Asp Gly Tyr His Asp
            580             585             590 aat ggg atg ttt gcg cca ggc gga gaa tcc tgt gaa gat att gac gaa   1824
Asn Gly Met Phe Ala Pro Gly Gly Glu Ser Cys Glu Asp Ile Asp Glu
            595             600             605 tgc ggg act ggg agg cac agc tgc acc aac gac acc att tgc ttc aac   1872
Cys Gly Thr Gly Arg His Ser Cys Thr Asn Asp Thr Ile Cys Phe Asn
            610             615             620
```

FIGURE 9C

```
ttg gac ggg gga tac gat tgc cgg tgt ccc cat ggg aag aac tgc act  1920   SEQ ID NO:11
Leu Asp Gly Gly Tyr Asp Cys Arg Cys Pro His Gly Lys Asn Cys Thr         SEQ ID NO:12
625                 630                 635                 640 ggg gac tgc gtg cac gag ggg aaa gtg aag cac acc ggc cag atc tgg  1968
Gly Asp Cys Val His Glu Gly Lys Val Lys His Thr Gly Gln Ile Trp
                645                 650                 655 gtg ctg gaa aac gac agg tgc tcc gtg tgt tcc tgg cag act ggg ttt  2016
Val Leu Glu Asn Asp Arg Cys Ser Val Cys Ser Trp Gln Thr Gly Phe
                    660                 665                 670 gtc atg tgt cga cgg atg gtc tgc gac tgc gaa aac ccc aca gat gac  2064
Val Met Cys Arg Arg Met Val Cys Asp Cys Glu Asn Pro Thr Asp Asp
            675                 680                 685 ctt tcc tgc tgc cct gag tgt gac cca agg ctg agc agt cag tgc ctg  2112
Leu Ser Cys Cys Pro Glu Cys Asp Pro Arg Leu Ser Ser Gln Cys Leu
        690                 695                 700 cat caa aac ggg gaa acc gtg tac aac agc ggc gac acc tgg gtc cag  2160
His Gln Asn Gly Glu Thr Val Tyr Asn Ser Gly Asp Thr Trp Val Gln
705                 710                 715                 720 gat tgc cgt cag tgc cgc tgc ttg caa gga gaa gtt gac tgt tgg ccc  2208
Asp Cys Arg Gln Cys Arg Cys Leu Gln Gly Glu Val Asp Cys Trp Pro
                725                 730                 735 ctg gct tgc cca gag gta gaa tgt gaa ttt agc gtc ctt cct gag aac  2256
Leu Ala Cys Pro Glu Val Glu Cys Glu Phe Ser Val Leu Pro Glu Asn
                    740                 745                 750 gag tgc tgc cca cgc tgt gtc acc gat cct tgt cag gcc gac acc atc  2304
Glu Cys Cys Pro Arg Cys Val Thr Asp Pro Cys Gln Ala Asp Thr Ile
            755                 760                 765 cgc aat gac atc acc aaa acc tgc ctg gac gag atg aac gtg gtt cgc  2352
Arg Asn Asp Ile Thr Lys Thr Cys Leu Asp Glu Met Asn Val Val Arg
        770                 775                 780 ttc acc ggg tct tcc tgg atc aag cac ggc acg gag tgt acc ctc tgc  2400
Phe Thr Gly Ser Ser Trp Ile Lys His Gly Thr Glu Cys Thr Leu Cys
785                 790                 795                 800 cag tgc aag aat ggc cat ttg tgc tgc tca gtg gat cca cag tgc ctt  2448
Gln Cys Lys Asn Gly His Leu Cys Cys Ser Val Asp Pro Gln Cys Leu
                805                 810                 815 cag gag ctg tga   2460    SEQ ID NO:11
Gln Glu Leu                SEQ ID NO:12
```

FIGURE 9D

```
atg gag tcc ggc tgc ggc tta ggc acg ctt tgc ctt ctc ctc tgc ctg   48  SEQ ID NO:13
Met Glu Ser Gly Cys Gly Leu Gly Thr Leu Cys Leu Leu Leu Cys Leu       SEQ ID NO:14
 1               5                  10                  15 ggg cca gtc gta ggc ttc ggc gtg gac ccc tcg ctg cag atc gac gtg   96
Gly Pro Val Val Gly Phe Gly Val Asp Pro Ser Leu Gln Ile Asp Val
                20                  25                  30 ctg tcc gag ctg ggg ctg ccg ggc tac gcg gcg ggc gtg cgc cag gtg   144
Leu Ser Glu Leu Gly Leu Pro Gly Tyr Ala Ala Gly Val Arg Gln Val
            35                  40                  45 ccg ggg ctg cac aac ggg agc aaa gcc ttc ctc ttc cca gat act tca   192
Pro Gly Leu His Asn Gly Ser Lys Ala Phe Leu Phe Pro Asp Thr Ser
        50                  55                  60 aga agt gta aag gcg tct cca gaa aca gct gaa atc ttt ttt cag aag   240
Arg Ser Val Lys Ala Ser Pro Glu Thr Ala Glu Ile Phe Phe Gln Lys
65                  70                  75                  80 ttg aga aat aaa tat gaa ttc aca atc ctg gtg acc tta aaa caa gcc   288
Leu Arg Asn Lys Tyr Glu Phe Thr Ile Leu Val Thr Leu Lys Gln Ala
                85                  90                  95 cat tta aat tca ggg gtt att ttc tct att cat cac tta gat cac agg   336
His Leu Asn Ser Gly Val Ile Phe Ser Ile His His Leu Asp His Arg
            100                 105                 110 tat ctg gaa ttg gaa agc agc ggt cat cga aat gaa atc agg ttg cat   384
Tyr Leu Glu Leu Glu Ser Ser Gly His Arg Asn Glu Ile Arg Leu His
        115                 120                 125 tac cgt aca ggc agt cat cgc tcc cac aca gaa gta ttc cca tac atc   432
Tyr Arg Thr Gly Ser His Arg Ser His Thr Glu Val Phe Pro Tyr Ile
    130                 135                 140 ctg gca gac gat aag tgg cac agg ctt tcc tta gca atc agt gcc tct   480
Leu Ala Asp Asp Lys Trp His Arg Leu Ser Leu Ala Ile Ser Ala Ser
145                 150                 155                 160 cac ttg att tta cac gtg gac tgc aat aaa atc tat gaa aga gtt gtg   528
His Leu Ile Leu His Val Asp Cys Asn Lys Ile Tyr Glu Arg Val Val
                165                 170                 175 gag aag ccc ttc atg gac tta cct gtg ggt aca acc ttt tgg cta gga   576
Glu Lys Pro Phe Met Asp Leu Pro Val Gly Thr Thr Phe Trp Leu Gly
            180                 185                 190 cag agg aat aat gca cac ggt tat ttt aag ggc ata atg caa gat gtg   624
Gln Arg Asn Asn Ala His Gly Tyr Phe Lys Gly Ile Met Gln Asp Val
        195                 200                 205
```

FIGURE 10A

```
caa tta ctt gtc atg cct caa gga ttt att tct cag tgc cca gat ctt   672   SEQ ID NO:13
Gln Leu Leu Val Met Pro Gln Gly Phe Ile Ser Gln Cys Pro Asp Leu         SEQ ID NO:14
    210             215                 220 aat cgg aca tgc cca act tgt aat gat ttc cat gga ctt gtg cag aaa   720
Asn Arg Thr Cys Pro Thr Cys Asn Asp Phe His Gly Leu Val Gln Lys
225             230                 235                 240 att atg gaa ctg caa gac att tta gct aaa acg tca gct aag ctg tcg   768
Ile Met Glu Leu Gln Asp Ile Leu Ala Lys Thr Ser Ala Lys Leu Ser
                245                 250                 255 caa gct gag cag agg atg aac aag ttg gat cag tgc tat tgt gaa agg   816
Gln Ala Glu Gln Arg Met Asn Lys Leu Asp Gln Cys Tyr Cys Glu Arg
            260                 265                 270 acc tgc aca atg aaa ggc atg aca tac aga gaa ttt gaa tcc tgg aca   864
Thr Cys Thr Met Lys Gly Met Thr Tyr Arg Glu Phe Glu Ser Trp Thr
        275                 280                 285 gat ggt tgt aag aac tgc act tgc atg aat ggc act gtg cag tgt gaa   912
Asp Gly Cys Lys Asn Cys Thr Cys Met Asn Gly Thr Val Gln Cys Glu
290                 295                 300 gct ttg att tgc tcc ctc tct gac tgt cca cct aat tct gcc ctg tca   960
Ala Leu Ile Cys Ser Leu Ser Asp Cys Pro Pro Asn Ser Ala Leu Ser
305             310                 315                 320 tac gtg gat ggc aag tgc tgc aaa gaa tgt caa tcg gtg tgc ata ttt   1008
Tyr Val Asp Gly Lys Cys Cys Lys Glu Cys Gln Ser Val Cys Ile Phe
                325                 330                 335 gaa ggc aga acc tac ttt gaa gga caa aga gaa acg gtg tat tca agc   1056
Glu Gly Arg Thr Tyr Phe Glu Gly Gln Arg Glu Thr Val Tyr Ser Ser
            340                 345                 350 tca ggg gac tgt gtt ctg ttt gag tgc aag gac cac aaa atg cag cgt   1104
Ser Gly Asp Cys Val Leu Phe Glu Cys Lys Asp His Lys Met Gln Arg
        355                 360                 365 att cca aaa gac agt tgt gca act ttg aac tgc ccg gaa tct caa cag   1152
Ile Pro Lys Asp Ser Cys Ala Thr Leu Asn Cys Pro Glu Ser Gln Gln
370                 375                 380 atc cca tta tct cac agt tgc tgc aaa atc tgt aaa ggc cat gac ttt   1200
Ile Pro Leu Ser His Ser Cys Cys Lys Ile Cys Lys Gly His Asp Phe
385             390                 395                 400 tgc act gaa gga cat aac tgt atg gag cat tct gtc tgc cga aac cta   1248
Cys Thr Glu Gly His Asn Cys Met Glu His Ser Val Cys Arg Asn Leu
                405                 410                 415
```

FIGURE 10B

```
gat gac aga gct gtc tgt agc tgc cga gat ggc ttc cgg gcc ctt cgg   1296   SEQ ID NO:13
Asp Asp Arg Ala Val Cys Ser Cys Arg Asp Gly Phe Arg Ala Leu Arg          SEQ ID NO:14
        420             425             430 gag gac aat gcc tac tgt gaa gat gtt gat gag tgt gcc gag ggg cag   1344
Glu Asp Asn Ala Tyr Cys Glu Asp Val Asp Glu Cys Ala Glu Gly Gln
        435             440             445 cac tac tgt cgg gag aac acc atg tgt gta aat aca cca gga tcc ttc   1392
His Tyr Cys Arg Glu Asn Thr Met Cys Val Asn Thr Pro Gly Ser Phe
        450             455             460 atg tgc atc tgc aaa aca gga tat ata cgc att gat gac tat tca tgt   1440
Met Cys Ile Cys Lys Thr Gly Tyr Ile Arg Ile Asp Asp Tyr Ser Cys
465             470             475             480 aca gag cac gat gaa tgt gta aca aac cag cac aac tgt gat gaa aat   1488
Thr Glu His Asp Glu Cys Val Thr Asn Gln His Asn Cys Asp Glu Asn
            485             490             495 gcg cta tgt ttc aac acg gtg ggt ggg cac aac tgt gtc tgc aag ctg   1536
Ala Leu Cys Phe Asn Thr Val Gly Gly His Asn Cys Val Cys Lys Leu
            500             505             510 ggt tac aca gga aat ggg acg gtg tgt aaa gca ttt tgc aaa gat ggg   1584
Gly Tyr Thr Gly Asn Gly Thr Val Cys Lys Ala Phe Cys Lys Asp Gly
            515             520             525 tgc agg aat gga gga gcc tgt att gct tcc aac gtg tgt gcc tgc cca   1632
Cys Arg Asn Gly Gly Ala Cys Ile Ala Ser Asn Val Cys Ala Cys Pro
        530             535             540 caa ggc ttc act ggc ccc agc tgt gaa act gac att gat gaa tgc tct   1680
Gln Gly Phe Thr Gly Pro Ser Cys Glu Thr Asp Ile Asp Glu Cys Ser
545             550             555             560 gat ggc ttt gtg cag tgt gac agc cgt gct aat tgc atc aat ctg cca   1728
Asp Gly Phe Val Gln Cys Asp Ser Arg Ala Asn Cys Ile Asn Leu Pro
            565             570             575 ggg tgg tac cac tgt gaa tgc agg gat ggc tac cat gac aat ggg atg   1776
Gly Trp Tyr His Cys Glu Cys Arg Asp Gly Tyr His Asp Asn Gly Met
            580             585             590 ttt tca cca agt gga gaa tcc tgt gaa gac att gat gaa tgt gca act   1824
Phe Ser Pro Ser Gly Glu Ser Cys Glu Asp Ile Asp Glu Cys Ala Thr
            595             600             605 gga agg cat agc tgt gcc aat gac act gtt tgc ttt aac ctg gat ggt   1872
Gly Arg His Ser Cys Ala Asn Asp Thr Val Cys Phe Asn Leu Asp Gly
            610             615             620
```

FIGURE 10C

```
ggg tat gac tgt cga tgt cca cat ggc aag aac tgc aca gga gac tgt   1920   SEQ ID NO:13
Gly Tyr Asp Cys Arg Cys Pro His Gly Lys Asn Cys Thr Gly Asp Cys          SEQ ID NO:14
625                 630                 635                 640 atc cat gaa gac aaa atc aag cac aat ggt cag att tgg gtg ctg gag   1968
Ile His Glu Asp Lys Ile Lys His Asn Gly Gln Ile Trp Val Leu Glu
            645                 650                 655 aac gac aga tgc tct gtc tgc tca tgc cag agt gga tac gtg atg tgc   2016
Asn Asp Arg Cys Ser Val Cys Ser Cys Gln Ser Gly Tyr Val Met Cys
                660                 665                 670 cgg cga atg gtc tgt gac tgt gaa aat ccc act gtt gac ctc ttt tgc   2064
Arg Arg Met Val Cys Asp Cys Glu Asn Pro Thr Val Asp Leu Phe Cys
            675                 680                 685 tgt cct gag tgt gac cca agg ctc agc agt caa tgt tta cat cag agt   2112
Cys Pro Glu Cys Asp Pro Arg Leu Ser Ser Gln Cys Leu His Gln Ser
        690                 695                 700 ggg gag ctt tcc tac aac agt ggt gac tcc tgg ata caa aac tgt cag   2160
Gly Glu Leu Ser Tyr Asn Ser Gly Asp Ser Trp Ile Gln Asn Cys Gln
705                 710                 715                 720 cag tgt cgc tgc ttg caa gga gag gtt gac tgt tgg ccc tta ccg tgc   2208
Gln Cys Arg Cys Leu Gln Gly Glu Val Asp Cys Trp Pro Leu Pro Cys
            725                 730                 735 cca gag gta gac tgt gag ttc agt gtc ctc cct gag aat gag tgc tgc   2256
Pro Glu Val Asp Cys Glu Phe Ser Val Leu Pro Glu Asn Glu Cys Cys
                740                 745                 750 cca cgc tgt gtc act gac ccc tgc caa gcg gac acc atc cgt aat gac   2304
Pro Arg Cys Val Thr Asp Pro Cys Gln Ala Asp Thr Ile Arg Asn Asp
        755                 760                 765 atc acc aaa acc tgc ctg gat gaa acc aat gtt gtt cgc ttc act gga   2352
Ile Thr Lys Thr Cys Leu Asp Glu Thr Asn Val Val Arg Phe Thr Gly
770                 775                 780 tct tct tgg att aag cat ggc aca gag tgc aca ctc tgc caa tgt aag   2400
Ser Ser Trp Ile Lys His Gly Thr Glu Cys Thr Leu Cys Gln Cys Lys
785                 790                 795                 800 aat ggc cac gtc tgt tgc tca gtg gat cca cag tgc ctt cag gaa ctg   2448
Asn Gly His Val Cys Cys Ser Val Asp Pro Gln Cys Leu Gln Glu Leu
            805                 810                 815 tga ca                                                            2453
```

FIGURE 10D

RECOMBINANT NEL-LIKE (NELL) PROTEIN PRODUCTION

CROSS-REFERENCE

This application is a continuation of U.S. patent application Ser. No. 13/121,394; which is a national stage entry of International Application No. PCT/US09/59893 filed on Oct. 7, 2009; which in turn claims the benefit of U.S. Provisional Application No. 61/103,534 filed on Oct. 7, 2008; the teaching of each of which is incorporated by reference in its entirety.

The application also claims priority as a continuation-in-part to U.S. patent application Ser. No. 13/253,859; which is a division of U.S. patent application Ser. No. 12/700,630 filed on Feb. 4, 2010 and issued as U.S. Pat. No. 8,053,412; which in turn is a division of U.S. patent application Ser. No. 11/601,529 filed on Nov. 17, 2006 and issued as U.S. Pat. No. 7,691,607; which is a continuation-in-part of U.S. patent application Ser. No. 10/544,553 filed on May 15, 2006 and issued as U.S. Pat. No. 7,544,486; which is a continuation-in-part of International Application No. PCT/US2006/005473 filed on Feb. 16, 2006 and a national stage entry of International Application No. PCT/US2004/003808 filed on Feb. 9, 2004 the teaching of each of which is incorporated by reference in its entirety.

STATEMENT OF GOVERNMENTAL SUPPORT

This invention was made with Government support under DE000422 and DE014649 awarded by the National Institutes of Health. The Government has certain rights in the invention.

FIELD OF THE INVENTION

The present invention is directed to a system and method of producing NELL peptides.

BACKGROUND OF THE INVENTION

Growth factors are substances, such as peptides, which affect the growth and differentiation of defined populations of cells in vivo or in vitro.

Bone formation occurs during development of long bones (endochondral bone formation) and flat bones (intramembranous bone formation). Further, bone formation occurs during bone remodeling which occurs continuously in adult life in order to preserve the integrity of the skeleton. Finally, bone formation occurs during bone repair, such as when bone wounds occur in a fracture or surgical situation, for example. While separate bone formation mechanisms are thought to be involved in the embryological development of long and flat bones and repair is thought to involve intramembranous bone formation.

Bone formation by either mechanism involves the activity of osteoblasts, which are regulated by growth factors. Osteoblasts are derived from a pool of marrow stromal cells (also known as mesenchymal stem cells; MSC). These cells are present in a variety of tissues and are prevalent in bone marrow stroma. MSC are pluripotent and can differentiate into a variety of cell types including osteoblasts, chondrocytes, fibroblasts, myocytes, and adipocytes. Growth factors are thought to impact osteogenic cell proliferation, differentiation and osteoblast mineralization, each of which impacts bone formation.

Autogenous bone has been used, such to repair bone in patients with craniosynostosis and cleft grafting, for example. Craniosynostosis (CS), the premature closure of cranial sutures, affects 1 in 3,000 infants and therefore is one of the most common human congenital craniofacial deformities. Premature suture closure results in cranial dimorphism, which can need surgical correction. Premature suture closure in human CS can occur by two possibly distinct processes: calvarial overgrowth and bony fusion. Recently, fibroblast growth factor 2 (FGF2) and fibroblast growth factor receptor 1 (FGFR1) have been implicated in premature cranial suture fusion via CBFA1-mediated pathways (8). Missense mutation of CBFA1 is linked to cleidocranial dysplasia, manifested as delayed suture closure.

Autologous bone grafting procedures have been performed utilizing autogenous bone, such as from the iliac crest or calvaria. These donor sites are not without associated morbidity including pain, gait disturbance, thigh paresthesia for iliac crest donor sites, and infection, neurologic deficits, and hematomas for calvarial grafts. Further, donor sites can have limited volume and can contribute to increased surgical time and hospital stay.

Alloplastic grafting materials have also been utilized, and growth factors have been tested in animal models. For example, bFGF has shown potential for use in bone regeneration and repair. Another family of osteogenic growth factors have been described as bone morphogenic protein (BMP). Specifically, BMP-2 recombinant protein has been demonstrated to regenerate mandibular continuity defects and cleft palate defects with results equal to or better than autogenous particulate bone and marrow. BMPs and other osteogenic factors have been studied for use in clinical applications. However, the cost of using minimally effective dosages of BMP has been a limiting factor in clinical use.

Spinal fusion is a surgical technique in which one more of the vertebrae of the spine are united together so that motion no longer occurs between them. Indications include: treatment of a fractured (broken) vertebra, correction of deformity, elimination of pain from motion, treatment of instability, and treatment of some cervical disc herniations. The surgery can involve placement of a bone graft between the vertebrae to obtain a solid union between the vertebrae. The procedure also can involve supplemental treatments including the placement of plates, screws, cages, and recently bone morphogenic protein 2 and 7 to assist in stabilizing and healing the bone graft. Autogenous bone grafting has been the clinically preferred method, and yet has about a 30-50% failure rate. Autogenous bone grafting is a separate surgery and also carries significant morbidity.

Cartilage is a type of dense connective tissue. It is composed of chondrocytes which are dispersed in a firm gel-like matrix. Cartilage is avascular (contains no blood vessels) and nutrients are diffused through the matrix. Cartilage is found in the joints, the rib cage, the ear, the nose, in the throat and between intervertebral disks. There are three main types of cartilage: hyaline (e.g., costal cartilages, the cartilages of the nose, trachea, and bronchi, and the articular cartilages of joints), elastic (e.g., external ear, external auditory meatus, part of the Eustachian tube, epiglottis, and in some of the laryngeal cartilages) and fibrocartilage [e.g. meniscus (e.g., wrist triangular fibrocartilage complex, knee meniscus), intervertebral discs, temporomandibular joint disc, the pubic symphysis, and in some tendons and ligaments at their attachment to bones. One of the main purposes of cartilage is to provide a framework upon which bone deposition could begin (i.e., during endochondral ossification). Another important purpose of cartilage is to provide smooth surfaces for the movement of articulating bones. For example, articular cartilage, most notably that which is found in the knee joint, is generally characterized by very low friction, high wear resistance, and poor regenerative qualities. It is responsible for much of the compressive resistance and load bearing qualities of the knee joint and, without it, walking is painful to impossible. Yet another important purpose of cartilage is to provide, firm, yet flexible support (e.g., nasal cartilage, spinal discs, tracheal cartilage, knee meniscus, bronchial cartilage). For instance, cartilage such as the meniscus plays a crucial role in joint stability, lubrication, and force transmission. Under a weight bearing load, the meniscus maintains the balanced position of the femur on the tibia and distributes the compressive forces by increasing the surface contact area, thereby decreasing the average stress two to three times. Additionally, the menisci interact with the joint fluid to produce a coefficient of friction that is five times as slick as ice on ice. In another example, the intervertebral disc has several important functions, including functioning as a spacer, as a shock absorber, and as a motion unit. The gelatinous central portion of the disc is called the nucleus pulposus. It is composed of 80-90% water. The solid portion of the nucleus is Type II collagen and non-aggregated proteoglycans. The outer ligamentous ring around the nucleus pulposus is called the annulus fibrosus, which hydraulically seals the nucleus, and allows intradiscal pressures to rise as the disc is loaded. The annulus has overlapping radial bands, not unlike the plies of a radial tire, and this allows torsional stresses to be distributed through the annulus under normal loading without rupture. The disc functions as a hydraulic cylinder. The annulus interacts with the nucleus. As the nucleus is pressurized, the annular fibers serve a containment function to prevent the nucleus from bulging or herniating.

Cartilage can be damaged by wear, injury or diseases. As we age, the water and protein content of the body's cartilage changes. This change results in weaker, more fragile and thin cartilage. Osteoarthritis is a common condition of cartilage failure that can lead to limited range of motion, bone damage and invariably, pain. Due to a combination of acute stress and chronic fatigue, osteoarthritis directly manifests itself in a wearing away of the articulating surface and, in extreme cases, bone can be exposed in the joint. In another example, loss of the protective stabilizing meniscus leads to increased joint laxity or abnormal motions that lead to joint instability. The excessive motion and narrowed contact area promotes early arthritic changes. At the cellular level, there is initially a loss of cells from the superficial layer of the articular cartilage followed by cartilage splitting, subsequent thinning and erosion occurs, and finally protrusion of the underlying raw bone. The earliest arthritic changes have been noted three weeks after loss of the entire meniscus. In yet another example, because both the discs and the joints that stack the vertebrae (facet joints) are partly composed of cartilage, these areas are subject to wear and tear over time (degenerative changes). As the inner nucleus dehydrates, the disc space narrows, and redundant annular ligaments bulge. With progressive nuclear dehydration, the annular fibers can crack and tear. Loss of normal soft tissue tension may allow the spinal segment to sublux (e.g. partial dislocation of the joint), leading to osteophyte formation (bone spurs), foraminal narrowing, mechanical instability, and pain. If the annular fibers stretch or rupture, allowing the pressurized nuclear material to bulge or herniate and compress neural tissues, pain and weakness may result. This is the condition called a pinched nerve, slipped disc, or herniated disc. Radiculopathy refers to nerve irritation caused by damage to the disc between the vertebrae. Mechanical dysfunction may also cause disc degeneration and pain (e.g. degenerative disc disease). For example, the disc may be damaged as the result of some trauma that overloads the capacity of the disc to withstand increased forces passing through it, and inner or outer portions of the annular fibers may tear. These torn fibers may be the focus for inflammatory response when they are subjected to increased stress, and may cause pain directly, or through the compensatory protective spasm of the deep paraspinal muscles.

NELL peptide has been documented to stimulate bone formation and cartilage formation. Existing methods and systems of producing NELL peptides have limited success with problems. A common problem of existing NELL peptide expression systems (e.g., a mammalian cell such as a CHO cell expression system) is low productivity. Low productivity is generally found to be caused by, for example, an inappropriate construct of the nucleic acid sequence expressing a NELL peptide and/or other additional sequences, e.g., a secretory signal peptide sequence, in a particular expression system, e.g., a CHO cell.

Therefore there is a continuous need for a method and system for producing NELL peptides.

SUMMARY OF THE INVENTION

The present invention relates to a system and method for producing a NELL peptide. The method comprises:

providing a nucleic acid construct including at least a nucleic acid encoding at least a NELL peptide in frame with a nucleic acid encoding a non-insect secretory signal peptide;

transfecting a mammalian cell with the nucleic acid construct; and culturing the mammalian cell under conditions that permit expression of the NELL peptide.

The mammalian cell can be, e.g., a Chinese hamster ovary cell. The nucleic acid encodes NELL1 or NELL2 or both.

In some embodiments, the method further comprises: collecting NELL peptide secreted from the cell line; and substantially purifying the NELL peptide.

In some embodiments, the method of the above various embodiments can further comprise testing the activity of the NELL peptide to induce bone formation.

The act of purifying can be any step of purifying a protein or peptide. In some embodiments, the act of purifying includes chromatography purification.

In some embodiments, the present invention provides a nucleic acid construct for expressing a NELL peptide in a mammalian cell. The nucleic acid construct comprises at least a nucleic acid encoding at least a NELL peptide in frame with a nucleic acid encoding a secretory signal peptide that is a non-insect secretory signal peptide. The nucleic acid encodes NELL1 or NELL2. In some embodiments, the mammalian cell can be a CHO cell.

In some embodiments, the present invention provides a mammalian cell line for expressing a NELL peptide. The cell line comprises a nucleic acid construct comprising at least a nucleic acid encoding at least a NELL peptide in frame with a nucleic acid encoding a secretory signal peptide that is a non-insect secretory signal peptide. The nucleic acid encodes NELL1 or NELL2. In some embodiments, the mammalian cell can be a CHO cell.

In some embodiments, the present invention provides a polypeptide comprising a NELL peptide and a non-insect secretory signal peptide.

In some embodiments, the mammalian cell can be human embryo kidney cell, such as HEK-293.

The present invention provides a method of purifying a NELL peptide, comprising providing a crude solution containing a NELL peptide, and subjecting the crude solution to membrane chromatography to obtain a purified NELL peptide.

In some embodiments, the membrane chromatography is anion-exchange membrane chromatography or cation-exchange membrane chromatography.

The present invention provides a method of purifying a NELL peptide, comprising providing a crude solution containing a NELL peptide, and subjecting the crude solution to chromatography process to obtain a purified NELL peptide, wherein the chromatography process comprises a medium comprising a metal ion bearing two or more charges. In some embodiments, the metal ion is calcium ion.

The NELL peptide can be NELL-1 peptide or NELL-2 peptide.

BRIEF DESCRIPTION OF THE DRAWINGS

FIGS. 1A-1D (SEQ ID NOs: 609 and 610) illustrate a signal peptide-NELL1-FLAG nucleic acid construct. The underlined amino acid sequence is from melittin signal peptide. The NELL1 peptide is from rat NELL1 peptide.

FIG. 2A is an illustration of a CBB-stained SDS-PAGE gel of UnoQ-eluate containing purified NELL1 peptide.

FIG. 2B shows a Western blot using anti-FLAG antibody depicting NELL1-FLAG expression in reference to a protein ladder.

FIG. 2C is an illustration of a CBB-stained SDS-PAGE gel of UnoQ-eluate containing NELL1-FLAG.

FIG. 2D shows a Western blot using anti-FLAG antibody depicting NELL1-FLAG expression.

FIGS. 4A-D show NELL1 (*homo sapiens*) nucleotide sequence and corresponding amino acid sequence (SEQ ID NOs: 1 and 2).

FIGS. 5A-D show NELL1 (*rattus norvegicus*) nucleotide sequence and corresponding amino acid sequence (SEQ ID NOs: 3 and 4).

FIGS. 6A-F show NELL1 (*Mus musculs*) nucleotide sequence and corresponding amino acid sequence (SEQ ID NOs: 5 and 6).

FIGS. 7A-D show NELL2 (*homo sapiens*) nucleotide sequence and corresponding amino acid sequence (SEQ ID NOs: 7 and 8).

FIGS. 8A-D show NELL2 (*rattus norvegicus*) nucleotide sequence and corresponding amino acid sequence (SEQ ID NOs: 9 and 10).

FIGS. 9A-D show NELL2 (*Mus musculs*) nucleotide sequence and corresponding amino acid sequence (SEQ ID NOs: 11 and 12).

FIGS. 10A-D show NELL2 (*Gallus gallus*) nucleotide sequence and corresponding amino acid sequence (SEQ ID NOs: 13 and 14).

DETAILED DESCRIPTION

Definitions

Figure 3A:
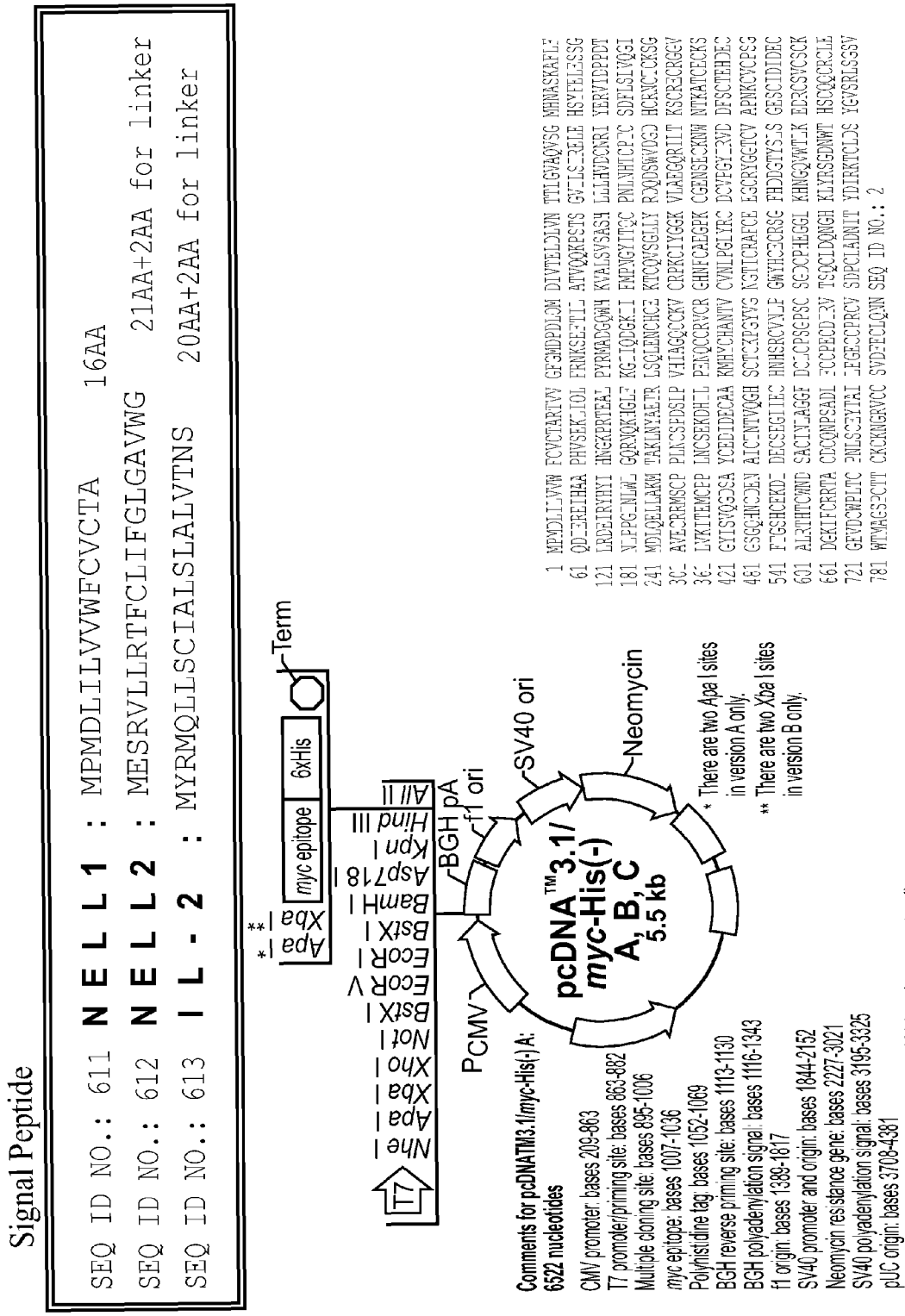
FIG. 3A depicts the nucleic acid sequence of the cDNA construct and amino acid sequences of three different signal peptides (SEQ ID NOs: 611-613) that were used for the constructs.

As used herein, the terms "polypeptide", "peptide" and "protein" can be used interchangeably to refer to a polymer of amino acid residues. The terms can apply to amino acid polymers in which one or more amino acid residues is an artificial chemical analogue of a corresponding naturally occurring amino acid, as well as to naturally occurring amino acid polymers.

The term "antibody" can include various forms of modified or altered antibodies, such as an intact immunoglobulin, an Fv fragment containing only the light and heavy chain variable regions, an Fv fragment linked by a disulfide bond, a Fab or F(ab')$^2$ fragment containing the variable regions and parts of the constant regions, a single-chain antibody and the like. An antibody can include intact molecules as well as fragments thereof, such as, Fab and F(ab')$^2$, and/or single-chain antibodies (e.g. scFv) which can bind an epitopic determinant. An antibody can be of animal, e.g., mouse or rat, or of human origin, or can be chimeric or humanized. Antibodies can be polyclonal or monoclonal antibodies (mAbs), such as monoclonal antibodies with specificity for a polypeptide encoded by a NELL1 or NELL 2 protein.

The term "capture agent" refers to molecules that specifically bind other molecules to form a binding complex such as, but not limited to, an antibody-antigen complex, a lectin-carbohydrate complex, a nucleic acid-nucleic acid complex or a biotin-avidin complex.

The term "specifically binds" refers to the binding property of a biomolecule (e.g., protein, nucleic acid, antibody, etc.), which is determinative of the presence of such a biomolecule in a heterogeneous population of molecules (e.g., proteins and other biologics). Thus, under designated conditions (e.g., immunoassay conditions in the case of an antibody or stringent hybridization conditions in the case of a nucleic acid), the specified ligand or antibody specifically binds to its particular "target" molecule and will not bind in a significant amount to other molecules present in the sample.

The terms "nucleic acid" or "oligonucleotide" refer to at least two nucleotides covalently linked together. A nucleic acid of the present invention can be single-stranded or double stranded and can contain phosphodiester bonds, although in some cases, nucleic acid analogs can be included that can have alternate backbones, comprising, for example, phosphoramide, phosphorothioate, phosphorodithioate, omethylphophoroamidite linkages, and/or peptide nucleic acid backbones and linkages. Analog nucleic acids can have positive backbones and/or non-ribose backbones. Nucleic acids can also include one or more carbocyclic sugars. Modifications of the ribose-phosphate backbone can be done to facilitate the addition of additional moieties such as labels, or to increase the stability and half-life of such molecules in physiological environments, for example.

The term "specific hybridization" refers to the preferential binding, duplexing, or hybridizing of a nucleic acid molecule to a particular nucleotide sequence under stringent conditions, including conditions under which a probe can hybridize preferentially to its target subsequence, and can hybridize to a lesser extent to other sequences.

The terms "NELL1 cDNA" refer to SEQ ID NO:1, 3 and 5, and "NELL2 cDNA" can refer to SEQ ID NO:7, 9, 11 and 13.

NELL Peptides

NELL1 is a 810 aa (amino acid) peptide, distributed primarily in bone. In adults, NELL1 is expressed at high levels in craniofacial bone, and lower levels in long bone. NELL1 has known roles in osteoblast differentiation, bone formation and bone regeneration. NELL1 has known rules in forming cartilage tissues without forming bone.

NELL 2 is a 816 aa peptide, distributed in neural cells and brain.

The human NELL1 gene includes at least 3 Cbfa1 response elements in the promoter region. Cbfa1 specifically binds to these response elements. NELL1 expression can be under the control of these transcription factors expressed endogenously at least in preosteoblasts, osteoblasts and hypertrophic chondrocytes in development and in adulthood. Cleidocranial disostosis is a developmental cranial defect thought to be caused at least in part by Cbfa disruption.

A NELL1 peptide can be encoded by the NELL1 gene or cDNA and includes SEQ ID NO: 2, 4, and 6. The NELL1 peptide can include a NELL1 peptide fragment that retains the ability to induce osteogenic cell differentiation, osteoblast differentiation or bone formation. In some embodiments, the NELL1 peptide can include a NELL 1 peptide fragment that retains the ability to induce cartilage formation without forming bone. A NELL2 peptide can be encoded by the NELL2 gene or cDNA and includes SEQ ID NO: 8, 10, 12 and 14. The NELL2 peptide can include NELL2 peptide fragments that retain similar activity to the full NELL2 peptide sequence.

In some embodiments, the amino acid sequence of the NELL peptide can be selected from the group including, but not limited to human NELL1 (SEQ ID NO:2), rat NELL1 (SEQ ID NO:4), mouse NELL1 (SEQ ID NO:6), or human NELL2 (SEQ ID NO:8), rat NELL2 (SEQ ID NO:10), mouse NELL2 (SEQ ID NO:12), chicken NELL2 (SEQ ID NO:14). The amino acid sequence can also include sequences such as those with substantial similarity, such as sequences having at least about 75% sequence similarity with any portion of the sequences listed above, or contain similar active binding domains as NELL1 peptides.

The term "derivative" as used herein, refers to any chemical or biological compound or material derived from a NELL peptide, structural equivalents thereof or conformational equivalents thereof. For example, such a derivative can include any pro-drug form, PEGylated form, or any other form of a NELL peptide that renders the NELL peptide more stable or more osteophilic or lipophilic. In some embodiments, the derivative can be a NELL peptide attached to poly(ethylene glycol), a poly(amino acid), a hydrocarbyl short chain having C1-C20 carbons, or a biocompatible polymer. In some embodiments, the term "derivative" can include NELL peptide mimetics. As used herein, the term "mimetic" refers to a peptide having at least one non-peptide bond in its backbone. A peptide bond is a chemical bond formed between the carboxylic acid group of an amino acid molecule and the amino group of another amino acid molecule. A NELL peptide mimetic can be any compound that exhibits at least one or more bone forming, bone repairing, cartilage forming, and/or cartilage repairing function of a NELL peptide.

Synthetic methods for making peptide mimetics are well known in the art. The following describes an example of the basic procedure for the synthesis of a peptide, including a peptide mimetics:

Before the peptide synthesis starts, the amine terminus of the amino acid (starting material) can protected with FMOC (9-fluoromethyl carbamate) or other protective groups, and a solid support such as a Merrifield resin (free amines) is used as an initiator. Then, step (1) through step (3) reactions are performed and repeated until the desired peptide is obtained: (1) a free-amine is reacted with carboxyl terminus using carbodiimide chemistry, (2) the amino acid sequence is purified, and (3) the protecting group, e.g., the FMOC protecting group, is removed under mildly acidic conditions to yield a free amine. The peptide can then be cleaved from the resin to yield a free standing peptide or peptide mimetics.

Systems Expressing NELL Peptides

Generally, the method of invention includes providing a nucleic acid sequence encoding a NELL peptide, such as NELL1 or NELL2 peptide, in frame with a nucleic acid sequence encoding a non-insect signal peptide.

In one embodiment, the method can include transfecting an insect cell line with a nucleic acid construct encoding a NELL peptide; and culturing the insect cell line under conditions that permit expression and/or secretion of the NELL peptide. For example, the cell line can be transfected transiently or stably with the nucleic acid construct encoding a NELL peptide.

In one embodiment, the method can include providing a nucleic acid sequence encoding a NELL peptide, such as NELL1 or NELL2 peptide. The nucleic acid sequence can be a cDNA or genomic DNA, encoding at least a functional portion of a NELL peptide. For example, the nucleic acid sequence can be selected from the group including, but not limited to human NELL1 (SEQ ID NO:1), rat NELL1 (SEQ ID NO:3), mouse NELL1 (SEQ ID NO:5), or human NELL2 (SEQ ID NO:7), rat NELL2 (SEQ ID NO:9), mouse NELL2 (SEQ ID NO:11), chicken NELL2 (SEQ ID NO:13). In some embodiments, the nucleic acid sequence can also include sequences such as those with substantial sequence similarity, such as sequences having at least about 75% sequence similarity with any portion of the sequences listed above.

Further the nucleic acid can include an expression vector for expressing the nucleic acid sequence encoding a NELL peptide, such as NELL1 or NELL2 peptide. For example, the expression vector can be pIZT/V5-His (Invitrogen), and selective markers can also include blasticidin and neomycin.

Such expression systems can include a carrier such as a viral carrier or viral vector, peptide carrier or a short polymer molecule.

Nucleic acid constructs can comprise expression and cloning vectors should contain a selection gene, also termed a selectable marker, such as a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g., ampicillin, neomycin, methotrexate or tetracycline, (b) complement auxotrophic deficiencies.

Further, the nucleic acid sequence can also include additional nucleic acids which encode reporter products to monitor levels of gene expression, or encode peptide tags which can be visualized using known methods in the art to monitor levels of peptide expression. Additional sequences can be selected so as to not interfere with the expression of the nucleic acid, or the functionality of the expressed peptide product.

A promoter is recognized by the host organism and is operatively linked to the NELL encoding nucleic acid. Promoters are untranslated sequences located upstream from the start codon of a structural gene (generally within about 100 to 1000 bp) that control the transcription and translation of nucleic acid under their control, including inducible and constitutive promoters. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known.

A nucleic acid can be operably linked when it is placed into a functional relationship with another nucleic acid sequence. For example, DNA for a presequence or secretory leader is operatively linked to DNA for a polypeptide if it is expressed as a preprotein which participates in the secretion of the polypeptide; a promoter or enhancer is operatively linked to a coding sequence if it affects the transcription of the sequence; or a ribosome binding site is operatively linked to a coding sequence if it is positioned so as to facilitate translation.

A NELL peptide can be expressed in any biological system. For example, a NELL peptide can be expressed in a bacterial system, a yeast system, a plant system or animal system.

In some embodiments, a NELL peptide can be expressed in a cell free expression system well known to those in the art. For example, E coli cell-free protein translation systems or wheat germ cell-free protein translation systems.

In some embodiments, a NELL peptide can be expressed in transgenic plant cell systems derived from tobacco, corn, rice or soybean.

In some embodiments, a NELL peptide can be expressed in insect cells. The NELL1 and NELL2 peptides expressed in an insect system are functional forms of the protein.

COS7 cells can be used to produce NELL1 and NELL2 proteins at low levels, such as about 10 micrograms per litter medium, but require serum-containing medium for the expression. As for the signal peptides, NELL1 and NELL2 endogenous signal peptides permit expression in COS7 cells.

In one embodiment, the invention includes a method of expressing a functional NELL peptide, such as NELL1 or NELL2 peptide, using an insect cell line. In one embodiment, the insect cell can be a high five cell, Sf9 and other Sf cells.

In one embodiment, the invention can include a nucleic acid construct for expressing a NELL peptide, such as NELL1 and/or NELL2 peptide in an insect cell. The nucleic acid sequence can be a cDNA or genomic DNA, encoding at least a functional portion of a NELL peptide. For example, the nucleic acid sequence can be selected from the group including, but not limited to human NELL1 (SEQ ID NO:1), rat NELL1 (SEQ ID NO:3), mouse NELL1 (SEQ ID NO:5), or human NELL2 (SEQ ID NO:7), rat NELL2 (SEQ ID NO:9), mouse NELL2 (SEQ ID NO:11), chicken NELL2 (SEQ ID NO:13). The nucleic acid sequence can also include sequences such as those with substantial sequence similarity, such as sequences having at least about 75% sequence similarity with any portion of the sequences listed above.

In one embodiment, the invention can include a nucleic acid construct for expressing a NELL peptide, such as NELL1 and/or NELL2 peptide in a mammalian cell such as a Chinese hamster ovary cell (CHO cell). The nucleic acid sequence can be a cDNA or genomic DNA, encoding at least a functional portion of a NELL peptide. For example, the nucleic acid sequence can be selected from the group including, but not limited to human NELL1 (SEQ ID NO:1), rat NELL1 (SEQ ID NO:3), mouse NELL1 (SEQ ID NO:5), or human NELL2 (SEQ ID NO:7), rat NELL2 (SEQ ID NO:9), mouse NELL2 (SEQ ID NO:11), chicken NELL2 (SEQ ID NO:13). In some embodiments, the nucleic acid sequence can also include sequences such as those with substantial sequence similarity, such as sequences having at least about 75% sequence similarity with any portion of the sequences listed above.

In one embodiment, the invention can include cells that express functional NELL peptides. For example, the cell can be a CHO cell. In one embodiment, the cell can be transfected with a nucleic acid construct encoding a NELL peptide. For example, the cell line can be transfected transiently or stably with the nucleic acid construct encoding a NELL peptide. In one embodiment, NELL expressing nucleic acids (e.g., cDNA(s) can be cloned into gene expression vector or viral particles that are competent to transfect cells (such as insect cells or Chinese hamster ovary cells (CHO cells)).

The nucleic acid construct can also include a nucleic acid sequence encoding a NELL peptide, such as NELL1 or NELL2 peptide, in frame with a nucleic acid sequence encoding a non-insect signal peptide that is a non-insect secretory signal peptide.

In one embodiment, the invention can include cells that express functional NELL peptides, and can secrete functional proteins.

In one embodiment, the invention can include a polypeptide (amino acid sequence) comprising a NELL peptide, such as NELL1 or NELL2 peptide, and can include a non-insect secretory signal peptide.

Non-Insect Secretory Signal Peptide

Useful non-insect secretory signal peptide for use in a NELL peptide expression system (e.g., a mammalian cell such as a CHO cell) can be any secretory signal peptide. Such non-insect secretory signal peptide can be, for example, plant secretory signal peptide, or animal secretory signal peptide, e.g., mammalian secretory signal peptide such as human secretory signal peptide. Various secretory signal peptide can be found at various publicly accessible sources, e.g., http<://> proline<dot>bic<dot>nus<dot>edu<dot>sg.

Human secretory signal peptides are well documented. Examples of human secretory signal peptides include, but are not limited to,
1A02_human secretory signal peptide, 1A11_human secretory signal peptide, 1A25_human secretory signal peptide, 1A26_human secretory signal peptide, 1A30_human secretory signal peptide, 1A31_human secretory signal peptide, 1A33_human secretory signal peptide, 1A68_human secretory signal peptide, 1A80_human secretory signal peptide, 1B07_human secretory signal peptide, 1B15_human secretory signal peptide, 1B37_human secretory signal peptide, 1B40_human secretory signal peptide, 1B47_human secretory signal peptide, 1B48_human secretory signal peptide, 1B57_human secretory signal peptide, 1B59_human secretory signal peptide, 1B78_human secretory signal peptide, 1C03_human secretory signal peptide, 1C04_human secretory signal peptide, 1C05_human secretory signal peptide, 1C07_human secretory signal peptide, 1C14_human secretory signal peptide, 1C15_human secretory signal peptide, 1C16_human secretory signal peptide, 1C17_human secretory signal peptide, 1C18_human secretory signal peptide, 2B11_human secretory signal peptide, 2B14_human secretory signal peptide, 2B17_human secretory signal peptide, 2B1A_human secretory signal peptide, 2B1B_human secretory signal peptide, 2B32_human secretory signal peptide, 2DOB_human secretory signal peptide, 7B2_human secretory signal peptide, A1AT_human secretory signal peptide, A2GL_human secretory signal peptide, A2MG_human secretory signal peptide, ABP1_human secretory signal peptide, ACET_human secretory signal peptide, ACHB_human secretory signal peptide, ACHE_human secretory signal peptide, ACRO_human secretory signal peptide, ADA32_human secretory signal peptide, ADIPO_human secretory signal peptide, ADML_human secretory signal peptide, AGAL_human secretory signal peptide, AGR2_human secretory signal peptide, AGR3_human secretory signal peptide, AMBP_human secretory signal peptide, AMTN_human secretory signal peptide, ANF_human secretory signal peptide, ANGI_human secretory signal peptide, ANGL3_human secretory signal peptide, ANGL7_human secretory signal peptide, ANGT_human secretory signal peptide, ANPRA_human secretory signal peptide, APOA2_human secretory signal peptide, APOA4_human secretory signal peptide, APOA_human secretory signal peptide, APOC1_human secretory signal peptide, APOC2_human secretory signal peptide, APOC3_human secretory signal peptide, APOD_human secretory signal peptide, APOE_human secretory signal peptide, APOH_human secretory signal peptide, APR3_human secretory signal peptide, ASM_human secretory signal peptide, ASPG_human secretory signal peptide, BAMBI_human secretory signal peptide, BASI_human secretory signal peptide, BGAL_human secretory signal peptide, BGLR_human secretory signal peptide, BOC_human secretory signal peptide, BPIL1_human secretory signal peptide, BPI_human secretory signal peptide, BT3A$^3$_human secretory signal peptide, BTNL8_human secretory signal peptide, C16L2_human secretory signal peptide, C1QT5_human secretory signal peptide, C1QT6_human secretory signal peptide, C1R_human secretory signal peptide, C1S_human secretory signal peptide, C4BPA_human secretory signal peptide, CA187_human secretory signal peptide, CADM3_human secretory signal peptide, CAH9_human secretory signal peptide, CALCR_human secretory signal peptide, CALRL_human secretory signal peptide, CALR_human secretory signal peptide, CAP7_human secretory signal peptide, CART_human secretory signal peptide, CASA1_human secretory signal peptide, CASB_human secretory signal peptide, CASK_human secretory signal peptide, CATC_human secretory signal peptide, CATE_human secretory signal peptide, CATG_human secretory signal peptide, CATW_human secretory signal peptide, CBG_human secretory signal peptide, CBLN3_human secretory signal peptide, CBLN4_human secretory signal peptide, CBPA1_human secretory signal peptide, CBPA3_human secretory signal peptide, CBPB1_human secretory signal peptide, CBPN_human secretory signal peptide, CCL11_human secretory signal peptide, CCL15_human secretory signal peptide, CCL19_human secretory signal peptide, CCL1_human secretory signal peptide, CCL22_human secretory signal peptide, CCL24_human secretory signal peptide, CCL2_human secretory signal peptide, CCL4_human secretory signal peptide, CCL5_human secretory signal peptide, CCL7_human secretory signal peptide, CD180_human secretory signal peptide, CD1A_human secretory signal peptide, CD244_human secretory signal peptide, CD276_human secretory signal peptide, CD27_human secretory signal peptide, CD28_human secretory signal peptide, CD2_human secretory signal peptide, CD320_human secretory signal peptide, CD34_human secretory signal peptide, CD3E_human secretory signal peptide, CD3G_human secretory signal peptide, CD3Z_human secretory signal peptide, CD45_human secretory signal peptide, CD5L_human secretory signal peptide, CD5_human secretory signal peptide, CD83_human secretory signal peptide, CD8B_human secretory signal peptide, CD99_human secretory signal peptide, CEAM1_human secretory signal peptide, CER1_human secretory signal peptide, CERU_human secretory signal peptide, CETP_human secretory signal peptide, CF126_human secretory signal peptide, CFAB_human secretory signal peptide, CFAH_human secretory signal peptide, CFAI_human secretory signal peptide, CH3L1_human secretory signal peptide, CH3L2_human secretory signal peptide, CHIT1_human secretory signal peptide, CL3L1_human secretory signal peptide, CLC11_human secretory signal peptide, CLC14_human secretory signal peptide, CLM1_human secretory signal peptide, CLM9_human secretory signal peptide, CLUS_human secretory signal peptide, CMA1_human secretory signal peptide, CMGA_human secretory signal peptide, CO1A1_human secretory signal peptide, CO2_human secretory signal peptide, CO3_human secretory signal peptide, CO4A2_human secretory signal peptide, CO5A2_human secretory signal peptide, CO6A1_human secretory signal peptide, CO6_human secretory signal peptide, CO7_human secretory signal peptide, CO9A1_human secretory signal peptide, CO9_human secretory signal peptide, COGA1_human secretory signal peptide, COLI_human secretory signal peptide, COL_human secretory signal peptide, CR2_human secretory signal peptide, CRDL2_human secretory signal peptide, CREG1_human secretory signal peptide, CRHBP_human secretory signal peptide, CRIM1_human secretory signal peptide, CRIS1_human secretory signal peptide, CRLF1_human secretory signal peptide, CRP_human secretory signal peptide, CSF2R_human secretory signal peptide, CSF2_human secretory signal peptide, CSF3R_human secretory signal peptide, CSPG2_human secretory signal peptide, CST9L_human secretory signal peptide, CST9_human secretory signal peptide, CTHR1_human secretory signal peptide, CTRB1_human secretory signal peptide, CXCL7_human secretory signal peptide, CXL10_human secretory signal peptide, CYTC_human secretory signal peptide, CYTL1_human secretory signal peptide, CYTN_human secretory signal peptide, CYTS_human secretory signal peptide, CYTT_human secretory signal peptide, D103A_human secretory signal peptide, DB127_human secretory signal peptide, DCD_human secretory signal peptide, DEF1_human secretory signal peptide, DKK1_human secretory signal peptide, DKK3_human secretory signal peptide, DKK4_human secretory signal peptide, DLK_human secretory signal peptide, DLL4_human secretory signal peptide, DNAS1_human secretory signal peptide, ECP_human secretory signal peptide, EDAR_human secretory signal peptide, EFNB1_human secretory signal peptide, EFNB3_human secretory signal peptide, EGFL8_human secretory signal peptide, EGFR_human secretory signal peptide, EGLN_human secretory signal peptide, ELA2A_human secretory signal peptide, ELA2B_human secretory signal peptide, ELAF_human secretory signal peptide, ENPL_human secretory signal peptide, ENPP7_human secretory signal peptide, EPGN_human secretory signal peptide, EPHB1_human secretory signal peptide, EPHB6_human secretory signal peptide, EPOR_human secretory signal peptide, EPO_human secretory signal peptide, ESAM_human secretory signal peptide, EST1_human secretory signal peptide, F13B_human secretory signal peptide, FA11_human secretory signal peptide, FA5_human secretory signal peptide, FA8_human secretory signal peptide, FCGR1_human secretory signal peptide, FCGRN_human secretory signal peptide, FCN1_human secretory signal peptide, FCN3_human secretory signal peptide, FCRL2_human secretory signal peptide, FCRLA_human secretory signal peptide, FETUA_human secretory signal peptide, FGF19_human secretory signal peptide, FGF21_human secretory signal peptide, FGF23_human secretory signal peptide, FGFR3_human secretory signal peptide, FGFR4_human secretory signal peptide, FGRL1_human secretory signal peptide, FIBA_human secretory signal peptide, FIBG_human secretory signal peptide, FKB14_human secretory signal peptide, FKBP2_human secretory signal peptide, FLRT2_human secretory signal peptide, FSHB_human secretory signal peptide, FSTL1_human secretory signal peptide, FSTL3_human secretory signal peptide, FST_human secretory signal peptide, FZD3_human secretory signal peptide, G6B_human secretory signal peptide, GALC_human secretory signal peptide, GDN_human secretory signal peptide, GELS_human secretory signal peptide, GI24_human secretory signal peptide, GLHA_human secretory signal peptide, GLPA_human secretory signal peptide, GLPB_human secretory signal peptide, GLPE_human secretory signal peptide, GLUC_human secretory signal peptide, GNS_human secretory signal peptide, GP1BA_human secretory signal peptide, GPI8_human secretory signal peptide, GPIX_human secretory signal peptide, GPR56_human secretory signal peptide, GPR97_human secretory signal peptide, GRAB_human secretory signal peptide, GREM1_human secretory signal peptide, GROA_human secretory signal peptide, GRP78_human secretory signal peptide, GRP_human secretory signal peptide, HA22_human secretory signal peptide, HA23_human secretory signal peptide, HA25_human secretory signal peptide, HA27_human secretory signal peptide, HB21_human secretory signal peptide, HB23_human secretory signal peptide, HB24_human secretory signal peptide, HB25_human secretory signal peptide, HB2B_human secretory signal peptide, HB2C_human secretory signal peptide, HB2K_human secretory signal peptide, HEP2_human secretory signal peptide, HGFA_human secretory signal peptide, HIS1_human secretory signal peptide, HIS3_human secretory signal peptide, HLAE_human secretory signal peptide, HPSE_human secretory signal peptide, HPT_human secretory signal peptide, HV103_human secretory signal peptide, HV303_human secretory signal peptide, I10R1_human secretory signal peptide, I10R2_human secretory signal peptide, I17RA_human secretory signal peptide, I17RB_human secretory signal peptide, I17RC_human secretory signal, I18BP_human secretory signal peptide, I20RA_human secretory signal peptide, I20RB_human secretory signal peptide, I22RA_human secretory signal peptide, IBP1_human secretory signal peptide, IBP2_human secretory signal peptide, IBP3_human secretory signal peptide, IBP7_human secretory signal peptide, IFN16_human secretory signal peptide, IFNA2_human secretory signal peptide, IFNA4_human secretory signal peptide, IFNA5_human secretory signal peptide, IFNA6_human secretory signal peptide, IFNA7_human secretory signal peptide, IFNK_human secretory signal peptide, IFNW1_human secretory signal peptide, IGF2_human secretory signal peptide, IGFL1_human secretory signal peptide, IGFL3_human secretory signal peptide, IL10_human secretory signal peptide, IL12A_human secretory signal peptide, IL12B_human secretory signal peptide, IL17F_human secretory signal peptide, IL17_human secretory signal peptide, IL19_human secretory signal peptide, IL1R1_human secretory signal peptide, IL1RA_human secretory signal peptide, IL20_human secretory signal peptide, IL21R_human secretory signal peptide, IL22_human secretory signal peptide, IL24_human secretory signal peptide, IL25_human secretory signal peptide, IL2RA_human secretory signal peptide, IL2RB_human secretory signal peptide, IL2RG_human secretory signal peptide, IL2_human secretory signal peptide, IL3_human secretory signal peptide, IL4_human secretory signal peptide, IL5RA_human secretory signal peptide, IL6RA_human secretory signal peptide, IL7RA_human secretory signal peptide, IL7_human secretory signal peptide, IL9_human secretory signal peptide, ILRL1_human secretory signal peptide, INAR2_human secretory signal peptide, INHA_human secretory signal peptide, INSL3_human secretory signal peptide, INSL4_human secretory signal peptide, INSL5_human secretory signal peptide, INS_human secretory signal peptide, IPSP_human secretory signal peptide, IRBP_human secretory signal peptide, ISK6_human secretory signal peptide, ITA2B_human secretory signal peptide, ITA2_human secretory signal peptide, ITA3_human secretory signal peptide, ITA4_human secretory signal peptide, ITA6_human secretory signal peptide, ITA7_human secretory signal peptide, ITAE_human secretory signal peptide, ITAL_human secretory signal peptide, ITAV_human secretory signal peptide, ITAX_human secretory signal peptide, ITB2_human secretory signal peptide, ITB4_human secretory signal peptide, ITIH4_human secretory signal peptide, JAM1_human secretory signal peptide, JAM2_human secretory signal peptide, JAM3_human secretory signal peptide, JAML1_human secretory signal peptide, KAZD1_human secretory signal peptide, KI2L1_human secretory signal peptide, KIRR2_human secretory signal peptide, KLK3_human secretory signal peptide, KLKB1_human secretory signal peptide, KNG1_human secretory signal peptide, KTEL1_human secretory signal peptide, KV403_human secretory signal peptide, KV404_human secretory signal peptide, L1CAM_human secretory signal peptide, LALBA_human secretory signal peptide, LAMB1_human secretory signal peptide, LAMC1_human secretory signal peptide, LAMP1_human secretory signal peptide, LAMP2_human secretory signal peptide, LBP_human secretory signal peptide, LCAT_human secretory signal peptide, LCN1_human secretory signal peptide, LCTL_human secretory signal peptide, LEUK_human secretory signal peptide, LG3BP_human secretory signal peptide, LIF_human secretory signal peptide, LIPG_human secretory signal peptide, LIPP_human secretory signal peptide, LIRA3_human secretory signal peptide, LMAN1_human secretory signal peptide, LPH_human secretory signal peptide, LRC55_human secretory signal peptide, LRRN1_human secretory signal peptide, LSHB_human secretory signal peptide, LUM_human secretory signal peptide, LU_human secretory signal peptide, LV605_human secretory signal peptide, LY86_human secretory signal peptide, LYAM2_human secretory signal peptide, LYPA3_human secretory signal peptide, LYPD6_human secretory signal peptide, LYSC_human secretory signal peptide, MBL2_human secretory signal peptide, MCP_human secretory signal peptide, MFAP4_human secretory signal peptide, MGP_human secretory signal peptide, MIA human secretory signal peptide, MIME_human secretory signal peptide, MIP2A_human secretory signal peptide, MIP2B_human secretory signal peptide, MK human secretory signal peptide, MMP1_human secretory signal peptide, MOTI_human secretory signal peptide, MOX2R_human secretory signal peptide, MPRD_human secretory signal peptide, MPRI_human secretory signal peptide, MPZL3_human secretory signal peptide, MSMB_human secretory signal peptide, MYPO_human secretory signal peptide, NAGAB_human secretory signal peptide, NELL1_human secretory signal peptide, NELL2_human secretory signal peptide, NETO2_human secretory signal peptide, NEU1_human secretory signal peptide, NEU2_human secretory signal peptide, NGAL_human secretory signal peptide, NID1_human secretory signal peptide, NID2_human secretory signal peptide, NLGNX_human secretory signal peptide, NMB_human secretory signal peptide, NOV_human secretory signal peptide, NPTN_human secretory signal peptide, NPY_human secretory signal peptide, NRP1_human secretory signal peptide, NTRK2_human secretory signal peptide, NXPH3_human secretory signal peptide, OLFL1_human secretory signal peptide, OTOR_human secretory signal peptide, OXLA_human secretory signal peptide, P3IP 1_human secretory signal peptide, PAHO_human secretory signal peptide, PARM1_human secretory signal peptide, PCDBA_human secretory signal peptide, PCOC2_human secretory signal peptide, PCYXL_human secretory signal peptide, PDGFA_human secretory signal peptide, PDIA1_human secretory signal peptide, PDIA3_human secretory signal peptide, PDYN_human secretory signal peptide, PEBP4_human secretory signal peptide, PECA1_human secretory signal peptide, PG12B_human secretory signal peptide, PGFRA_human secretory signal peptide, PGFRB_human secretory signal peptide, PGH1_human secretory signal peptide, PGRP2_human secretory signal peptide, PIGT_human secretory signal peptide, PIP_human secretory signal peptide, PLBL2_human secretory signal peptide, PLF4_human secretory signal peptide, PLOD1_human secretory signal peptide, PORIM_human secretory signal peptide, PPA6_human secretory signal peptide, PPAP_human secretory signal peptide, PPGB_human secretory signal peptide, PPIB_human secretory signal peptide, PRB4_human secretory signal peptide, PRLR_human secretory signal peptide, PRL_human secretory signal peptide, PROK1_human secretory signal peptide, PROK2_human secretory signal peptide, PROP_human secretory signal peptide, PROZ_human secretory signal peptide, PRP1_human secretory signal peptide, PRPC_human secretory signal peptide, PRRT3_human secretory signal peptide, PTGDS_human secretory signal peptide, PTHY_human secretory signal peptide, PTPRG_human secretory signal peptide, PYY_human secretory signal peptide, PZP_human secretory signal peptide, REG1A_human secretory signal peptide, REG3G_human secretory signal peptide, RIB1_human secretory signal peptide, RIB2_human secretory signal peptide, RISC_human secretory signal peptide, RNAS1_human secretory signal peptide, RNAS4_human secretory signal peptide, S39A6_human secretory signal peptide, SAA4_human secretory signal peptide, SAA_human secretory signal peptide, SAMP_human secretory signal peptide, SCG1_human secretory signal peptide, SCRG1_human secretory signal peptide, SEM4B_human secretory signal peptide, SEM6B_human secretory signal peptide, SEMG1_human secretory signal peptide, SEMG2_human secretory signal peptide, SEPP1_human secretory signal peptide, SFRP2_human secretory signal peptide, SFRP3_human secretory signal peptide, SFTPG_human secretory signal peptide, SG1D4_human secretory signal peptide, SG3A1_human secretory signal peptide, SHBG_human secretory signal peptide, SIAL_human secretory signal peptide, SIDT2_human secretory signal peptide, SLAF6_human secretory signal peptide, SLAF7_human secretory signal peptide, SLAF8_human secretory signal peptide, SLPI_human secretory signal peptide, SMR3B_human secretory signal peptide, SMS_human secretory signal peptide, SODS_human secretory signal peptide, SOSD1_human secretory signal peptide, SOST_human secretory signal peptide, SPIT1_human secretory signal peptide, SPIT2_human secretory signal peptide, SRCH_human secretory signal peptide, SRGN_human secretory signal peptide, STAT_human secretory signal peptide, STC1_human secretory signal peptide, TCO1_human secretory signal peptide, TCO2_human secretory signal peptide, TENA_human secretory signal peptide, TETN_human secretory signal peptide, TFF1_human secretory signal peptide, TFF3_human secretory signal peptide, TFPI1_human secretory signal peptide, TGFR2_human secretory signal peptide, THBG_human secretory signal peptide, THYG_human secretory signal peptide, TICN2_human secretory signal peptide, TIE1_human secretory signal peptide, TIE2_human secretory signal peptide, TIMP1_human secretory signal peptide, TIMP2_human secretory signal peptide, TIMP3_human secretory signal peptide, TINAL_human secretory signal peptide, TLR1_human secretory signal peptide, TLR3_human secretory signal peptide, TLR4_human secretory signal peptide, TLR5_human secretory signal peptide, TM2D1_human secretory signal peptide, TMIG2_human secretory signal peptide, TMM25_human secretory signal peptide, TMM46_human secretory signal peptide, TMM66_human secretory signal peptide, TMM9B_human secretory signal peptide, TNFB_human secretory signal peptide, TNR14_human secretory signal peptide, TNR16_human secretory signal peptide, TNR18_human secretory signal peptide, TNR19_human secretory signal peptide, TNR1B_human secretory signal peptide, TNR5_human secretory signal peptide, TNR6B_human secretory signal peptide, TNR8_human secretory signal peptide, TNR9_human secretory signal peptide, TPO_human secretory signal peptide, TPSNR_human secretory signal peptide, TPSN_human secretory signal peptide, TR10D_human secretory signal peptide, TR11B_human secretory signal peptide, TR19L_human secretory signal peptide, TRBM_human secretory signal peptide, TRFE_human secretory signal peptide, TRFL_human secretory signal peptide, TRY1_human secretory signal peptide, TRY2_human secretory signal peptide, TSHB_human secretory signal peptide, TSP1_human secretory signal peptide, TVA2_human secretory signal peptide, TVB2_human secretory signal peptide, TXD12_human secretory signal peptide, TXND4_human secretory signal peptide, TYRP1_human secretory signal peptide, UROK_human secretory signal peptide, UTER_human secretory signal peptide, UTS2_human secretory signal peptide, VCAM1_human secretory signal peptide, VEGFA_human secretory signal peptide, VEGFC_human secretory signal peptide, VGFR3_human secretory signal peptide, VMO1_human secretory signal peptide, VSIG2_human secretory signal peptide, VSIG4_human secretory signal peptide, VSTM1_human secretory signal peptide, VTNC_human secretory signal peptide, VWF_human secretory signal peptide, WISP2_human secretory signal peptide, X3CL1_human secretory signal peptide, XCL2_human secretory signal peptide, YK001_human secretory signal peptide, YQ001_human secretory signal peptide, ZA2G_human secretory signal peptide, ZG16_human secretory signal peptide, ZP2_human secretory signal peptide.

The sequences of these secretory signal peptides are as following:

```
1A02_HUMAN SPdb195 Homo sapiens (Human)
                                    (SEQ ID NO: 15)
MAVMAPRTLVLLLSGALALTQTWA 1A11_HUMAN SPdb208 Homo sapiens (Human)
                                    (SEQ ID NO: 16)
MAVMAPRTLLLLLSGALALTQTWA 1A25_HUMAN SPdb276 Homo sapiens (Human)
                                    (SEQ ID NO: 17)
MAVMAPRTLVLLLSGALALTQTWA 1A26_HUMAN SPdb277 Homo sapiens (Human)
                                    (SEQ ID NO: 18)
MAVMAPRTLVLLLSGALALTQTWA 1A30_HUMAN SPdb279 Homo sapiens (Human)
                                    (SEQ ID NO: 19)
MAVMAPRTLLLLLSGALALTHTWA 1A31_HUMAN SPdb280 Homo sapiens (Human)
                                    (SEQ ID NO: 20)
MAVMAPRTLLLLLLGALALTQTWA 1A33_HUMAN SPdb282 Homo sapiens (Human)
                                    (SEQ ID NO: 21)
MAVMAPRTLLLLLLGALALTQTWA 1A68_HUMAN SPdb287 Homo sapiens (Human)
                                    (SEQ ID NO: 22)
MAVMAPRTLVLLLSGALALTQTWA 1A80_HUMAN SPdb290 Homo sapiens (Human)
                                    (SEQ ID NO: 23)
MAVMPPRTLLLLLSGALALTQTWA 1B07_HUMAN SPdb298 Homo sapiens (Human)
                                    (SEQ ID NO: 24)
MLVMAPRTVLLLLSAALALTETWA 1B15_HUMAN SPdb302 Homo sapiens (Human)
                                    (SEQ ID NO: 25)
MRVTAPRTVLLLLSGALALTETWA 1B37_HUMAN SPdb306 Homo sapiens (Human)
                                    (SEQ ID NO: 26)
MRVTAPRTLLLLLWGAVALTETWA 1B40_HUMAN SPdb309 Homo sapiens (Human)
                                    (SEQ ID NO: 27)
MRVTAPRTLLLLLWGAVALTETWA 1B47_HUMAN SPdb315 Homo sapiens (Human)
                                    (SEQ ID NO: 28)
MRVTAPRTLLLLLWGAVALTETWA 1B48_HUMAN SPdb316 Homo sapiens (Human)
                                    (SEQ ID NO: 29)
MLVMAPRTVLLLLSAALALTETWA 1B57_HUMAN SPdb325 Homo sapiens (Human)
                                    (SEQ ID NO: 30)
MRVTAPRTVLLLLWGAVALTETWA 1B59_HUMAN SPdb327 Homo sapiens (Human)
                                    (SEQ ID NO: 31)
MRVTAPRTLLLLLWGALALTETWA 1B78_HUMAN SPdb330 Homo sapiens (Human)
                                    (SEQ ID NO: 32)
MRVTAPRTVLLLLWGAVALTETWA 1C03_HUMAN SPdb340 Homo sapiens (Human)
                                    (SEQ ID NO: 33)
MRVMAPRTLILLLSGALALTETWA 1C04_HUMAN SPdb342 Homo sapiens (Human)
                                    (SEQ ID NO: 34)
MRVMAPRTLILLLSGALALTETWA 1C05_HUMAN SPdb343 Homo sapiens (Human)
                                    (SEQ ID NO: 35)
MRVMAPRTLILLLSGALALTETWA 1C07_HUMAN SPdb345 Homo sapiens (Human)
                                    (SEQ ID NO: 36)
MRVMAPRALLLLLSGGLALTETWA 1C14_HUMAN SPdb348 Homo sapiens (Human)
                                    (SEQ ID NO: 37)
MRVMAPRTLILLLSGALALTETWA 1C15_HUMAN SPdb349 Homo sapiens (Human)
                                    (SEQ ID NO: 38)
MRVMAPRTLLLLLSGALALTETWA 1C16_HUMAN SPdb350 Homo sapiens (Human)
                                    (SEQ ID NO: 39)
MRVMAPRTLILLLSGALALTETWA 1C17_HUMAN SPdb351 Homo sapiens (Human)
                                    (SEQ ID NO: 40)
MRVMAPQALLLLLSGALALIETWA 1C18_HUMAN SPdb352 Homo sapiens (Human)
                                    (SEQ ID NO: 41)
MRVMAPRALLLLLSGGLALTETWA 2B11_HUMAN SPdb440 Homo sapiens (Human)
                                    (SEQ ID NO: 42)
MVCLKLPGGSCMTALTVTLMVLSSPLALA 2B14_HUMAN SPdb441 Homo sapiens (Human)
                                    (SEQ ID NO: 43)
MVCLKFPGGSCMAALTVTLMVLSSPLALA 2B17_HUMAN SPdb442 Homo sapiens (Human)
                                    (SEQ ID NO: 44)
MVCLKLPGGSCMAALTVTLMVLSSPLALA 2B1A_HUMAN SPdb445 Homo sapiens (Human)
                                    (SEQ ID NO: 45)
MVCLRLPGGSCMAVLTVTLMVLSSPLALA 2B1B_HUMAN SPdb446 Homo sapiens (Human)
                                    (SEQ ID NO: 46)
MVCLRLPGGSCMAVLTVTLMVLSSPLALA 2B32_HUMAN SPdb449 Homo sapiens (Human)
                                    (SEQ ID NO: 47)
MVCLKLPGGSSLAALTVTLMVLSSRLAFA 2DOB_HUMAN SPdb458 Homo sapiens (Human)
                                    (SEQ ID NO: 48)
MGSGWVPWVVALLVNLTRLDSSMTQG 7B2_HUMAN SPdb1113 Homo sapiens (Human)
                                    (SEQ ID NO: 49)
MVSRMVSTMLSGLLFWLASGWTPAFA
```

-continued

A1AT_HUMAN SPdb1182 *Homo sapiens* (Human)
(SEQ ID NO: 50)
MPSSVSWGILLLAGLCCLVPVSLA A2GL_HUMAN SPdb1223 *Homo sapiens* (Human)
(SEQ ID NO: 51)
MSSWSRQRPKSPGGIQPHVSRTLFLLLLLAASAWG A2MG_HUMAN SPdb1225 *Homo sapiens* (Human)
(SEQ ID NO: 52)
MGKNKLLHPSLVLLLLVLLPTDA ABP1_HUMAN SPdb2047 *Homo sapiens* (Human)
(SEQ ID NO: 53)
MPALGWAVAAILMLQTAMA ACET_HUMAN SPdb2859 *Homo sapiens* (Human)
(SEQ ID NO: 54)
MGQGWATAGLPSLLFLLLCYGHPLLVPSQEA ACHB_HUMAN SPdb2984 *Homo sapiens* (Human)
(SEQ ID NO: 55)
MTPGALLMLLGALGAPLAPGVRG ACHE_HUMAN SPdb2999 *Homo sapiens* (Human)
(SEQ ID NO: 56)
MARAPLGVLLLLGLLGRGVG ACRO_HUMAN SPdb4311 *Homo sapiens* (Human)
(SEQ ID NO: 57)
MVEMLPTAILLVLAVSVVA ADA32_HUMAN SPdb5197 *Homo sapiens* (Human)
(SEQ ID NO: 58)
MFRLWLLLAGLCGLLA ADIPO_HUMAN SPdb5938 *Homo sapiens* (Human)
(SEQ ID NO: 59)
MLLLGAVLLLLALPGHDQ ADML_HUMAN SPdb5966 *Homo sapiens* (Human)
(SEQ ID NO: 60)
MKLVSVALMYLGSLAFLGADT AGAL_HUMAN SPdb6382 *Homo sapiens* (Human)
(SEQ ID NO: 61)
MQLRNPELHLGCALALRFLALVSWDIPGARA AGR2_HUMAN SPdb6560 *Homo sapiens* (Human)
(SEQ ID NO: 62)
MEKIPVSAFLLLVALSYTLA AGR3_HUMAN SPdb6563 *Homo sapiens* (Human)
(SEQ ID NO: 63)
MMLHSALGLCLLLVTVSSNLA AMBP_HUMAN SPdb8414 *Homo sapiens* (Human)
(SEQ ID NO: 64)
MRSLGALLLLLSACLAVSA AMTN_HUMAN SPdb9141 *Homo sapiens* (Human)
(SEQ ID NO: 65)
MRSTILLFCLLGSTRS ANF_HUMAN SPdb9494 *Homo sapiens* (Human)
(SEQ ID NO: 66)
MSSFSTTTVSFLLLLAFQLLGQTRA ANGI_HUMAN SPdb9521 *Homo sapiens* (Human)
(SEQ ID NO: 67)
MVMGLGVLLLVFVLGLGLTPPTLA ANGL3_HUMAN SPdb9540 *Homo sapiens* (Human)
(SEQ ID NO: 68)
MFTIKLLLFIVPLVIS ANGL7_HUMAN SPdb9551 *Homo sapiens* (Human)
(SEQ ID NO: 69)
MLKKPLSAVTWLCIFIVAFVSHPAWL -continued ANGT_HUMAN SPdb9580 *Homo sapiens* (Human)
(SEQ ID NO: 70)
MRKRAPQSEMAPAGVSLRATILCLLAWAGLAAG ANPRA_HUMAN SPdb9903 *Homo sapiens* (Human)
(SEQ ID NO: 71)
MPGPRRPAGSRLRLLLLLLLPPLLLLLRGSHA APOA2_HUMAN SPdb10884 *Homo sapiens* (Human)
(SEQ ID NO: 72)
MKLLAATVLLLTICSLEG APOA4_HUMAN SPdb10891 *Homo sapiens* (Human)
(SEQ ID NO: 73)
MFLKAVVLTLALVAVAGARA APOA_HUMAN SPdb10900 *Homo sapiens* (Human)
(SEQ ID NO: 74)
MEHKEVVLLLLLFLKSAAP APOC1_HUMAN SPdb10907 *Homo sapiens* (Human)
(SEQ ID NO: 75)
MRLFLSLPVLVVVLSIVLEGPAPAQG APOC2_HUMAN SPdb10917 *Homo sapiens* (Human)
(SEQ ID NO: 76)
MGTRLLPALFLVLLVLGFEVQG APOC3_HUMAN SPdb10924 *Homo sapiens* (Human)
(SEQ ID NO: 77)
MQPRVLLVVALLALLASARA APOD_HUMAN SPdb10936 *Homo sapiens* (Human)
(SEQ ID NO: 78)
MVMLLLLLSALAGLFGAAEG APOE_HUMAN SPdb10946 *Homo sapiens* (Human)
(SEQ ID NO: 79)
MKVLWAALLVTFLAGCQA APOH_HUMAN SPdb10966 *Homo sapiens* (Human)
(SEQ ID NO: 80)
MISPVLILFSSFLCHVAIA APR3_HUMAN SPdb11011 *Homo sapiens* (Human)
(SEQ ID NO: 81)
MAPHGPGSLTTLVPWAAALLLALGVERALA ASM_HUMAN SPdb16794 *Homo sapiens* (Human)
(SEQ ID NO: 82)
MPRYGASLRQSCPRSGREQGQDGTAGAPGLLWMGLVLALALALALA ASPG_HUMAN SPdb17050 Homo sapiens (Human)
(SEQ ID NO: 83)
MARKSNLPVLLVPFLLCQALVRC BAMBI_HUMAN SPdb23773 *Homo sapiens* (Human)
(SEQ ID NO: 84)
MDRHSSYIFIWLQLELCAMA BASI_HUMAN SPdb23850 *Homo sapiens* (Human)
(SEQ ID NO: 85)
MAAALFVLLGFALLGTHGASG BGAL_HUMAN SPdb24876 *Homo sapiens* (Human)
(SEQ ID NO: 86)
MPGFLVRILLLLLVLLLLGPTRG BGLR_HUMAN SPdb24971 *Homo sapiens* (Human)
(SEQ ID NO: 87)
MARGSAVAWAALGPLLWGCALG BOC_HUMAN SPdb25928 *Homo sapiens* (Human)
(SEQ ID NO: 88)
MLRGTMTAWRGMRPEVTLACLLLATAGCFA BPIL1_HUMAN SPdb26090 *Homo sapiens* (Human)
(SEQ ID NO: 89)
MAWASRLGLLLALLLPVVGA BPI_HUMAN SPdb26097 Homo sapiens (Human)
(SEQ ID NO: 90)
MRENMARGPCNAPRWVSLMVLVAIGTAVTAA BT3A3_HUMAN SPdb26592 Homo sapiens (Human)
(SEQ ID NO: 91)
MKMASSLAFLLLNFHVSLFLVQLLTPCSA BTNL8_HUMAN SPdb26692 Homo sapiens (Human)
(SEQ ID NO: 92)
MALMLSLVLSLLKLGSG C16L2_HUMAN SPdb27156 Homo sapiens (Human)
(SEQ ID NO: 93)
MEAPGPRALRTALCGGCCCLLLCAQLAVA C1QT5_HUMAN SPdb27240 Homo sapiens (Human)
(SEQ ID NO: 94)
MRPLLVLLLLGLAAG C1QT6_HUMAN SPdb27243 Homo sapiens (Human)
(SEQ ID NO: 95)
MVTAALGPVWAALLLFLLMCEIPMVEL C1R_HUMAN SPdb27257 Homo sapiens (Human)
(SEQ ID NO: 96)
MWLLYLLVPALFCRAGG C1S_HUMAN SPdb27262 Homo sapiens (Human)
(SEQ ID NO: 97)
MWCIVLFSLLAWVYA C4BPA_HUMAN SPdb27346 Homo sapiens (Human)
(SEQ ID NO: 98)
MHPPKTPSGALHRKRKMAAWPFSRLWKVSDPILFQMTLIAALLPAVLG CA187_HUMAN SPdb27946 Homo sapiens (Human)
(SEQ ID NO: 99)
MAGPAIHTAPMLFLVLLLPLELSLA CADM3_HUMAN SPdb28390 Homo sapiens (Human)
(SEQ ID NO: 100)
MGAPAASLLLLLLLFACCWAPGGA CAH9_HUMAN SPdb28555 Homo sapiens (Human)
(SEQ ID NO: 101)
MAPLCPSPWLPLLIPAPAPGLTVQLLLSLLLLVPVHP CALCR_HUMAN SPdb28726 Homo sapiens (Human)
(SEQ ID NO: 102)
MRFTFTSRCLALFLLLNHPTPILP CALRL_HUMAN SPdb28899 Homo sapiens (Human)
(SEQ ID NO: 103)
MEKKCTLYFLVLLPFFMILVTA CALR_HUMAN SPdb28916 Homo sapiens (Human)
(SEQ ID NO: 104)
MLLSVPLLLGLLGLAVA CAP7_HUMAN SPdb29157 Homo sapiens (Human)
(SEQ ID NO: 105)
MTRLTVLALLAGLLASSRAGSSPLLD CART_HUMAN SPdb29961 Homo sapiens (Human)
(SEQ ID NO: 106)
MESSRVRLLPLLGAALLLMLPLLGTRA CASA1_HUMAN SPdb29986 Homo sapiens (Human)
(SEQ ID NO: 107)
MRLLILTCLVAVALA CASB_HUMAN SPdb30005 Homo sapiens (Human)
(SEQ ID NO: 108)
MKVLILACLVALALA CASK_HUMAN SPdb30048 Homo sapiens (Human)
(SEQ ID NO: 109)
MKSFLLVVNALALTLPFLAV CATC_HUMAN SPdb30354 Homo sapiens (Human)
(SEQ ID NO: 110)
MGAGPSLLLAALLLLLSGDGAVRC CATE_HUMAN SPdb30381 Homo sapiens (Human)
(SEQ ID NO: 111)
MKTLLLLLLVLLELGEA CATG_HUMAN SPdb30393 Homo sapiens (Human)
(SEQ ID NO: 112)
MQPLLLLLAFLLPTGAEA CATW_HUMAN SPdb30490 Homo sapiens (Human)
(SEQ ID NO: 113)
MALTAHPSCLLALLVAGLAQG CBG_HUMAN SPdb30913 Homo sapiens (Human)
(SEQ ID NO: 114)
MPLLLYTCLLWLPTSGLWTVQA CBLN3_HUMAN SPdb31375 Homo sapiens (Human)
(SEQ ID NO: 115)
MLGAKPHWLPGPLHSPGLPLVLVLLALGAGWA CBLN4_HUMAN SPdb31377 Homo sapiens (Human)
(SEQ ID NO: 116)
MGSGRRALSAVPAVLLVLTLPGLPVWA CBPA1_HUMAN SPdb31413 Homo sapiens (Human)
(SEQ ID NO: 117)
MRGLLVLSVLLGAVFG CBPA3_HUMAN SPdb31420 Homo sapiens (Human)
(SEQ ID NO: 118)
MRLILPVGLIATTLA CBPB1_HUMAN SPdb31459 Homo sapiens (Human)
(SEQ ID NO: 119)
MLALLVLVTVALASA CBPN_HUMAN SPdb31531 Homo sapiens (Human)
(SEQ ID NO: 120)
MSDLLSVFLHLLLLFKLVAP CCL11_HUMAN SPdb32635 Homo sapiens (Human)
(SEQ ID NO: 121)
MKVSAALLWLLLIAAAFSPQGLA CCL15_HUMAN SPdb32644 Homo sapiens (Human)
(SEQ ID NO: 122)
MKVSVAALSCLMLVAVLGSQA CCL19_HUMAN SPdb32652 Homo sapiens (Human)
(SEQ ID NO: 123)
MALLLALSLLVLWTSPAPTLS CCL1_HUMAN SPdb32654 Homo sapiens (Human)
(SEQ ID NO: 124)
MQIITTALVCLLLAGMWPEDVDS CCL22_HUMAN SPdb32663 Homo sapiens (Human)
(SEQ ID NO: 125)
MARLQTALLVVLVLLAVALQATEA CCL24_HUMAN SPdb32668 Homo sapiens (Human)
(SEQ ID NO: 126)
MAGLMTIVTSLLFLGVCAHHIIPTGS CCL2_HUMAN SPdb32684 Homo sapiens (Human)
(SEQ ID NO: 127)
MKVSAALLCLLLIAATFIPQGLA CCL4_HUMAN SPdb32700 Homo sapiens (Human)
(SEQ ID NO: 128)
MKLCVTVLSLLMLVAAFCSPALS CCL5_HUMAN SPdb32709 Homo sapiens (Human)
(SEQ ID NO: 129)
MKVSAAALAVILIATALCAPASA CCL7_HUMAN SPdb32717 Homo sapiens (Human)
(SEQ ID NO: 130)
MKASAALLCLLLTAAAFSPQGLA CD180_HUMAN SPdb33618 Homo sapiens (Human)
(SEQ ID NO: 131)
MAFDVSCFFWVVLFSAGCKVITS CD1A_HUMAN SPdb33624 Homo sapiens (Human)
(SEQ ID NO: 132)
MLFLLLPLLAVLPGDG CD244_HUMAN SPdb33672 Homo sapiens (Human)
(SEQ ID NO: 133)
MLGQVVTLILLLLLKVYQGKG CD276_HUMAN SPdb33680 Homo sapiens (Human)
(SEQ ID NO: 134)
MLRRRGSPGMGVHVGAALGALWFCLTGA CD27_HUMAN SPdb33684 Homo sapiens (Human)
(SEQ ID NO: 135)
MARPHPWWLCVLGTLVGLS CD28_HUMAN SPdb33689 Homo sapiens (Human)
(SEQ ID NO: 136)
MLRLLLALNLFPSIQVTG CD2_HUMAN SPdb33718 Homo sapiens (Human)
(SEQ ID NO: 137)
MSFPCKFVASFLLIFNVSSKGAVS CD320_HUMAN SPdb33725 Homo sapiens (Human)
(SEQ ID NO: 138)
MSGGWMAQVGAWRTGALGLALLLLLGLGLGLEAAA CD34_HUMAN SPdb33729 Homo sapiens (Human)
(SEQ ID NO: 139)
MLVRRGARAGPRMPRGWTALCLLSLLPSGFM CD3E_HUMAN SPdb33763 Homo sapiens (Human)
(SEQ ID NO: 140)
MQSGTHWRVLGLCLLSVGVWGQ CD3G_HUMAN SPdb33770 Homo sapiens (Human)
(SEQ ID NO: 141)
MEQGKGLAVLILAIILLQGTLA CD3Z_HUMAN SPdb33777 Homo sapiens (Human)
(SEQ ID NO: 142)
MKWKALFTAAILQAQLPITEA CD45_HUMAN SPdb33804 Homo sapiens (Human)
(SEQ ID NO: 143)
MYLWLKLLAFGFAFLDTEVFVTG CD5L_HUMAN SPdb33861 Homo sapiens (Human)
(SEQ ID NO: 144)
MALLFSLILAICTRPGFLA CD5_HUMAN SPdb33872 Homo sapiens (Human)
(SEQ ID NO: 145)
MPMGSLQPLATLYLLGMLVASCLG CD83_HUMAN SPdb33912 Homo sapiens (Human)
(SEQ ID NO: 146)
MSRGLQLLLLSCAYSLAPA CD8B_HUMAN SPdb33924 Homo sapiens (Human)
(SEQ ID NO: 147)
MRPRLWLLLAAQLTVLHGNSV CD99_HUMAN SPdb33932 Homo sapiens (Human)
(SEQ ID NO: 148)
MARGAALALLLFGLLGVLVAAP CEAM1_HUMAN SPdb34729 Homo sapiens (Human)
(SEQ ID NO: 149)
MGHLSAPLHRVRVPWQGLLLTASLLTFWNPPTTA CER1_HUMAN SPdb35232 Homo sapiens (Human)
(SEQ ID NO: 150)
MHLLLFQLLVLLPLGKT CERU_HUMAN SPdb35241 Homo sapiens (Human)
(SEQ ID NO: 151)
MKILILGIFLFLCSTPAWA CETP_HUMAN SPdb35298 Homo sapiens (Human)
(SEQ ID NO: 152)
MLAATVLTLALLGNAHA CF126_HUMAN SPdb35387 Homo sapiens (Human)
(SEQ ID NO: 153)
MAAALALVAGVLSGAVLPLWS CFAB_HUMAN SPdb35492 Homo sapiens (Human)
(SEQ ID NO: 154)
MGSNLSPQLCLMPFILGLLSGGVTT CFAH_HUMAN SPdb35506 Homo sapiens (Human)
(SEQ ID NO: 155)
MRLLAKIICLMLWAICVA CFAI_HUMAN SPdb35508 Homo sapiens (Human)
(SEQ ID NO: 156)
MKLLHVFLLFLCFHLRFC CH3L1_HUMAN SPdb36470 Homo sapiens (Human)
(SEQ ID NO: 157)
MGVKASQTGFVVLVLLQCCSA CH3L2_HUMAN SPdb36476 Homo sapiens (Human)
(SEQ ID NO: 158)
MGATTMDQKSLWAGVVVLLLLQGGSA CHIT1_HUMAN SPdb37892 Homo sapiens (Human)
(SEQ ID NO: 159)
MVRSVAWAGFMVLLMIPWGSA CL3L1_HUMAN SPdb39759 Homo sapiens (Human)
(SEQ ID NO: 160)
MQVSTAALAVLLCTMALCNQVLS CLC11_HUMAN SPdb39795 Homo sapiens (Human)
(SEQ ID NO: 161)
MQAAWLLGALVVPQLLGFGHG CLC14_HUMAN SPdb39798 Homo sapiens (Human)
(SEQ ID NO: 162)
MRPAFALCLLWQALWPGPGGG CLM1_HUMAN SPdb40173 Homo sapiens (Human)
(SEQ ID NO: 163)
MPLLTLYLLLFWLSGYSIA CLM9_HUMAN SPdb40190 Homo sapiens (Human)
(SEQ ID NO: 164)
MRLLVLLWGCLLLPGYEA CLUS_HUMAN SPdb41741 Homo sapiens (Human)
(SEQ ID NO: 165)
MMKTLLLFVGLLLTWESGQVLG CMA1_HUMAN SPdb41778 Homo sapiens (Human)
(SEQ ID NO: 166)
MLLLPLPLLLFLLCSRAEA CMGA_HUMAN SPdb41825 Homo sapiens (Human)
(SEQ ID NO: 167)
MRSAAVLALLLCAGQVTA CO1A1_HUMAN SPdb42643 Homo sapiens (Human)
(SEQ ID NO: 168)
MFSFVDLRLLLLLAATALLTHG CO2_HUMAN SPdb42671 Homo sapiens (Human)
(SEQ ID NO: 169)
MGPLMVLFCLLFLYPGLADS CO3_HUMAN SPdb42683 Homo sapiens (Human)
(SEQ ID NO: 170)
MGPTSGPSLLLLLLTHLPLALG CO4A2_HUMAN SPdb42702 Homo sapiens (Human)
(SEQ ID NO: 171)
MGRDQRAVAGPALRRWLLLGTVTVG CO5A2_HUMAN SPdb42724 Homo sapiens (Human)
(SEQ ID NO: 172)
MMANWAEARPLLILIVLLGQFVSIKA CO6A1_HUMAN SPdb42733 Homo sapiens (Human)
(SEQ ID NO: 173)
MRAARALLPLLLQACWTAA CO6_HUMAN SPdb42741 Homo sapiens (Human)
(SEQ ID NO: 174)
MARRSVLYFILLNALINKGQA CO7_HUMAN SPdb42748 Homo sapiens (Human)
(SEQ ID NO: 175)
MKVISLFILVGFIGEFQSFSSA CO9A1_HUMAN SPdb42770 Homo sapiens (Human)
(SEQ ID NO: 176)
MKTCWKIPVFFFVCSFLEPWASA CO9_HUMAN SPdb42781 Homo sapiens (Human)
(SEQ ID NO: 177)
MSACRSFAVAICILEISILTA COGA1_HUMAN SPdb44971 Homo sapiens (Human)
(SEQ ID NO: 178)
MWVSWAPGLWLLGLWATFGHG COLI_HUMAN SPdb45068 Homo sapiens (Human)
(SEQ ID NO: 179)
MPRSCCSRSGALLLALLLQASMEVRG COL_HUMAN SPdb45103 Homo sapiens (Human)
(SEQ ID NO: 180)
MEKILILLLVALSVAYA CR2_HUMAN SPdb47985 Homo sapiens (Human)
(SEQ ID NO: 181)
MGAAGLLGVFLALVAPGVLG CRDL2_HUMAN SPdb48539 Homo sapiens (Human)
(SEQ ID NO: 182)
MVPEVRVLSSLLGLALLWFPLDSHA CREG1_HUMAN SPdb48576 Homo sapiens (Human)
(SEQ ID NO: 183)
MAGLSRGSARALLAALLASTLLALLVSPARG CRHBP_HUMAN SPdb48678 Homo sapiens (Human)
(SEQ ID NO: 184)
MSPNFKLQCHFILIFLTALRGESR CRIM1_HUMAN SPdb48688 Homo sapiens (Human)
(SEQ ID NO: 185)
MYLVAGDRGLAGCGHLLVSLLGLLLLARSGTRA CRIS1_HUMAN SPdb48712 Homo sapiens (Human)
(SEQ ID NO: 186)
MEIKHLLFLVAAACLLPMLSM CRLF1_HUMAN SPdb48785 Homo sapiens (Human)
(SEQ ID NO: 187)
MPAGRRGPAAQSARRPPPLLPLLLLLCVLGAPRAGSG CRP_HUMAN SPdb48875 Homo sapiens (Human)
(SEQ ID NO: 188)
MEKLLCFLVLTSLSHAFG CSF2R_HUMAN SPdb49487 Homo sapiens (Human)
(SEQ ID NO: 189)
MLLLVTSLLLCELPHPAFLLIP CSF2_HUMAN SPdb49495 Homo sapiens (Human)
(SEQ ID NO: 190)
MWLQSLLLLGTVACSIS CSF3R_HUMAN SPdb49500 Homo sapiens (Human)
(SEQ ID NO: 191)
MARLGNCSLTWAALIILLLPGSLE CSPG2_HUMAN SPdb50031 Homo sapiens (Human)
(SEQ ID NO: 192)
MFINIKSILWMCSTLIVTHA CST9L_HUMAN SPdb50299 Homo sapiens (Human)
(SEQ ID NO: 193)
MLGLPWKGGLSWALLLLLLGSQILLIYA CST9_HUMAN SPdb50302 Homo sapiens (Human)
(SEQ ID NO: 194)
MSSPQRRKAMPWALSLLLMGFQLLVTYA CTHR1_HUMAN SPdb50661 Homo sapiens (Human)
(SEQ ID NO: 195)
MRPQGPAASPQRLRGLLLLLLLQLPAPSSA CTRB1_HUMAN SPdb50822 Homo sapiens (Human)
(SEQ ID NO: 196)
MAFLWLLSCWALLGTTFG CXCL7_HUMAN SPdb52153 Homo sapiens (Human)
(SEQ ID NO: 197)
MSLRLDTTPSCNSARPLHALQVLLLLSLLLTALA CXL10_HUMAN SPdb52338 Homo sapiens (Human)
(SEQ ID NO: 198)
MNQTAILICCLIFLTLSGIQG CYTC_HUMAN SPdb56121 Homo sapiens (Human)
(SEQ ID NO: 199)
MAGPLRAPLLLLAILAVALAVSPAAG CYTL1_HUMAN SPdb56131 Homo sapiens (Human)
(SEQ ID NO: 200)
MRTPGPLPVLLLLLAGAPAARP CYTN_HUMAN SPdb56136 Homo sapiens (Human)
(SEQ ID NO: 201)
MAQHLSTLLLLLATLAVALA CYTS_HUMAN SPdb56151 Homo sapiens (Human)
(SEQ ID NO: 202)
MARPLCTLLLLMATLAGALA CYTT_HUMAN SPdb56153 Homo sapiens (Human)
(SEQ ID NO: 203)
MAWPLCTLLLLLATQAVALA D103A_HUMAN SPdb56224 Homo sapiens (Human)
(SEQ ID NO: 204)
MRIHYLLFALLFLFLVPVPGHG DB127_HUMAN SPdb57844 Homo sapiens (Human)
(SEQ ID NO: 205)
MGLFMIIAILLFQKPTVTEQ DCD_HUMAN SPdb58564 Homo sapiens (Human)
(SEQ ID NO: 206)
MRFMTLLFLTALAGALVCA DEF1_HUMAN SPdb60113 Homo sapiens (Human)
(SEQ ID NO: 207)
MRTLAILAAILLVALQAQA DKK1_HUMAN SPdb62795 Homo sapiens (Human)
(SEQ ID NO: 208)
MMALGAAGATRVFVAMVAAALGGHPLLGVSA DKK3_HUMAN SPdb62800 Homo sapiens (Human)
(SEQ ID NO: 209)
MQRLGATLLCLLLAAAVPTAP DKK4_HUMAN SPdb62802 Homo sapiens (Human)
(SEQ ID NO: 210)
MVAAVLLGLSWLCSPLGA DLK_HUMAN SPdb62960 Homo sapiens (Human)
(SEQ ID NO: 211)
MTATEALLRVLLLLLAFGHSTYG DLL4_HUMAN SPdb62971 Homo sapiens (Human)
(SEQ ID NO: 212)
MAAASRSASGWALLLLVALWQQRAAG DNAS1_HUMAN SPdb64678 Homo sapiens (Human)
(SEQ ID NO: 213)
MRGMKLLGALLALAALLQGAVS ECP_HUMAN SPdb69940 Homo sapiens (Human)
(SEQ ID NO: 214)
MVPKLFTSQICLLLLLGLMGVEGSLHA EDAR_HUMAN SPdb70101 Homo sapiens (Human)
(SEQ ID NO: 215)
MAHVGDCTQTPWLPVLVVSLMCSARA EFNB1_HUMAN SPdb71207 Homo sapiens (Human)
(SEQ ID NO: 216)
MARPGQRWLGKWLVAMVVWALCRLATP EFNB3_HUMAN SPdb71214 Homo sapiens (Human)
(SEQ ID NO: 217)
MGPPHSGPGGVRVGALLLLGVLGLVSG EGFL8_HUMAN SPdb72652 Homo sapiens (Human)
(SEQ ID NO: 218)
MGSRAELCTLLGGFSFLLLLIPGEG EGFR_HUMAN SPdb72662 Homo sapiens (Human)
(SEQ ID NO: 219)
MRPSGTAGAALLALLAALCPASRA EGLN_HUMAN SPdb72697 Homo sapiens (Human)
(SEQ ID NO: 220)
MDRGTLPLAVALLLASCSLSPTSLA ELA2A_HUMAN SPdb73024 Homo sapiens (Human)
(SEQ ID NO: 221)
MIRTLLLSTLVAGALS ELA2B_HUMAN SPdb73028 Homo sapiens (Human)
(SEQ ID NO: 222)
MIRTLLLSTLVAGALS ELAF_HUMAN SPdb73040 Homo sapiens (Human)
(SEQ ID NO: 223)
MRASSFLIVVVFLIAGTLVLEA ENPL_HUMAN SPdb75253 Homo sapiens (Human)
(SEQ ID NO: 224)
MRALWVLGLCCVLLTFGSVRA ENPP7_HUMAN SPdb75282 Homo sapiens (Human)
(SEQ ID NO: 225)
MRGLAVLLTVALATLLAPGAG EPGN_HUMAN SPdb75639 Homo sapiens (Human)
(SEQ ID NO: 226)
MALGVPISVYLLFNAMTALTEE EPHB1_HUMAN SPdb75671 Homo sapiens (Human)
(SEQ ID NO: 227)
MALDYLLLLLLASAVAA EPHB6_HUMAN SPdb75686 Homo sapiens (Human)
(SEQ ID NO: 228)
MVCSLWVLLLVSSVLA EPOR_HUMAN SPdb75734 Homo sapiens (Human)
(SEQ ID NO: 229)
MDHLGASLWPQVGSLCLLLAGAAW EPO_HUMAN SPdb75747 Homo sapiens (Human)
(SEQ ID NO: 230)
MGVHECPAWLWLLLSLLSLPLGLPVLG ESAM_HUMAN SPdb76640 Homo sapiens (Human)
(SEQ ID NO: 231)
MISLPGPLVTNLLRFLFLGLSALAPPSRA EST1_HUMAN SPdb76818 Homo sapiens (Human)
(SEQ ID NO: 232)
MWLRAFILATLSASAAWG F13B_HUMAN SPdb78523 Homo sapiens (Human)
(SEQ ID NO: 233)
MRLKNLTFIIILIISGELYA FA111_HUMAN SPdb78712 Homo sapiens (Human)
(SEQ ID NO: 234)
MIFLYQVVHFILFTSVSG FA5_HUMAN SPdb78865 Homo sapiens (Human)
(SEQ ID NO: 235)
MFPGCPRLWVLVVLGTSWVGWGSQGTEA FA8_HUMAN SPdb78981 Homo sapiens (Human)
(SEQ ID NO: 236)
MQIELSTCFFLCLLRFCFS FCGR1_HUMAN SPdb81611 Homo sapiens (Human)
(SEQ ID NO: 237)
MWFLTTLLLWVPVDG FCGRN_HUMAN SPdb81622 Homo sapiens (Human)
(SEQ ID NO: 238)
MGVPRPQPWALGLLLFLLPGSLG FCN1_HUMAN SPdb81643 Homo sapiens (Human)
(SEQ ID NO: 239)
MELSGATMARGLAVLLVLFLHIKNLPAQA FCN3_HUMAN SPdb81652 Homo sapiens (Human)
(SEQ ID NO: 240)
MDLLWILPSLWLLLLGGPACLKT FCRL2_HUMAN SPdb81673 Homo sapiens (Human)
(SEQ ID NO: 241)
MLLWSLLVIFDAVTEQADS FCRLA_HUMAN SPdb81677 Homo sapiens (Human)
(SEQ ID NO: 242)
MKLGCVLMAWALYLSLGVLWVAQMLLA FETUA_HUMAN SPdb82655 Homo sapiens (Human)
(SEQ ID NO: 243)
MKSLVLLLCLAQLWGCHS FGF19_HUMAN SPdb82742 Homo sapiens (Human)
(SEQ ID NO: 244)
MRSGCVVVHVWILAGLWLAVAGRP FGF21_HUMAN SPdb82761 Homo sapiens (Human)
(SEQ ID NO: 245)
MDSDETGFEHSGLWVSVLAGLLLGACQA FGF23_HUMAN SPdb82765 Homo sapiens (Human)
(SEQ ID NO: 246)
MLGARLRLWVCALCSVCSMSVLRA FGFR3_HUMAN SPdb82845 Homo sapiens (Human)
(SEQ ID NO: 247)
MGAPACALALCVAVAIVAGASS FGFR4_HUMAN SPdb82851 Homo sapiens (Human)
(SEQ ID NO: 248)
MRLLLALLGVLLSVPGPPVLS FGRL1_HUMAN SPdb82874 Homo sapiens (Human)
(SEQ ID NO: 249)
MTPSPLLLLLLPPLLLGAFPPAAA FIBA_HUMAN SPdb83006 Homo sapiens (Human)
(SEQ ID NO: 250)
MFSMRIVCLVLSVVGTAWT FIBG_HUMAN SPdb83075 Homo sapiens (Human)
(SEQ ID NO: 251)
MSWSLHPRNLILYFYALLFLSSTCVA FKB14_HUMAN SPdb83515 Homo sapiens (Human)
(SEQ ID NO: 252)
MRLFLWNAVLTLFVTSLIG FKBP2_HUMAN SPdb83570 Homo sapiens (Human)
(SEQ ID NO: 253)
MRLSWFRVLTVLSICLSAVAT FLRT2_HUMAN SPdb84949 Homo sapiens (Human)
(SEQ ID NO: 254)
MGLQTTKWPSHGAFFLKSWLIISLGLYSQVSKLLA FSHB_HUMAN SPdb87356 Homo sapiens (Human)
(SEQ ID NO: 255)
MKTLQFFFLFCCWKAICC FSTL1_HUMAN SPdb87403 Homo sapiens (Human)
(SEQ ID NO: 256)
MWKRWLALALALVAVAWVRA FSTL3_HUMAN SPdb87408 Homo sapiens (Human)
(SEQ ID NO: 257)
MRPGAPGPLWPLPWGALAWAVGFVSS FST_HUMAN SPdb87422 Homo sapiens (Human)
(SEQ ID NO: 258)
MVRARHQPGGLCLLLLLLCQFMEDRSAQA FZD3_HUMAN SPdb88844 Homo sapiens (Human)
(SEQ ID NO: 259)
MAMTWIVFSLWPLTVFMGHIGG G6B_HUMAN SPdb89267 Homo sapiens (Human)
(SEQ ID NO: 260)
MAVFLQLLPLLLSRAQG GALC_HUMAN SPdb90251 Homo sapiens (Human)
(SEQ ID NO: 261)
MTAAAGSAGRAAVPLLLCALLAPGGA GDN_HUMAN SPdb94028 Homo sapiens (Human)
(SEQ ID NO: 262)
MNWHLPLFLLASVTLPSIC GELS_HUMAN SPdb94075 Homo sapiens (Human)
(SEQ ID NO: 263)
MAPHRPAPALLCALSLALCALSLPVRA GI24_HUMAN SPdb94473 Homo sapiens (Human)
(SEQ ID NO: 264)
MGVPTALEAGSWRWGSLLFALFLAASLGPVAA GLHA_HUMAN SPdb96435 Homo sapiens (Human)
(SEQ ID NO: 265)
MDYYRKYAAIFLVTLSVFLHVLHS GLPA_HUMAN SPdb98215 Homo sapiens (Human)
(SEQ ID NO: 266)
MYGKIIFVLLLSAIVSISA GLPB_HUMAN SPdb98238 Homo sapiens (Human)
(SEQ ID NO: 267)
MYGKIIFVLLLSEIVSISA GLPE_HUMAN SPdb98310 Homo sapiens (Human)
(SEQ ID NO: 268)
MYGKIIFVLLLSGIVSISA GLUC_HUMAN SPdb99110 Homo sapiens (Human)
(SEQ ID NO: 269)
MKSIYFVAGLFVMLVQGSWQ GNS_HUMAN SPdb100194 Homo sapiens (Human)
(SEQ ID NO: 270)
MRLLPLAPGRLRRGSPRHLPSCSPALLLLVLGGCLG GP1BA_HUMAN SPdb100593 Homo sapiens (Human)
(SEQ ID NO: 271)
MPLLLLLLLLPSPLHP GPI8_HUMAN SPdb101405 Homo sapiens (Human)
(SEQ ID NO: 272)
MAVTDSLSRAATVLATVLLLSFGSVAA GPIX_HUMAN SPdb101411 Homo sapiens (Human)
(SEQ ID NO: 273)
MPAWGALFLLWATAEA GPR56_HUMAN SPdb102058 Homo sapiens (Human)
(SEQ ID NO: 274)
MTPQSLLQTTLFLLSLLFLVQGAHG GPR97_HUMAN SPdb102106 Homo sapiens (Human)
(SEQ ID NO: 275)
MATPRGLGALLLLLLLPTSG GRAB_HUMAN SPdb102370 Homo sapiens (Human)
(SEQ ID NO: 276)
MQPILLLLAFLLLPRADA GREM1_HUMAN SPdb102718 Homo sapiens (Human)
(SEQ ID NO: 277)
MSRTAYTVGALLLLLGTLLPAAEG GROA_HUMAN SPdb102897 Homo sapiens (Human)
(SEQ ID NO: 278)
MARAALSAAPSNPRLLRVALLLLLLVAAGRRAAG GRP78_HUMAN SPdb102967 Homo sapiens (Human)
(SEQ ID NO: 279)
MKLSLVAAMLLLLSAARA GRP_HUMAN SPdb103369 Homo sapiens (Human)
(SEQ ID NO: 280)
MRGSELPLVLLALVLCLAPRGRA HA22_HUMAN SPdb106653 Homo sapiens (Human)
(SEQ ID NO: 281)
MILNKALMLGALALTTVMSPCGG HA23_HUMAN SPdb106655 Homo sapiens (Human)
(SEQ ID NO: 282)
MILNKALMLGALALTTVMSPCGG HA25_HUMAN SPdb106658 Homo sapiens (Human)
(SEQ ID NO: 283)
MILNKALLLGALALTTVMSPCGG HA27_HUMAN SPdb106660 Homo sapiens (Human)
(SEQ ID NO: 284)
MILNKALMLGSLALTTVMSPCGG HB21_HUMAN SPdb106943 Homo sapiens (Human)
(SEQ ID NO: 285)
MSWKKALRIPGGLRAATVTLMLSMLSTPVAEG HB23_HUMAN SPdb106948 Homo sapiens (Human)
(SEQ ID NO: 286)
MSWKKALRIPGGLRVATVTLMLAMLSTSVAEG HB24_HUMAN SPdb106950 Homo sapiens (Human)
(SEQ ID NO: 287)
MSWKKALRIPGGLRVATVTLMLAMLSTPVAEG HB25_HUMAN SPdb106952 Homo sapiens (Human)
(SEQ ID NO: 288)
MSWKKALRIPGDLRVATVTLMLAMLSSLLAEG HB2B_HUMAN SPdb106955 Homo sapiens (Human)
(SEQ ID NO: 289)
MVCLRLPGGSCMAVLTVTLMVLSSPLALA HB2C_HUMAN SPdb106957 Homo sapiens (Human)
(SEQ ID NO: 290)
MVCLRLPGGSCMAVLTVTLMVLSSPLALA HB2K_HUMAN SPdb106966 Homo sapiens (Human)
(SEQ ID NO: 291)
MVCLKLPGGSCMAALTVTLTVLSSPLALA HEP2_HUMAN SPdb110024 Homo sapiens (Human)
(SEQ ID NO: 292)
MKHSLNALLIFLIITSAWG HGFA_HUMAN SPdb110611 Homo sapiens (Human)
(SEQ ID NO: 293)
MGRWAWVPSPWPPPGLGPFLLLLLLLLLPRGFQP HIS1_HUMAN SPdb111008 Homo sapiens (Human)
(SEQ ID NO: 294)
MKFFVFALVLALMISMISA HIS3_HUMAN SPdb111571 Homo sapiens (Human)
(SEQ ID NO: 295)
MKFFVFALILALMLSMTGA HLAE_HUMAN SPdb113899 Homo sapiens (Human)
(SEQ ID NO: 296)
MVDGTLLLLLSEALALTQTWA HPSE_HUMAN SPdb115516 Homo sapiens (Human)
(SEQ ID NO: 297)
MLLRSKPALPPPLMLLLLGPLGPLSPGALPRPAQA HPT_HUMAN SPdb115541 Homo sapiens (Human)
(SEQ ID NO: 298)
MSALGAVIALLLWGQLFA HV103_HUMAN SPdb118845 Homo sapiens (Human)
(SEQ ID NO: 299)
MDWTWRILFLVAAATGAHS HV303_HUMAN SPdb118866 Homo sapiens (Human)
(SEQ ID NO: 300)
MEFGLSWLFLVAILKGVQC I10R1_HUMAN SPdb119663 Homo sapiens (Human)
(SEQ ID NO: 301)
MLPCLVVLLAALLSLRLGSDA I10R2_HUMAN SPdb119665 Homo sapiens (Human)
(SEQ ID NO: 302)
MAWSLGSWLGGCLLVSALG I17RA_HUMAN SPdb119686 Homo sapiens (Human)
(SEQ ID NO: 303)
MGAARSPPSAVPGPLLGLLLLLLGVLAPGGAS I17RB_HUMAN SPdb119688 Homo sapiens (Human)
(SEQ ID NO: 304)
MSLVLLSLAALCRSAVP I17RC_HUMAN SPdb119690 Homo sapiens (Human)
(SEQ ID NO: 305)
MPVPWFLLSLALGRSPVVLS I18BP_HUMAN SPdb119699 Homo sapiens (Human)
(SEQ ID NO: 306)
MRHNWTPDLSPLWVLLLCAHVVTLLVRA I20RA_HUMAN SPdb119707 Homo sapiens (Human)
(SEQ ID NO: 307)
MRAPGRPALRPLPLPPLLLLLLAAPWGRA I20RB_HUMAN SPdb119709 Homo sapiens (Human)
(SEQ ID NO: 308)
MQTFTMVLEEIWTSLFMWFFYALIPCLLT I22RA_HUMAN SPdb119711 Homo sapiens (Human)
(SEQ ID NO: 309)
MMPKHCFLGFLISFFLTGVAG IBP1_HUMAN SPdb119979 Homo sapiens (Human)
(SEQ ID NO: 310)
MSEVPVARVWLVLLLLTVQVGVTAG IBP2_HUMAN SPdb119988 Homo sapiens (Human)
(SEQ ID NO: 311)
MLPRVGCPALPLPPPPLLPLLPLLLLLLGASGGGGARA IBP3_HUMAN SPdb119995 Homo sapiens (Human)
(SEQ ID NO: 312)
MQRARPTLWAAALTLLVLLRGPPVARA IBP7_HUMAN SPdb120015 Homo sapiens (Human)
(SEQ ID NO: 313)
MERPSLRALLLGAAGLLLLLLPLSSS IFN16_HUMAN SPdb122381 Homo sapiens (Human)
(SEQ ID NO: 314)
MALSFSLLMAVLVLSYKSICSLG IFNA2_HUMAN SPdb122393 Homo sapiens (Human)
(SEQ ID NO: 315)
MALTFALLVALLVLSCKSSCSVG IFNA4_HUMAN SPdb122399 Homo sapiens (Human)
(SEQ ID NO: 316)
MALSFSLLMAVLVLSYKSICSLG IFNA5_HUMAN SPdb122401 Homo sapiens (Human)
(SEQ ID NO: 317)
MALPFVLLMALVVLNCKSICS IFNA6_HUMAN SPdb122403 Homo sapiens (Human)
(SEQ ID NO: 318)
MALPFALLMALVVLSCKSSC IFNA7_HUMAN SPdb122405 Homo sapiens (Human)
(SEQ ID NO: 319)
MARSFSLLMVVLVLSYKSICSLG IFNK_HUMAN SPdb122481 Homo sapiens (Human)
(SEQ ID NO: 320)
MSTKPDMIQKCLWLEILMGIFIAGTLS IFNW1_HUMAN SPdb122503 Homo sapiens (Human)
(SEQ ID NO: 321)
MALLFPLLAALVMTSYSPVGS IGF2_HUMAN SPdb122603 Homo sapiens (Human)
(SEQ ID NO: 322)
MGIPMGKSMLVLLTFLAFASCCIA IGFL1_HUMAN SPdb122611 Homo sapiens (Human)
(SEQ ID NO: 323)
MAPRGCIVAVFAIFCISRLLCSHG IGFL3_HUMAN SPdb122613 Homo sapiens (Human)
(SEQ ID NO: 324)
MRPRCCILALVCWITVFLLQCSKG IL10_HUMAN SPdb123103 Homo sapiens (Human)
(SEQ ID NO: 325)
MHSSALLCCLVLLTGVRA IL12A_HUMAN SPdb123133 Homo sapiens (Human)
(SEQ ID NO: 326)
MCPARSLLLVATLVLLDHLSLA IL12B_HUMAN SPdb123153 Homo sapiens (Human)
(SEQ ID NO: 327)
MCHQQLVISWFSLVFLASPLVA IL17F_HUMAN SPdb123200 Homo sapiens (Human)
(SEQ ID NO: 328)
MVKYLLLSILGLAFLSEAAA IL17_HUMAN SPdb123202 Homo sapiens (Human)
(SEQ ID NO: 329)
MTPGKTSLVSLLLLLSLEAIVKA IL19_HUMAN SPdb123221 Homo sapiens (Human)
(SEQ ID NO: 330)
MKLQCVSLWLLGTILILCSVDNHG IL1R1_HUMAN SPdb123285 Homo sapiens (Human)
(SEQ ID NO: 331)
MKVLLRLICFIALLISS IL1RA_HUMAN SPdb123295 Homo sapiens (Human)
(SEQ ID NO: 332)
MEICRGLRSHLITLLLFLFHSETIC IL20_HUMAN SPdb123302 Homo sapiens (Human)
(SEQ ID NO: 333)
MKASSLAFSLLSAAFYLLWTPSTG IL21R_HUMAN SPdb123304 Homo sapiens (Human)
(SEQ ID NO: 334)
MPRGWAAPLLLLLQGGWG IL22_HUMAN SPdb123314 Homo sapiens (Human)
(SEQ ID NO: 335)
MAALQKSVSSFLMGTLATSCLLLLALLVQGGAA IL24_HUMAN SPdb123324 Homo sapiens (Human)
(SEQ ID NO: 336)
MNFQQRLQSLWTLARPFCPPLLATASQMQMVVLPCLGFTLLLWSQVSGAQ
G IL25_HUMAN SPdb123327 Homo sapiens (Human)
(SEQ ID NO: 337)
MRERPRLGEDSSLISLFLQVVAFLAMVMGTHT IL2RA_HUMAN SPdb123341 Homo sapiens (Human)
(SEQ ID NO: 338)
MDSYLLMWGLLTFIMVPGCQA IL2RB_HUMAN SPdb123348 Homo sapiens (Human)
(SEQ ID NO: 339)
MAAPALSWRLPLLILLLPLATSWASA IL2RG_HUMAN SPdb123355 Homo sapiens (Human)
(SEQ ID NO: 340)
MLKPSLPFTSLLFLQLPLLGVG IL2_HUMAN SPdb123376 Homo sapiens (Human)
(SEQ ID NO: 341)
MYRMQLLSCIALSLALVTNS IL3_HUMAN SPdb123414 Homo sapiens (Human)
(SEQ ID NO: 342)
MSRLPVLLLLQLLVRPGLQ IL4_HUMAN SPdb123438 Homo sapiens (Human)
(SEQ ID NO: 343)
MGLTSQLLPPLFFLLACAGNFVHG IL5RA_HUMAN SPdb123452 Homo sapiens (Human)
(SEQ ID NO: 344)
MIIVAHVLLILLGATEILQA IL6RA_HUMAN SPdb123469 Homo sapiens (Human)
(SEQ ID NO: 345)
MLAVGCALLAALLAAPGAA IL7RA_HUMAN SPdb123503 Homo sapiens (Human)
(SEQ ID NO: 346)
MTILGTTFGMVFSLLQVVSG IL7_HUMAN SPdb123506 Homo sapiens (Human)
(SEQ ID NO: 347)
MFHVSFRYIFGLPPLILVLLPVASS IL9_HUMAN SPdb123527 Homo sapiens (Human)
(SEQ ID NO: 348)
MLLAMVLTSALLLCSVAG ILRL1_HUMAN SPdb123591 Homo sapiens (Human)
(SEQ ID NO: 349)
MGFWILAILTILMYSTAA INAR2_HUMAN SPdb124806 Homo sapiens (Human)
(SEQ ID NO: 350)
MLLSQNAFIFRSLNLVLMVYISLVFG INHA_HUMAN SPdb124863 Homo sapiens (Human)
(SEQ ID NO: 351)
MVLHLLLFLLLTPQGGHS INSL3_HUMAN SPdb125047 Homo sapiens (Human)
(SEQ ID NO: 352)
MDPRLPAWALVLLGPALVFA INSL4_HUMAN SPdb125053 Homo sapiens (Human)
(SEQ ID NO: 353)
MASLFRSYLPAIWLLLSQLLRESLA INSL5_HUMAN SPdb125056 Homo sapiens (Human)
(SEQ ID NO: 354)
MKGSIFTLFLFSVLFAISEVRS INS_HUMAN SPdb125119 Homo sapiens (Human)
(SEQ ID NO: 355)
MALWMRLLPLLALLALWGPDPAAA IPSP_HUMAN SPdb125761 Homo sapiens (Human)
(SEQ ID NO: 356)
MQLFLLLCLVLLSPQGASL IRBP_HUMAN SPdb126007 Homo sapiens (Human)
(SEQ ID NO: 357)
MMREWVLLMSVLLCGLA ISK6_HUMAN SPdb126513 Homo sapiens (Human)
(SEQ ID NO: 358)
MKLSGMFLLLSLALFCFLTGVFS ITA2B_HUMAN SPdb128319 Homo sapiens (Human)
(SEQ ID NO: 359)
MARALCPLQALWLLEWVLLLLGPCAAPPAWA ITA2_HUMAN SPdb128324 Homo sapiens (Human)
(SEQ ID NO: 360)
MGPERTGAAPLPLLLVLALSQGILNCCLA ITA3_HUMAN SPdb128328 Homo sapiens (Human)
(SEQ ID NO: 361)
MGPGPSRAPRAPRLMLCALALMVAAGGCVVSA ITA4_HUMAN SPdb128331 Homo sapiens (Human)
(SEQ ID NO: 362)
MFPTESAWLGKRGANPGPEAAVRETVMLLLCLGVPTGRP ITA6_HUMAN SPdb128340 Homo sapiens (Human)
(SEQ ID NO: 363)
MAAAGQLCLLYLSAGLLSRLGAA ITA7_HUMAN SPdb128342 Homo sapiens (Human)
(SEQ ID NO: 364)
MAGARSRDPWGASGICYLFGSLLVELLFSRAVA ITAE_HUMAN SPdb128352 Homo sapiens (Human)
(SEQ ID NO: 365)
MWLFHTLLCIASLALLAA ITAL_HUMAN SPdb128355 Homo sapiens (Human)
(SEQ ID NO: 366)
MKDSCITVMAMALLSGFFFFAPASS ITAV_HUMAN SPdb128362 Homo sapiens (Human)
(SEQ ID NO: 367)
MAFPPRRRLRLGPRGLPLLLSGLLLPLCRA ITAX_HUMAN SPdb128364 Homo sapiens (Human)
(SEQ ID NO: 368)
MTRTRAALLLFTALATSLG ITB2_HUMAN SPdb128379 Homo sapiens (Human)
(SEQ ID NO: 369)
MLGLRPPLLALVGLLSLGCVLS ITB4_HUMAN SPdb128387 Homo sapiens (Human)
(SEQ ID NO: 370)
MAGPRPSPWARLLLAALISVSLSGTLA ITIH4_HUMAN SPdb128480 Homo sapiens (Human)
(SEQ ID NO: 371)
MKPPRPVRTCSKVLVLLSLLAIHQTTTA JAM1_HUMAN SPdb128758 Homo sapiens (Human)
(SEQ ID NO: 372)
MGTKAQVERKLLCLFILAILLCSLALG JAM2_HUMAN SPdb128761 Homo sapiens (Human)
(SEQ ID NO: 373)
MARRSRHRLLLLLLRYLVVALGYHKAYG JAM3_HUMAN SPdb128763 Homo sapiens (Human)
(SEQ ID NO: 374)
MALRRPPRLRLCARLPDFFLLLLFRGCLIGA JAML1_HUMAN SPdb128766 Homo sapiens (Human)
(SEQ ID NO: 375)
MFCPLKLILLPVLLDYSLG KAZD1_HUMAN SPdb130734 Homo sapiens (Human)
(SEQ ID NO: 376)
MLPPPRPAAALALPVLLLLLVVLTPPPTGA KI2L1_HUMAN SPdb132984 Homo sapiens (Human)
(SEQ ID NO: 377)
MSLLVVSMACVGFFLLQGAWP KIRR2_HUMAN SPdb133175 Homo sapiens (Human)
(SEQ ID NO: 378)
MLRMRVPALLVLLFCFRGRA KLK3_HUMAN SPdb133637 Homo sapiens (Human)
(SEQ ID NO: 379)
MWVPVVFLTLSVTWIGA KLKB1_HUMAN SPdb133654 Homo sapiens (Human)
(SEQ ID NO: 380)
MILFKQATYFISLFATVSC KNG1_HUMAN SPdb133744 Homo sapiens (Human)
(SEQ ID NO: 381)
MKLITILFLCSRLLLSLT KTEL1_HUMAN SPdb135048 Homo sapiens (Human)
(SEQ ID NO: 382)
MEWWASSPLRLWLLLFLLPSAQG KV403_HUMAN SPdb135854 Homo sapiens (Human)
(SEQ ID NO: 383)
MVLQTQVFISLLLWISGAYG KV404_HUMAN SPdb135855 Homo sapiens (Human)
(SEQ ID NO: 384)
MVLQTQVFISLLLWISGAYG L1CAM_HUMAN SPdb135937 Homo sapiens (Human)
(SEQ ID NO: 385)
MVVALRYVWPLLLCSPCLL LALBA_HUMAN SPdb136381 Homo sapiens (Human)
(SEQ ID NO: 386)
MRFFVPLFLVGILFPAILA LAMB1_HUMAN SPdb136411 Homo sapiens (Human)
(SEQ ID NO: 387)
MGLLQLLAFSFLALCRARVRA LAMC1_HUMAN SPdb136476 Homo sapiens (Human)
(SEQ ID NO: 388)
MRGSHRAAPALRPRGRLWPVLAVLAAAAAGCA LAMP1_HUMAN SPdb136491 Homo sapiens (Human)
(SEQ ID NO: 389)
MAPRSARRPLLLLLPVAAARPHALSSA LAMP2_HUMAN SPdb136496 Homo sapiens (Human)
(SEQ ID NO: 390)
MVCFRLFPVPGSGLVLVCLVLGAVRSYA LBP_HUMAN SPdb136757 Homo sapiens (Human)
(SEQ ID NO: 391)
MGALARALPSILLALLLTSTPEALG LCAT_HUMAN SPdb136799 Homo sapiens (Human)
(SEQ ID NO: 392)
MGPPGSPWQWVTLLLGLLLPPAAP LCN1_HUMAN SPdb136934 Homo sapiens (Human)
(SEQ ID NO: 393)
MKPLLLAVSLGLIAALQA LCTL_HUMAN SPdb137082 Homo sapiens (Human)
(SEQ ID NO: 394)
MKPVWVATLLWMLLLVPRLGA LEUK_HUMAN SPdb139543 Homo sapiens (Human)
(SEQ ID NO: 395)
MATLLLLLGVLVVSPDALG LG3BP_HUMAN SPdb140022 Homo sapiens (Human)
(SEQ ID NO: 396)
MTPPRLFWVWLLVAGTQG LIF_HUMAN SPdb140701 Homo sapiens (Human)
(SEQ ID NO: 397)
MKVLAAGVVPLLLVLHWKHGAG LIPG_HUMAN SPdb141547 Homo sapiens (Human)
(SEQ ID NO: 398)
MWLLLTMASLISVLGTTHG LIPP_HUMAN SPdb141584 Homo sapiens (Human)
(SEQ ID NO: 399)
MLPLWTLSLLLGAVAG LIRA3_HUMAN SPdb141630 Homo sapiens (Human)
(SEQ ID NO: 400)
MTPILTVLICLGLSLDPRTHVQA LMAN1_HUMAN SPdb141882 Homo sapiens (Human)
(SEQ ID NO: 401)
MAGSRQRGLRARVRPLFCALLLSLGRFVRG LPH_HUMAN SPdb142734 Homo sapiens (Human)
(SEQ ID NO: 402)
MELSWHVVFIALLSFSCWG LRC55_HUMAN SPdb144275 Homo sapiens (Human)
(SEQ ID NO: 403)
MGSLQHCCCLLPKMGDTWAQLPWPGPPHPAMLLISLLLAAGLMHSDA LRRN1_HUMAN SPdb144478 Homo sapiens (Human)
(SEQ ID NO: 404)
MARMSFVIAACQLVLGLLMTSLTES LSHB_HUMAN SPdb144551 Homo sapiens (Human)
(SEQ ID NO: 405)
MEMLQGLLLLLLLSMGGAWA LUM_HUMAN SPdb145084 Homo sapiens (Human)
(SEQ ID NO: 406)
MSLSAFTLFLALIGGTSG LU_HUMAN SPdb145367 Homo sapiens (Human)
(SEQ ID NO: 407)
MEPPDAPAQARGAPRLLLLAVLLAAHPDAQA LV605_HUMAN SPdb145410 Homo sapiens (Human)
(SEQ ID NO: 408)
MAWAPLLLTLLAHCTDCWA LY86_HUMAN SPdb145461 Homo sapiens (Human)
(SEQ ID NO: 409)
MKGFTATLFLWTLIFPSCSG LYAM2_HUMAN SPdb145485 *Homo sapiens* (Human)
(SEQ ID NO: 410)
MIASQFLSALTLVLLIKESGA LYPA3_HUMAN SPdb145568 *Homo sapiens* (Human)
(SEQ ID NO: 411)
MGLHLRPYRVGLLPDGLLFLLLLLMLLADPALP LYPD6_HUMAN SPdb145583 *Homo sapiens* (Human)
(SEQ ID NO: 412)
MEPGPALAWLLLLSLLADCLKA LYSC_HUMAN SPdb145736 *Homo sapiens* (Human)
(SEQ ID NO: 413)
MKALIVLGLVLLSVTVQG MBL2_HUMAN SPdb148469 *Homo sapiens* (Human)
(SEQ ID NO: 414)
MSLFPSLPLLLLSMVAASYS MCP_HUMAN SPdb149004 *Homo sapiens* (Human)
(SEQ ID NO: 415)
MEPPGRRECPFPSWRFPGLLLAAMVLLLYSFSDA MFAP4_HUMAN SPdb152514 *Homo sapiens* (Human)
(SEQ ID NO: 416)
MKALLALPLLLLLSTPPCAPQ MGP_HUMAN SPdb152777 *Homo sapiens* (Human)
(SEQ ID NO: 417)
MKSLILLAILAALAVVTLC MIA_HUMAN SPdb153344 *Homo sapiens* (Human)
(SEQ ID NO: 418)
MARSLVCLGVIILLSAFSGPGVRG MIME_HUMAN SPdb153448 *Homo sapiens* (Human)
(SEQ ID NO: 419)
MKTLQSTLLLLLLVPLIKPA MIP2A_HUMAN SPdb153896 *Homo sapiens* (Human)
(SEQ ID NO: 420)
MARATLSAAPSNPRLLRVALLLLLLVAASRRAAG MIP2B_HUMAN SPdb153898 *Homo sapiens* (Human)
(SEQ ID NO: 421)
MAHATLSAAPSNPRLLRVALLLLLLVAASRRAAG MK_HUMAN SPdb154137 *Homo sapiens* (Human)
(SEQ ID NO: 422)
MQHRGFLLLTLLALLALTSA MMP1_HUMAN SPdb154439 *Homo sapiens* (Human)
(SEQ ID NO: 423)
MHSFPPLLLLLLFWGVVSHS MOTI_HUMAN SPdb155899 *Homo sapiens* (Human)
(SEQ ID NO: 424)
MVSRKAVAALLVVHVAAMLASQTEA MOX2R_HUMAN SPdb155983 *Homo sapiens* (Human)
(SEQ ID NO: 425)
MLCPWRTANLGLLLILTIFLVAASSSLC MPRD_HUMAN SPdb156360 *Homo sapiens* (Human)
(SEQ ID NO: 426)
MFPFYSCWRTGLLLLLLAVAVRESWQ MPRI_HUMAN SPdb156380 *Homo sapiens* (Human)
(SEQ ID NO: 427)
MGAAAGRSPHLGPAPARRPQRSLLLLQLLLLVAAPGSTQA MPZL3_HUMAN SPdb156425 *Homo sapiens* (Human)
(SEQ ID NO: 428)
MQQRGAAGSRGCALFPLLGVLFFQGVYIVFS MSMB_HUMAN SPdb158422 *Homo sapiens* (Human)
(SEQ ID NO: 429)
MNVLLGSVVIFATFVTLCNA MYP0_HUMAN SPdb164385 *Homo sapiens* (Human)
(SEQ ID NO: 430)
MAPGAPSSSPSPILAVLLFSSLVLSPAQA NAGAB_HUMAN SPdb165267 *Homo sapiens* (Human)
(SEQ ID NO: 431)
MLLKTVLLLGHVAQVLM NELL2_HUMAN SPdb168581 *Homo sapiens* (Human)
(SEQ ID NO: 432)
MESRVLLRTFCLIFGLGAVWG NET02_HUMAN SPdb168760 *Homo sapiens* (Human)
(SEQ ID NO: 433)
MALERLCSVLKVLLITVLVVEG NEU1_HUMAN SPdb168777 *Homo sapiens* (Human)
(SEQ ID NO: 434)
MAGPSLACCLLGLLALTSA NEU2_HUMAN SPdb168794 *Homo sapiens* (Human)
(SEQ ID NO: 435)
MPDTMLPACFLGLLAFSSA NGAL_HUMAN SPdb169201 *Homo sapiens* (Human)
(SEQ ID NO: 436)
MPLGLLWLGLALLGALHAQA NID1_HUMAN SPdb169544 *Homo sapiens* (Human)
(SEQ ID NO: 437)
MLASSSRIRAAWTRALLLPLLLAGPVGC NID2_HUMAN SPdb169547 *Homo sapiens* (Human)
(SEQ ID NO: 438)
MEGDRVAGRPVLSSLPVLLLLQLLMLRAAA NLGNX_HUMAN SPdb170305 *Homo sapiens* (Human)
(SEQ ID NO: 439)
MSRPQGLLWLPLLFTPVCVMLNSNVLLWLTALAIKFTLIDS NMB_HUMAN SPdb170485 *Homo sapiens* (Human)
(SEQ ID NO: 440)
MARRAGGARMFGSLLLLFALLAAGV NOV_HUMAN SPdb171434 *Homo sapiens* (Human)
(SEQ ID NO: 441)
MQSVQSTSFCLRKQCLCLTFLLLHLLGQVAA NPTN_HUMAN SPdb171815 *Homo sapiens* (Human)
(SEQ ID NO: 442)
MSGSSLPSALALSLLLVSGSLLPGPGAA NPY_HUMAN SPdb171875 *Homo sapiens* (Human)
(SEQ ID NO: 443)
MLGNKRLGLSGLTLALSLLVCLGALAEA NRP1_HUMAN SPdb172978 *Homo sapiens* (Human)
(SEQ ID NO: 444)
MERGLPLLCAVLALVLAPAGA NTRK2_HUMAN SPdb173863 *Homo sapiens* (Human)
(SEQ ID NO: 445)
MSSWIRWHGPAMARLWGFCWLVVGFWRAAFA NXPH3_HUMAN SPdb177361 *Homo sapiens* (Human)
(SEQ ID NO: 446)
MQLTRCCFVFLVQGSLYLVICG OLFL1_HUMAN SPdb178511 *Homo sapiens* (Human)
(SEQ ID NO: 447)
MMVALRGASALLVLFLAAFLPPPQCTQD OTOR_HUMAN SPdb180733 *Homo sapiens* (Human)
(SEQ ID NO: 448)
MARILLLFLPGLVAVCA OXLA_HUMAN SPdb181241 *Homo sapiens* (Human)
(SEQ ID NO: 449)
MAPLALHLLVLVPILLSLVAS P3IP1_HUMAN SPdb181543 Homo sapiens (Human)
(SEQ ID NO: 450)
MLLAWVQAFLVSNMLLAEAYG PAHO_HUMAN SPdb182446 Homo sapiens (Human)
(SEQ ID NO: 451)
MAAARLCLSLLLLSTCVALLLQPLLGAQG PARM1_HUMAN SPdb184104 Homo sapiens (Human)
(SEQ ID NO: 452)
MVYKTLFALCILTAGWRVQS PCDBA_HUMAN SPdb184878 Homo sapiens (Human)
(SEQ ID NO: 453)
MAVRELCFPRQRQVLFLFLFWGVSLA PCOC2_HUMAN SPdb185137 Homo sapiens (Human)
(SEQ ID NO: 454)
MRGANAWAPLCLLLAAATQLSRQ PCYXL_HUMAN SPdb185474 Homo sapiens (Human)
(SEQ ID NO: 455)
MARAPPLLAALTALLAAAAAGG PDGFA_HUMAN SPdb185687 Homo sapiens (Human)
(SEQ ID NO: 456)
MRTLACLLLLGCGYLAHVLA PDIA1_HUMAN SPdb185732 Homo sapiens (Human)
(SEQ ID NO: 457)
MLRRALLCLAVAALVRA PDIA3_HUMAN SPdb185743 Homo sapiens (Human)
(SEQ ID NO: 458)
MRLRRLALFPGVALLLAAARLAAA PDYN_HUMAN SPdb186941 Homo sapiens (Human)
(SEQ ID NO: 459)
MAWQGLVLAACLLMFPSTTA PEBP4_HUMAN SPdb187068 Homo sapiens (Human)
(SEQ ID NO: 460)
MGWTMRLVTAALLLGLMMVVTG PECA1_HUMAN SPdb187074 Homo sapiens (Human)
(SEQ ID NO: 461)
MQPRWAQGATMWLGVLLTLLLCSSLEG PG12B_HUMAN SPdb188887 Homo sapiens (Human)
(SEQ ID NO: 462)
MKLASGFLVLWLSLGGGLA PGFRA_HUMAN SPdb189004 Homo sapiens (Human)
(SEQ ID NO: 463)
MGTSHPAFLVLGCLLTGLSLILC PGFRB_HUMAN SPdb189010 Homo sapiens (Human)
(SEQ ID NO: 464)
MRLPGAMPALALKGELLLLSLLLLLEPQISQG PGH1_HUMAN SPdb189021 Homo sapiens (Human)
(SEQ ID NO: 465)
MSRSLLLRFLLFLLLLPPLPVLL PGRP2_HUMAN SPdb189713 Homo sapiens (Human)
(SEQ ID NO: 466)
MAQGVLWILLGLLLWSDPGTA PIGT_HUMAN SPdb191467 Homo sapiens (Human)
(SEQ ID NO: 467)
MAAAMPLALLVLLLLGPGGWC PIP_HUMAN SPdb191771 Homo sapiens (Human)
(SEQ ID NO: 468)
MRLLQLLFRASPATLLLVLCLQLGANKA PLBL2_HUMAN SPdb192296 Homo sapiens (Human)
(SEQ ID NO: 469)
MVGQMYCYPGSHLARALTRALALALVLALLVGPFLSGLAGA PLF4_HUMAN SPdb192496 Homo sapiens (Human)
(SEQ ID NO: 470)
MSSAAGFCASRPGLLFLGLLLLPLVVAFASA PLOD1_HUMAN SPdb192587 Homo sapiens (Human)
(SEQ ID NO: 471)
MRPLLLLALLGWLLLAEA PORIM_HUMAN SPdb194575 Homo sapiens (Human)
(SEQ ID NO: 472)
MGLGARGAWAALLLGTLQVLALLGAA PPA6_HUMAN SPdb195079 Homo sapiens (Human)
(SEQ ID NO: 473)
MITGVFSMRLWTPVGVLTSLAYCLHQRRVALA PPAP_HUMAN SPdb195174 Homo sapiens (Human)
(SEQ ID NO: 474)
MRAAPLLLARAASLSLGFLFLLFFWLDRSVLA PPGB_HUMAN SPdb195573 Homo sapiens (Human)
(SEQ ID NO: 475)
MIRAAPPPLFLLLLLLLLLVSWASRGEA PPIB_HUMAN SPdb195662 Homo sapiens (Human)
(SEQ ID NO: 476)
MKVLLAAALIAGSVFFLLLPGPSAA PRB4_HUMAN SPdb196833 Homo sapiens (Human)
(SEQ ID NO: 477)
MLLILLSVALLALSSA PRLR_HUMAN SPdb197321 Homo sapiens (Human)
(SEQ ID NO: 478)
MKENVASATVFTLLLFLNTCLLNG PRL_HUMAN SPdb197346 Homo sapiens (Human)
(SEQ ID NO: 479)
MNIKGSPWKGSLLLLLVSNLLLCQSVAP PROK1_HUMAN SPdb198420 Homo sapiens (Human)
(SEQ ID NO: 480)
MRGATRVSIMLLLVTVSDC PROK2_HUMAN SPdb198424 Homo sapiens (Human)
(SEQ ID NO: 481)
MRSLCCAPLLLLLLLPPLLLLTPRAGDA PROP_HUMAN SPdb198449 Homo sapiens (Human)
(SEQ ID NO: 482)
MITEGAQAPRLLLPPLLLLLTLPATGS PROZ_HUMAN SPdb198539 Homo sapiens (Human)
(SEQ ID NO: 483)
MAGCVPLLQGLVLVLALHRVEPS PRP1_HUMAN SPdb198570 Homo sapiens (Human)
(SEQ ID NO: 484)
MLLILLSVALLALSSA PRPC_HUMAN SPdb198723 Homo sapiens (Human)
(SEQ ID NO: 485)
MLLILLSVALLAFSSA PRRT3_HUMAN SPdb198854 Homo sapiens (Human)
(SEQ ID NO: 486)
MASSPWGCVCGLLLLLLPLLGTGPALG PTGDS_HUMAN SPdb203865 Homo sapiens (Human)
(SEQ ID NO: 487)
MATHHTLWMGLALLGVLGDLQA PTHY_HUMAN SPdb203993 Homo sapiens (Human)
(SEQ ID NO: 488)
MIPAKDMAKVMIVMLAICFLTKSDG PTPRG_HUMAN SPdb204842 Homo sapiens (Human)
(SEQ ID NO: 489)
MRRLLEPCWWILFLKITSS PYY_HUMAN SPdb210515 Homo sapiens (Human)
                                         (SEQ ID NO: 490)
MVFVRRPWPALTTVLLALLVCLGALVDA PZP_HUMAN SPdb210532 Homo sapiens (Human)
                                         (SEQ ID NO: 491)
MRKDRLLHLCLVLLLILLSASDSNS REG1A_HUMAN SPdb217426 Homo sapiens (Human)
                                         (SEQ ID NO: 492)
MAQTSSYFMLISCLMFLSQSQG REG3G_HUMAN SPdb217443 Homo sapiens (Human)
                                         (SEQ ID NO: 493)
MLPPMALPSVSWMLLSCLILLCQVQG RIB1_HUMAN SPdb220194 Homo sapiens (Human)
                                         (SEQ ID NO: 494)
MEAPAAGLFLLLLLGTWAPAPGS RIB2_HUMAN SPdb220201 Homo sapiens (Human)
                                         (SEQ ID NO: 495)
MAPPGSSTVFLLALTIIASTWA RISC_HUMAN SPdb221907 Homo sapiens (Human)
                                         (SEQ ID NO: 496)
MELALRRSPVPRWLLLLPLLLGLNAG RNAS1_HUMAN SPdb241351 Homo sapiens (Human)
                                         (SEQ ID NO: 497)
MALEKSLVRLLLLVLILLVLGWVQPSLG RNAS4_HUMAN SPdb241408 Homo sapiens (Human)
                                         (SEQ ID NO: 498)
MALQRTHSLLLLLLLTLLGLGLVQPSYG S39A6_HUMAN SPdb264754 Homo sapiens (Human)
                                         (SEQ ID NO: 499)
MARKLSVILILTFALSVTNPLHELKAAA SAA4_HUMAN SPdb264973 Homo sapiens (Human)
                                         (SEQ ID NO: 500)
MRLFTGIVFCSLVMGVTS SAA_HUMAN SPdb264986 Homo sapiens (Human)
                                         (SEQ ID NO: 501)
MKLLTGLVFCSLVLGVSS SAMP_HUMAN SPdb265378 Homo sapiens (Human)
                                         (SEQ ID NO: 502)
MNKPLLWISVLTSLLEAFA SCG1_HUMAN SPdb266260 Homo sapiens (Human)
                                         (SEQ ID NO: 503)
MQPTLLLSLLGAVGLAAVNS SCRG1_HUMAN SPdb266759 Homo sapiens (Human)
                                         (SEQ ID NO: 504)
MKLMVLVFTIGLTLLLGVQA SEM4B_HUMAN SPdb269059 Homo sapiens (Human)
                                         (SEQ ID NO: 505)
MGLRSWLAAPWGALPPRPPLLLLLLLLLLLQPPPPTWA SEM6B_HUMAN SPdb269079 Homo sapiens (Human)
                                         (SEQ ID NO: 506)
MQTPRASPPRPALLLLLLLGGAHG SEMG1_HUMAN SPdb269090 Homo sapiens (Human)
                                         (SEQ ID NO: 507)
MKPNIIFVLSLLLILEKQAAVMG SEMG2_HUMAN SPdb269095 Homo sapiens (Human)
                                         (SEQ ID NO: 508)
MKSIILFVLSLLLILEKQAAVMG SEPP1_HUMAN SPdb269196 Homo sapiens (Human)
                                         (SEQ ID NO: 509)
MWRSLGLALALCLLPSGGT SFRP2_HUMAN SPdb269743 Homo sapiens (Human)
                                         (SEQ ID NO: 510)
MLQGPGSLLLLFLASHCCLGSARG SFRP3_HUMAN SPdb269747 Homo sapiens (Human)
                                         (SEQ ID NO: 511)
MVCGSPGGMLLLRAGLLALAALCLLRVPGARA SFTPG_HUMAN SPdb269980 Homo sapiens (Human)
                                         (SEQ ID NO: 512)
MGSGLPLVLLLTLLGSSHG SG1D4_HUMAN SPdb270016 Homo sapiens (Human)
                                         (SEQ ID NO: 513)
MRLSVCLLMVSLALCCYQAHA SG3A1_HUMAN SPdb270025 Homo sapiens (Human)
                                         (SEQ ID NO: 514)
MKLAALLGLCVALSCSSAAA SHBG_HUMAN SPdb270301 Homo sapiens (Human)
                                         (SEQ ID NO: 515)
MESRGPLATSRLLLLLLLLLLRHTRQGWA SIAL_HUMAN SPdb270534 Homo sapiens (Human)
                                         (SEQ ID NO: 516)
MKTALILLSILGMACA SIDT2_HUMAN SPdb270589 Homo sapiens (Human)
                                         (SEQ ID NO: 517)
MFALGLPFLVLLVASVES SLAF6_HUMAN SPdb271065 Homo sapiens (Human)
                                         (SEQ ID NO: 518)
MLWLFQSLLFVFCFGPGNVVS SLAF7_HUMAN SPdb271067 Homo sapiens (Human)
                                         (SEQ ID NO: 519)
MAGSPTCLTLIYILWQLTGSAA SLAF8_HUMAN SPdb271069 Homo sapiens (Human)
                                         (SEQ ID NO: 520)
MVMRPLWSLLLWEALLPITVTG SLPI_HUMAN SPdb271309 Homo sapiens (Human)
                                         (SEQ ID NO: 521)
MKSSGLFPFLVLLALGTLAPWAVEG SMR3B_HUMAN SPdb271976 Homo sapiens (Human)
                                         (SEQ ID NO: 522)
MKSLTWILGLWALAACFTPGES SMS_HUMAN SPdb272029 Homo sapiens (Human)
                                         (SEQ ID NO: 523)
MLSCRLQCALAALSIVLALGCVTG SODE_HUMAN SPdb272720 Homo sapiens (Human)
                                         (SEQ ID NO: 524)
MLALLCSCLLLAAGASDA SOSD1_HUMAN SPdb273214 Homo sapiens (Human)
                                         (SEQ ID NO: 525)
MLPPAIHFYLLPLACILMKSCLA SOST_HUMAN SPdb273220 Homo sapiens (Human)
                                         (SEQ ID NO: 526)
MQLPLALCLVCLLVHTAFRVVEG SPIT1_HUMAN SPdb274564 Homo sapiens (Human)
                                         (SEQ ID NO: 527)
MAPARTMARARLAPAGIPAVALWLLCTLGLQGTQA SPIT2_HUMAN SPdb274566 Homo sapiens (Human)
                                         (SEQ ID NO: 528)
MAQLCGLRRSRAFLALLGSLLLSGVLA SRCH_HUMAN SPdb275436 Homo sapiens (Human)
                                         (SEQ ID NO: 529)
MGHHRPWLHASVLWAGVASLLLPPAMTQ -continued SRGN_HUMAN SPdb275551 Homo sapiens (Human)
(SEQ ID NO: 530)
MMQKLLKCSRLVLALALILVLESSVQG STAT_HUMAN SPdb277447 Homo sapiens (Human)
(SEQ ID NO: 531)
MKFLVFAFILALMVSMIGA STC1_HUMAN SPdb277483 Homo sapiens (Human)
(SEQ ID NO: 532)
MLQNSAVLLVLVISASA TCO1_HUMAN SPdb290388 Homo sapiens (Human)
(SEQ ID NO: 533)
MRQSHQLPLVGLLLFSFIPSQLC TCO2_HUMAN SPdb290391 Homo sapiens (Human)
(SEQ ID NO: 534)
MRHLGAFLFLLGVLGALT TENA_HUMAN SPdb291090 Homo sapiens (Human)
(SEQ ID NO: 535)
MGAMTQLLAGVFLAFLALATEG TETN_HUMAN SPdb291269 Homo sapiens (Human)
(SEQ ID NO: 536)
MELWGAYLLLCLFSLLTQVTT TFF1_HUMAN SPdb291574 Homo sapiens (Human)
(SEQ ID NO: 537)
MATMENKVICALVLVSMLALGTLA TFF3_HUMAN SPdb291583 Homo sapiens (Human)
(SEQ ID NO: 538)
MAARALCMLGLVLALLSSSSA TFPI1_HUMAN SPdb291601 Homo sapiens (Human)
(SEQ ID NO: 539)
MIYTMKKVHALWASVCLLLNLAPAPLNA TGFR2_HUMAN SPdb291788 Homo sapiens (Human)
(SEQ ID NO: 540)
MGRGLLRGLWPLHIVLWTRIAS THBG_HUMAN SPdb292195 Homo sapiens (Human)
(SEQ ID NO: 541)
MSPFLYLVLLVLGLHATIHC THYG_HUMAN SPdb293853 Homo sapiens (Human)
(SEQ ID NO: 542)
MALVLEIFTLLASICWVSA TICN2_HUMAN SPdb293959 Homo sapiens (Human)
(SEQ ID NO: 543)
MRAPGCGRLVLPLLLLAAAALA TIE1_HUMAN SPdb293968 Homo sapiens (Human)
(SEQ ID NO: 544)
MVWRVPPFLLPILFLASHVGA TIE2_HUMAN SPdb293972 Homo sapiens (Human)
(SEQ ID NO: 545)
MDSLASLVLCGVSLLLSGTVEG TIMP1_HUMAN SPdb294965 Homo sapiens (Human)
(SEQ ID NO: 546)
MAPFEPLASGILLLLWLIAPSRA TIMP2_HUMAN SPdb294980 Homo sapiens (Human)
(SEQ ID NO: 547)
MGAAARTLRLALGLLLLATLLRPADA TIMP3_HUMAN SPdb294987 Homo sapiens (Human)
(SEQ ID NO: 548)
MTPWLGLIVLLGSWSLGDWGAEA TINAL_HUMAN SPdb295015 Homo sapiens (Human)
(SEQ ID NO: 549)
MWRCPLGLLLLLPLAGHLALG -continued TLR1_HUMAN SPdb295471 Homo sapiens (Human)
(SEQ ID NO: 550)
MTSIFHFAIIFMLILQIRIQLSEE TLR3_HUMAN SPdb295485 Homo sapiens (Human)
(SEQ ID NO: 551)
MRQTLPCIYFWGGLLPFGMLCAS TLR4_HUMAN SPdb295493 Homo sapiens (Human)
(SEQ ID NO: 552)
MMSASRLAGTLIPAMAFLSCVRP TLR5_HUMAN SPdb295500 Homo sapiens (Human)
(SEQ ID NO: 553)
MGDHLDLLLGVVLMAGPVFG TM2D1_HUMAN SPdb295869 Homo sapiens (Human)
(SEQ ID NO: 554)
MAAAWPSGPSAPEAVTARLVGVLWFVSVTTGPWGAVA TMIG2_HUMAN SPdb296142 Homo sapiens (Human)
(SEQ ID NO: 555)
MGSPGMVLGLLVQIWALQEASS TMM25_HUMAN SPdb296188 Homo sapiens (Human)
(SEQ ID NO: 556)
MALPPGPAALRHTLLLLPALLSSGWG TMM46_HUMAN SPdb296232 Homo sapiens (Human)
(SEQ ID NO: 557)
MWGARRSSVSSSWNAASLLQLLLAALLAAGARA TMM66_HUMAN SPdb296282 Homo sapiens (Human)
(SEQ ID NO: 558)
MAAACGPGAAGYCLLLGLHLFLLTAGPALG TMM9B_HUMAN SPdb296355 Homo sapiens (Human)
(SEQ ID NO: 559)
MATLWGGLLRLGSLLSLSCLALSVLLLAQLSDA TNFB_HUMAN SPdb296533 Homo sapiens (Human)
(SEQ ID NO: 560)
MTPPERLFLPRVCGTTLHLLLLGLLLVLLPGAQG TNR14_HUMAN SPdb296702 Homo sapiens (Human)
(SEQ ID NO: 561)
MEPPGDWGPPPWRSTPKTDVLRLVLYLTFLGAPCYAPA TNR16_HUMAN SPdb296704 Homo sapiens (Human)
(SEQ ID NO: 562)
MGAGATGRAMDGPRLLLLLLLGVSLGGA TNR18_HUMAN SPdb296709 Homo sapiens (Human)
(SEQ ID NO: 563)
MAQHGAMGAFRALCGLALLCALSLG TNR19_HUMAN SPdb296711 Homo sapiens (Human)
(SEQ ID NO: 564)
MALKVLLEQEKTFFTLLVLLGYLSCKVTC TNR1B_HUMAN SPdb296718 Homo sapiens (Human)
(SEQ ID NO: 565)
MAPVAVWAALAVGLELWAAAHA TNR5_HUMAN SPdb296744 Homo sapiens (Human)
(SEQ ID NO: 566)
MVRLPLQCVLWGCLLTAVHP TNR6B_HUMAN SPdb296751 Homo sapiens (Human)
(SEQ ID NO: 567)
MRALEGPGLSLLCLVLALPALLPVPAVRG TNR8_HUMAN SPdb296768 Homo sapiens (Human)
(SEQ ID NO: 568)
MRVLLAALGLLFLGALRA TNR9_HUMAN SPdb296771 Homo sapiens (Human)
(SEQ ID NO: 569)
MGNSCYNIVATLLLVLNFERTRS TPO_HUMAN SPdb298326 Homo sapiens (Human)
(SEQ ID NO: 570)
MELTELLLVVMLLLTARLTLS TPSNR_HUMAN SPdb298428 Homo sapiens (Human)
(SEQ ID NO: 571)
MGTQEGWCLLLCLALSGA TPSN_HUMAN SPdb298434 Homo sapiens (Human)
(SEQ ID NO: 572)
MKSLSLLLAVALGLATAVSA TR10D_HUMAN SPdb298538 Homo sapiens (Human)
(SEQ ID NO: 573)
MGLWGQSVPTASSARAGRYPGARTASGTRPWLLDPKILKFVVFIVAVLLP
VRVDS TR11B_HUMAN SPdb298559 Homo sapiens (Human)
(SEQ ID NO: 574)
MNKLLCCALVFLDISIKWTTQ TR19L_HUMAN SPdb298594 Homo sapiens (Human)
(SEQ ID NO: 575)
MKPSLLCRPLSCFLMLLPWPLATLT TRBM_HUMAN SPdb298866 Homo sapiens (Human)
(SEQ ID NO: 576)
MLGVLVLGALALAGLGFP TRFE_HUMAN SPdb299004 Homo sapiens (Human)
(SEQ ID NO: 577)
MRLAVGALLVCAVLGLCLA TRFL_HUMAN SPdb299019 Homo sapiens (Human)
(SEQ ID NO: 578)
MKLVFLVLLFLGALGLCLA TRY1_HUMAN SPdb303488 Homo sapiens (Human)
(SEQ ID NO: 579)
MNPLLILTFVAAALA TRY2_HUMAN SPdb303496 Homo sapiens (Human)
(SEQ ID NO: 580)
MNLLLILTFVAAAVA TSHB_HUMAN SPdb303727 Homo sapiens (Human)
(SEQ ID NO: 581)
MTALFLMSMLFGLACGQAMS TSP1_HUMAN SPdb303853 Homo sapiens (Human)
(SEQ ID NO: 582)
MGLAWGLGVLFLMHVCGT TVA2_HUMAN SPdb304532 Homo sapiens (Human)
(SEQ ID NO: 583)
MAMLLGASVLILWLQPDWVNSQQKNDD TVB2_HUMAN SPdb304538 Homo sapiens (Human)
(SEQ ID NO: 584)
MGTSLLCWMALCLLGADHADT TXD12_HUMAN SPdb304820 Homo sapiens (Human)
(SEQ ID NO: 585)
METRPRLGATCLLGFSFLLLVISSDG TXND4_HUMAN SPdb304996 Homo sapiens (Human)
(SEQ ID NO: 586)
MHPAVFLSLPDLRCSLLLLVTWVFTPVTT TYRP1_HUMAN SPdb305383 Homo sapiens (Human)
(SEQ ID NO: 587)
MSAPKLLSLGCIFFPLLLFQQARA UROK_HUMAN SPdb311443 Homo sapiens (Human)
(SEQ ID NO: 588)
MRALLARLLLCVLVVSDSKG UTER_HUMAN SPdb311731 Homo sapiens (Human)
(SEQ ID NO: 589)
MKLAVTLTLVTLALCCSSASA UTS2_HUMAN SPdb311840 Homo sapiens (Human)
(SEQ ID NO: 590)
MYKLASCCLLFIGFLNPLLS VCAM1_HUMAN SPdb314239 Homo sapiens (Human)
(SEQ ID NO: 591)
MPGKMVVILGASNILWIMFAASQA VEGFA_HUMAN SPdb314841 Homo sapiens (Human)
(SEQ ID NO: 592)
MNFLLSWVHWSLALLLYLHHAKWSQA VEGFC_HUMAN SPdb314852 Homo sapiens (Human)
(SEQ ID NO: 593)
MHLLGFFSVACSLLAAALLPGPREAPAAAA VGFR3_HUMAN SPdb315610 Homo sapiens (Human)
(SEQ ID NO: 594)
MQRGAALCLRLWLCLGLLDGLVSG VMO1_HUMAN SPdb317004 Homo sapiens (Human)
(SEQ ID NO: 595)
MERGAGAKLLPLLLLLRATGFTCA VSIG2_HUMAN SPdb318531 Homo sapiens (Human)
(SEQ ID NO: 596)
MAELPGPFLCGALLGFLCLSGLA VSIG4_HUMAN SPdb318533 Homo sapiens (Human)
(SEQ ID NO: 597)
MGILLGLLLLGHLTVDTYG VSTM1_HUMAN SPdb318698 Homo sapiens (Human)
(SEQ ID NO: 598)
MTAEFLSLLCLGLCLG VTNC_HUMAN SPdb318799 Homo sapiens (Human)
(SEQ ID NO: 599)
MAPLRPLLILALLAWVALA VWF_HUMAN SPdb318878 Homo sapiens (Human)
(SEQ ID NO: 600)
MIPARFAGVLLALALILPGTLC WISP2_HUMAN SPdb319573 Homo sapiens (Human)
(SEQ ID NO: 601)
MRGTPKTHLLAFSLLCLLSKVRT X3CL1_HUMAN SPdb320112 Homo sapiens (Human)
(SEQ ID NO: 602)
MAPISLSWLLRLATFCHLTVLLAG XCL2_HUMAN SPdb320139 Homo sapiens (Human)
(SEQ ID NO: 603)
MRLLILALLGICSLTAYIVEG YK001_HUMAN SPdb348747 Homo sapiens (Human)
(SEQ ID NO: 604)
MDSLRKMLISVAMLGAGAGVGYA YQ001_HUMAN SPdb352137 Homo sapiens (Human)
(SEQ ID NO: 605)
MGLPGLFCLAVLAASSFSKA ZA2G_HUMAN SPdb354335 Homo sapiens (Human)
(SEQ ID NO: 606)
MVPVLLSLLLLLGPAVP ZG16_HUMAN SPdb354803 Homo sapiens (Human)
(SEQ ID NO: 607)
MLTVALLALLCASASG ZP2_HUMAN SPdb355981 Homo sapiens (Human)
(SEQ ID NO: 608)
MACRQRGGSWSPSGWFNAGWSTYRSISLFFALVTSGNS A preferred expression system using each specific human secretory signal peptide listed above is a CHO cell expression system.

In some embodiments, the human secretory signal peptide can include any combination of the aforelisted secretory signal peptide. In some embodiments, the human secretory signal peptide can specifically exclude any one or more of the aforelisted secretory signal peptide. For the sake of providing a concise description of the invention, listing of the above human secretory signal peptides is not repeated. Nonetheless this invention encompasses specific exclusion of any one of the human secretory signal peptide or nucleic acid sequences encoding each one of the secretory signal peptide listed above.

For the sake of providing a concise description of the invention, listing of nucleic acid sequences encoding each one of the secretory signal peptide listed above is omitted. Nonetheless, such nucleic acid sequences are publicly available and can be readily ascertained by a person of ordinary skill in the art. One public source of such nucleic acid sequence information is, e.g., http<://>proline<dot>bic<dot>nus<dot>edu<dot>sg.

In some embodiments, for mammalian expression systems, a protrypsin leading sequence can also be used.

In some embodiments, for production of NELL1 and/or NELL2 peptides in mammalian cells (e.g., CHO cells), the expression system for NELL1 and/or NELL2 can include the nucleic acid or cDNA that expresses an endogenous NELL signal peptide. In some embodiments, the method and system described herein specifically excludes an endogenous NELL signal peptide.

Peptide Purification

In some embodiments, the invention includes a method purifying NELL1 and/or NELL2 peptides secreted into culture media, according to standard peptide purification protocols, including, but not limited to those described below.

The method can also include collecting secreted NELL peptides and/or purifying NELL peptides for use. Peptide products can be tested for activity in a variety of functional or expression assays. For example in any assay, if a NELL peptide has a significant effect over a control substance on a given parameter, the NELL peptides can be functional to effect the measured parameter in a functional or expression assay.

In one embodiment, whether a selected cell expresses a selected nucleic acid sequence to express and/or secrete a NELL peptide can be examined. In one embodiment, the presence, amount or and/or activity of NELL peptides can be examined.

In one embodiment, NELL peptides detected and quantified by any of a number of methods well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one embodiment, Western blot (immunoblot) analysis can be used to detect and quantify the presence of NELL peptide(s) in a selected sample. Western blot analysis is well known in the art.

The assays of this invention can be scored (as positive or negative or quantity of target polypeptide) according to standard methods well known to those of skill in the art. The particular method of scoring can depend on the assay format and choice of label. For example, a Western Blot assay can be scored by visualizing the colored product produced by an enzymatic label. A clearly visible colored band or spot at the correct molecular weight can be scored as a positive result, while the absence of a clearly visible spot or band can be scored as a negative. The intensity of the band or spot can provide a quantitative measure of target polypeptide concentration.

NELL peptides, when in non-monomeric forms can be a large molecule and many of the techniques that work for purification of smaller proteins may not work as well for NELL peptides. The unusually large size of NELL oligomeric protein molecules causes it to be incompatible with the industry standard techniques used to purify smaller proteins, such as monoclonal antibodies and blood clotting factors. Specifically, the industry standard media is made by cross-linking agarose (e.g., agarose columns) into round beads with dead-end channels. The channels are lined with a functional group and interaction of this functional group with a protein forms the basis for purification. Because the channels are dead-ends, a protein molecule enters the channels by the forces of diffusion. As the protein of interest increases in size, diffusion into the channel slows and purification efficiently drops.

Instead of traditional porous media (e.g., agarose columns), other media not traditionally used for proteins may be used to purify NELL peptides in a more efficient fashion both in terms of speed and amount of NELL peptides purified/recovered. The present invention provides a method for purifying NELL peptides with a higher productivity. A low productivity in purification of protein is generally considered a production rate limiting factor in protein production. Therefore achieving a higher productivity is important in protein production.

In some embodiments, the method includes subjecting crude NELL peptides to membrane chromatography to obtain purified NELL peptides. In some embodiments, the method includes using commercially available purification media in membrane format. In some embodiments, the NELL peptide is NELL-1 peptide. In some embodiments, the NELL peptide is NELL-2 peptide. By employing membrane purification media, an efficient purification process for the NELL peptide was developed whereas analogous efforts with porous media was much less efficient.

The ion-exchange membrane can be anion-exchange membrane or cation-exchange membrane. It is not at all obvious that membrane chromatography can be used to purify NELL peptides.

Further, it is particularly surprising that cation-exchange chromatography is effective for NELL peptide purification. For example, analysis of the NELL-1 primary protein sequence indicates that its theoretical pI is 5.8. Under the pH ranges of 7-8.5 typically used to purify proteins, NELL-1 would be predicted to carry a net negative charge and therefore bind to anion exchange functional groups such as quaternary or secondary amines and not necessarily cation exchanges. Unexpectedly, however, NELL-1 is found to bind to both cation and anion exchange functional groups.

In some embodiments, purification of Nell-1 peptide/protein can be effected through a chromatography process using a medium including a metal cation bearing two, three or more charges, e.g., an earth metal cation, a rare earth metal cation. Examples of such metal ions are, e.g., $Mg(++)$, $Ca(++)$, $Al(+++)$, and any rare earth ions $Ln(+++)$. Such metal ions can be included in a buffer solution or eluting solution.

In some embodiments, purification can sequentially employ a cation exchange chromatography, an anion exchange chromatography and an hydroxyapatite medium. In other embodiments, it can also sequentially employ an anion exchange chromatography, a cation exchange chromotography and an hydroxyapatite medium. Alternatively, other combinations or steps can be introduced in between the aforementioned sequences.

The following examples are offered to illustrate, but not to limit the claimed invention.

EXAMPLES

In general, expression hosts can be bacteria, yeast and fungi, mammalian cells, plants, transgenic animals or it can also be cell-free expression systems such as those based on wheat germ or *E. coli* extracts. In general, expression elements can be Prokaryotic, Yeast, Mammalian and Plant promoters or viral promoters. Protein expression strategies can be: intra- or extracellular, fusion proteins and display strategies. Downstream processing of recombinant proteins can include: harvest, lysis, filtration, ultrafiltration, precipitation, and/or other protein processing/purification strategies that encompass protein capture, purification, polishing, and optimization.

Example 1

Expression of NELL Peptides

A cDNA fragment was ligated into the expression vector PiZT/V5-His (3.4 kb) (EcoRV site, Invitrogen) and included a melittin signal peptide, BamHI-EcoRI cDNA fragment of the mature rat NELL1 and a FLAG tag sequence. FIGS. 1A-1B are a depiction of the nucleic acid sequence of the cDNA construct used in this example, and corresponding predicted peptide sequence.

The High five cells (BTI-TN-5B1-4) were adapted to serum-free medium, and cells were transfected with the NELL1 peptide expression vector. Cells were treated with zeocin so as to select only cell populations expressing the NELL1 FLAG constructs. Surviving cell populations were confirmed to be stable transformants. Extracellular media was collected and tested for the presence of NELL1 peptide. NELL1 peptide was purified and used in functional assays described below.

FIG. 2A is an illustration of a CBB-stained SDS-PAGE gel of UnoQ-eluate containing purified NELL1 peptide. The medium was applied onto UnoQ column (Bio-Rad) as described herein. FIG. 2B shows a Western blot using anti-FLAG antibody depicting NELL1-FLAG expression in reference to a protein ladder. Peptide: 140 kDa (intracellular precursor), 130 kDa (mature form; 90 kDa peptide), 400 kDa (secreted form, homotrimer). In the example above, the productivity of the expression system was about 3 mg NELL1 peptide/L medium.

Relative to other expression systems which did not express or secrete peptide at all (such as bacterial expression, including yeast) or whose peptide production was extremely low (e.g., *E. coli* fused peptide system, CHO-dhfr cells, >10 mcg/L) production with the systems described (mammalian and insect cells) was surprisingly and substantially more effective at producing large amounts of functional protein.

Expression and Purification of Recombinant Rat NELL1 Protein.

For production of the C-terminally FLAG-tagged NELL1 peptide by insect cells, a pIZT-NELL1-FLC plasmid was constructed by inserting the rat NELL1 cDNA fused to a FLAG epitope sequence derived from the pTB701-NELL1-FLC plasmid (Kuroda, BBRC, 265, 752-757, 1999) into insect expression vector pIZT/V5-His (Invitrogen). Furthermore, NELL1 original secretory signal sequence was replaced to honeybee mellitin signal sequence using PCR methods. High Five cells were purchased from Invitrogen, and were cultured in High Five Serum-Free Medium (Invitrogen). High Five cells were transfected with the pIZT-NELL1-FLC plasmid using FuGene6 (Roche). Forty-eight hours after transfection, cells were selected with 400 mg/ml of Zeocin (Invitrogen). Replace selective medium every 3 to 4 days until the stable expression cell line was established. NELL1 secretion was confirmed using immunoprecipitation and Western blot analyses. High five cells were found to express NELL1 peptides (140-kDa) in the culture medium.

The recombinant rat NELL1-FLC peptide was purified from the culture medium of Zeocin-resistant High Five cells by anion exchange chromatography using a UNO Q-1 column (Bio-Rad). NELL1 peptide was eluted at 500 mM NaCl.

For production of the C-terminally FLAG-tagged NELL1 peptide by COS7 cells, a pcDNA3.1-NELL1-FLC plasmid was constructed by inserting the rat NELL1 cDNA linked to a FLAG epitope sequence derived from the pTB701-NELL1-FLC plasmid into mammalian expression vector pcDNA3.1 (Invitrogen). COS7 cells were cultured in DMEM supplemented with 10% FBS. COS7 cells were transfected with the pcDNA3.1-NELL1-FLC using the endogenous NELL signal peptide plasmid and using electroporation method. Forty-eight hours after transfection, culture medium was subjected to immunoprecipitation and Western blot analyses for NELL1 peptide.

FIG. 2C is an illustration of a CBB-stained SDS-PAGE gel of UnoQ-eluate including NELL1-FLAG. These expression studies showed that COS cells did not express functional NELL peptide, without modifying the N terminal of the NELL to increase secretion efficiency such as including a signal sequence. FIG. 2D is an illustration of a Western blot using anti-FLAG antibody depicting NELL1-FLAG expression.

Expression and Purification of Recombinant Rat NELL2 Protein.

For production of the C-terminally FLAG-tagged NELL2 peptide by insect cells, a pIZT-NELL2-FLC plasmid was constructed by inserting the rat NELL2 cDNA fused to a FLAG epitope sequence derived from the pTB701-NELL2-FLC plasmid into insect expression vector pIZT/V5-His (Invitrogen). High Five cells were purchased from Invitrogen, and were cultured in High Five Serum-Free Medium (Invitrogen). High Five cells were transfected with the pIZT-NELL2-FLC plasmid using FuGene6 (Roche). Forty-eight hours after transfection, cells were selected with 400 mg/ml of Zeocin (Invitrogen). Selective media was replaced every 3 to 4 days, until the stable expression cell line was established. NELL2 expression was confirmed in culture medium was confirmed using immunoprecipitation and Western blot analyses. High five cells were found to express NELL2 peptides (140-kDa) in the culture medium.

The recombinant rat NELL2-FLC peptide was purified from the culture medium of Zeocin-resistant High Five cells by anion exchange chromatography using a UNO Q-1 column (Bio-Rad). NELL2-FLC peptide was eluted at 500 mM NaCl.

Example 2

Expression of NELL1 in Mammalian Systems

The mammalian expression system used for production of rhNELL1 by non-viral DNA delivery in this invention may include, but not limit to these commonly used stable suspension systems listed in Table 1. The relatively detailed protocols including vector design, host cell line culture, transfection and selection of stable cell line as well as purification of rhNell-1 in HEK 293 and CHO system are described below, but are well known to those in the art.

TABLE 1

Mammalian Expression System for production of rhNell-1

| System | Parental vector | Leader sequence | Gene amplification |
|---|---|---|---|
| CHO | p3Xflag-CMV | preprotrypsin | No/optinal |
| DXB11 | mp19-Lp | human tPA | DHFR/MTX |
| HEK293 | pSecTag | immunoglobulin | No/optinal |
| NS/0 or Sp2/0 | pdCs-Fc-X | light chain of Ig and Fc fragment | DHFR/MTX |
| | pEE12 | N/A | GS/MSX |

DHFR: dihydrofolate reductase; MTX: methotrexate; GS: glutamine synthetase; MSX: methionine sulphoximine.

A. CHO System #1
Vector Design:
A cDNA fragment was ligated into the expression vector p3×Flag-CMV (Sigma). The resulting expression construct, pCMV-rhNELL3×flag, includes a preprotrypsin leading sequence, cDNA fragment of the mature human NELL1 coding region and a 3×flag sequences at c-terminal.

Host Cell Line:
The CHO-K1 were adherent cell line and can be adapted to suspension culture in serum-free medium. The construct of pCMV-rhNell-1-3×flag was transfected by either lipofectamin (Invitrogen) or calcium phosphates treatment. The stable cell lines were selected by adding G418 (400-600 ug/ml) into the cell culture medium for about two weeks. The stable transformants were further screened for single clones with high productivity of rhNELL1 by limiting dilution. The selected stable cell lines can be expended in laboratory or industrial scale bioreactors for rhNell-1 production.

Purification Procedure:
rhNELL1 peptide containing media or cell lysate were purified through anti-flag antibody M2 (Sigma) affinity column at its native condition and eluted with 3×flag peptide.

B. CHO System #2
Vector Design:
FIG. 3A depicts the nucleic acid sequence of the cDNA construct and amino acid sequences of three different signal peptides that were used for the constructs.

Host Cell Line:
The CHO-K1 were adherent cell line and can be adapted to suspension culture in serum-free medium. The construct of pcDNA3.1-hNELL1-c-myc/His, pIL2-hNELL1-c-myc/His, or pN2-hNELL1-c-myc/His were transfected by either lipofectamin (Invitrogen) or calcium phosphates treatment. The stable cell lines were selected by adding G418 (400-600 ug/ml) into the cell culture medium for about two weeks. The stable transformants were further screened for single clones with high productivity of rhNELL1 by limiting dilution. The selected stable cell lines can be expended in laboratory or industrial scale bioreactors for rhNELL1 production.

Figure 3B:
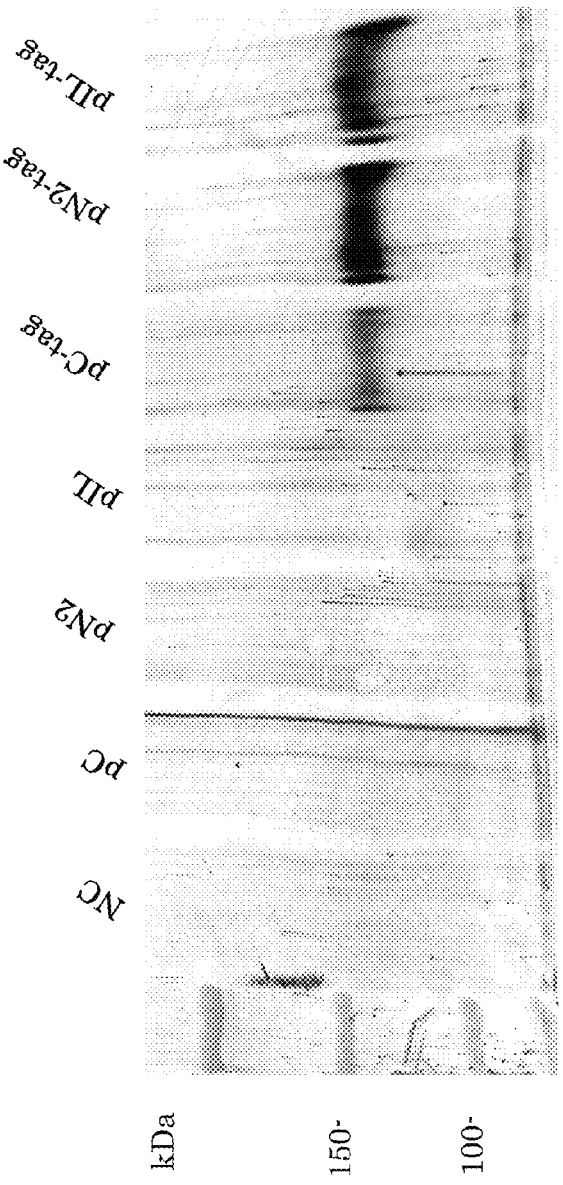
FIG. 3B is a Western blot with anti-c-myc antibody detecting secreting NELL1 from transfections with different constructs after immunoprecipitation using anti-c-myc agarose.
Figure 3C:
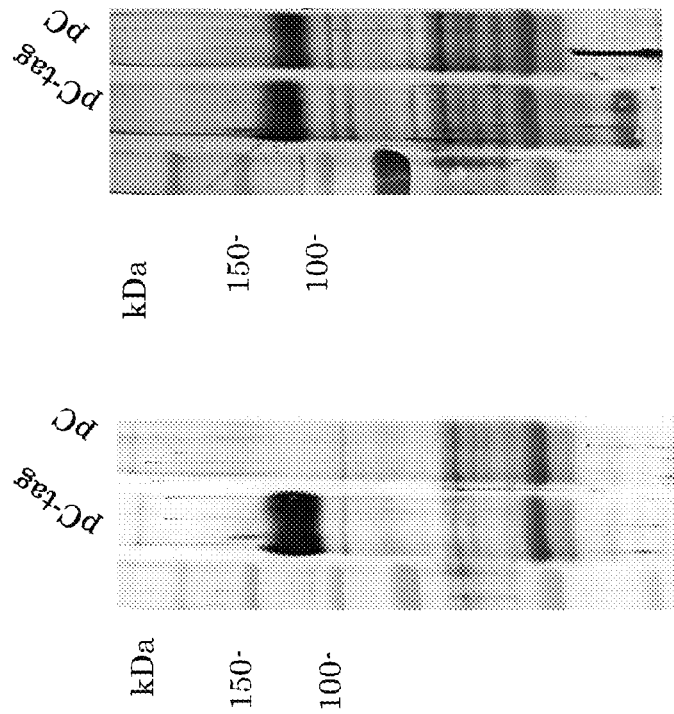
FIG. 3C is a Western blot with anti-c-myc or mouse anti-human NELL1 antibodies detecting secreting NELL1 after immunoprecipitation using rabbit anti-human Nell-1 antibody-NHS activated sepharose.

Purification Procedure:
rhNELL1 peptide containing media or cell lysate were purified through immunoprecipitation through anti-c-myc agarose. FIG. 3B is a Western blot with anti-c-myc antibody detecting secreting NELL1 from transfections with different constructs after immunoprecipitation using anti-c-myc agarose. FIG. 3C is a Western blot with anti-c-myc or mouse anti-human NELL1 antibodies detecting secreting NELL1 after immunoprecipitation using rabbit anti-human Nell-1 antibody-NHS activated sepharose.

C. CHO System #3
Vector Design:
Proprietary cDNA constructs expressing a NELL1 peptide was constructed according to the general procedures described above.

Host Cell Line:
The proprietary CHO cell lines were adherent cell line and can be adapted to suspension culture in serum-free medium. The proprietary constructs were transfected. The stable cell lines were selected by adding appropriate factors into the cell culture medium for about two weeks. The stable transformants were further screened for single clones with high productivity of rhNELL1 by limiting dilution. The selected stable cell lines can be expended in laboratory or industrial scale bioreactors for rhNELL1 production.

Purification Procedure:
rhNELL1 peptide containing media or cell lysate were purified through analytical and preparative protein purifications methods well known to those in the art (e.g., size, exclusion chromatography, ion exchange chromatography, affinity chromatography, immunoaffinity chromatography, high performance liquid chromatography, Concentration Procedure:
rhNELL1 was concentrated using lyophilization or ultrafiltration.

D: HEK293 System
Vector Design:
A cDNA fragment was ligated into the expression vector pSecTagA (Invitrogen). The resulting expression construct, pSec-hNell-1-Tag, includes a murine immunoglobulin □-chain leader sequence, cDNA fragment of the mature human NELL1 coding region and dual tag of Myc and His sequences at c-terminal.

Host Cell Line:
The human embryo kidney cell line, HEK-293 which was adapted to serum-free medium and grown in suspension format, was transfected with the NELL1 peptide expression vector, pSec-hNell-1-Tag. Cells were either cultured for a couple of days as transient transfection before collecting conditioned medium for purification of rhNell-1 or treated with Zeocin (250 ug/ml) for selection of stable expression cell line. The stable transformants were further screened for single clones with high productivity of rhNell-1 by limiting dilution. The selected stable cell lines can be expended in laboratory or industrial scale bioreactors for rhNell-1 production.

Purification Procedure:
rhNell-1 peptide containing media were purified through $Ni^{2+}$ affinity column at its native condition and eluted with 1M imidazole. The rhNell-1 was tested for its integrity, purity and bioactivity after extensively dialysis against at least 1000 volumes of PBS (pH 7.4) at 4° C. for 20 hrs.

In addition, the modifications of parental vectors for replacing existing leader sequence with a new one such as rat serum albumin, CD33, tPA and human interlukin-2 leader sequence or adding gene amplification target such as DHFR or GS into the backbone sequence will result in new expression vectors and systems. In this invention, the native signal peptide of human Nell-1 is not effective enough to guide the protein secretion and sometimes even the external leading sequence didn't work well, either. Thus, the construction of expression vector with in frame fusion of a small natural secretory protein such as human granulocyte-macrophage colony stimulating factor (GM-CSF) by a spacer containing intraprotein His tag and proteolytic cleavage site as "MPH-HHHHHGGGDDDDKDPM" (SEQ ID NO: 614) might be needed. The epitope tags used for purification of NELL1 can be one of the following: 6×Histidines, 3×Flag, Myc, GST (glutathione S-transferase), EGFP or CTHS (C-terminal half of SUMO which stands for small ubiquitin modifying protein) etc, but also could be dual of His plus Myc as listed plasmid pSecTag in Table 1 (supra).

Furthermore, the dicistronic or multicistronic vectors using IRES might be constructed for regulatory or inducible expression of rhNell-1 under certain circumstances. The genetic modifications of host cell lines for gaining longer lasting proliferation and delayed apoptosis or compatible with special requests such as Tet (tetracycline) inducible system and Flp-In specific site integration system will be considered for improvement of rhNell-1 production.

Besides the stable expression of system for production of rhNell-1 mentioned above, we would not exclude the possibility to establish a large-scale transient transfection (LST) approach using multi-milligram purified plasmid vector (pREP4) to transfect HEK 293 or BHK suspension cells with cationic polymer PEI as backup alternative or complimentary to stable system.

Example 3

Purification of NELL2 Protein from Culture Medium

High Five cells carrying pIZT-FLC-NELL2 were cultured for about three days in serum free culture medium (1 L). The culture medium was centrifuged at. 3000×g for 5 minutes and the supernatant was collected. PMSF was added to a final concentration of 1 mM. Saturated ammonium sulfate solution (80% saturation (v/v) was added and the solution kept at 4 degrees for 1 hour. The solution was centrifuged at 15000×g for 30 min. and precipitate collected. Precipitate was dissolved in 50 ml of 20 mM Tris-HCl (pH 8.0), 1 mm EDTA at 4 degree and applied onto an anion-exchange chromatography UnoQ column (6 ml, Bio-Rad) equilibrated in 20 mM Tris-HCl (pH 8.0), 1 mM EDTA at 4 degree (1 ml/min speed by FPLC (Amersham-Pharmacia). The column was thoroughly washed with the same buffer.

The binding protein was then eluted by the gradation from 0 M to 1.5 M NaCl in the same buffer. The NELL2-FLAG fractions were identified by Western blotting using anti-Flag M2 (Sigma) Ab. The positive fractions were collected into one tube. Final product was dialyzed in the seamless cellulose tube (Wako, cutoff MW 12000) against 1 L PBS for overnight at 4 degree. The product was stored at −70 degree.

Example 4

Cell Line Development and Expression of NELL-1

A series of Chinese Hamster Ovary (CHO) cell lines expressing recombinant human Nell-1 protein were developed according to procedures described above or procedures known in the art. The cell lines were screened according to known methods (please see references 1-8, below). The top 12 clones were cultured in a medium to amplify expression. The cell pools exhibiting the highest expression of human Nell-1 by ELISA were subcloned. They were then subjected to amplification, after which the cell pools were rescreened by ELISA. From this procedure, the ten highest expressing MTX-amplified subclones from transfection were expanded.

The six highest expressing subclones were adapted to grow in protein-free medium. All serum-free adapted clones were evaluated for Nell-1 expression by ELISA and by SDS gel. The clones that were observed to express the best at 1,000 nM MTX were identified as N2-1.9E10.1F9.4C2, N2-1.9E10.1F9.5H6, N2-1.9E10.1F9.5H2. All expressed Nell-1 protein at levels=40 ug/ml by ELISA.

(1) Urlaub, G. & Chasin, L. (1980) Isolation of Chinese Hamster Cell Mutants Deficient in Dihydrofolate Reductase Activity. Proc Natl. Acad. Sci. 77: 4216-4220

(2) Kao, F.-T. and Puck, T. T. (1967) Genetics of somatic mammalian cells. IV. Properties of Chinese hamster cells with respect to the requirement for proline. Genetics 55: 513-524

(3) Wigler, M., Perucho, M., Kurtz, D., Dana, S., Pellicer, A, Axel, R., and Silverstein, S. (1980) Transformation of mammalian genes with an amplifiable dominant-acting gene. Proc. Natl. Acad. Sci. USA Vol 77: 3567-3570.

(4) Bourouis, M. and Jury, B. (1983) Vectors containing a prokaryotic dihydrofolate reductase gene transform *Drosophila* cells to methotrexate resistance. EMBO J. 2: 1099-1104.

(5) Ringold, G., Dieckmann, B., and Lee, F. (1982) Co-expression and amplification of dihydrofolate reductase cDNA and the *Escherichia coli* XGPRT gene in Chinese hamster ovary cells. Journal of Molecular and Applied Genetics, Vol. 1:3: 165-175.

(6) Gasser C. S., Simonsen C. C., Schilling J. W., Schimke R. T. (1982) Expression of abbreviated mouse dihydrofolate reductase genes in cultured hamster cells. Proc. Natl. Acad. Sci. V 79: 6522-6526.

(7) Kaufman, R. J., Wasley, L. C., Spiliotes, A. J., Gossels, S. D., Latt, S. A., Larsen, G. R. and Kay, R. M. (1985) Co-amplification and co-expression of human tissue type plasminogen activator and murine dihydrofolate reductase sequences in Chinese hamster ovary cells. Mol. Cell. Biol. Vol 5: 1750-1759.

(8) Simonsen, C. C. and Levinson, A. D. (1983) Isolation and expression of an altered mouse dihydrofolate reductase cDNA. Proc. Natl. Acad. Sci. U.S.A. 80: 2495-2499.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true sprit and scope of this invention.

What is claimed is:

1. A method of expressing a peptide in a mammalian cell comprising:

providing a nucleic acid construct including at least a nucleic acid encoding at least a NEL-like protein (NELL) peptide in frame with a nucleic acid encoding a heterologous, non-insect secretory signal peptide;

transfecting a mammalian cell with the nucleic acid construct;

culturing the mammalian cell under conditions that permit expression of the NELL peptide;

collecting NELL peptide secreted from the cell; and substantially purifying the NELL peptide using a chromatography process that uses membrane chromatography or affinity chromatography;

wherein the nucleic acid encodes NELL1 or NELL2, wherein NELL1 is selected from the group consisting of: SEQ ID NO:1, SEQ ID NO:2, SEQ ID NO:3, SEQ ID NO:4, SEQ ID NO:5, and SEQ ID NO:6, wherein NELL2 is selected from the group consisting of: SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

2. The method of claim 1, wherein the mammalian cell is a Chinese hamster ovary (CHO) cell.

3. The method of claim 1, wherein substantially purifying comprises membrane chromatography.

4. The method of claim 3, further comprising
testing the activity of the NELL peptide to induce bone formation.

5. The method of claim 1, further comprising
testing the activity of the NELL peptide to induce bone formation.

6. The method of claim 1, wherein substantially purifying comprises affinity chromatography.

7. The method of claim 1, wherein the non-insect secretory signal peptide is a plant secretory signal peptide or an animal secretory signal peptide, wherein the animal secretory signal peptide is a mammalian secretory signal peptide.

8. A nucleic acid construct for expressing a NEL-like protein (NELL peptide) in a mammalian cell, the nucleic acid construct comprising at least a nucleic acid encoding at least a NELL peptide in frame with a nucleic acid encoding a heterologous non-insect signal peptide that is a non-insect secretory signal peptide;
wherein the nucleic acid encodes NELL1 or NELL2, wherein the NELL1 is selected from the group consisting of: SEQ ID NO:1, SEQ ID NO:2, SEQ ID NO:3, SEQ ID NO:4, SEQ ID NO:5, and SEQ ID NO:6; and
wherein NELL2 is selected from the group consisting of: SEQ ID NO:7, SEQ ID NO: 8, SEQ ID NO:9, SEQ ID NO:10, SEQ ID NO:11, SEQ ID NO:12, SEQ ID NO:13, and SEQ ID NO:14.

9. The nucleic acid construct of claim 8, wherein the mammalian cell is a CHO cell.

10. The nucleic acid construct of claim 8, wherein the non-insect secretory signal peptide is a plant secretory signal peptide or an animal secretory signal peptide, wherein the animal secretory signal peptide is a mammalian secretory signal peptide.

11. A mammalian cell line for expressing a NEL-like protein (NELL) peptide, the cell line including a nucleic acid construct comprising at least a nucleic acid encoding at least a NELL peptide in frame with a nucleic acid encoding a heterologous non-insect signal peptide that is a non-insect secretory signal peptide;
wherein the nucleic acid encodes NELL or NELL2 peptide, wherein NELL1 is selected from the group consisting of: SEQ ID NO:1, SEQ ID NO:2, SEQ ID NO:3, SEQ ID NO:4, SEQ ID NO:5, or SEQ ID NO:6; and
wherein NELL2 is selected from the group consisting of: SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

12. The cell of claim 11, wherein the mammalian cell line comprises a CHO cell.

13. The cell of claim 12, wherein the CHO cell secretes NELL1 or NELL2 peptide.

14. The cell line of claim 11, wherein the non-insect secretory signal peptide is a plant secretory signal peptide or an animal secretory signal peptide, and wherein the animal secretory signal peptide is a mammalian secretory signal peptide.

* * * * *

SEQUENCE LISTING

<160> NUMBER OF SEQ ID NOS: 614

<210> SEQ ID NO 1
<211> LENGTH: 2433
<212> TYPE: DNA
<213> ORGANISM: Homo sapiens
<220> FEATURE:
<221> NAME/KEY: CDS
<222> LOCATION: (1)..(2433)

<400> SEQUENCE: 1

| | | | | | | | | | | | | | | | | |
|---|---|---|---|---|---|---|---|---|---|---|---|---|---|---|---|---|
| atg | ccg | atg | gat | ttg | att | tta | gtt | gtg | tgg | ttc | tgt | gtg | tgc | act | gcc | 48 |
| Met | Pro | Met | Asp | Leu | Ile | Leu | Val | Val | Trp | Phe | Cys | Val | Cys | Thr | Ala | |
| 1 | | | | 5 | | | | | 10 | | | | | 15 | | |
| agg | aca | gtg | gtg | ggc | ttt | ggg | atg | gac | cct | gac | ctt | cag | atg | gat | atc | 96 |
| Arg | Thr | Val | Val | Gly | Phe | Gly | Met | Asp | Pro | Asp | Leu | Gln | Met | Asp | Ile | |
| | | | 20 | | | | | 25 | | | | | 30 | | | |
| gtc | acc | gag | ctt | gac | ctt | gtg | aac | acc | acc | ctt | gga | gtt | gct | cag | gtg | 144 |
| Val | Thr | Glu | Leu | Asp | Leu | Val | Asn | Thr | Thr | Leu | Gly | Val | Ala | Gln | Val | |
| | | 35 | | | | | 40 | | | | | 45 | | | | |
| tct | gga | atg | cac | aat | gcc | agc | aaa | gca | ttt | tta | ttt | caa | gac | ata | gaa | 192 |
| Ser | Gly | Met | His | Asn | Ala | Ser | Lys | Ala | Phe | Leu | Phe | Gln | Asp | Ile | Glu | |
| | 50 | | | | | 55 | | | | | 60 | | | | | |
| aga | gag | atc | cat | gca | gct | cct | cat | gtg | agt | gag | aaa | tta | att | cag | ctg | 240 |
| Arg | Glu | Ile | His | Ala | Ala | Pro | His | Val | Ser | Glu | Lys | Leu | Ile | Gln | Leu | |
| 65 | | | | | 70 | | | | | 75 | | | | | 80 | |
| ttc | cag | aac | aag | agt | gaa | ttc | acc | att | ttg | gcc | act | gta | cag | cag | aag | 288 |
| Phe | Gln | Asn | Lys | Ser | Glu | Phe | Thr | Ile | Leu | Ala | Thr | Val | Gln | Gln | Lys | |
| | | | | 85 | | | | | 90 | | | | | 95 | | |
| cca | tcc | act | tca | gga | gtg | ata | ctg | tcc | att | cga | gaa | ctg | gag | cac | agc | 336 |
| Pro | Ser | Thr | Ser | Gly | Val | Ile | Leu | Ser | Ile | Arg | Glu | Leu | Glu | His | Ser | |
| | | | 100 | | | | | 105 | | | | | 110 | | | |
| tat | ttt | gaa | ctg | gag | agc | agt | ggc | ctg | agg | gat | gag | att | cgg | tat | cac | 384 |
| Tyr | Phe | Glu | Leu | Glu | Ser | Ser | Gly | Leu | Arg | Asp | Glu | Ile | Arg | Tyr | His | |
| | | 115 | | | | | 120 | | | | | 125 | | | | |
| tac | ata | cac | aat | ggg | aag | cca | agg | aca | gag | gca | ctt | cct | tac | cgc | atg | 432 |
| Tyr | Ile | His | Asn | Gly | Lys | Pro | Arg | Thr | Glu | Ala | Leu | Pro | Tyr | Arg | Met | |
| | 130 | | | | | 135 | | | | | 140 | | | | | |
| gca | gat | gga | caa | tgg | cac | aag | gtt | gca | ctg | tca | gtt | agc | gcc | tct | cat | 480 |
| Ala | Asp | Gly | Gln | Trp | His | Lys | Val | Ala | Leu | Ser | Val | Ser | Ala | Ser | His | |
| 145 | | | | | 150 | | | | | 155 | | | | | 160 | |
| ctc | ctg | ctc | cat | gtc | gac | tgt | aac | agg | att | tat | gag | cgt | gtg | ata | gac | 528 |
| Leu | Leu | Leu | His | Val | Asp | Cys | Asn | Arg | Ile | Tyr | Glu | Arg | Val | Ile | Asp | |
| | | | | 165 | | | | | 170 | | | | | 175 | | |
| cct | cca | gat | acc | aac | ctt | ccc | cca | gga | atc | aat | tta | tgg | ctt | ggc | cag | 576 |
| Pro | Pro | Asp | Thr | Asn | Leu | Pro | Pro | Gly | Ile | Asn | Leu | Trp | Leu | Gly | Gln | |
| | | | 180 | | | | | 185 | | | | | 190 | | | |
| cgc | aac | caa | aag | cat | ggc | tta | ttc | aaa | ggg | atc | atc | caa | gat | ggg | aag | 624 |
| Arg | Asn | Gln | Lys | His | Gly | Leu | Phe | Lys | Gly | Ile | Ile | Gln | Asp | Gly | Lys | |
| | | 195 | | | | | 200 | | | | | 205 | | | | |
| atc | atc | ttt | atg | ccg | aat | gga | tat | ata | aca | cag | tgt | cca | aat | cta | aat | 672 |
| Ile | Ile | Phe | Met | Pro | Asn | Gly | Tyr | Ile | Thr | Gln | Cys | Pro | Asn | Leu | Asn | |
| | 210 | | | | | 215 | | | | | 220 | | | | | |
| cac | act | tgc | cca | acc | tgc | agt | gat | ttc | tta | agc | ctg | gtg | caa | gga | ata | 720 |
| His | Thr | Cys | Pro | Thr | Cys | Ser | Asp | Phe | Leu | Ser | Leu | Val | Gln | Gly | Ile | |
| 225 | | | | | 230 | | | | | 235 | | | | | 240 | |
| atg | gat | tta | caa | gag | ctt | ttg | gcc | aag | atg | act | gca | aaa | cta | aat | tat | 768 |
| Met | Asp | Leu | Gln | Glu | Leu | Leu | Ala | Lys | Met | Thr | Ala | Lys | Leu | Asn | Tyr | |
| | | | | 245 | | | | | 250 | | | | | 255 | | |
| gca | gag | aca | aga | ctt | agt | caa | ttg | gaa | aac | tgt | cat | tgt | gag | aag | act | 816 |
| Ala | Glu | Thr | Arg | Leu | Ser | Gln | Leu | Glu | Asn | Cys | His | Cys | Glu | Lys | Thr | |

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 260 |     |     |     |     | 265 |     |     |     |     | 270 |     |     |      |
| tgt | caa | gtg | agt | gga | ctg | ctc | tat | cga | gat | caa | gac | tct | tgg | gta | gat | 864  |
| Cys | Gln | Val | Ser | Gly | Leu | Leu | Tyr | Arg | Asp | Gln | Asp | Ser | Trp | Val | Asp |      |
|     |     |     | 275 |     |     |     |     | 280 |     |     |     |     | 285 |     |     |      |
| ggt | gac | cat | tgc | agg | aac | tgc | act | tgc | aaa | agt | ggt | gcc | gtg | gaa | tgc | 912  |
| Gly | Asp | His | Cys | Arg | Asn | Cys | Thr | Cys | Lys | Ser | Gly | Ala | Val | Glu | Cys |      |
|     |     |     | 290 |     |     |     |     | 295 |     |     |     |     | 300 |     |     |      |
| cga | agg | atg | tcc | tgt | ccc | cct | ctc | aat | tgc | tcc | cca | gac | tcc | ctc | cca | 960  |
| Arg | Arg | Met | Ser | Cys | Pro | Pro | Leu | Asn | Cys | Ser | Pro | Asp | Ser | Leu | Pro |      |
| 305 |     |     |     |     | 310 |     |     |     |     | 315 |     |     |     |     | 320 |      |
| gta | cac | att | gct | ggc | cag | tgc | tgt | aag | gtc | tgc | cga | cca | aaa | tgt | atc | 1008 |
| Val | His | Ile | Ala | Gly | Gln | Cys | Cys | Lys | Val | Cys | Arg | Pro | Lys | Cys | Ile |      |
|     |     |     |     | 325 |     |     |     |     | 330 |     |     |     |     | 335 |     |      |
| tat | gga | gga | aaa | gtt | ctt | gca | gaa | ggc | cag | cgg | att | tta | acc | aag | agc | 1056 |
| Tyr | Gly | Gly | Lys | Val | Leu | Ala | Glu | Gly | Gln | Arg | Ile | Leu | Thr | Lys | Ser |      |
|     |     |     | 340 |     |     |     |     | 345 |     |     |     |     | 350 |     |     |      |
| tgt | cgg | gaa | tgc | cga | ggt | gga | gtt | tta | gta | aaa | att | aca | gaa | atg | tgt | 1104 |
| Cys | Arg | Glu | Cys | Arg | Gly | Gly | Val | Leu | Val | Lys | Ile | Thr | Glu | Met | Cys |      |
|     |     |     | 355 |     |     |     |     | 360 |     |     |     |     | 365 |     |     |      |
| cct | cct | ttg | aac | tgc | tca | gaa | aag | gat | cac | att | ctt | cct | gag | aat | cag | 1152 |
| Pro | Pro | Leu | Asn | Cys | Ser | Glu | Lys | Asp | His | Ile | Leu | Pro | Glu | Asn | Gln |      |
|     | 370 |     |     |     |     | 375 |     |     |     |     | 380 |     |     |     |     |      |
| tgc | tgc | cgt | gtc | tgt | aga | ggt | cat | aac | ttt | tgt | gca | gaa | gga | cct | aaa | 1200 |
| Cys | Cys | Arg | Val | Cys | Arg | Gly | His | Asn | Phe | Cys | Ala | Glu | Gly | Pro | Lys |      |
| 385 |     |     |     |     | 390 |     |     |     |     | 395 |     |     |     |     | 400 |      |
| tgt | ggt | gaa | aac | tca | gag | tgc | aaa | aac | tgg | aat | aca | aaa | gct | act | tgt | 1248 |
| Cys | Gly | Glu | Asn | Ser | Glu | Cys | Lys | Asn | Trp | Asn | Thr | Lys | Ala | Thr | Cys |      |
|     |     |     |     | 405 |     |     |     |     | 410 |     |     |     |     | 415 |     |      |
| gag | tgc | aag | agt | ggt | tac | atc | tct | gtc | cag | gga | gac | tct | gcc | tac | tgt | 1296 |
| Glu | Cys | Lys | Ser | Gly | Tyr | Ile | Ser | Val | Gln | Gly | Asp | Ser | Ala | Tyr | Cys |      |
|     |     |     | 420 |     |     |     |     | 425 |     |     |     |     | 430 |     |     |      |
| gaa | gat | att | gat | gag | tgt | gca | gct | aag | atg | cat | tac | tgt | cat | gcc | aat | 1344 |
| Glu | Asp | Ile | Asp | Glu | Cys | Ala | Ala | Lys | Met | His | Tyr | Cys | His | Ala | Asn |      |
|     |     |     | 435 |     |     |     |     | 440 |     |     |     |     | 445 |     |     |      |
| act | gtg | tgt | gtc | aac | ctt | cct | ggg | tta | tat | cgc | tgt | gac | tgt | gtc | cca | 1392 |
| Thr | Val | Cys | Val | Asn | Leu | Pro | Gly | Leu | Tyr | Arg | Cys | Asp | Cys | Val | Pro |      |
| 450 |     |     |     |     | 455 |     |     |     |     | 460 |     |     |     |     |     |      |
| gga | tac | att | cgt | gtg | gat | gac | ttc | tct | tgt | aca | gaa | cac | gat | gaa | tgt | 1440 |
| Gly | Tyr | Ile | Arg | Val | Asp | Asp | Phe | Ser | Cys | Thr | Glu | His | Asp | Glu | Cys |      |
| 465 |     |     |     |     | 470 |     |     |     |     | 475 |     |     |     |     | 480 |      |
| ggc | agc | ggc | cag | cac | aac | tgt | gat | gag | aat | gcc | atc | tgc | acc | aac | act | 1488 |
| Gly | Ser | Gly | Gln | His | Asn | Cys | Asp | Glu | Asn | Ala | Ile | Cys | Thr | Asn | Thr |      |
|     |     |     |     | 485 |     |     |     |     | 490 |     |     |     |     | 495 |     |      |
| gtc | cag | gga | cac | agc | tgc | acc | tgc | aaa | ccg | ggc | tac | gtg | ggg | aac | ggg | 1536 |
| Val | Gln | Gly | His | Ser | Cys | Thr | Cys | Lys | Pro | Gly | Tyr | Val | Gly | Asn | Gly |      |
|     |     |     | 500 |     |     |     |     | 505 |     |     |     |     | 510 |     |     |      |
| acc | atc | tgc | aga | gct | ttc | tgt | gaa | gag | ggc | tgc | aga | tac | ggt | gga | acg | 1584 |
| Thr | Ile | Cys | Arg | Ala | Phe | Cys | Glu | Glu | Gly | Cys | Arg | Tyr | Gly | Gly | Thr |      |
|     |     |     | 515 |     |     |     |     | 520 |     |     |     |     | 525 |     |     |      |
| tgt | gtg | gct | ccc | aac | aaa | tgt | gtc | tgt | cca | tct | gga | ttc | aca | gga | agc | 1632 |
| Cys | Val | Ala | Pro | Asn | Lys | Cys | Val | Cys | Pro | Ser | Gly | Phe | Thr | Gly | Ser |      |
|     |     |     | 530 |     |     |     |     | 535 |     |     |     |     | 540 |     |     |      |
| cac | tgc | gag | aaa | gat | att | gat | gaa | tgt | tca | gag | gga | atc | att | gag | tgc | 1680 |
| His | Cys | Glu | Lys | Asp | Ile | Asp | Glu | Cys | Ser | Glu | Gly | Ile | Ile | Glu | Cys |      |
| 545 |     |     |     |     | 550 |     |     |     |     | 555 |     |     |     |     | 560 |      |
| cac | aac | cat | tcc | cgc | tgc | gtt | aac | ctg | cca | ggg | tgg | tac | cac | tgt | gag | 1728 |
| His | Asn | His | Ser | Arg | Cys | Val | Asn | Leu | Pro | Gly | Trp | Tyr | His | Cys | Glu |      |
|     |     |     |     | 565 |     |     |     |     | 570 |     |     |     |     | 575 |     |      |
| tgc | aga | agc | ggt | ttc | cat | gac | gat | ggg | acc | tat | tca | ctg | tcc | ggg | gag | 1776 |

| | | | | | | | | | | | | | | | |
|---|---|---|---|---|---|---|---|---|---|---|---|---|---|---|---|
|Cys|Arg|Ser|Gly|Phe|His|Asp|Asp|Gly|Thr|Tyr|Ser|Leu|Ser|Gly|Glu|
| | | |580| | | |585| | | |590| | | | |

```
tcc tgt att gac att gat gaa tgt gcc tta aga act cac acc tgt tgg    1824
Ser Cys Ile Asp Ile Asp Glu Cys Ala Leu Arg Thr His Thr Cys Trp
        595                 600                 605 aac gat tct gcc tgc atc aac ctg gca ggg ggt ttt gac tgt ctc tgc    1872
Asn Asp Ser Ala Cys Ile Asn Leu Ala Gly Gly Phe Asp Cys Leu Cys
610                 615                 620 ccc tct ggg ccc tcc tgc tct ggt gac tgt cct cat gaa ggg ggg ctg    1920
Pro Ser Gly Pro Ser Cys Ser Gly Asp Cys Pro His Glu Gly Gly Leu
625                 630                 635                 640 aag cac aat ggc cag gtg tgg acc ttg aaa gaa gac agg tgt tct gtc    1968
Lys His Asn Gly Gln Val Trp Thr Leu Lys Glu Asp Arg Cys Ser Val
                645                 650                 655 tgc tcc tgc aag gat ggc aag ata ttc tgc cga cgg aca gct tgt gat    2016
Cys Ser Cys Lys Asp Gly Lys Ile Phe Cys Arg Arg Thr Ala Cys Asp
            660                 665                 670 tgc cag aat cca agt gct gac cta ttc tgt tgc cca gaa tgt gac acc    2064
Cys Gln Asn Pro Ser Ala Asp Leu Phe Cys Cys Pro Glu Cys Asp Thr
        675                 680                 685 aga gtc aca agt caa tgt tta gac caa aat ggt cac aag ctg tat cga    2112
Arg Val Thr Ser Gln Cys Leu Asp Gln Asn Gly His Lys Leu Tyr Arg
690                 695                 700 agt gga gac aat tgg acc cat agc tgt cag cag tgt cgg tgt ctg gaa    2160
Ser Gly Asp Asn Trp Thr His Ser Cys Gln Gln Cys Arg Cys Leu Glu
705                 710                 715                 720 gga gag gta gat tgc tgg cca ctc act tgc ccc aac ttg agc tgt gag    2208
Gly Glu Val Asp Cys Trp Pro Leu Thr Cys Pro Asn Leu Ser Cys Glu
                725                 730                 735 tat aca gct atc tta gaa ggg gaa tgt tgt ccc cgc tgt gtc agt gac    2256
Tyr Thr Ala Ile Leu Glu Gly Glu Cys Cys Pro Arg Cys Val Ser Asp
            740                 745                 750 ccc tgc cta gct gat aac atc acc tat gac atc aga aaa act tgc ctg    2304
Pro Cys Leu Ala Asp Asn Ile Thr Tyr Asp Ile Arg Lys Thr Cys Leu
        755                 760                 765 gac agc tat ggt gtt tca cgg ctt agt ggc tca gtg tgg acg atg gct    2352
Asp Ser Tyr Gly Val Ser Arg Leu Ser Gly Ser Val Trp Thr Met Ala
770                 775                 780 gga tct ccc tgc aca acc tgt aaa tgc aag aat gga aga gtc tgt tgt    2400
Gly Ser Pro Cys Thr Thr Cys Lys Cys Lys Asn Gly Arg Val Cys Cys
785                 790                 795                 800 tct gtg gat ttt gag tgt ctt caa aat aat tga                        2433
Ser Val Asp Phe Glu Cys Leu Gln Asn Asn
                805                 810

<210> SEQ ID NO 2
<211> LENGTH: 810
<212> TYPE: PRT
<213> ORGANISM: Homo sapiens

<400> SEQUENCE: 2

Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
            20                  25                  30

Val Thr Glu Leu Asp Leu Val Asn Thr Thr Leu Gly Val Ala Gln Val
        35                  40                  45

Ser Gly Met His Asn Ala Ser Lys Ala Phe Leu Phe Gln Asp Ile Glu
    50                  55                  60
```

```
Arg Glu Ile His Ala Ala Pro His Val Ser Glu Lys Leu Ile Gln Leu
 65                  70                  75                  80

Phe Gln Asn Lys Ser Glu Phe Thr Ile Leu Ala Thr Val Gln Gln Lys
                 85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp His Cys Arg Asn Cys Thr Cys Lys Ser Gly Ala Val Glu Cys
290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
            340                 345                 350

Cys Arg Glu Cys Arg Gly Gly Val Leu Val Lys Ile Thr Glu Met Cys
        355                 360                 365

Pro Pro Leu Asn Cys Ser Glu Lys Asp His Ile Leu Pro Glu Asn Gln
370                 375                 380

Cys Cys Arg Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
                405                 410                 415

Glu Cys Lys Ser Gly Tyr Ile Ser Val Gln Gly Asp Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Val Pro
450                 455                 460

Gly Tyr Ile Arg Val Asp Asp Phe Ser Cys Thr Glu His Asp Glu Cys
465                 470                 475                 480

Gly Ser Gly Gln His Asn Cys Asp Glu Asn Ala Ile Cys Thr Asn Thr
```

|   |   |   |   | 485 |   |   |   | 490 |   |   |   | 495 |   |   |
|---|---|---|---|---|---|---|---|---|---|---|---|---|---|---|---|

Val Gln Gly His Ser Cys Thr Cys Lys Pro Gly Tyr Val Gly Asn Gly
            500                 505                 510

Thr Ile Cys Arg Ala Phe Cys Glu Glu Gly Cys Arg Tyr Gly Gly Thr
            515                 520                 525

Cys Val Ala Pro Asn Lys Cys Val Cys Pro Ser Gly Phe Thr Gly Ser
        530                 535                 540

His Cys Glu Lys Asp Ile Asp Glu Cys Ser Glu Gly Ile Ile Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
            595                 600                 605

Asn Asp Ser Ala Cys Ile Asn Leu Ala Gly Gly Phe Asp Cys Leu Cys
        610                 615                 620

Pro Ser Gly Pro Ser Cys Ser Gly Asp Cys Pro His Glu Gly Gly Leu
625                 630                 635                 640

Lys His Asn Gly Gln Val Trp Thr Leu Lys Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Ser Ala Asp Leu Phe Cys Cys Pro Glu Cys Asp Thr
        675                 680                 685

Arg Val Thr Ser Gln Cys Leu Asp Gln Asn Gly His Lys Leu Tyr Arg
690                 695                 700

Ser Gly Asp Asn Trp Thr His Ser Cys Gln Gln Cys Arg Cys Leu Glu
705                 710                 715                 720

Gly Glu Val Asp Cys Trp Pro Leu Thr Cys Pro Asn Leu Ser Cys Glu
                725                 730                 735

Tyr Thr Ala Ile Leu Glu Gly Glu Cys Cys Pro Arg Cys Val Ser Asp
            740                 745                 750

Pro Cys Leu Ala Asp Asn Ile Thr Tyr Asp Ile Arg Lys Thr Cys Leu
        755                 760                 765

Asp Ser Tyr Gly Val Ser Arg Leu Ser Gly Ser Val Trp Thr Met Ala
770                 775                 780

Gly Ser Pro Cys Thr Thr Cys Lys Cys Lys Asn Gly Arg Val Cys Cys
785                 790                 795                 800

Ser Val Asp Phe Glu Cys Leu Gln Asn Asn
                805                 810

```
<210> SEQ ID NO 3
<211> LENGTH: 2433
<212> TYPE: DNA
<213> ORGANISM: Rattus norvegicus
<220> FEATURE:
<221> NAME/KEY: CDS
<222> LOCATION: (1)..(2433)

<400> SEQUENCE: 3
``` atg ccg atg gat gtg att tta gtt ttg tgg ttc tgt gta tgc acc gcc     48
Met Pro Met Asp Val Ile Leu Val Leu Trp Phe Cys Val Cys Thr Ala
1               5                   10                  15 agg aca gtg ttg ggc ttt ggg atg gac cct gac ctt cag ctg gac atc     96
Arg Thr Val Leu Gly Phe Gly Met Asp Pro Asp Leu Gln Leu Asp Ile

```
                        20                  25                  30
atc tca gag ctc gac ctg gtg aac acc acc ctg gga gtc acg cag gtg      144
Ile Ser Glu Leu Asp Leu Val Asn Thr Thr Leu Gly Val Thr Gln Val
         35                  40                  45 gct gga ctg cac aac gcc agt aaa gca ttt cta ttt caa gat gta cag      192
Ala Gly Leu His Asn Ala Ser Lys Ala Phe Leu Phe Gln Asp Val Gln
 50                  55                  60 aga gag atc cat tcg gcc cct cac gtg agt gag aag ctg atc cag cta      240
Arg Glu Ile His Ser Ala Pro His Val Ser Glu Lys Leu Ile Gln Leu
65                  70                  75                  80 ttc cgg aat aag agc gag ttc acc ttt ttg gct aca gtg cag cag aaa      288
Phe Arg Asn Lys Ser Glu Phe Thr Phe Leu Ala Thr Val Gln Gln Lys
                 85                  90                  95 cca tcc acc tca ggg gtg ata ctg tcc atc cgg gag ctg gag cac agc      336
Pro Ser Thr Ser Gly Val Ile Leu Ser Ile Arg Glu Leu Glu His Ser
            100                 105                 110 tat ttt gaa ctg gag agc agt ggc cca aga gaa gag ata cgc tac cat      384
Tyr Phe Glu Leu Glu Ser Ser Gly Pro Arg Glu Glu Ile Arg Tyr His
        115                 120                 125 tac ata cat ggt gga aag ccc agg act gag gcc ctt ccc tac cgc atg      432
Tyr Ile His Gly Gly Lys Pro Arg Thr Glu Ala Leu Pro Tyr Arg Met
    130                 135                 140 gca gac gga caa tgg cac aag gtc gcg ctg tca gtg agc gcc tct cac      480
Ala Asp Gly Gln Trp His Lys Val Ala Leu Ser Val Ser Ala Ser His
145                 150                 155                 160 ctc ctg ctc cac atc gac tgc aat agg att tac gag cgt gtg ata gac      528
Leu Leu Leu His Ile Asp Cys Asn Arg Ile Tyr Glu Arg Val Ile Asp
                165                 170                 175 cct ccg gag acc aac ctt cct cca gga agc aat ctg tgg ctt ggg caa      576
Pro Pro Glu Thr Asn Leu Pro Pro Gly Ser Asn Leu Trp Leu Gly Gln
            180                 185                 190 cgt aac caa aag cat ggc ttt ttc aaa gga atc atc caa gat ggt aag      624
Arg Asn Gln Lys His Gly Phe Phe Lys Gly Ile Ile Gln Asp Gly Lys
        195                 200                 205 atc atc ttc atg ccg aat ggt ttc atc aca cag tgt ccc aac ctc aat      672
Ile Ile Phe Met Pro Asn Gly Phe Ile Thr Gln Cys Pro Asn Leu Asn
    210                 215                 220 cgc act tgc cca aca tgc agt gac ttc ctg agc ctg gtt caa gga ata      720
Arg Thr Cys Pro Thr Cys Ser Asp Phe Leu Ser Leu Val Gln Gly Ile
225                 230                 235                 240 atg gat ttg caa gag ctt ttg gcc aag atg act gca aaa ctg aat tat      768
Met Asp Leu Gln Glu Leu Leu Ala Lys Met Thr Ala Lys Leu Asn Tyr
                245                 250                 255 gca gag acg aga ctt ggt caa ctg gaa aat tgc cac tgt gag aag acc      816
Ala Glu Thr Arg Leu Gly Gln Leu Glu Asn Cys His Cys Glu Lys Thr
            260                 265                 270 tgc caa gtg agt ggg ctg ctc tac agg gac caa gac tcc tgg gtg gat      864
Cys Gln Val Ser Gly Leu Leu Tyr Arg Asp Gln Asp Ser Trp Val Asp
        275                 280                 285 ggt gac aac tgt ggg aac tgc acg tgc aaa agt ggt gcc gtg gag tgc      912
Gly Asp Asn Cys Gly Asn Cys Thr Cys Lys Ser Gly Ala Val Glu Cys
    290                 295                 300 cgc agg atg tcc tgt ccc ccg ctc aac tgt tcc ccg gac tca ctt cct      960
Arg Arg Met Ser Cys Pro Pro Leu Asn Cys Ser Pro Asp Ser Leu Pro
305                 310                 315                 320 gtg cac att tcc ggc cag tgt tgt aaa gtt tgc aga cca aaa tgt atc     1008
Val His Ile Ser Gly Gln Cys Cys Lys Val Cys Arg Pro Lys Cys Ile
                325                 330                 335 tat gga gga aaa gtt ctt gct gag ggc cag cgg att tta acc aag acc     1056
Tyr Gly Gly Lys Val Leu Ala Glu Gly Gln Arg Ile Leu Thr Lys Thr
```

```
                Tyr Gly Gly Lys Val Leu Ala Glu Gly Gln Arg Ile Leu Thr Lys Thr
                                340                 345                 350 tgc cgg gaa tgt cga ggt gga gtc ttg gta aaa atc aca gaa gct tgc        1104
Cys Arg Glu Cys Arg Gly Gly Val Leu Val Lys Ile Thr Glu Ala Cys
            355                 360                 365 cct cct ttg aac tgc tca gca aag gat cat att ctt cca gag aat cag        1152
Pro Pro Leu Asn Cys Ser Ala Lys Asp His Ile Leu Pro Glu Asn Gln
370                 375                 380 tgc tgc agg gtc tgc cca ggt cat aac ttc tgt gca gaa gca cct aag        1200
Cys Cys Arg Val Cys Pro Gly His Asn Phe Cys Ala Glu Ala Pro Lys
385                 390                 395                 400 tgc gga gaa aac tcg gaa tgc aaa aat tgg aat aca aaa gca acc tgt        1248
Cys Gly Glu Asn Ser Glu Cys Lys Asn Trp Asn Thr Lys Ala Thr Cys
                405                 410                 415 gag tgc aag aat gga tac atc tct gtc cag ggc aac tct gca tac tgt        1296
Glu Cys Lys Asn Gly Tyr Ile Ser Val Gln Gly Asn Ser Ala Tyr Cys
            420                 425                 430 gaa gat att gat gag tgt gca gct aaa atg cac tat tgt cat gcc aac        1344
Glu Asp Ile Asp Glu Cys Ala Ala Lys Met His Tyr Cys His Ala Asn
        435                 440                 445 acc gtg tgt gtc aac ttg ccg ggg ttg tat cgc tgt gac tgc gtc cca        1392
Thr Val Cys Val Asn Leu Pro Gly Leu Tyr Arg Cys Asp Cys Val Pro
450                 455                 460 ggg tac atc cgt gtg gat gac ttc tct tgt acg gag cat gat gat tgt        1440
Gly Tyr Ile Arg Val Asp Asp Phe Ser Cys Thr Glu His Asp Asp Cys
465                 470                 475                 480 ggc agc gga caa cac aac tgc gac aaa aat gcc atc tgt acc aac aca        1488
Gly Ser Gly Gln His Asn Cys Asp Lys Asn Ala Ile Cys Thr Asn Thr
                485                 490                 495 gtc cag gga cac agc tgc acc tgc cag ccg ggt tac gtg gga aat ggc        1536
Val Gln Gly His Ser Cys Thr Cys Gln Pro Gly Tyr Val Gly Asn Gly
            500                 505                 510 acc atc tgc aaa gca ttc tgt gaa gag ggt tgc aga tac gga ggt acc        1584
Thr Ile Cys Lys Ala Phe Cys Glu Glu Gly Cys Arg Tyr Gly Gly Thr
        515                 520                 525 tgt gtg gct cct aac aag tgt gtc tgt cct tct gga ttc acg gga agc        1632
Cys Val Ala Pro Asn Lys Cys Val Cys Pro Ser Gly Phe Thr Gly Ser
530                 535                 540 cac tgt gag aaa gat att gat gaa tgc gca gag gga ttc gtt gaa tgc        1680
His Cys Glu Lys Asp Ile Asp Glu Cys Ala Glu Gly Phe Val Glu Cys
545                 550                 555                 560 cac aac tac tcc cgc tgt gtt aac ctg cca ggg tgg tac cac tgt gag        1728
His Asn Tyr Ser Arg Cys Val Asn Leu Pro Gly Trp Tyr His Cys Glu
                565                 570                 575 tgc aga agc ggt ttc cat gac gat ggg acc tac tca ctg tcc ggg gag        1776
Cys Arg Ser Gly Phe His Asp Asp Gly Thr Tyr Ser Leu Ser Gly Glu
            580                 585                 590 tcc tgc att gat atc gat gaa tgt gcc tta aga act cac act tgt tgg        1824
Ser Cys Ile Asp Ile Asp Glu Cys Ala Leu Arg Thr His Thr Cys Trp
        595                 600                 605 aat gac tct gcc tgc atc aac tta gca gga gga ttt gac tgc ctg tgt        1872
Asn Asp Ser Ala Cys Ile Asn Leu Ala Gly Gly Phe Asp Cys Leu Cys
610                 615                 620 ccc tct ggg ccc tcc tgc tct ggt gac tgt ccc cac gaa gga ggg ctg        1920
Pro Ser Gly Pro Ser Cys Ser Gly Asp Cys Pro His Glu Gly Gly Leu
625                 630                 635                 640 aag cat aat ggg cag gtg tgg att ctg aga gaa gac agg tgt tca gtc        1968
Lys His Asn Gly Gln Val Trp Ile Leu Arg Glu Asp Arg Cys Ser Val
                645                 650                 655
```

```
tgt tcc tgc aag gat ggg aag ata ttc tgc cgg cgg aca gct tgt gat      2016
Cys Ser Cys Lys Asp Gly Lys Ile Phe Cys Arg Arg Thr Ala Cys Asp
            660                 665                 670 tgc cag aat cca aat gtt gac ctt ttt tgc tgc cca gag tgc gat acc      2064
Cys Gln Asn Pro Asn Val Asp Leu Phe Cys Cys Pro Glu Cys Asp Thr
        675                 680                 685 agg gtc acc agc caa tgt tta gat caa agt gga cag aag ctc tat cga      2112
Arg Val Thr Ser Gln Cys Leu Asp Gln Ser Gly Gln Lys Leu Tyr Arg
    690                 695                 700 agt gga gac aac tgg acc cac agc tgc cag cag tgc cga tgt ctg gaa      2160
Ser Gly Asp Asn Trp Thr His Ser Cys Gln Gln Cys Arg Cys Leu Glu
705                 710                 715                 720 gga gag gca gac tgc tgg cct ctg gct tgc cct agt ttg ggc tgt gaa      2208
Gly Glu Ala Asp Cys Trp Pro Leu Ala Cys Pro Ser Leu Gly Cys Glu
                725                 730                 735 tac aca gcc atg ttt gaa ggg gag tgt tgt ccc cga tgt gtc agt gac      2256
Tyr Thr Ala Met Phe Glu Gly Glu Cys Cys Pro Arg Cys Val Ser Asp
            740                 745                 750 ccc tgc ctg gct ggt aat att gcc tat gac atc aga aaa act tgc ctg      2304
Pro Cys Leu Ala Gly Asn Ile Ala Tyr Asp Ile Arg Lys Thr Cys Leu
        755                 760                 765 gac agc ttt ggt gtt tcg agg ctg agc gga gcc gtg tgg aca atg gct      2352
Asp Ser Phe Gly Val Ser Arg Leu Ser Gly Ala Val Trp Thr Met Ala
    770                 775                 780 gga tct cct tgt aca acc tgc aaa tgc aag aat ggg aga gtc tgc tgc      2400
Gly Ser Pro Cys Thr Thr Cys Lys Cys Lys Asn Gly Arg Val Cys Cys
785                 790                 795                 800 tct gtg gat ctg gag tgt att gag aat aac tga                          2433
Ser Val Asp Leu Glu Cys Ile Glu Asn Asn
                805                 810

<210> SEQ ID NO 4
<211> LENGTH: 810
<212> TYPE: PRT
<213> ORGANISM: Rattus norvegicus

<400> SEQUENCE: 4

Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Leu Asp Ile
            20                  25                  30

Ile Ser Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Ile Asp Cys Asn Arg Ile Tyr Glu Arg Val Ile Asp
```

```
              165                 170                 175
Pro Pro Glu Thr Asn Leu Pro Pro Gly Ser Asn Leu Trp Leu Gly Gln
                180                 185                 190

Arg Asn Gln Lys His Gly Phe Phe Lys Gly Ile Ile Gln Asp Gly Lys
            195                 200                 205

Ile Ile Phe Met Pro Asn Gly Phe Ile Thr Gln Cys Pro Asn Leu Asn
        210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Gly Asn Cys Thr Cys Lys Ser Gly Ala Val Glu Cys
        290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
            340                 345                 350

Cys Arg Glu Cys Arg Gly Gly Val Leu Val Lys Ile Thr Glu Ala Cys
        355                 360                 365

Pro Pro Leu Asn Cys Ser Ala Lys Asp His Ile Leu Pro Glu Asn Gln
    370                 375                 380

Cys Cys Arg Val Cys Pro Gly His Asn Phe Cys Ala Glu Ala Pro Lys
385                 390                 395                 400

Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asn Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Val Pro
    450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
            500                 505                 510

Thr Ile Cys Lys Ala Phe Cys Glu Glu Gly Cys Arg Tyr Gly Gly Thr
        515                 520                 525

Cys Val Ala Pro Asn Lys Cys Val Cys Pro Ser Gly Phe Thr Gly Ser
    530                 535                 540

His Cys Glu Lys Asp Ile Asp Glu Cys Ala Glu Gly Phe Val Glu Cys
545                 550                 555                 560

His Asn Tyr Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590
```

```
Ser Cys Ile Asp Ile Asp Glu Cys Ala Leu Arg Thr His Thr Cys Trp
        595                 600                 605
Asn Asp Ser Ala Cys Ile Asn Leu Ala Gly Gly Phe Asp Cys Leu Cys
    610                 615                 620
Pro Ser Gly Pro Ser Cys Ser Gly Asp Cys Pro His Glu Gly Leu
625                 630                 635                 640
Lys His Asn Gly Gln Val Trp Ile Leu Arg Glu Asp Arg Cys Ser Val
                645                 650                 655
Cys Ser Cys Lys Asp Gly Lys Ile Phe Cys Arg Arg Thr Ala Cys Asp
                660                 665                 670
Cys Gln Asn Pro Asn Val Asp Leu Phe Cys Cys Pro Glu Cys Asp Thr
            675                 680                 685
Arg Val Thr Ser Gln Cys Leu Asp Gln Ser Gly Gln Lys Leu Tyr Arg
    690                 695                 700
Ser Gly Asp Asn Trp Thr His Ser Cys Gln Gln Cys Arg Cys Leu Glu
705                 710                 715                 720
Gly Glu Ala Asp Cys Trp Pro Leu Ala Cys Pro Ser Leu Gly Cys Glu
                725                 730                 735
Tyr Thr Ala Met Phe Glu Gly Cys Cys Pro Arg Cys Val Ser Asp
            740                 745                 750
Pro Cys Leu Ala Gly Asn Ile Ala Tyr Asp Ile Arg Lys Thr Cys Leu
        755                 760                 765
Asp Ser Phe Gly Val Ser Arg Leu Ser Gly Ala Val Trp Thr Met Ala
    770                 775                 780
Gly Ser Pro Cys Thr Thr Cys Lys Cys Lys Asn Gly Arg Val Cys Cys
785                 790                 795                 800
Ser Val Asp Leu Glu Cys Ile Glu Asn Asn
                805                 810

<210> SEQ ID NO 5
<211> LENGTH: 2433
<212> TYPE: DNA
<213> ORGANISM: Mus musculus

<400> SEQUENCE: 5
atgccgatgg atgtgatttt agttttgtgg ttctgtgtgt gcaccgccag gacagtgctg     60
ggctttggga tggaccctga ccttcagatg gacatcatca ctgaacttga ccttgtgaac    120
accaccctgg gcgtcactca ggtggctgga ctacacaatg ccagtaaggc atttctgttt    180
caagatgtac agagagagat ccactcagcc cctcatgtga gtgagaagct gatccagcta    240
ttccggaata agagtgagtt tacctttttg gctacagtgc agcagaagcc gtccacctca    300
ggggtgatac tgtcgatccg ggagctggaa cacagctatt ttgaactgga gagcagtggc    360
ccaagagaag agatacgcta tcattacatc catggcggca agcccaggac tgaggccctt    420
ccctaccgca tggccgatgg acagtggcac aaggtcgcgc tgtctgtgag cgcctctcac    480
ctcctactcc atgtcgactg caataggatt tatgagcgtg tgatagatcc tccggagacc    540
aaccttcctc aggaagcaa tctatggctt gggcaacgta atcaaaagca tggcttttc    600
aaaggaatca tccaagatgg caagatcatc ttcatgccga acggcttcat cacacagtgc    660
cccaacctaa atcgcacttg cccaacatgc agtgatttcc tgagcctggt tcaaggaata    720
atggatttgc aagagctttt ggccaagatg actgcaaaac tgaattatgc agagacgaga    780
cttggtcaac tggaaaattg ccactgtgag aagacctgcc aagtgagtgg gctgctctac    840
```

```
agggaccaag actcctgggt agatggtgac aactgcagga actgcacatg caaaagtggt    900
gctgtggagt gccgaaggat gtcctgtccc ccactcaact gttccccaga ctcacttcct    960
gtgcatattt ctggccaatg ttgtaaagtt tgcagaccaa aatgtatcta tggaggaaaa   1020
gttcttgctg agggccagcg gattttaacc aagacctgcc gggaatgtcg aggtggagtc   1080
ttggtaaaaa tcacagaagc ttgccctcct ttgaactgct cagagaagga tcatattctt   1140
ccggagaacc agtgctgcag ggtctgccga ggtcataact tctgtgcaga agcacctaag   1200
tgtggagaaa actcggaatg caaaaattgg aatacaaaag cgacttgtga gtgcaagaat   1260
ggatacatct ctgtccaggg caactctgca tactgtgaag atatcgatga gtgtgcagca   1320
aagatgcact actgtcatgc aacacggtg tgtgtcaact gccggggtt atatcgctgt    1380
gactgcatcc aggatacat ccgtgtggat gacttctctt gtacgagca tgatgattgt    1440
ggcagcggac aacacaactg tgacaaaaat gccatctgta ccaacacagt ccagggacac   1500
agctgtacct gccagccagg ctacgtggga atggtactg tctgcaaagc attctgtgaa   1560
gagggttgca gatacggagg tacctgtgtg ccccctaaca aatgtgtctg tccttctgga   1620
ttcacaggaa gccactgtga gaaagatatt gatgaatgtg cagagggatt cgttgagtgc   1680
cacaaccact cccgctgcgt taaccttcca gggtggtacc actgtgagtg cagaagcggt   1740
ttccatgacg atgggaccta ttcactgtcc ggggagtcct gcattgatat tgatgaatgt   1800
gccttaagaa ctcacacttg ttggaatgac tctgcctgca tcaacttagc aggaggattt   1860
gactgcctgt gtccctctgg gccctcctgc tctggtgact gtccccacga agggggctg    1920
aagcataatg gcaggtgtg gattctgaga aagacaggt gttcagtctg ttcctgtaag    1980
gatgggaaga tattctgccg gcggacagct tgtgattgcc agaatccaaa tgttgaccttt  2040
ttctgctgcc cagagtgtga caccagggtc actagccaat gtttagatca aagcggacag   2100
aagctctatc gaagtggaga caactggacc cacagctgcc agcagtgccg atgtctggaa   2160
ggagaggcag actgctggcc tctagcttgc cctagtttga gctgtgaata cacagccatc   2220
tttgaaggag agtgttgtcc ccgctgtgtc agtgaccct gcctggctga taatattgcc   2280
tatgacatca gaaaaacttg cctggacagc tctggtattt cgaggctgag cggcgcagtg   2340
tggacaatgg ctggatctcc ctgtacaacc tgtcaatgca agaatgggag agtctgctgc   2400
tctgtggatc tggtgtgtct tgagaataac tga                                2433

<210> SEQ ID NO 6
<211> LENGTH: 810
<212> TYPE: PRT
<213> ORGANISM: Mus musculus

<400> SEQUENCE: 6

Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Met Asp Ile
            20                  25                  30

Ile Thr Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95
```

```
Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
            340                 345                 350

Cys Arg Glu Cys Arg Gly Gly Val Leu Val Lys Ile Thr Glu Ala Cys
        355                 360                 365

Pro Pro Leu Asn Cys Ser Glu Lys Asp His Ile Leu Pro Glu Asn Gln
    370                 375                 380

Cys Cys Arg Val Cys Arg Gly His Asn Phe Cys Ala Glu Ala Pro Lys
385                 390                 395                 400

Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asn Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Ile Pro
    450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
            500                 505                 510
```

```
Thr Val Cys Lys Ala Phe Cys Glu Glu Gly Cys Arg Tyr Gly Gly Thr
            515                 520                 525

Cys Val Ala Pro Asn Lys Cys Val Cys Pro Ser Gly Phe Thr Gly Ser
    530                 535                 540

His Cys Glu Lys Asp Ile Asp Glu Cys Ala Glu Gly Phe Val Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
    610                 615                 620

Pro Ser Gly Pro Ser Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
        675                 680                 685

Arg Val Thr Ser Gln Cys Leu Asp Gln Ser Gly Gln Lys Leu Tyr Arg
    690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Ser Cys Glu
                725                 730                 735

Tyr Thr Ala Ile Phe Glu Gly Glu Cys Cys Pro Arg Cys Val Ser Asp
            740                 745                 750

Pro Cys Leu Ala Asp Asn Ile Ala Tyr Asp Ile Arg Lys Thr Cys Leu
        755                 760                 765

Asp Ser Ser Gly Ile Ser Arg Leu Ser Gly Ala Val Trp Thr Met Ala
    770                 775                 780

Gly Ser Pro Cys Thr Thr Cys Gln Cys Lys Asn Gly Arg Val Cys Cys
785                 790                 795                 800

Ser Val Asp Leu Val Cys Leu Glu Asn Asn
                805                 810

<210> SEQ ID NO 7
<211> LENGTH: 2451
<212> TYPE: DNA
<213> ORGANISM: Homo sapiens
<220> FEATURE:
<221> NAME/KEY: CDS
<222> LOCATION: (1)..(2448)

<400> SEQUENCE: 7 atg gag tct cgg gtc tta ctg aga aca ttc tgt ttg atc ttc ggt ctc     48
Met Glu Ser Arg Val Leu Leu Arg Thr Phe Cys Leu Ile Phe Gly Leu
1               5                   10                  15 gga gca gtt tgg ggg ctt ggt gtg gac cct tcc cta cag att gac gtc     96
Gly Ala Val Trp Gly Leu Gly Val Asp Pro Ser Leu Gln Ile Asp Val
            20                  25                  30 tta aca gag tta gaa ctt ggg gag tcc acg acc gga gtg cgt cag gtc    144
Leu Thr Glu Leu Glu Leu Gly Glu Ser Thr Thr Gly Val Arg Gln Val
        35                  40                  45
```

| | | |
|---|---|---|
| ccg ggg ctg cat aat ggg acg aaa gcc ttt ctc ttt caa gat act ccc<br>Pro Gly Leu His Asn Gly Thr Lys Ala Phe Leu Phe Gln Asp Thr Pro<br>50                      55                      60 | | 192 |
| aga agc ata aaa gca tcc act gct aca gct gaa cag ttt ttt cag aag<br>Arg Ser Ile Lys Ala Ser Thr Ala Thr Ala Glu Gln Phe Phe Gln Lys<br>65                      70                      75                      80 | | 240 |
| ctg aga aat aaa cat gaa ttt act att ttg gtg acc cta aaa cag acc<br>Leu Arg Asn Lys His Glu Phe Thr Ile Leu Val Thr Leu Lys Gln Thr<br>                      85                      90                      95 | | 288 |
| cac tta aat tca gga gtt att ctc tca att cac cac ttg gat cac agg<br>His Leu Asn Ser Gly Val Ile Leu Ser Ile His His Leu Asp His Arg<br>                100                      105                      110 | | 336 |
| tac ctg gaa ctg gaa agt agt ggc cat cgg aat gaa gtc aga ctg cat<br>Tyr Leu Glu Leu Glu Ser Ser Gly His Arg Asn Glu Val Arg Leu His<br>                115                      120                      125 | | 384 |
| tac cgc tca ggc agt cac cgc cct cac aca gaa gtg ttt cct tac att<br>Tyr Arg Ser Gly Ser His Arg Pro His Thr Glu Val Phe Pro Tyr Ile<br>130                      135                      140 | | 432 |
| ttg gct gat gac aag tgg cac aag ctc tcc tta gcc atc agt gct tcc<br>Leu Ala Asp Asp Lys Trp His Lys Leu Ser Leu Ala Ile Ser Ala Ser<br>145                      150                      155                      160 | | 480 |
| cat ttg att tta cac att gac tgc aat aaa att tat gaa agg gta gta<br>His Leu Ile Leu His Ile Asp Cys Asn Lys Ile Tyr Glu Arg Val Val<br>                165                      170                      175 | | 528 |
| gaa aag ccc tcc aca gac ttg cct cta ggc aca aca ttt tgg cta gga<br>Glu Lys Pro Ser Thr Asp Leu Pro Leu Gly Thr Thr Phe Trp Leu Gly<br>                  180                      185                      190 | | 576 |
| cag aga aat aat gcg cat gga tat ttt aag ggt ata atg caa gat gtc<br>Gln Arg Asn Asn Ala His Gly Tyr Phe Lys Gly Ile Met Gln Asp Val<br>                195                      200                      205 | | 624 |
| caa tta ctt gtc atg ccc cag gga ttt att gct cag tgc cca gat ctt<br>Gln Leu Leu Val Met Pro Gln Gly Phe Ile Ala Gln Cys Pro Asp Leu<br>210                      215                      220 | | 672 |
| aat cgc acc tgt cca act tgc aat gac ttc cat gga ctt gtg cag aaa<br>Asn Arg Thr Cys Pro Thr Cys Asn Asp Phe His Gly Leu Val Gln Lys<br>225                      230                      235                      240 | | 720 |
| atc atg gag cta cag gat att tta gcc aaa aca tca gcc aag ctg tct<br>Ile Met Glu Leu Gln Asp Ile Leu Ala Lys Thr Ser Ala Lys Leu Ser<br>                      245                      250                      255 | | 768 |
| cga gct gaa cag cga atg aat aga ttg gat cag tgc tat tgt gaa agg<br>Arg Ala Glu Gln Arg Met Asn Arg Leu Asp Gln Cys Tyr Cys Glu Arg<br>                260                      265                      270 | | 816 |
| act tgc acc atg aag gga acc acc tac cga gaa ttt gag tcc tgg ata<br>Thr Cys Thr Met Lys Gly Thr Thr Tyr Arg Glu Phe Glu Ser Trp Ile<br>                275                      280                      285 | | 864 |
| gac ggc tgt aag aac tgc aca tgc ctg aat gga acc atc cag tgt gaa<br>Asp Gly Cys Lys Asn Cys Thr Cys Leu Asn Gly Thr Ile Gln Cys Glu<br>290                      295                      300 | | 912 |
| act cta atc tgc cca aat cct gac tgc cca ctt aag tcg gct ctt gcg<br>Thr Leu Ile Cys Pro Asn Pro Asp Cys Pro Leu Lys Ser Ala Leu Ala<br>305                      310                      315                      320 | | 960 |
| tat gtg gat ggc aaa tgc tgt aag gaa tgc aaa tcg ata tgc caa ttt<br>Tyr Val Asp Gly Lys Cys Cys Lys Glu Cys Lys Ser Ile Cys Gln Phe<br>                      325                      330                      335 | | 1008 |
| caa gga cga acc tac ttt gaa gga gaa aga aat aca gtc tat tcc tct<br>Gln Gly Arg Thr Tyr Phe Glu Gly Glu Arg Asn Thr Val Tyr Ser Ser<br>                      340                      345                      350 | | 1056 |
| tct gga gta tgt gtt ctc tat gag tgc aag gac cag acc atg aaa ctt<br>Ser Gly Val Cys Val Leu Tyr Glu Cys Lys Asp Gln Thr Met Lys Leu | | 1104 |

|                                                                                                 |      |
|-------------------------------------------------------------------------------------------------|------|
| gtt gag agt tca ggc tgt cca gct ttg gat tgt cca gag tct cat cag<br>Val Glu Ser Ser Gly Cys Pro Ala Leu Asp Cys Pro Glu Ser His Gln<br>370                  375                  380 | 1152 |
| ata acc ttg tct cac agc tgt tgc aaa gtt tgt aaa ggt tat gac ttt<br>Ile Thr Leu Ser His Ser Cys Cys Lys Val Cys Lys Gly Tyr Asp Phe<br>385                  390                395              400 | 1200 |
| tgt tct gaa agg cat aac tgc atg gag aat tcc atc tgc aga aat ctg<br>Cys Ser Glu Arg His Asn Cys Met Glu Asn Ser Ile Cys Arg Asn Leu<br>                  405                410                415 | 1248 |
| aat gac agg gct gtt tgt agc tgt cga gat ggt ttt agg gct ctt cga<br>Asn Asp Arg Ala Val Cys Ser Cys Arg Asp Gly Phe Arg Ala Leu Arg<br>420                  425                430 | 1296 |
| gag gat aat gcc tac tgt gaa gac atc gat gag tgt gct gaa ggg cgc<br>Glu Asp Asn Ala Tyr Cys Glu Asp Ile Asp Glu Cys Ala Glu Gly Arg<br>435                  440                445 | 1344 |
| cat tac tgt cgt gaa aat aca atg tgt gtc aac acc ccg ggt tct ttt<br>His Tyr Cys Arg Glu Asn Thr Met Cys Val Asn Thr Pro Gly Ser Phe<br>450                  455                460 | 1392 |
| atg tgc atc tgc aaa act gga tac atc aga att gat gat tat tca tgt<br>Met Cys Ile Cys Lys Thr Gly Tyr Ile Arg Ile Asp Asp Tyr Ser Cys<br>465                  470                475              480 | 1440 |
| aca gaa cat gat gag tgt atc aca aat cag cac aac tgt gat gaa aat<br>Thr Glu His Asp Glu Cys Ile Thr Asn Gln His Asn Cys Asp Glu Asn<br>                  485                490              495 | 1488 |
| gct tta tgc ttc aac act gtt gga gga cac aac tgt gtt tgc aag ccg<br>Ala Leu Cys Phe Asn Thr Val Gly Gly His Asn Cys Val Cys Lys Pro<br>500                  505                510 | 1536 |
| ggc tat aca ggg aat gga acg aca tgc aaa gca ttt tgc aaa gat ggc<br>Gly Tyr Thr Gly Asn Gly Thr Thr Cys Lys Ala Phe Cys Lys Asp Gly<br>515                  520                525 | 1584 |
| tgt agg aat gga gga gcc tgt att gcc gct aat gtg tgt gcc tgc cca<br>Cys Arg Asn Gly Gly Ala Cys Ile Ala Ala Asn Val Cys Ala Cys Pro<br>530                  535                540 | 1632 |
| caa ggc ttc act gga ccc agc tgt gaa acg gac att gat gaa tgc tct<br>Gln Gly Phe Thr Gly Pro Ser Cys Glu Thr Asp Ile Asp Glu Cys Ser<br>545                  550                555              560 | 1680 |
| gat ggt ttt gtt caa tgt gac agt cgt gct aat tgc att aac ctg cct<br>Asp Gly Phe Val Gln Cys Asp Ser Arg Ala Asn Cys Ile Asn Leu Pro<br>                  565                570              575 | 1728 |
| gga tgg tac cac tgt gag tgc aga gat ggc tac cat gac aat ggg atg<br>Gly Trp Tyr His Cys Glu Cys Arg Asp Gly Tyr His Asp Asn Gly Met<br>580                  585                590 | 1776 |
| ttt tca cca agt gga gaa tcg tgt gaa gat att gat gag tgt ggg acc<br>Phe Ser Pro Ser Gly Glu Ser Cys Glu Asp Ile Asp Glu Cys Gly Thr<br>595                  600                605 | 1824 |
| ggg agg cac agc tgt gcc aat gat acc att tgc ttc aat ttg gat ggc<br>Gly Arg His Ser Cys Ala Asn Asp Thr Ile Cys Phe Asn Leu Asp Gly<br>610                  615                620 | 1872 |
| gga tat gat tgt cga tgt cct cat gga aag aat tgc aca ggg gac tgc<br>Gly Tyr Asp Cys Arg Cys Pro His Gly Lys Asn Cys Thr Gly Asp Cys<br>625                  630                635              640 | 1920 |
| atc cat gat gga aaa gtt aag cac aat ggt cag att tgg gtg ttg gaa<br>Ile His Asp Gly Lys Val Lys His Asn Gly Gln Ile Trp Val Leu Glu<br>                  645                650              655 | 1968 |
| aat gac agg tgc tct gtg tgc tca tgt cag aat gga ttc gtt atg tgt<br>Asn Asp Arg Cys Ser Val Cys Ser Cys Gln Asn Gly Phe Val Met Cys<br>660                  665                670 | 2016 |
| cga cgg atg gtc tgt gac tgt gag aat ccc aca gtt gat ctt ttt tgc | 2064 |

-continued

```
             Arg Arg Met Val Cys Asp Cys Glu Asn Pro Thr Val Asp Leu Phe Cys
                     675                 680                 685 tgc cct gaa tgt gac cca agg ctt agt agt cag tgc ctc cat caa aat        2112
Cys Pro Glu Cys Asp Pro Arg Leu Ser Ser Gln Cys Leu His Gln Asn
690                 695                 700 ggg gaa act ttg tat aac agt ggt gac acc tgg gtc cag aat tgt caa        2160
Gly Glu Thr Leu Tyr Asn Ser Gly Asp Thr Trp Val Gln Asn Cys Gln
705                 710                 715                 720 cag tgc cgc tgc ttg caa ggg gaa gtt gat tgt tgg ccc ctg cct tgc        2208
Gln Cys Arg Cys Leu Gln Gly Glu Val Asp Cys Trp Pro Leu Pro Cys
            725                 730                 735 cca gat gtg gag tgt gaa ttc agc att ctc cca gag aat gag tgc tgc        2256
Pro Asp Val Glu Cys Glu Phe Ser Ile Leu Pro Glu Asn Glu Cys Cys
            740                 745                 750 ccg cgc tgt gtc aca gac cct tgc cag gct gac acc atc cgc aat gac        2304
Pro Arg Cys Val Thr Asp Pro Cys Gln Ala Asp Thr Ile Arg Asn Asp
            755                 760                 765 atc acc aag act tgc ctg gac gaa atg aat gtg gtt cgc ttc acc ggg        2352
Ile Thr Lys Thr Cys Leu Asp Glu Met Asn Val Val Arg Phe Thr Gly
770                 775                 780 tcc tct tgg atc aaa cat ggc act gag tgt act ctc tgc cag tgc aag        2400
Ser Ser Trp Ile Lys His Gly Thr Glu Cys Thr Leu Cys Gln Cys Lys
785                 790                 795                 800 aat ggc cac atc tgt tgc tca gtg gat cca cag tgc ctt cag gaa ctg        2448
Asn Gly His Ile Cys Cys Ser Val Asp Pro Gln Cys Leu Gln Glu Leu
            805                 810                 815 tga                                                                    2451
```

<210> SEQ ID NO 8
<211> LENGTH: 816
<212> TYPE: PRT
<213> ORGANISM: Homo sapiens

<400> SEQUENCE: 8

```
Met Glu Ser Arg Val Leu Leu Arg Thr Phe Cys Leu Ile Phe Gly Leu
1               5                   10                  15

Gly Ala Val Trp Gly Leu Gly Val Asp Pro Ser Leu Gln Ile Asp Val
            20                  25                  30

Leu Thr Glu Leu Glu Leu Gly Glu Ser Thr Thr Gly Val Arg Gln Val
        35                  40                  45

Pro Gly Leu His Asn Gly Thr Lys Ala Phe Leu Phe Gln Asp Thr Pro
    50                  55                  60

Arg Ser Ile Lys Ala Ser Thr Ala Thr Ala Glu Gln Phe Phe Gln Lys
65                  70                  75                  80

Leu Arg Asn Lys His Glu Phe Thr Ile Leu Val Thr Leu Lys Gln Thr
                85                  90                  95

His Leu Asn Ser Gly Val Ile Leu Ser Ile His His Leu Asp His Arg
            100                 105                 110

Tyr Leu Glu Leu Glu Ser Ser Gly His Arg Asn Glu Val Arg Leu His
        115                 120                 125

Tyr Arg Ser Gly Ser His Arg Pro His Thr Glu Val Phe Pro Tyr Ile
    130                 135                 140

Leu Ala Asp Asp Lys Trp His Lys Leu Ser Leu Ala Ile Ser Ala Ser
145                 150                 155                 160

His Leu Ile Leu His Ile Asp Cys Asn Lys Ile Tyr Glu Arg Val Val
                165                 170                 175

Glu Lys Pro Ser Thr Asp Leu Pro Leu Gly Thr Thr Phe Trp Leu Gly
```

-continued

```
                180                 185                 190
Gln Arg Asn Asn Ala His Gly Tyr Phe Lys Gly Ile Met Gln Asp Val
            195                 200                 205
Gln Leu Leu Val Met Pro Gln Gly Phe Ile Ala Gln Cys Pro Asp Leu
            210                 215                 220
Asn Arg Thr Cys Pro Thr Cys Asn Asp Phe His Gly Leu Val Gln Lys
225                 230                 235                 240
Ile Met Glu Leu Gln Asp Ile Leu Ala Lys Thr Ser Ala Lys Leu Ser
                245                 250                 255
Arg Ala Glu Gln Arg Met Asn Arg Leu Asp Gln Cys Tyr Cys Glu Arg
            260                 265                 270
Thr Cys Thr Met Lys Gly Thr Thr Tyr Arg Glu Phe Glu Ser Trp Ile
        275                 280                 285
Asp Gly Cys Lys Asn Cys Thr Cys Leu Asn Gly Thr Ile Gln Cys Glu
        290                 295                 300
Thr Leu Ile Cys Pro Asn Pro Asp Cys Pro Leu Lys Ser Ala Leu Ala
305                 310                 315                 320
Tyr Val Asp Gly Lys Cys Cys Lys Glu Cys Lys Ser Ile Cys Gln Phe
                325                 330                 335
Gln Gly Arg Thr Tyr Phe Glu Gly Glu Arg Asn Thr Val Tyr Ser Ser
            340                 345                 350
Ser Gly Val Cys Val Leu Tyr Glu Cys Lys Asp Gln Thr Met Lys Leu
        355                 360                 365
Val Glu Ser Ser Gly Cys Pro Ala Leu Asp Cys Pro Glu Ser His Gln
    370                 375                 380
Ile Thr Leu Ser His Ser Cys Cys Lys Val Cys Lys Gly Tyr Asp Phe
385                 390                 395                 400
Cys Ser Glu Arg His Asn Cys Met Glu Asn Ser Ile Cys Arg Asn Leu
                405                 410                 415
Asn Asp Arg Ala Val Cys Ser Cys Arg Asp Gly Phe Arg Ala Leu Arg
            420                 425                 430
Glu Asp Asn Ala Tyr Cys Glu Asp Ile Asp Glu Cys Ala Glu Gly Arg
        435                 440                 445
His Tyr Cys Arg Glu Asn Thr Met Cys Val Asn Thr Pro Gly Ser Phe
        450                 455                 460
Met Cys Ile Cys Lys Thr Gly Tyr Ile Arg Ile Asp Asp Tyr Ser Cys
465                 470                 475                 480
Thr Glu His Asp Glu Cys Ile Thr Asn Gln His Asn Cys Asp Glu Asn
                485                 490                 495
Ala Leu Cys Phe Asn Thr Val Gly Gly His Asn Cys Val Cys Lys Pro
            500                 505                 510
Gly Tyr Thr Gly Asn Gly Thr Thr Cys Lys Ala Phe Cys Lys Asp Gly
        515                 520                 525
Cys Arg Asn Gly Gly Ala Cys Ile Ala Ala Asn Val Cys Ala Cys Pro
    530                 535                 540
Gln Gly Phe Thr Gly Pro Ser Cys Glu Thr Asp Ile Asp Glu Cys Ser
545                 550                 555                 560
Asp Gly Phe Val Gln Cys Asp Ser Arg Ala Asn Cys Ile Asn Leu Pro
                565                 570                 575
Gly Trp Tyr His Cys Glu Cys Arg Asp Gly Tyr His Asp Asn Gly Met
            580                 585                 590
Phe Ser Pro Ser Gly Glu Ser Cys Glu Asp Ile Asp Glu Cys Gly Thr
        595                 600                 605
```

```
Gly Arg His Ser Cys Ala Asn Asp Thr Ile Cys Phe Asn Leu Asp Gly
    610                 615                 620

Gly Tyr Asp Cys Arg Cys Pro His Gly Lys Asn Cys Thr Gly Asp Cys
625                 630                 635                 640

Ile His Asp Gly Lys Val Lys His Asn Gly Gln Ile Trp Val Leu Glu
                645                 650                 655

Asn Asp Arg Cys Ser Val Cys Ser Cys Gln Asn Gly Phe Val Met Cys
                660                 665                 670

Arg Arg Met Val Cys Asp Cys Glu Asn Pro Thr Val Asp Leu Phe Cys
            675                 680                 685

Cys Pro Glu Cys Asp Pro Arg Leu Ser Ser Gln Cys Leu His Gln Asn
690                 695                 700

Gly Glu Thr Leu Tyr Asn Ser Gly Asp Thr Trp Val Gln Asn Cys Gln
705                 710                 715                 720

Gln Cys Arg Cys Leu Gln Gly Glu Val Asp Cys Trp Pro Leu Pro Cys
                725                 730                 735

Pro Asp Val Glu Cys Glu Phe Ser Ile Leu Pro Glu Asn Glu Cys Cys
            740                 745                 750

Pro Arg Cys Val Thr Asp Pro Cys Gln Ala Asp Thr Ile Arg Asn Asp
            755                 760                 765

Ile Thr Lys Thr Cys Leu Asp Glu Met Asn Val Val Arg Phe Thr Gly
770                 775                 780

Ser Ser Trp Ile Lys His Gly Thr Glu Cys Thr Leu Cys Gln Cys Lys
785                 790                 795                 800

Asn Gly His Ile Cys Cys Ser Val Asp Pro Gln Cys Leu Gln Glu Leu
                805                 810                 815

<210> SEQ ID NO 9
<211> LENGTH: 2451
<212> TYPE: DNA
<213> ORGANISM: Rattus norvegicus
<220> FEATURE:
<221> NAME/KEY: CDS
<222> LOCATION: (1)..(2448)

<400> SEQUENCE: 9 atg gaa tcc cgg gta tta ctg aga acg ttc tgc gtg atc ctc ggg ctc      48
Met Glu Ser Arg Val Leu Leu Arg Thr Phe Cys Val Ile Leu Gly Leu
1               5                   10                  15 gaa gcg gtt tgg gga ctt ggt gtg gac ccc tcc cta cag att gac gtc      96
Glu Ala Val Trp Gly Leu Gly Val Asp Pro Ser Leu Gln Ile Asp Val
            20                  25                  30 tta tca gag tta gaa ctt ggg gag tcc aca gct gga gtg cgc caa gtc     144
Leu Ser Glu Leu Glu Leu Gly Glu Ser Thr Ala Gly Val Arg Gln Val
        35                  40                  45 cca gga ctg cat aat ggg acg aaa gcc ttc ctc ttc caa gat tcc ccc     192
Pro Gly Leu His Asn Gly Thr Lys Ala Phe Leu Phe Gln Asp Ser Pro
    50                  55                  60 aga agc ata aaa gca ccc att gct aca gct gag cgg ttt ttc cag aag     240
Arg Ser Ile Lys Ala Pro Ile Ala Thr Ala Glu Arg Phe Phe Gln Lys
65                  70                  75                  80 ctg agg aat aaa cac gag ttc aca att ctg gtg acc ctg aaa cag atc     288
Leu Arg Asn Lys His Glu Phe Thr Ile Leu Val Thr Leu Lys Gln Ile
                85                  90                  95 cac tta aat tcg gga gtc att ctc tcc atc cac cac ttg gat cac agg     336
His Leu Asn Ser Gly Val Ile Leu Ser Ile His His Leu Asp His Arg
            100                 105                 110
```

| | |
|---|---|
| tac ctg gaa ctg gaa agc agc ggc cac cgg aat gag atc aga ctg cat<br>Tyr Leu Glu Leu Glu Ser Ser Gly His Arg Asn Glu Ile Arg Leu His<br>115                    120                    125 | 384 |
| tac cgc tct gga act cac cgc ccg cac acg gaa gtg ttt cct tat att<br>Tyr Arg Ser Gly Thr His Arg Pro His Thr Glu Val Phe Pro Tyr Ile<br>130                    135                    140 | 432 |
| ttg gct gat gcc aag tgg cac aag ctc tcc tta gcc ttc agt gcc tcc<br>Leu Ala Asp Ala Lys Trp His Lys Leu Ser Leu Ala Phe Ser Ala Ser<br>145                    150                    155                    160 | 480 |
| cac tta att tta cac atc gac tgc aac aag atc tat gaa cga gtg gtg<br>His Leu Ile Leu His Ile Asp Cys Asn Lys Ile Tyr Glu Arg Val Val<br>                    165                    170                    175 | 528 |
| gaa atg cct tct aca gac ttg cct ctg ggc acc aca ttt tgg ttg gga<br>Glu Met Pro Ser Thr Asp Leu Pro Leu Gly Thr Thr Phe Trp Leu Gly<br>                180                    185                    190 | 576 |
| cag aga aat aac gca cac ggg tat ttt aag gga ata atg caa gat gtg<br>Gln Arg Asn Asn Ala His Gly Tyr Phe Lys Gly Ile Met Gln Asp Val<br>                    195                    200                    205 | 624 |
| caa tta ctt gtc atg ccc cag ggg ttc atc gct cag tgc ccg gat ctt<br>Gln Leu Leu Val Met Pro Gln Gly Phe Ile Ala Gln Cys Pro Asp Leu<br>210                    215                    220 | 672 |
| aat cga acc tgt cca aca tgc aac gac ttc cat ggg ctt gtg cag aaa<br>Asn Arg Thr Cys Pro Thr Cys Asn Asp Phe His Gly Leu Val Gln Lys<br>225                    230                    235                    240 | 720 |
| atc atg gag ctg cag gac att tta tcg aag acg tca gcc aag ttg tct<br>Ile Met Glu Leu Gln Asp Ile Leu Ser Lys Thr Ser Ala Lys Leu Ser<br>                    245                    250                    255 | 768 |
| aga gct gaa caa cga atg aac agg ctg gat cag tgc tac tgt gag cgg<br>Arg Ala Glu Gln Arg Met Asn Arg Leu Asp Gln Cys Tyr Cys Glu Arg<br>                    260                    265                    270 | 816 |
| acg tgc acc atg aag gga gcc acc tac cgg gag ttc gag tcc tgg aca<br>Thr Cys Thr Met Lys Gly Ala Thr Tyr Arg Glu Phe Glu Ser Trp Thr<br>                    275                    280                    285 | 864 |
| gac ggc tgc aag aac tgc aca tgc ttg aat ggg acc atc cag tgc gag<br>Asp Gly Cys Lys Asn Cys Thr Cys Leu Asn Gly Thr Ile Gln Cys Glu<br>290                    295                    300 | 912 |
| act ctg gtc tgc cct gct ccc gac tgc ccg gct aaa tcg gct cca gcg<br>Thr Leu Val Cys Pro Ala Pro Asp Cys Pro Ala Lys Ser Ala Pro Ala<br>305                    310                    315                    320 | 960 |
| tac gtg gat ggc aag tgc tgt aag gag tgc aag tcc acc tgc cag ttc<br>Tyr Val Asp Gly Lys Cys Cys Lys Glu Cys Lys Ser Thr Cys Gln Phe<br>                    325                    330                    335 | 1008 |
| cag ggg cgg agc tac ttt gag gga gaa agg agc aca gtc ttc tca gct<br>Gln Gly Arg Ser Tyr Phe Glu Gly Glu Arg Ser Thr Val Phe Ser Ala<br>                    340                    345                    350 | 1056 |
| tcc gga atg tgc gtc ttg tat gaa tgc aag gat cag acc atg aag ctt<br>Ser Gly Met Cys Val Leu Tyr Glu Cys Lys Asp Gln Thr Met Lys Leu<br>                    355                    360                    365 | 1104 |
| gtt gag aac gcc ggc tgc ccg gct tta gat tgc ccc gag tct cat cag<br>Val Glu Asn Ala Gly Cys Pro Ala Leu Asp Cys Pro Glu Ser His Gln<br>370                    375                    380 | 1152 |
| atc gcc ttg tct cac agc tgc tgc aag gtt tgc aaa ggt tat gac ttc<br>Ile Ala Leu Ser His Ser Cys Cys Lys Val Cys Lys Gly Tyr Asp Phe<br>385                    390                    395                    400 | 1200 |
| tgt tct gag aag cat aca tgc atg gag aac tca gtc tgc agg aac ctg<br>Cys Ser Glu Lys His Thr Cys Met Glu Asn Ser Val Cys Arg Asn Leu<br>                    405                    410                    415 | 1248 |
| aac gac agg gca gtg tgc agc tgc cgg gat ggt ttc cgg gcc ctc cgg<br>Asn Asp Arg Ala Val Cys Ser Cys Arg Asp Gly Phe Arg Ala Leu Arg<br>                    420                    425                    430 | 1296 |

-continued

| | |
|---|---|
| gag gac aat gcc tac tgt gaa gac att gac gag tgt gca gag ggg cgc<br>Glu Asp Asn Ala Tyr Cys Glu Asp Ile Asp Glu Cys Ala Glu Gly Arg<br>          435                  440                445 | 1344 |
| cat tac tgc cgt gag aac acc atg tgt gtg aac aca ccg ggc tct ttc<br>His Tyr Cys Arg Glu Asn Thr Met Cys Val Asn Thr Pro Gly Ser Phe<br>450                       455                  460 | 1392 |
| ctg tgt atc tgc caa aca ggg tac atc aga atc gac gat tac tcg tgt<br>Leu Cys Ile Cys Gln Thr Gly Tyr Ile Arg Ile Asp Asp Tyr Ser Cys<br>465                     470                   475                  480 | 1440 |
| acg gaa cat gac gag tgc ctc aca aac cag cac aac tgt gac gag aac<br>Thr Glu His Asp Glu Cys Leu Thr Asn Gln His Asn Cys Asp Glu Asn<br>                   485                   490                   495 | 1488 |
| gct ttg tgc ttt aac acc gtt gga ggt cac aac tgt gtc tgc aag cct<br>Ala Leu Cys Phe Asn Thr Val Gly Gly His Asn Cys Val Cys Lys Pro<br>          500                  505                  510 | 1536 |
| ggg tac act ggg aat gga acc acg tgc aaa gct ttc tgc aaa gac ggc<br>Gly Tyr Thr Gly Asn Gly Thr Thr Cys Lys Ala Phe Cys Lys Asp Gly<br>         515                  520                  525 | 1584 |
| tgc aaa aac gga ggt gcc tgc att gct gcc aat gtc tgt gct tgc cca<br>Cys Lys Asn Gly Gly Ala Cys Ile Ala Ala Asn Val Cys Ala Cys Pro<br>530                     535                  540 | 1632 |
| caa ggc ttc acc gga ccc agc tgt gag aca gac att gat gag tgc tct<br>Gln Gly Phe Thr Gly Pro Ser Cys Glu Thr Asp Ile Asp Glu Cys Ser<br>545                     550                   555                  560 | 1680 |
| gag ggc ttt gtt cag tgt gac agc cgt gcc aac tgc att aac ctg cct<br>Glu Gly Phe Val Gln Cys Asp Ser Arg Ala Asn Cys Ile Asn Leu Pro<br>                   565                   570                   575 | 1728 |
| ggg tgg tac cac tgt gag tgc aga gat ggc tac cat gac aat ggg atg<br>Gly Trp Tyr His Cys Glu Cys Arg Asp Gly Tyr His Asp Asn Gly Met<br>         580                  585                  590 | 1776 |
| ttt gcg cca ggt gga gaa tcc tgt gaa gat att gat gaa tgt ggg act<br>Phe Ala Pro Gly Gly Glu Ser Cys Glu Asp Ile Asp Glu Cys Gly Thr<br>         595                  600                  605 | 1824 |
| ggg agg cac agc tgt gcc aat gac acc att tgc ttc aac ttg gac ggt<br>Gly Arg His Ser Cys Ala Asn Asp Thr Ile Cys Phe Asn Leu Asp Gly<br>         610                  615                  620 | 1872 |
| ggc tac gat tgc cgg tgt ccc cat gga aag aac tgc aca ggg gac tgc<br>Gly Tyr Asp Cys Arg Cys Pro His Gly Lys Asn Cys Thr Gly Asp Cys<br>625                     630                   635                  640 | 1920 |
| gtg cac gac ggg aaa gtc aaa cac aac ggc cag atc tgg gtg ctg gag<br>Val His Asp Gly Lys Val Lys His Asn Gly Gln Ile Trp Val Leu Glu<br>                   645                   650                   655 | 1968 |
| aac gac agg tgc tct gtg tgt tcc tgc cag act gga ttt gtt atg tgc<br>Asn Asp Arg Cys Ser Val Cys Ser Cys Gln Thr Gly Phe Val Met Cys<br>                   660                   665                  670 | 2016 |
| caa cgg atg gtc tgt gac tgc gaa aac ccc aca gtt gac ctc tcc tgc<br>Gln Arg Met Val Cys Asp Cys Glu Asn Pro Thr Val Asp Leu Ser Cys<br>         675                  680                  685 | 2064 |
| tgc cct gag tgc gac cca agg ctg agc agc cag tgc ctg cat caa aac<br>Cys Pro Glu Cys Asp Pro Arg Leu Ser Ser Gln Cys Leu His Gln Asn<br>690                     695                  700 | 2112 |
| ggg gaa acc gtg tac aac agc ggt gac acc tgg gcc cag gat tgc cgt<br>Gly Glu Thr Val Tyr Asn Ser Gly Asp Thr Trp Ala Gln Asp Cys Arg<br>705                     710                   715                  720 | 2160 |
| cag tgc cgc tgc ttg caa gaa gaa gtt gac tgc tgg ccc ctg gct tgc<br>Gln Cys Arg Cys Leu Gln Glu Glu Val Asp Cys Trp Pro Leu Ala Cys<br>                   725                   730                  735 | 2208 |
| cca gag gta gag tgt gaa ttt agt gtc ctt cct gag aac gag tgc tgc<br>Pro Glu Val Glu Cys Glu Phe Ser Val Leu Pro Glu Asn Glu Cys Cys | 2256 |

```
                        740                 745                 750
cca cgc tgt gtc acc gat cct tgt cag gct gac acc atc cgc aat gac    2304
Pro Arg Cys Val Thr Asp Pro Cys Gln Ala Asp Thr Ile Arg Asn Asp
        755                 760                 765 atc acc aaa acc tgc ctg gac gag atg aac gtg gtt cgc ttc act ggg    2352
Ile Thr Lys Thr Cys Leu Asp Glu Met Asn Val Val Arg Phe Thr Gly
770                 775                 780 tct tcc tgg atc aag cac ggc acg gag tgc acc ctc tgc cag tgc aag    2400
Ser Ser Trp Ile Lys His Gly Thr Glu Cys Thr Leu Cys Gln Cys Lys
785                 790                 795                 800 aac ggc cac gtg tgc tgc tca gtg gac cca cag tgc ctc cag gag ctg    2448
Asn Gly His Val Cys Cys Ser Val Asp Pro Gln Cys Leu Gln Glu Leu
            805                 810                 815 tga                                                                 2451

<210> SEQ ID NO 10
<211> LENGTH: 816
<212> TYPE: PRT
<213> ORGANISM: Rattus norvegicus

<400> SEQUENCE: 10

Met Glu Ser Arg Val Leu Leu Arg Thr Phe Cys Val Ile Leu Gly Leu
1               5                   10                  15

Glu Ala Val Trp Gly Leu Gly Val Asp Pro Ser Leu Gln Ile Asp Val
            20                  25                  30

Leu Ser Glu Leu Glu Leu Gly Glu Ser Thr Ala Gly Val Arg Gln Val
        35                  40                  45

Pro Gly Leu His Asn Gly Thr Lys Ala Phe Leu Phe Gln Asp Ser Pro
    50                  55                  60

Arg Ser Ile Lys Ala Pro Ile Ala Thr Ala Glu Arg Phe Phe Gln Lys
65                  70                  75                  80

Leu Arg Asn Lys His Glu Phe Thr Ile Leu Val Thr Leu Lys Gln Ile
                85                  90                  95

His Leu Asn Ser Gly Val Ile Leu Ser Ile His His Leu Asp His Arg
            100                 105                 110

Tyr Leu Glu Leu Glu Ser Ser Gly His Arg Asn Glu Ile Arg Leu His
        115                 120                 125

Tyr Arg Ser Gly Thr His Arg Pro His Thr Glu Val Phe Pro Tyr Ile
    130                 135                 140

Leu Ala Asp Ala Lys Trp His Lys Leu Ser Leu Ala Phe Ser Ala Ser
145                 150                 155                 160

His Leu Ile Leu His Ile Asp Cys Asn Lys Ile Tyr Glu Arg Val Val
                165                 170                 175

Glu Met Pro Ser Thr Asp Leu Pro Leu Gly Thr Thr Phe Trp Leu Gly
            180                 185                 190

Gln Arg Asn Asn Ala His Gly Tyr Phe Lys Gly Ile Met Gln Asp Val
        195                 200                 205

Gln Leu Leu Val Met Pro Gln Gly Phe Ile Ala Gln Cys Pro Asp Leu
    210                 215                 220

Asn Arg Thr Cys Pro Thr Cys Asn Asp Phe His Gly Leu Val Gln Lys
225                 230                 235                 240

Ile Met Glu Leu Gln Asp Ile Leu Ser Lys Thr Ser Ala Lys Leu Ser
                245                 250                 255

Arg Ala Glu Gln Arg Met Asn Arg Leu Asp Gln Cys Tyr Cys Glu Arg
            260                 265                 270
```

```
Thr Cys Thr Met Lys Gly Ala Thr Tyr Arg Glu Phe Glu Ser Trp Thr
            275                 280                 285

Asp Gly Cys Lys Asn Cys Thr Cys Leu Asn Gly Thr Ile Gln Cys Glu
        290                 295                 300

Thr Leu Val Cys Pro Ala Pro Asp Cys Pro Ala Lys Ser Ala Pro Ala
305                 310                 315                 320

Tyr Val Asp Gly Lys Cys Cys Lys Glu Cys Lys Ser Thr Cys Gln Phe
                325                 330                 335

Gln Gly Arg Ser Tyr Phe Glu Gly Glu Arg Ser Thr Val Phe Ser Ala
            340                 345                 350

Ser Gly Met Cys Val Leu Tyr Glu Cys Lys Asp Gln Thr Met Lys Leu
        355                 360                 365

Val Glu Asn Ala Gly Cys Pro Ala Leu Asp Cys Pro Glu Ser His Gln
370                 375                 380

Ile Ala Leu Ser His Ser Cys Cys Lys Val Cys Lys Gly Tyr Asp Phe
385                 390                 395                 400

Cys Ser Glu Lys His Thr Cys Met Glu Asn Ser Val Cys Arg Asn Leu
                405                 410                 415

Asn Asp Arg Ala Val Cys Ser Cys Arg Asp Gly Phe Arg Ala Leu Arg
            420                 425                 430

Glu Asp Asn Ala Tyr Cys Glu Asp Ile Asp Glu Cys Ala Glu Gly Arg
        435                 440                 445

His Tyr Cys Arg Glu Asn Thr Met Cys Val Asn Thr Pro Gly Ser Phe
    450                 455                 460

Leu Cys Ile Cys Gln Thr Gly Tyr Ile Arg Ile Asp Asp Tyr Ser Cys
465                 470                 475                 480

Thr Glu His Asp Glu Cys Leu Thr Asn Gln His Asn Cys Asp Glu Asn
                485                 490                 495

Ala Leu Cys Phe Asn Thr Val Gly Gly His Asn Cys Val Cys Lys Pro
            500                 505                 510

Gly Tyr Thr Gly Asn Gly Thr Thr Cys Lys Ala Phe Cys Lys Asp Gly
        515                 520                 525

Cys Lys Asn Gly Gly Ala Cys Ile Ala Ala Asn Val Cys Ala Cys Pro
530                 535                 540

Gln Gly Phe Thr Gly Pro Ser Cys Glu Thr Asp Ile Asp Glu Cys Ser
545                 550                 555                 560

Glu Gly Phe Val Gln Cys Asp Ser Arg Ala Asn Cys Ile Asn Leu Pro
                565                 570                 575

Gly Trp Tyr His Cys Glu Cys Arg Asp Gly Tyr His Asp Asn Gly Met
            580                 585                 590

Phe Ala Pro Gly Gly Glu Ser Cys Glu Asp Ile Asp Glu Cys Gly Thr
        595                 600                 605

Gly Arg His Ser Cys Ala Asn Asp Thr Ile Cys Phe Asn Leu Asp Gly
610                 615                 620

Gly Tyr Asp Cys Arg Cys Pro His Gly Lys Asn Cys Thr Gly Asp Cys
625                 630                 635                 640

Val His Asp Gly Lys Val Lys His Asn Gly Gln Ile Trp Val Leu Glu
                645                 650                 655

Asn Asp Arg Cys Ser Val Cys Ser Cys Gln Thr Gly Phe Val Met Cys
            660                 665                 670

Gln Arg Met Val Cys Asp Cys Glu Asn Pro Thr Val Asp Leu Ser Cys
        675                 680                 685

Cys Pro Glu Cys Asp Pro Arg Leu Ser Ser Gln Cys Leu His Gln Asn
```

```
                690              695              700
Gly Glu Thr Val Tyr Asn Ser Gly Asp Thr Trp Ala Gln Asp Cys Arg
705              710              715              720

Gln Cys Arg Cys Leu Gln Glu Val Asp Cys Trp Pro Leu Ala Cys
            725              730              735

Pro Glu Val Glu Cys Glu Phe Ser Val Leu Pro Glu Asn Glu Cys Cys
            740              745              750

Pro Arg Cys Val Thr Asp Pro Cys Gln Ala Asp Thr Ile Arg Asn Asp
            755              760              765

Ile Thr Lys Thr Cys Leu Asp Glu Met Asn Val Val Arg Phe Thr Gly
            770              775              780

Ser Ser Trp Ile Lys His Gly Thr Glu Cys Thr Leu Cys Gln Cys Lys
785              790              795              800

Asn Gly His Val Cys Cys Ser Val Asp Pro Gln Cys Leu Gln Glu Leu
            805              810              815

<210> SEQ ID NO 11
<211> LENGTH: 2460
<212> TYPE: DNA
<213> ORGANISM: Mus musculus
<220> FEATURE:
<221> NAME/KEY: CDS
<222> LOCATION: (1)..(2457)

<400> SEQUENCE: 11 atg cac gcc atg gaa tcc cgg gtg tta ctg aga acg ttc tgc gtg atc     48
Met His Ala Met Glu Ser Arg Val Leu Leu Arg Thr Phe Cys Val Ile
1               5                  10                  15 ctc ggc ctt gga gcg gtt tgg ggg ctt ggt gtg gac ccc tcc cta cag     96
Leu Gly Leu Gly Ala Val Trp Gly Leu Gly Val Asp Pro Ser Leu Gln
            20                  25                  30 att gac gtc tta aca gag tta gaa ctt ggg gag tct aca gat gga gtg    144
Ile Asp Val Leu Thr Glu Leu Glu Leu Gly Glu Ser Thr Asp Gly Val
        35                  40                  45 cgc caa gtc ccg gga ctg cat aat ggg acg aaa gcc ttc ctc ttc caa    192
Arg Gln Val Pro Gly Leu His Asn Gly Thr Lys Ala Phe Leu Phe Gln
    50                  55                  60 gag tcc ccc aga agc ata aag gca tcc act gct aca gct gag cgg ttt    240
Glu Ser Pro Arg Ser Ile Lys Ala Ser Thr Ala Thr Ala Glu Arg Phe
65                  70                  75                  80 ctc cag aag ctg aga aat aaa cac gag ttc aca atc ttg gtg acc tta    288
Leu Gln Lys Leu Arg Asn Lys His Glu Phe Thr Ile Leu Val Thr Leu
                85                  90                  95 aaa cag atc cac tta aat tcg gga gtt atc ctc tcc atc cac cac ttg    336
Lys Gln Ile His Leu Asn Ser Gly Val Ile Leu Ser Ile His His Leu
            100                 105                 110 gat cac agg tac ctg gaa ctg gaa agc agt ggc cat cgg aat gag atc    384
Asp His Arg Tyr Leu Glu Leu Glu Ser Ser Gly His Arg Asn Glu Ile
        115                 120                 125 aga ctc cac tac cgc tct ggc act cac cgc ccc cac acg gaa gtg ttt    432
Arg Leu His Tyr Arg Ser Gly Thr His Arg Pro His Thr Glu Val Phe
    130                 135                 140 cct tat att ttg gct gat gcc aag tgg cac aag ctc tcc tta gcc ttc    480
Pro Tyr Ile Leu Ala Asp Ala Lys Trp His Lys Leu Ser Leu Ala Phe
145                 150                 155                 160 agt gcc tct cac tta att tta cac atc gac tgc aat aag atc tat gaa    528
Ser Ala Ser His Leu Ile Leu His Ile Asp Cys Asn Lys Ile Tyr Glu
                165                 170                 175 cga gtg gtg gaa atg ccc ttc aca gac ttg gct ctg ggc aca aca ttt    576
Arg Val Val Glu Met Pro Phe Thr Asp Leu Ala Leu Gly Thr Thr Phe
```

-continued

```
                Arg Val Val Glu Met Pro Phe Thr Asp Leu Ala Leu Gly Thr Thr Phe
                                180             185                 190 tgg ttg gga cag aga aat aat gca cat ggc tat ttt aag gga ata atg      624
Trp Leu Gly Gln Arg Asn Asn Ala His Gly Tyr Phe Lys Gly Ile Met
            195                 200                 205 cag gat gtg cac gtc ctt gtc atg cct cag ggc ttc att gct cag tgc      672
Gln Asp Val His Val Leu Val Met Pro Gln Gly Phe Ile Ala Gln Cys
210                 215                 220 ccg gac ctt aat cga acc tgt cca aca tgc aac gac ttc cat ggg ctt      720
Pro Asp Leu Asn Arg Thr Cys Pro Thr Cys Asn Asp Phe His Gly Leu
225                 230                 235                 240 gtg cag aaa atc atg gag ctg cag gac att tta tca aag acg tca gcc      768
Val Gln Lys Ile Met Glu Leu Gln Asp Ile Leu Ser Lys Thr Ser Ala
                245                 250                 255 aag ctg tcc cga gct gaa caa aga atg aac agg ctg gat cag tgc tac      816
Lys Leu Ser Arg Ala Glu Gln Arg Met Asn Arg Leu Asp Gln Cys Tyr
            260                 265                 270 tgt gag cgg aca tgc act gtg aag gga acc acc tac cga gag tct gag      864
Cys Glu Arg Thr Cys Thr Val Lys Gly Thr Thr Tyr Arg Glu Ser Glu
        275                 280                 285 tcc tgg aca gac ggc tgt aag aac tgc aca tgc ttg aac ggg acc atc      912
Ser Trp Thr Asp Gly Cys Lys Asn Cys Thr Cys Leu Asn Gly Thr Ile
290                 295                 300 cag tgc gag act ctg gtc tgc cct gct cct gac tgc cct cct aaa tcg      960
Gln Cys Glu Thr Leu Val Cys Pro Ala Pro Asp Cys Pro Pro Lys Ser
305                 310                 315                 320 gcc cct gcg tat gtg gat ggc aag tgc tgt aag gag tgc aaa tca acc     1008
Ala Pro Ala Tyr Val Asp Gly Lys Cys Cys Lys Glu Cys Lys Ser Thr
                325                 330                 335 tgc cag ttc cag gga cgg agc tac ttt gag gga gaa agg aac acg gca     1056
Cys Gln Phe Gln Gly Arg Ser Tyr Phe Glu Gly Glu Arg Asn Thr Ala
            340                 345                 350 tac tca tct tct gga atg tgt gtc tta tat gaa tgc aag gat cag acc     1104
Tyr Ser Ser Ser Gly Met Cys Val Leu Tyr Glu Cys Lys Asp Gln Thr
        355                 360                 365 atg aag ctt gtt gag aac att ggc tgc cca ccc tta gat tgt ccc gag     1152
Met Lys Leu Val Glu Asn Ile Gly Cys Pro Pro Leu Asp Cys Pro Glu
370                 375                 380 tct cat cag att gcc ttg tct cac agc tgc tgc aag gtt tgt aaa ggt     1200
Ser His Gln Ile Ala Leu Ser His Ser Cys Cys Lys Val Cys Lys Gly
385                 390                 395                 400 tat gac ttc tgt tct gag aag cat acc tgc atg gag aac tcg gtc tgc     1248
Tyr Asp Phe Cys Ser Glu Lys His Thr Cys Met Glu Asn Ser Val Cys
                405                 410                 415 agg aac ctg aac gac agg gtt gtg tgc agc tgc agg gat ggt ttt cgg     1296
Arg Asn Leu Asn Asp Arg Val Val Cys Ser Cys Arg Asp Gly Phe Arg
            420                 425                 430 gct ctc cga gag gac aac gcc tac tgt gaa gac att gac gag tgt gca     1344
Ala Leu Arg Glu Asp Asn Ala Tyr Cys Glu Asp Ile Asp Glu Cys Ala
        435                 440                 445 gaa ggg cgc cat tac tgc cgt gag aac acc atg tgt gtg aat aca cct     1392
Glu Gly Arg His Tyr Cys Arg Glu Asn Thr Met Cys Val Asn Thr Pro
450                 455                 460 ggt tct ttc atg tgt gtc tgc aaa act ggg tac atc agg atc gac gat     1440
Gly Ser Phe Met Cys Val Cys Lys Thr Gly Tyr Ile Arg Ile Asp Asp
465                 470                 475                 480 tac tca tgt aca gaa cat gat gag tgt ctc aca acc cag cac aat tgt     1488
Tyr Ser Cys Thr Glu His Asp Glu Cys Leu Thr Thr Gln His Asn Cys
                485                 490                 495
```

-continued

| | |
|---|---|
| gat gaa aac gct ttg tgc ttt aac act gtt gga gga cac aac tgt gtc<br>Asp Glu Asn Ala Leu Cys Phe Asn Thr Val Gly Gly His Asn Cys Val<br>            500                  505                  510 | 1536 |
| tgc aag cct ggc tac acc ggg aat gga acc acg tgt aaa gct ttc tgc<br>Cys Lys Pro Gly Tyr Thr Gly Asn Gly Thr Thr Cys Lys Ala Phe Cys<br>            515                  520                  525 | 1584 |
| aaa gat ggc tgt aga aac gga gga gcg tgt att gct gcc aat gtg tgt<br>Lys Asp Gly Cys Arg Asn Gly Gly Ala Cys Ile Ala Ala Asn Val Cys<br>530                  535                  540 | 1632 |
| gcc tgc cca caa ggc ttc acg gga ccc agc tgt gag aca gac att gac<br>Ala Cys Pro Gln Gly Phe Thr Gly Pro Ser Cys Glu Thr Asp Ile Asp<br>545                  550                  555                  560 | 1680 |
| gag tgc tct gag ggc ttt gtt cag tgt gac agc cgt gcc aac tgc atc<br>Glu Cys Ser Glu Gly Phe Val Gln Cys Asp Ser Arg Ala Asn Cys Ile<br>            565                  570                  575 | 1728 |
| aac ctg cct ggg tgg tat cac tgt gag tgc aga gac ggc tac cat gac<br>Asn Leu Pro Gly Trp Tyr His Cys Glu Cys Arg Asp Gly Tyr His Asp<br>                  580                  585                  590 | 1776 |
| aat ggg atg ttt gcg cca ggc gga gaa tcc tgt gaa gat att gac gaa<br>Asn Gly Met Phe Ala Pro Gly Gly Glu Ser Cys Glu Asp Ile Asp Glu<br>            595                  600                  605 | 1824 |
| tgc ggg act ggg agg cac agc tgc acc aac gac acc att tgc ttc aac<br>Cys Gly Thr Gly Arg His Ser Cys Thr Asn Asp Thr Ile Cys Phe Asn<br>610                  615                  620 | 1872 |
| ttg gac ggg gga tac gat tgc cgg tgt ccc cat ggg aag aac tgc act<br>Leu Asp Gly Gly Tyr Asp Cys Arg Cys Pro His Gly Lys Asn Cys Thr<br>625                  630                  635                  640 | 1920 |
| ggg gac tgc gtg cac gag ggg aaa gtg aag cac acc ggc cag atc tgg<br>Gly Asp Cys Val His Glu Gly Lys Val Lys His Thr Gly Gln Ile Trp<br>                  645                  650                  655 | 1968 |
| gtg ctg gaa aac gac agg tgc tcc gtg tgt tcc tgg cag act ggg ttt<br>Val Leu Glu Asn Asp Arg Cys Ser Val Cys Ser Trp Gln Thr Gly Phe<br>            660                  665                  670 | 2016 |
| gtc atg tgt cga cgg atg gtc tgc gac tgc gaa aac ccc aca gat gac<br>Val Met Cys Arg Arg Met Val Cys Asp Cys Glu Asn Pro Thr Asp Asp<br>              675                  680                  685 | 2064 |
| ctt tcc tgc tgc cct gag tgt gac cca agg ctg agc agt cag tgc ctg<br>Leu Ser Cys Cys Pro Glu Cys Asp Pro Arg Leu Ser Ser Gln Cys Leu<br>690                  695                  700 | 2112 |
| cat caa aac ggg gaa acc gtg tac aac agc ggc gac acc tgg gtc cag<br>His Gln Asn Gly Glu Thr Val Tyr Asn Ser Gly Asp Thr Trp Val Gln<br>705                  710                  715                  720 | 2160 |
| gat tgc cgt cag tgc cgc tgc ttg caa gga gaa gtt gac tgt tgg ccc<br>Asp Cys Arg Gln Cys Arg Cys Leu Gln Gly Glu Val Asp Cys Trp Pro<br>            725                  730                  735 | 2208 |
| ctg gct tgc cca gag gta gaa tgt gaa ttt agc gtc ctt cct gag aac<br>Leu Ala Cys Pro Glu Val Glu Cys Glu Phe Ser Val Leu Pro Glu Asn<br>                  740                  745                  750 | 2256 |
| gag tgc tgc cca cgc tgt gtc acc gat cct tgt cag gcc gac acc atc<br>Glu Cys Cys Pro Arg Cys Val Thr Asp Pro Cys Gln Ala Asp Thr Ile<br>            755                  760                  765 | 2304 |
| cgc aat gac atc acc aaa acc tgc ctg gac gag atg aac gtg gtt cgc<br>Arg Asn Asp Ile Thr Lys Thr Cys Leu Asp Glu Met Asn Val Val Arg<br>770                  775                  780 | 2352 |
| ttc acc ggg tct tcc tgg atc aag cac ggc acg gag tgt acc ctc tgc<br>Phe Thr Gly Ser Ser Trp Ile Lys His Gly Thr Glu Cys Thr Leu Cys<br>785                  790                  795                  800 | 2400 |
| cag tgc aag aat ggc cat ttg tgc tgc tca gtg gat cca cag tgc ctt<br>Gln Cys Lys Asn Gly His Leu Cys Cys Ser Val Asp Pro Gln Cys Leu<br>            805                  810                  815 | 2448 |

```
cag gag ctg tga                                                    2460
Gln Glu Leu <210> SEQ ID NO 12
<211> LENGTH: 819
<212> TYPE: PRT
<213> ORGANISM: Mus musculus

<400> SEQUENCE: 12

Met His Ala Met Glu Ser Arg Val Leu Leu Arg Thr Phe Cys Val Ile
1               5                   10                  15

Leu Gly Leu Gly Ala Val Trp Gly Leu Gly Val Asp Pro Ser Leu Gln
            20                  25                  30

Ile Asp Val Leu Thr Glu Leu Glu Leu Gly Glu Ser Thr Asp Gly Val
        35                  40                  45

Arg Gln Val Pro Gly Leu His Asn Gly Thr Lys Ala Phe Leu Phe Gln
    50                  55                  60

Glu Ser Pro Arg Ser Ile Lys Ala Ser Thr Ala Thr Ala Glu Arg Phe
65                  70                  75                  80

Leu Gln Lys Leu Arg Asn Lys His Glu Phe Thr Ile Leu Val Thr Leu
                85                  90                  95

Lys Gln Ile His Leu Asn Ser Gly Val Ile Leu Ser Ile His His Leu
            100                 105                 110

Asp His Arg Tyr Leu Glu Leu Glu Ser Ser Gly His Arg Asn Glu Ile
        115                 120                 125

Arg Leu His Tyr Arg Ser Gly Thr His Arg Pro His Thr Glu Val Phe
    130                 135                 140

Pro Tyr Ile Leu Ala Asp Ala Lys Trp His Lys Leu Ser Leu Ala Phe
145                 150                 155                 160

Ser Ala Ser His Leu Ile Leu His Ile Asp Cys Asn Lys Ile Tyr Glu
                165                 170                 175

Arg Val Val Glu Met Pro Phe Thr Asp Leu Ala Leu Gly Thr Thr Phe
            180                 185                 190

Trp Leu Gly Gln Arg Asn Asn Ala His Gly Tyr Phe Lys Gly Ile Met
        195                 200                 205

Gln Asp Val His Val Leu Val Met Pro Gln Gly Phe Ile Ala Gln Cys
    210                 215                 220

Pro Asp Leu Asn Arg Thr Cys Pro Thr Cys Asn Asp Phe His Gly Leu
225                 230                 235                 240

Val Gln Lys Ile Met Glu Leu Gln Asp Ile Leu Ser Lys Thr Ser Ala
                245                 250                 255

Lys Leu Ser Arg Ala Glu Gln Arg Met Asn Arg Leu Asp Gln Cys Tyr
            260                 265                 270

Cys Glu Arg Thr Cys Thr Val Lys Gly Thr Thr Tyr Arg Glu Ser Glu
        275                 280                 285

Ser Trp Thr Asp Gly Cys Lys Asn Cys Thr Cys Leu Asn Gly Thr Ile
    290                 295                 300

Gln Cys Glu Thr Leu Val Cys Pro Ala Pro Asp Cys Pro Pro Lys Ser
305                 310                 315                 320

Ala Pro Ala Tyr Val Asp Gly Lys Cys Cys Lys Glu Cys Lys Ser Thr
                325                 330                 335

Cys Gln Phe Gln Gly Arg Ser Tyr Phe Glu Gly Glu Arg Asn Thr Ala
            340                 345                 350

Tyr Ser Ser Ser Gly Met Cys Val Leu Tyr Glu Cys Lys Asp Gln Thr
```

-continued

```
                355                 360                 365
Met Lys Leu Val Glu Asn Ile Gly Cys Pro Pro Leu Asp Cys Pro Glu
    370                 375                 380

Ser His Gln Ile Ala Leu Ser His Ser Cys Cys Lys Val Cys Lys Gly
385                 390                 395                 400

Tyr Asp Phe Cys Ser Glu Lys His Thr Cys Met Glu Asn Ser Val Cys
                405                 410                 415

Arg Asn Leu Asn Asp Arg Val Val Cys Ser Cys Arg Asp Gly Phe Arg
                420                 425                 430

Ala Leu Arg Glu Asp Asn Ala Tyr Cys Glu Asp Ile Asp Glu Cys Ala
            435                 440                 445

Glu Gly Arg His Tyr Cys Arg Glu Asn Thr Met Cys Val Asn Thr Pro
        450                 455                 460

Gly Ser Phe Met Cys Val Cys Lys Thr Gly Tyr Ile Arg Ile Asp Asp
465                 470                 475                 480

Tyr Ser Cys Thr Glu His Asp Glu Cys Leu Thr Thr Gln His Asn Cys
                485                 490                 495

Asp Glu Asn Ala Leu Cys Phe Asn Thr Val Gly Gly His Asn Cys Val
                500                 505                 510

Cys Lys Pro Gly Tyr Thr Gly Asn Gly Thr Thr Cys Lys Ala Phe Cys
            515                 520                 525

Lys Asp Gly Cys Arg Asn Gly Gly Ala Cys Ile Ala Ala Asn Val Cys
530                 535                 540

Ala Cys Pro Gln Gly Phe Thr Gly Pro Ser Cys Glu Thr Asp Ile Asp
545                 550                 555                 560

Glu Cys Ser Glu Gly Phe Val Gln Cys Asp Ser Arg Ala Asn Cys Ile
                565                 570                 575

Asn Leu Pro Gly Trp Tyr His Cys Glu Cys Arg Asp Gly Tyr His Asp
            580                 585                 590

Asn Gly Met Phe Ala Pro Gly Gly Glu Ser Cys Glu Asp Ile Asp Glu
        595                 600                 605

Cys Gly Thr Gly Arg His Ser Cys Thr Asn Asp Thr Ile Cys Phe Asn
    610                 615                 620

Leu Asp Gly Gly Tyr Asp Cys Arg Cys Pro His Gly Lys Asn Cys Thr
625                 630                 635                 640

Gly Asp Cys Val His Glu Gly Lys Val Lys His Thr Gly Gln Ile Trp
                645                 650                 655

Val Leu Glu Asn Asp Arg Cys Ser Val Cys Ser Trp Gln Thr Gly Phe
                660                 665                 670

Val Met Cys Arg Arg Met Val Cys Asp Cys Glu Asn Pro Thr Asp Asp
            675                 680                 685

Leu Ser Cys Cys Pro Glu Cys Asp Pro Arg Leu Ser Gln Cys Leu
        690                 695                 700

His Gln Asn Gly Glu Thr Val Tyr Asn Ser Gly Asp Thr Trp Val Gln
705                 710                 715                 720

Asp Cys Arg Gln Cys Arg Cys Leu Gln Gly Glu Val Asp Cys Trp Pro
                725                 730                 735

Leu Ala Cys Pro Glu Val Glu Cys Glu Phe Ser Val Leu Pro Glu Asn
                740                 745                 750

Glu Cys Cys Pro Arg Cys Val Thr Asp Pro Cys Gln Ala Asp Thr Ile
            755                 760                 765

Arg Asn Asp Ile Thr Lys Thr Cys Leu Asp Glu Met Asn Val Val Arg
770                 775                 780
```

```
Phe Thr Gly Ser Ser Trp Ile Lys His Gly Thr Glu Cys Thr Leu Cys
785                 790                 795                 800

Gln Cys Lys Asn Gly His Leu Cys Cys Ser Val Asp Pro Gln Cys Leu
                805                 810                 815

Gln Glu Leu

<210> SEQ ID NO 13
<211> LENGTH: 2453
<212> TYPE: DNA
<213> ORGANISM: Gallus gallus
<220> FEATURE:
<221> NAME/KEY: CDS
<222> LOCATION: (1)..(2448)

<400> SEQUENCE: 13 atg gag tcc ggc tgc ggc tta ggc acg ctt tgc ctt ctc ctc tgc ctg    48
Met Glu Ser Gly Cys Gly Leu Gly Thr Leu Cys Leu Leu Leu Cys Leu
1               5                   10                  15 ggg cca gtc gta ggc ttc ggc gtg gac ccc tcg ctg cag atc gac gtg    96
Gly Pro Val Val Gly Phe Gly Val Asp Pro Ser Leu Gln Ile Asp Val
            20                  25                  30 ctg tcc gag ctg ggg ctg ccg ggc tac gcg gcg ggc gtg cgc cag gtg   144
Leu Ser Glu Leu Gly Leu Pro Gly Tyr Ala Ala Gly Val Arg Gln Val
        35                  40                  45 ccg ggg ctg cac aac ggg agc aaa gcc ttc ctc ttc cca gat act tca   192
Pro Gly Leu His Asn Gly Ser Lys Ala Phe Leu Phe Pro Asp Thr Ser
    50                  55                  60 aga agt gta aag gcg tct cca gaa aca gct gaa atc ttt ttt cag aag   240
Arg Ser Val Lys Ala Ser Pro Glu Thr Ala Glu Ile Phe Phe Gln Lys
65                  70                  75                  80 ttg aga aat aaa tat gaa ttc aca atc ctg gtg acc tta aaa caa gcc   288
Leu Arg Asn Lys Tyr Glu Phe Thr Ile Leu Val Thr Leu Lys Gln Ala
                85                  90                  95 cat tta aat tca ggg gtt att ttc tct att cat cac tta gat cac agg   336
His Leu Asn Ser Gly Val Ile Phe Ser Ile His His Leu Asp His Arg
            100                 105                 110 tat ctg gaa ttg gaa agc agc ggt cat cga aat gaa atc agg ttg cat   384
Tyr Leu Glu Leu Glu Ser Ser Gly His Arg Asn Glu Ile Arg Leu His
        115                 120                 125 tac cgt aca ggc agt cat cgc tcc cac aca gaa gta ttc cca tac atc   432
Tyr Arg Thr Gly Ser His Arg Ser His Thr Glu Val Phe Pro Tyr Ile
    130                 135                 140 ctg gca gac gat aag tgg cac agg ctt tcc tta gca atc agt gcc tct   480
Leu Ala Asp Asp Lys Trp His Arg Leu Ser Leu Ala Ile Ser Ala Ser
145                 150                 155                 160 cac ttg att tta cac gtg gac tgc aat aaa atc tat gaa aga gtt gtg   528
His Leu Ile Leu His Val Asp Cys Asn Lys Ile Tyr Glu Arg Val Val
                165                 170                 175 gag aag ccc ttc atg gac tta cct gtg ggt aca acc ttt tgg cta gga   576
Glu Lys Pro Phe Met Asp Leu Pro Val Gly Thr Thr Phe Trp Leu Gly
            180                 185                 190 cag agg aat aat gca cac ggt tat ttt aag ggc ata atg caa gat gtg   624
Gln Arg Asn Asn Ala His Gly Tyr Phe Lys Gly Ile Met Gln Asp Val
        195                 200                 205 caa tta ctt gtc atg cct caa gga ttt att tct cag tgc cca gat ctt   672
Gln Leu Leu Val Met Pro Gln Gly Phe Ile Ser Gln Cys Pro Asp Leu
    210                 215                 220 aat cgg aca tgc cca act tgt aat gat ttc cat gga ctt gtg cag aaa   720
Asn Arg Thr Cys Pro Thr Cys Asn Asp Phe His Gly Leu Val Gln Lys
225                 230                 235                 240
```

```
att atg gaa ctg caa gac att tta gct aaa acg tca gct aag ctg tcg      768
Ile Met Glu Leu Gln Asp Ile Leu Ala Lys Thr Ser Ala Lys Leu Ser
            245                 250                 255 caa gct gag cag agg atg aac aag ttg gat cag tgc tat tgt gaa agg      816
Gln Ala Glu Gln Arg Met Asn Lys Leu Asp Gln Cys Tyr Cys Glu Arg
        260                 265                 270 acc tgc aca atg aaa ggc atg aca tac aga gaa ttt gaa tcc tgg aca      864
Thr Cys Thr Met Lys Gly Met Thr Tyr Arg Glu Phe Glu Ser Trp Thr
    275                 280                 285 gat ggt tgt aag aac tgc act tgc atg aat ggc act gtg cag tgt gaa      912
Asp Gly Cys Lys Asn Cys Thr Cys Met Asn Gly Thr Val Gln Cys Glu
290                 295                 300 gct ttg att tgc tcc ctc tct gac tgt cca cct aat tct gcc ctg tca      960
Ala Leu Ile Cys Ser Leu Ser Asp Cys Pro Pro Asn Ser Ala Leu Ser
305                 310                 315                 320 tac gtg gat ggc aag tgc tgc aaa gaa tgt caa tcg gtg tgc ata ttt     1008
Tyr Val Asp Gly Lys Cys Cys Lys Glu Cys Gln Ser Val Cys Ile Phe
                325                 330                 335 gaa ggc aga acc tac ttt gaa gga caa aga gaa acg gtg tat tca agc     1056
Glu Gly Arg Thr Tyr Phe Glu Gly Gln Arg Glu Thr Val Tyr Ser Ser
            340                 345                 350 tca ggg gac tgt gtt ctg ttt gag tgc aag gac cac aaa atg cag cgt     1104
Ser Gly Asp Cys Val Leu Phe Glu Cys Lys Asp His Lys Met Gln Arg
        355                 360                 365 att cca aaa gac agt tgt gca act ttg aac tgc ccg gaa tct caa cag     1152
Ile Pro Lys Asp Ser Cys Ala Thr Leu Asn Cys Pro Glu Ser Gln Gln
    370                 375                 380 atc cca tta tct cac agt tgc tgc aaa atc tgt aaa ggc cat gac ttt     1200
Ile Pro Leu Ser His Ser Cys Cys Lys Ile Cys Lys Gly His Asp Phe
385                 390                 395                 400 tgc act gaa gga cat aac tgt atg gag cat tct gtc tgc cga aac cta     1248
Cys Thr Glu Gly His Asn Cys Met Glu His Ser Val Cys Arg Asn Leu
                405                 410                 415 gat gac aga gct gtc tgt agc tgc cga gat ggc ttc cgg gcc ctt cgg     1296
Asp Asp Arg Ala Val Cys Ser Cys Arg Asp Gly Phe Arg Ala Leu Arg
            420                 425                 430 gag gac aat gcc tac tgt gaa gat gtt gat gag tgt gcc gag ggg cag     1344
Glu Asp Asn Ala Tyr Cys Glu Asp Val Asp Glu Cys Ala Glu Gly Gln
        435                 440                 445 cac tac tgt cgg gag aac acc atg tgt gta aat aca cca gga tcc ttc     1392
His Tyr Cys Arg Glu Asn Thr Met Cys Val Asn Thr Pro Gly Ser Phe
    450                 455                 460 atg tgc atc tgc aaa aca gga tat ata cgc att gat gac tat tca tgt     1440
Met Cys Ile Cys Lys Thr Gly Tyr Ile Arg Ile Asp Asp Tyr Ser Cys
465                 470                 475                 480 aca gag cac gat gaa tgt gta aca aac cag cac aac tgt gat gaa aat     1488
Thr Glu His Asp Glu Cys Val Thr Asn Gln His Asn Cys Asp Glu Asn
                485                 490                 495 gcg cta tgt ttc aac acg gtg ggt ggg cac aac tgt gtc tgc aag ctg     1536
Ala Leu Cys Phe Asn Thr Val Gly Gly His Asn Cys Val Cys Lys Leu
            500                 505                 510 ggt tac aca gga aat ggg acg gtg tgt aaa gca ttt tgc aaa gat ggg     1584
Gly Tyr Thr Gly Asn Gly Thr Val Cys Lys Ala Phe Cys Lys Asp Gly
        515                 520                 525 tgc agg aat gga gga gcc tgt att gct tcc aac gtg tgt gcc tgc cca     1632
Cys Arg Asn Gly Gly Ala Cys Ile Ala Ser Asn Val Cys Ala Cys Pro
    530                 535                 540 caa ggc ttc act ggc ccc agc tgt gaa act gac att gat gaa tgc tct     1680
Gln Gly Phe Thr Gly Pro Ser Cys Glu Thr Asp Ile Asp Glu Cys Ser
```

```
                                                                              1728
gat ggc ttt gtg cag tgt gac agc cgt gct aat tgc atc aat ctg cca
Asp Gly Phe Val Gln Cys Asp Ser Arg Ala Asn Cys Ile Asn Leu Pro
            565                 570                 575 ggg tgg tac cac tgt gaa tgc agg gat ggc tac cat gac aat ggg atg      1776
Gly Trp Tyr His Cys Glu Cys Arg Asp Gly Tyr His Asp Asn Gly Met
        580                 585                 590 ttt tca cca agt gga gaa tcc tgt gaa gac att gat gaa tgt gca act      1824
Phe Ser Pro Ser Gly Glu Ser Cys Glu Asp Ile Asp Glu Cys Ala Thr
    595                 600                 605 gga agg cat agc tgt gcc aat gac act gtt tgc ttt aac ctg gat ggt      1872
Gly Arg His Ser Cys Ala Asn Asp Thr Val Cys Phe Asn Leu Asp Gly
610                 615                 620 ggg tat gac tgt cga tgt cca cat ggc aag aac tgc aca gga gac tgt      1920
Gly Tyr Asp Cys Arg Cys Pro His Gly Lys Asn Cys Thr Gly Asp Cys
625                 630                 635                 640 atc cat gaa gac aaa atc aag cac aat ggt cag att tgg gtg ctg gag      1968
Ile His Glu Asp Lys Ile Lys His Asn Gly Gln Ile Trp Val Leu Glu
                645                 650                 655 aac gac aga tgc tct gtc tgc tca tgc cag agt gga tac gtg atg tgc      2016
Asn Asp Arg Cys Ser Val Cys Ser Cys Gln Ser Gly Tyr Val Met Cys
            660                 665                 670 cgg cga atg gtc tgt gac tgt gaa aat ccc act gtt gac ctc ttt tgc      2064
Arg Arg Met Val Cys Asp Cys Glu Asn Pro Thr Val Asp Leu Phe Cys
        675                 680                 685 tgt cct gag tgt gac cca agg ctc agc agt caa tgt tta cat cag agt      2112
Cys Pro Glu Cys Asp Pro Arg Leu Ser Ser Gln Cys Leu His Gln Ser
    690                 695                 700 ggg gag ctt tcc tac aac agt ggt gac tcc tgg ata caa aac tgt cag      2160
Gly Glu Leu Ser Tyr Asn Ser Gly Asp Ser Trp Ile Gln Asn Cys Gln
705                 710                 715                 720 cag tgt cgc tgc ttg caa gga gag gtt gac tgt tgg ccc tta ccg tgc      2208
Gln Cys Arg Cys Leu Gln Gly Glu Val Asp Cys Trp Pro Leu Pro Cys
                725                 730                 735 cca gag gta gac tgt gag ttc agt gtc ctc cct gag aat gag tgc tgc      2256
Pro Glu Val Asp Cys Glu Phe Ser Val Leu Pro Glu Asn Glu Cys Cys
            740                 745                 750 cca cgc tgt gtc act gac ccc tgc caa gcg gac acc atc cgt aat gac      2304
Pro Arg Cys Val Thr Asp Pro Cys Gln Ala Asp Thr Ile Arg Asn Asp
        755                 760                 765 atc acc aaa acc tgc ctg gat gaa acc aat gtt gtt cgc ttc act gga      2352
Ile Thr Lys Thr Cys Leu Asp Glu Thr Asn Val Val Arg Phe Thr Gly
    770                 775                 780 tct tct tgg att aag cat ggc aca gag tgc aca ctc tgc caa tgt aag      2400
Ser Ser Trp Ile Lys His Gly Thr Glu Cys Thr Leu Cys Gln Cys Lys
785                 790                 795                 800 aat ggc cac gtc tgt tgc tca gtg gat cca cag tgc ctt cag gaa ctg      2448
Asn Gly His Val Cys Cys Ser Val Asp Pro Gln Cys Leu Gln Glu Leu
                805                 810                 815 tgaca                                                                 2453

<210> SEQ ID NO 14
<211> LENGTH: 816
<212> TYPE: PRT
<213> ORGANISM: Gallus gallus

<400> SEQUENCE: 14

Met Glu Ser Gly Cys Gly Leu Gly Thr Leu Cys Leu Leu Leu Cys Leu
1               5                   10                  15
```

```
Gly Pro Val Val Gly Phe Gly Val Asp Pro Ser Leu Gln Ile Asp Val
             20                  25                  30
Leu Ser Glu Leu Gly Leu Pro Gly Tyr Ala Ala Gly Val Arg Gln Val
         35                  40                  45
Pro Gly Leu His Asn Gly Ser Lys Ala Phe Leu Phe Pro Asp Thr Ser
     50                  55                  60
Arg Ser Val Lys Ala Ser Pro Glu Thr Ala Glu Ile Phe Phe Gln Lys
 65                  70                  75                  80
Leu Arg Asn Lys Tyr Glu Phe Thr Ile Leu Val Thr Leu Lys Gln Ala
                 85                  90                  95
His Leu Asn Ser Gly Val Ile Phe Ser Ile His His Leu Asp His Arg
             100                 105                 110
Tyr Leu Glu Leu Glu Ser Ser Gly His Arg Asn Glu Ile Arg Leu His
         115                 120                 125
Tyr Arg Thr Gly Ser His Arg Ser His Thr Glu Val Phe Pro Tyr Ile
     130                 135                 140
Leu Ala Asp Asp Lys Trp His Arg Leu Ser Leu Ala Ile Ser Ala Ser
145                 150                 155                 160
His Leu Ile Leu His Val Asp Cys Asn Lys Ile Tyr Glu Arg Val Val
                 165                 170                 175
Glu Lys Pro Phe Met Asp Leu Pro Val Gly Thr Thr Phe Trp Leu Gly
             180                 185                 190
Gln Arg Asn Asn Ala His Gly Tyr Phe Lys Gly Ile Met Gln Asp Val
         195                 200                 205
Gln Leu Leu Val Met Pro Gln Gly Phe Ile Ser Gln Cys Pro Asp Leu
     210                 215                 220
Asn Arg Thr Cys Pro Thr Cys Asn Asp Phe His Gly Leu Val Gln Lys
225                 230                 235                 240
Ile Met Glu Leu Gln Asp Ile Leu Ala Lys Thr Ser Ala Lys Leu Ser
                 245                 250                 255
Gln Ala Glu Gln Arg Met Asn Lys Leu Asp Gln Cys Tyr Cys Glu Arg
             260                 265                 270
Thr Cys Thr Met Lys Gly Met Thr Tyr Arg Glu Phe Glu Ser Trp Thr
         275                 280                 285
Asp Gly Cys Lys Asn Cys Thr Cys Met Asn Gly Thr Val Gln Cys Glu
     290                 295                 300
Ala Leu Ile Cys Ser Leu Ser Asp Cys Pro Pro Asn Ser Ala Leu Ser
305                 310                 315                 320
Tyr Val Asp Gly Lys Cys Cys Lys Glu Cys Gln Ser Val Cys Ile Phe
                 325                 330                 335
Glu Gly Arg Thr Tyr Phe Glu Gly Gln Arg Glu Thr Val Tyr Ser Ser
             340                 345                 350
Ser Gly Asp Cys Val Leu Phe Glu Cys Lys Asp His Lys Met Gln Arg
         355                 360                 365
Ile Pro Lys Asp Ser Cys Ala Thr Leu Asn Cys Pro Glu Ser Gln Gln
     370                 375                 380
Ile Pro Leu Ser His Ser Cys Cys Lys Ile Cys Lys Gly His Asp Phe
385                 390                 395                 400
Cys Thr Glu Gly His Asn Cys Met Glu His Ser Val Cys Arg Asn Leu
                 405                 410                 415
Asp Asp Arg Ala Val Cys Ser Cys Arg Asp Gly Phe Arg Ala Leu Arg
             420                 425                 430
Glu Asp Asn Ala Tyr Cys Glu Asp Val Asp Glu Cys Ala Glu Gly Gln
```

```
                435                 440                 445
His Tyr Cys Arg Glu Asn Thr Met Cys Val Asn Thr Pro Gly Ser Phe
450                 455                 460

Met Cys Ile Cys Lys Thr Gly Tyr Ile Arg Ile Asp Asp Tyr Ser Cys
465                 470                 475                 480

Thr Glu His Asp Glu Cys Val Thr Asn Gln His Asn Cys Asp Glu Asn
                485                 490                 495

Ala Leu Cys Phe Asn Thr Val Gly Gly His Asn Cys Val Cys Lys Leu
            500                 505                 510

Gly Tyr Thr Gly Asn Gly Thr Val Cys Lys Ala Phe Cys Lys Asp Gly
            515                 520                 525

Cys Arg Asn Gly Gly Ala Cys Ile Ala Ser Asn Val Cys Ala Cys Pro
530                 535                 540

Gln Gly Phe Thr Gly Pro Ser Cys Glu Thr Asp Ile Asp Glu Cys Ser
545                 550                 555                 560

Asp Gly Phe Val Gln Cys Asp Ser Arg Ala Asn Cys Ile Asn Leu Pro
                565                 570                 575

Gly Trp Tyr His Cys Glu Cys Arg Asp Gly Tyr His Asp Asn Gly Met
            580                 585                 590

Phe Ser Pro Ser Gly Glu Ser Cys Glu Asp Ile Asp Glu Cys Ala Thr
            595                 600                 605

Gly Arg His Ser Cys Ala Asn Asp Thr Val Cys Phe Asn Leu Asp Gly
610                 615                 620

Gly Tyr Asp Cys Arg Cys Pro His Gly Lys Asn Cys Thr Gly Asp Cys
625                 630                 635                 640

Ile His Glu Asp Lys Ile Lys His Asn Gly Gln Ile Trp Val Leu Glu
                645                 650                 655

Asn Asp Arg Cys Ser Val Cys Ser Cys Gln Ser Gly Tyr Val Met Cys
            660                 665                 670

Arg Arg Met Val Cys Asp Cys Glu Asn Pro Thr Val Asp Leu Phe Cys
            675                 680                 685

Cys Pro Glu Cys Asp Pro Arg Leu Ser Ser Gln Cys Leu His Gln Ser
690                 695                 700

Gly Glu Leu Ser Tyr Asn Ser Gly Asp Ser Trp Ile Gln Asn Cys Gln
705                 710                 715                 720

Gln Cys Arg Cys Leu Gln Gly Glu Val Asp Cys Trp Pro Leu Pro Cys
                725                 730                 735

Pro Glu Val Asp Cys Glu Phe Ser Val Leu Pro Glu Asn Glu Cys Cys
            740                 745                 750

Pro Arg Cys Val Thr Asp Pro Cys Gln Ala Asp Thr Ile Arg Asn Asp
            755                 760                 765

Ile Thr Lys Thr Cys Leu Asp Glu Thr Asn Val Val Arg Phe Thr Gly
770                 775                 780

Ser Ser Trp Ile Lys His Gly Thr Glu Cys Thr Leu Cys Gln Cys Lys
785                 790                 795                 800

Asn Gly His Val Cys Cys Ser Val Asp Pro Gln Cys Leu Gln Glu Leu
                805                 810                 815
```

<210> SEQ ID NO 15
<211> LENGTH: 24
<212> TYPE: PRT
<213> ORGANISM: Homo sapiens

<400> SEQUENCE: 15

-continued

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 16
<211> LENGTH: 24
<212> TYPE: PRT
<213> ORGANISM: Homo sapiens

<400> SEQUENCE: 16

Met Ala Val Met Ala Pro Arg Thr Leu Leu Leu Leu Leu Ser Gly Ala
1               5                   10                  15

Leu Ala Leu Thr Gln Thr Trp Ala
            20

<210> SEQ ID NO 17
<211> LENGTH: 24
<212> TYPE: PRT
<213> ORGANISM: Homo sapiens

<400> SEQUENCE: 17

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 18
<211> LENGTH: 24
<212> TYPE: PRT
<213> ORGANISM: Homo sapiens

<400> SEQUENCE: 18

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 19
<211> LENGTH: 24
<212> TYPE: PRT
<213> ORGANISM: Homo sapiens

<400> SEQUENCE: 19

Met Ala Val Met Ala Pro Arg Thr Leu Leu Leu Leu Leu Ser Gly Ala
1               5                   10                  15

Leu Ala Leu Thr His Thr Trp Ala
            20

<210> SEQ ID NO 20
<211> LENGTH: 24
<212> TYPE: PRT
<213> ORGANISM: Homo sapiens

<400> SEQUENCE: 20

Met Ala Val Met Ala Pro Arg Thr Leu Leu Leu Leu Leu Leu Gly Ala
1               5                   10                  15

Leu Ala Leu Thr Gln Thr Trp Ala
            20

<210> SEQ ID NO 21
<211> LENGTH: 24

```
<212> TYPE: PRT
<213> ORGANISM: Homo sapiens

<400> SEQUENCE: 21

Met Ala Val Met Ala Pro Arg Thr Leu Leu Leu Leu Leu Gly Ala
1               5                   10                  15

Leu Ala Leu Thr Gln Thr Trp Ala
            20

<210> SEQ ID NO 22
<211> LENGTH: 24
<212> TYPE: PRT
<213> ORGANISM: Homo sapiens

<400> SEQUENCE: 22

Met Ala Val Met Ala Pro Arg Thr Leu Val Leu Leu Leu Ser Gly Ala
1               5                   10                  15

Leu Ala Leu Thr Gln Thr Trp Ala
            20

<210> SEQ ID NO 23
<211> LENGTH: 24
<212> TYPE: PRT
<213> ORGANISM: Homo sapiens

<400> SEQUENCE: 23

Met Ala Val Met Pro Pro Arg Thr Leu Leu Leu Leu Leu Ser Gly Ala
1               5                   10                  15

Leu Ala Leu Thr Gln Thr Trp Ala
            20

<210> SEQ ID NO 24
<211> LENGTH: 24
<212> TYPE: PRT
<213> ORGANISM: Homo sapiens

<400> SEQUENCE: 24

Met Leu Val Met Ala Pro Arg Thr Val Leu Leu Leu Leu Ser Ala Ala
1               5                   10                  15

Leu Ala Leu Thr Glu Thr Trp Ala
            20

<210> SEQ ID NO 25
<211> LENGTH: 24
<212> TYPE: PRT
<213> ORGANISM: Homo sapiens

<400> SEQUENCE: 25

Met Arg Val Thr Ala Pro Arg Thr Val Leu Leu Leu Leu Ser Gly Ala
1               5                   10                  15

Leu Ala Leu Thr Glu Thr Trp Ala
            20

<210> SEQ ID NO 26
<211> LENGTH: 24
<212> TYPE: PRT
<213> ORGANISM: Homo sapiens

<400> SEQUENCE: 26

Met Arg Val Thr Ala Pro Arg Thr Leu Leu Leu Leu Leu Trp Gly Ala
1               5                   10                  15

Val Ala Leu Thr Glu Thr Trp Ala
```

<210> SEQ ID NO 27
<211> LENGTH: 24
<212> TYPE: PRT
<213> ORGANISM: Homo sapiens

<400> SEQUENCE: 27

Met Arg Val Thr Ala Pro Arg Thr Leu Leu Leu Leu Trp Gly Ala
1               5                   10                  15

Val Ala Leu Thr Glu Thr Trp Ala
            20

<210> SEQ ID NO 28
<211> LENGTH: 24
<212> TYPE: PRT
<213> ORGANISM: Homo sapiens

<400> SEQUENCE: 28

Met Arg Val Thr Ala Pro Arg Thr Leu Leu Leu Leu Trp Gly Ala
1               5                   10                  15

Val Ala Leu Thr Glu Thr Trp Ala
            20

<210> SEQ ID NO 29
<211> LENGTH: 24
<212> TYPE: PRT
<213> ORGANISM: Homo sapiens

<400> SEQUENCE: 29

Met Leu Val Met Ala Pro Arg Thr Val Leu Leu Leu Ser Ala Ala
1               5                   10                  15

Leu Ala Leu Thr Glu Thr Trp Ala
            20

<210> SEQ ID NO 30
<211> LENGTH: 24
<212> TYPE: PRT
<213> ORGANISM: Homo sapiens

<400> SEQUENCE: 30

Met Arg Val Thr Ala Pro Arg Thr Val Leu Leu Leu Trp Gly Ala
1               5                   10                  15

Val Ala Leu Thr Glu Thr Trp Ala
            20

<210> SEQ ID NO 31
<211> LENGTH: 24
<212> TYPE: PRT
<213> ORGANISM: Homo sapiens

<400> SEQUENCE: 31

Met Arg Val Thr Ala Pro Arg Thr Leu Leu Leu Leu Trp Gly Ala
1               5                   10                  15

Leu Ala Leu Thr Glu Thr Trp Ala
            20

<210> SEQ ID NO 32
<211> LENGTH: 24
<212> TYPE: PRT
<213> ORGANISM: Homo sapiens

<400> SEQUENCE: 32

```
Met Arg Val Thr Ala Pro Arg Thr Val Leu Leu Leu Trp Gly Ala
1               5                   10                  15

Val Ala Leu Thr Glu Thr Trp Ala
            20
```

<210> SEQ ID NO 33
<211> LENGTH: 24
<212> TYPE: PRT
<213> ORGANISM: Homo sapiens

<400> SEQUENCE: 33

```
Met Arg Val Met Ala Pro Arg Thr Leu Ile Leu Leu Ser Gly Ala
1               5                   10                  15

Leu Ala Leu Thr Glu Thr Trp Ala
            20
```

<210> SEQ ID NO 34
<211> LENGTH: 24
<212> TYPE: PRT
<213> ORGANISM: Homo sapiens

<400> SEQUENCE: 34

```
Met Arg Val Met Ala Pro Arg Thr Leu Ile Leu Leu Ser Gly Ala
1               5                   10                  15

Leu Ala Leu Thr Glu Thr Trp Ala
            20
```

<210> SEQ ID NO 35
<211> LENGTH: 24
<212> TYPE: PRT
<213> ORGANISM: Homo sapiens

<400> SEQUENCE: 35

```
Met Arg Val Met Ala Pro Arg Thr Leu Ile Leu Leu Ser Gly Ala
1               5                   10                  15

Leu Ala Leu Thr Glu Thr Trp Ala
            20
```

<210> SEQ ID NO 36
<211> LENGTH: 24
<212> TYPE: PRT
<213> ORGANISM: Homo sapiens

<400> SEQUENCE: 36

```
Met Arg Val Met Ala Pro Arg Ala Leu Leu Leu Leu Ser Gly Gly
1               5                   10                  15

Leu Ala Leu Thr Glu Thr Trp Ala
            20
```

<210> SEQ ID NO 37
<211> LENGTH: 24
<212> TYPE: PRT
<213> ORGANISM: Homo sapiens

<400> SEQUENCE: 37

```
Met Arg Val Met Ala Pro Arg Thr Leu Ile Leu Leu Ser Gly Ala
1               5                   10                  15

Leu Ala Leu Thr Glu Thr Trp Ala
            20
```

<210> SEQ ID NO 38

```
<211> LENGTH: 24
<212> TYPE: PRT
<213> ORGANISM: Homo sapiens

<400> SEQUENCE: 38

Met Arg Val Met Ala Pro Arg Thr Leu Leu Leu Leu Ser Gly Ala
1               5                   10                  15

Leu Ala Leu Thr Glu Thr Trp Ala
            20

<210> SEQ ID NO 39
<211> LENGTH: 24
<212> TYPE: PRT
<213> ORGANISM: Homo sapiens

<400> SEQUENCE: 39

Met Arg Val Met Ala Pro Arg Thr Leu Ile Leu Leu Ser Gly Ala
1               5                   10                  15

Leu Ala Leu Thr Glu Thr Trp Ala
            20

<210> SEQ ID NO 40
<211> LENGTH: 24
<212> TYPE: PRT
<213> ORGANISM: Homo sapiens

<400> SEQUENCE: 40

Met Arg Val Met Ala Pro Gln Ala Leu Leu Leu Leu Ser Gly Ala
1               5                   10                  15

Leu Ala Leu Ile Glu Thr Trp Ala
            20

<210> SEQ ID NO 41
<211> LENGTH: 24
<212> TYPE: PRT
<213> ORGANISM: Homo sapiens

<400> SEQUENCE: 41

Met Arg Val Met Ala Pro Arg Ala Leu Leu Leu Leu Ser Gly Gly
1               5                   10                  15

Leu Ala Leu Thr Glu Thr Trp Ala
            20

<210> SEQ ID NO 42
<211> LENGTH: 29
<212> TYPE: PRT
<213> ORGANISM: Homo sapiens

<400> SEQUENCE: 42

Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ala
            20                  25

<210> SEQ ID NO 43
<211> LENGTH: 29
<212> TYPE: PRT
<213> ORGANISM: Homo sapiens

<400> SEQUENCE: 43

Met Val Cys Leu Lys Phe Pro Gly Gly Ser Cys Met Ala Ala Leu Thr
1               5                   10                  15
```

Val Thr Leu Met Val Leu Ser Ser Pro Leu Ala Leu Ala
            20                  25

<210> SEQ ID NO 44
<211> LENGTH: 29
<212> TYPE: PRT
<213> ORGANISM: Homo sapiens

<400> SEQUENCE: 44

Met Val Cys Leu Lys Leu Pro Gly Gly Ser Cys Met Ala Ala Leu Thr
1               5                   10                  15

Val Thr Leu Met Val Leu Ser Ser Pro Leu Ala Leu Ala
            20                  25

<210> SEQ ID NO 45
<211> LENGTH: 29
<212> TYPE: PRT
<213> ORGANISM: Homo sapiens

<400> SEQUENCE: 45

Met Val Cys Leu Arg Leu Pro Gly Gly Ser Cys Met Ala Val Leu Thr
1               5                   10                  15

Val Thr Leu Met Val Leu Ser Ser Pro Leu Ala Leu Ala
            20                  25

<210> SEQ ID NO 46
<211> LENGTH: 29
<212> TYPE: PRT
<213> ORGANISM: Homo sapiens

<400> SEQUENCE: 46

Met Val Cys Leu Arg Leu Pro Gly Gly Ser Cys Met Ala Val Leu Thr
1               5                   10                  15

Val Thr Leu Met Val Leu Ser Ser Pro Leu Ala Leu Ala
            20                  25

<210> SEQ ID NO 47
<211> LENGTH: 29
<212> TYPE: PRT
<213> ORGANISM: Homo sapiens

<400> SEQUENCE: 47

Met Val Cys Leu Lys Leu Pro Gly Gly Ser Ser Leu Ala Ala Leu Thr
1               5                   10                  15

Val Thr Leu Met Val Leu Ser Ser Arg Leu Ala Phe Ala
            20                  25

<210> SEQ ID NO 48
<211> LENGTH: 26
<212> TYPE: PRT
<213> ORGANISM: Homo sapiens

<400> SEQUENCE: 48

Met Gly Ser Gly Trp Val Pro Trp Val Val Ala Leu Leu Val Asn Leu
1               5                   10                  15

Thr Arg Leu Asp Ser Ser Met Thr Gln Gly
            20                  25

<210> SEQ ID NO 49
<211> LENGTH: 26
<212> TYPE: PRT
<213> ORGANISM: Homo sapiens

```
<400> SEQUENCE: 49

Met Val Ser Arg Met Val Ser Thr Met Leu Ser Gly Leu Leu Phe Trp
1               5                   10                  15

Leu Ala Ser Gly Trp Thr Pro Ala Phe Ala
            20                  25

<210> SEQ ID NO 50
<211> LENGTH: 24
<212> TYPE: PRT
<213> ORGANISM: Homo sapiens

<400> SEQUENCE: 50

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 51
<211> LENGTH: 35
<212> TYPE: PRT
<213> ORGANISM: Homo sapiens

<400> SEQUENCE: 51

Met Ser Ser Trp Ser Arg Gln Arg Pro Lys Ser Pro Gly Gly Ile Gln
1               5                   10                  15

Pro His Val Ser Arg Thr Leu Phe Leu Leu Leu Leu Leu Ala Ala Ser
            20                  25                  30

Ala Trp Gly
        35

<210> SEQ ID NO 52
<211> LENGTH: 23
<212> TYPE: PRT
<213> ORGANISM: Homo sapiens

<400> SEQUENCE: 52

Met Gly Lys Asn Lys Leu Leu His Pro Ser Leu Val Leu Leu Leu Leu
1               5                   10                  15

Val Leu Leu Pro Thr Asp Ala
            20

<210> SEQ ID NO 53
<211> LENGTH: 19
<212> TYPE: PRT
<213> ORGANISM: Homo sapiens

<400> SEQUENCE: 53

Met Pro Ala Leu Gly Trp Ala Val Ala Ala Ile Leu Met Leu Gln Thr
1               5                   10                  15

Ala Met Ala

<210> SEQ ID NO 54
<211> LENGTH: 31
<212> TYPE: PRT
<213> ORGANISM: Homo sapiens

<400> SEQUENCE: 54

Met Gly Gln Gly Trp Ala Thr Ala Gly Leu Pro Ser Leu Leu Phe Leu
1               5                   10                  15

Leu Leu Cys Tyr Gly His Pro Leu Leu Val Pro Ser Gln Glu Ala
            20                  25                  30
```

<210> SEQ ID NO 55
<211> LENGTH: 23
<212> TYPE: PRT
<213> ORGANISM: Homo sapiens

<400> SEQUENCE: 55

Met Thr Pro Gly Ala Leu Leu Met Leu Leu Gly Ala Leu Gly Ala Pro
1               5                   10                  15

Leu Ala Pro Gly Val Arg Gly
            20

<210> SEQ ID NO 56
<211> LENGTH: 20
<212> TYPE: PRT
<213> ORGANISM: Homo sapiens

<400> SEQUENCE: 56

Met Ala Arg Ala Pro Leu Gly Val Leu Leu Leu Gly Leu Leu Gly
1               5                   10                  15

Arg Gly Val Gly
            20

<210> SEQ ID NO 57
<211> LENGTH: 19
<212> TYPE: PRT
<213> ORGANISM: Homo sapiens

<400> SEQUENCE: 57

Met Val Glu Met Leu Pro Thr Ala Ile Leu Leu Val Leu Ala Val Ser
1               5                   10                  15

Val Val Ala

<210> SEQ ID NO 58
<211> LENGTH: 16
<212> TYPE: PRT
<213> ORGANISM: Homo sapiens

<400> SEQUENCE: 58

Met Phe Arg Leu Trp Leu Leu Leu Ala Gly Leu Cys Gly Leu Leu Ala
1               5                   10                  15

<210> SEQ ID NO 59
<211> LENGTH: 18
<212> TYPE: PRT
<213> ORGANISM: Homo sapiens

<400> SEQUENCE: 59

Met Leu Leu Leu Gly Ala Val Leu Leu Leu Ala Leu Pro Gly His
1               5                   10                  15

Asp Gln

<210> SEQ ID NO 60
<211> LENGTH: 21
<212> TYPE: PRT
<213> ORGANISM: Homo sapiens

<400> SEQUENCE: 60

Met Lys Leu Val Ser Val Ala Leu Met Tyr Leu Gly Ser Leu Ala Phe
1               5                   10                  15

Leu Gly Ala Asp Thr
            20

```
<210> SEQ ID NO 61
<211> LENGTH: 31
<212> TYPE: PRT
<213> ORGANISM: Homo sapiens

<400> SEQUENCE: 61

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala
            20                  25                  30

<210> SEQ ID NO 62
<211> LENGTH: 20
<212> TYPE: PRT
<213> ORGANISM: Homo sapiens

<400> SEQUENCE: 62

Met Glu Lys Ile Pro Val Ser Ala Phe Leu Leu Leu Val Ala Leu Ser
1               5                   10                  15

Tyr Thr Leu Ala
            20

<210> SEQ ID NO 63
<211> LENGTH: 21
<212> TYPE: PRT
<213> ORGANISM: Homo sapiens

<400> SEQUENCE: 63

Met Met Leu His Ser Ala Leu Gly Leu Cys Leu Leu Leu Val Thr Val
1               5                   10                  15

Ser Ser Asn Leu Ala
            20

<210> SEQ ID NO 64
<211> LENGTH: 19
<212> TYPE: PRT
<213> ORGANISM: Homo sapiens

<400> SEQUENCE: 64

Met Arg Ser Leu Gly Ala Leu Leu Leu Leu Leu Ser Ala Cys Leu Ala
1               5                   10                  15

Val Ser Ala

<210> SEQ ID NO 65
<211> LENGTH: 16
<212> TYPE: PRT
<213> ORGANISM: Homo sapiens

<400> SEQUENCE: 65

Met Arg Ser Thr Ile Leu Leu Phe Cys Leu Leu Gly Ser Thr Arg Ser
1               5                   10                  15

<210> SEQ ID NO 66
<211> LENGTH: 25
<212> TYPE: PRT
<213> ORGANISM: Homo sapiens

<400> SEQUENCE: 66

Met Ser Ser Phe Ser Thr Thr Thr Val Ser Phe Leu Leu Leu Leu Ala
1               5                   10                  15

Phe Gln Leu Leu Gly Gln Thr Arg Ala
```

```
                    20                  25

<210> SEQ ID NO 67
<211> LENGTH: 24
<212> TYPE: PRT
<213> ORGANISM: Homo sapiens

<400> SEQUENCE: 67

Met Val Met Gly Leu Gly Val Leu Leu Val Phe Val Leu Gly Leu
1               5                   10                  15

Gly Leu Thr Pro Pro Thr Leu Ala
            20

<210> SEQ ID NO 68
<211> LENGTH: 16
<212> TYPE: PRT
<213> ORGANISM: Homo sapiens

<400> SEQUENCE: 68

Met Phe Thr Ile Lys Leu Leu Leu Phe Ile Val Pro Leu Val Ile Ser
1               5                   10                  15

<210> SEQ ID NO 69
<211> LENGTH: 26
<212> TYPE: PRT
<213> ORGANISM: Homo sapiens

<400> SEQUENCE: 69

Met Leu Lys Lys Pro Leu Ser Ala Val Thr Trp Leu Cys Ile Phe Ile
1               5                   10                  15

Val Ala Phe Val Ser His Pro Ala Trp Leu
            20                  25

<210> SEQ ID NO 70
<211> LENGTH: 33
<212> TYPE: PRT
<213> ORGANISM: Homo sapiens

<400> SEQUENCE: 70

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
            20                  25                  30

Gly

<210> SEQ ID NO 71
<211> LENGTH: 32
<212> TYPE: PRT
<213> ORGANISM: Homo sapiens

<400> SEQUENCE: 71

Met Pro Gly Pro Arg Arg Pro Ala Gly Ser Arg Leu Arg Leu Leu Leu
1               5                   10                  15

Leu Leu Leu Leu Pro Pro Leu Leu Leu Leu Leu Arg Gly Ser His Ala
            20                  25                  30

<210> SEQ ID NO 72
<211> LENGTH: 18
<212> TYPE: PRT
<213> ORGANISM: Homo sapiens

<400> SEQUENCE: 72
```

Met Lys Leu Leu Ala Ala Thr Val Leu Leu Thr Ile Cys Ser Leu
1               5                   10                  15

Glu Gly

<210> SEQ ID NO 73
<211> LENGTH: 20
<212> TYPE: PRT
<213> ORGANISM: Homo sapiens

<400> SEQUENCE: 73

Met Phe Leu Lys Ala Val Val Leu Thr Leu Ala Leu Val Ala Val Ala
1               5                   10                  15

Gly Ala Arg Ala
            20

<210> SEQ ID NO 74
<211> LENGTH: 19
<212> TYPE: PRT
<213> ORGANISM: Homo sapiens

<400> SEQUENCE: 74

Met Glu His Lys Glu Val Val Leu Leu Leu Leu Leu Phe Leu Lys Ser
1               5                   10                  15

Ala Ala Pro

<210> SEQ ID NO 75
<211> LENGTH: 26
<212> TYPE: PRT
<213> ORGANISM: Homo sapiens

<400> SEQUENCE: 75

Met Arg Leu Phe Leu Ser Leu Pro Val Leu Val Val Val Leu Ser Ile
1               5                   10                  15

Val Leu Glu Gly Pro Ala Pro Ala Gln Gly
            20                  25

<210> SEQ ID NO 76
<211> LENGTH: 22
<212> TYPE: PRT
<213> ORGANISM: Homo sapiens

<400> SEQUENCE: 76

Met Gly Thr Arg Leu Leu Pro Ala Leu Phe Leu Val Leu Leu Val Leu
1               5                   10                  15

Gly Phe Glu Val Gln Gly
            20

<210> SEQ ID NO 77
<211> LENGTH: 20
<212> TYPE: PRT
<213> ORGANISM: Homo sapiens

<400> SEQUENCE: 77

Met Gln Pro Arg Val Leu Leu Val Val Ala Leu Leu Ala Leu Leu Ala
1               5                   10                  15

Ser Ala Arg Ala
            20

<210> SEQ ID NO 78
<211> LENGTH: 20
<212> TYPE: PRT
<213> ORGANISM: Homo sapiens

```
<400> SEQUENCE: 78

Met Val Met Leu Leu Leu Leu Ser Ala Leu Ala Gly Leu Phe Gly
1               5                   10                  15

Ala Ala Glu Gly
            20

<210> SEQ ID NO 79
<211> LENGTH: 18
<212> TYPE: PRT
<213> ORGANISM: Homo sapiens

<400> SEQUENCE: 79

Met Lys Val Leu Trp Ala Ala Leu Leu Val Thr Phe Leu Ala Gly Cys
1               5                   10                  15

Gln Ala

<210> SEQ ID NO 80
<211> LENGTH: 19
<212> TYPE: PRT
<213> ORGANISM: Homo sapiens

<400> SEQUENCE: 80

Met Ile Ser Pro Val Leu Ile Leu Phe Ser Ser Phe Leu Cys His Val
1               5                   10                  15

Ala Ile Ala

<210> SEQ ID NO 81
<211> LENGTH: 30
<212> TYPE: PRT
<213> ORGANISM: Homo sapiens

<400> SEQUENCE: 81

Met Ala Pro His Gly Pro Gly Ser Leu Thr Thr Leu Val Pro Trp Ala
1               5                   10                  15

Ala Ala Leu Leu Leu Ala Leu Gly Val Glu Arg Ala Leu Ala
            20                  25                  30

<210> SEQ ID NO 82
<211> LENGTH: 46
<212> TYPE: PRT
<213> ORGANISM: Homo sapiens

<400> SEQUENCE: 82

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala
        35                  40                  45

<210> SEQ ID NO 83
<211> LENGTH: 23
<212> TYPE: PRT
<213> ORGANISM: Homo sapiens

<400> SEQUENCE: 83

Met Ala Arg Lys Ser Asn Leu Pro Val Leu Leu Val Pro Phe Leu Leu
1               5                   10                  15

Cys Gln Ala Leu Val Arg Cys
            20
```

<210> SEQ ID NO 84
<211> LENGTH: 20
<212> TYPE: PRT
<213> ORGANISM: Homo sapiens

<400> SEQUENCE: 84

Met Asp Arg His Ser Ser Tyr Ile Phe Ile Trp Leu Gln Leu Glu Leu
1               5                   10                  15

Cys Ala Met Ala
            20

<210> SEQ ID NO 85
<211> LENGTH: 21
<212> TYPE: PRT
<213> ORGANISM: Homo sapiens

<400> SEQUENCE: 85

Met Ala Ala Ala Leu Phe Val Leu Leu Gly Phe Ala Leu Leu Gly Thr
1               5                   10                  15

His Gly Ala Ser Gly
            20

<210> SEQ ID NO 86
<211> LENGTH: 23
<212> TYPE: PRT
<213> ORGANISM: Homo sapiens

<400> SEQUENCE: 86

Met Pro Gly Phe Leu Val Arg Ile Leu Leu Leu Leu Val Leu Leu
1               5                   10                  15

Leu Leu Gly Pro Thr Arg Gly
            20

<210> SEQ ID NO 87
<211> LENGTH: 22
<212> TYPE: PRT
<213> ORGANISM: Homo sapiens

<400> SEQUENCE: 87

Met Ala Arg Gly Ser Ala Val Ala Trp Ala Ala Leu Gly Pro Leu Leu
1               5                   10                  15

Trp Gly Cys Ala Leu Gly
            20

<210> SEQ ID NO 88
<211> LENGTH: 30
<212> TYPE: PRT
<213> ORGANISM: Homo sapiens

<400> SEQUENCE: 88

Met Leu Arg Gly Thr Met Thr Ala Trp Arg Gly Met Arg Pro Glu Val
1               5                   10                  15

Thr Leu Ala Cys Leu Leu Leu Ala Thr Ala Gly Cys Phe Ala
            20                  25                  30

<210> SEQ ID NO 89
<211> LENGTH: 20
<212> TYPE: PRT
<213> ORGANISM: Homo sapiens

<400> SEQUENCE: 89

```
Met Ala Trp Ala Ser Arg Leu Gly Leu Leu Ala Leu Leu Leu Pro
1               5                   10                  15

Val Val Gly Ala
            20
```

<210> SEQ ID NO 90
<211> LENGTH: 31
<212> TYPE: PRT
<213> ORGANISM: Homo sapiens

<400> SEQUENCE: 90

```
Met Arg Glu Asn Met Ala Arg Gly Pro Cys Asn Ala Pro Arg Trp Val
1               5                   10                  15

Ser Leu Met Val Leu Val Ala Ile Gly Thr Ala Val Thr Ala Ala
            20                  25                  30
```

<210> SEQ ID NO 91
<211> LENGTH: 29
<212> TYPE: PRT
<213> ORGANISM: Homo sapiens

<400> SEQUENCE: 91

```
Met Lys Met Ala Ser Ser Leu Ala Phe Leu Leu Leu Asn Phe His Val
1               5                   10                  15

Ser Leu Phe Leu Val Gln Leu Leu Thr Pro Cys Ser Ala
            20                  25
```

<210> SEQ ID NO 92
<211> LENGTH: 17
<212> TYPE: PRT
<213> ORGANISM: Homo sapiens

<400> SEQUENCE: 92

```
Met Ala Leu Met Leu Ser Leu Val Leu Ser Leu Leu Lys Leu Gly Ser
1               5                   10                  15

Gly
```

<210> SEQ ID NO 93
<211> LENGTH: 29
<212> TYPE: PRT
<213> ORGANISM: Homo sapiens

<400> SEQUENCE: 93

```
Met Glu Ala Pro Gly Pro Arg Ala Leu Arg Thr Ala Leu Cys Gly Gly
1               5                   10                  15

Cys Cys Cys Leu Leu Leu Cys Ala Gln Leu Ala Val Ala
            20                  25
```

<210> SEQ ID NO 94
<211> LENGTH: 15
<212> TYPE: PRT
<213> ORGANISM: Homo sapiens

<400> SEQUENCE: 94

```
Met Arg Pro Leu Leu Val Leu Leu Leu Gly Leu Ala Ala Gly
1               5                   10                  15
```

<210> SEQ ID NO 95
<211> LENGTH: 27
<212> TYPE: PRT
<213> ORGANISM: Homo sapiens

<400> SEQUENCE: 95

Met Val Thr Ala Ala Leu Gly Pro Val Trp Ala Ala Leu Leu Leu Phe
1               5                   10                  15

Leu Leu Met Cys Glu Ile Pro Met Val Glu Leu
            20                  25

<210> SEQ ID NO 96
<211> LENGTH: 17
<212> TYPE: PRT
<213> ORGANISM: Homo sapiens

<400> SEQUENCE: 96

Met Trp Leu Leu Tyr Leu Leu Val Pro Ala Leu Phe Cys Arg Ala Gly
1               5                   10                  15

Gly

<210> SEQ ID NO 97
<211> LENGTH: 15
<212> TYPE: PRT
<213> ORGANISM: Homo sapiens

<400> SEQUENCE: 97

Met Trp Cys Ile Val Leu Phe Ser Leu Leu Ala Trp Val Tyr Ala
1               5                   10                  15

<210> SEQ ID NO 98
<211> LENGTH: 48
<212> TYPE: PRT
<213> ORGANISM: Homo sapiens

<400> SEQUENCE: 98

Met His Pro Pro Lys Thr Pro Ser Gly Ala Leu His Arg Lys Arg Lys
1               5                   10                  15

Met Ala Ala Trp Pro Phe Ser Arg Leu Trp Lys Val Ser Asp Pro Ile
            20                  25                  30

Leu Phe Gln Met Thr Leu Ile Ala Ala Leu Leu Pro Ala Val Leu Gly
        35                  40                  45

<210> SEQ ID NO 99
<211> LENGTH: 25
<212> TYPE: PRT
<213> ORGANISM: Homo sapiens

<400> SEQUENCE: 99

Met Ala Gly Pro Ala Ile His Thr Ala Pro Met Leu Phe Leu Val Leu
1               5                   10                  15

Leu Leu Pro Leu Glu Leu Ser Leu Ala
            20                  25

<210> SEQ ID NO 100
<211> LENGTH: 24
<212> TYPE: PRT
<213> ORGANISM: Homo sapiens

<400> SEQUENCE: 100

Met Gly Ala Pro Ala Ala Ser Leu Leu Leu Leu Leu Leu Phe Ala
1               5                   10                  15

Cys Cys Trp Ala Pro Gly Gly Ala
            20

<210> SEQ ID NO 101
<211> LENGTH: 37

```
<212> TYPE: PRT
<213> ORGANISM: Homo sapiens

<400> SEQUENCE: 101

Met Ala Pro Leu Cys Pro Ser Pro Trp Leu Pro Leu Ile Pro Ala
1               5                   10                  15

Pro Ala Pro Gly Leu Thr Val Gln Leu Leu Ser Leu Leu Leu Leu
                20                  25                  30

Val Pro Val His Pro
                35

<210> SEQ ID NO 102
<211> LENGTH: 24
<212> TYPE: PRT
<213> ORGANISM: Homo sapiens

<400> SEQUENCE: 102

Met Arg Phe Thr Phe Thr Ser Arg Cys Leu Ala Leu Phe Leu Leu Leu
1               5                   10                  15

Asn His Pro Thr Pro Ile Leu Pro
                20

<210> SEQ ID NO 103
<211> LENGTH: 22
<212> TYPE: PRT
<213> ORGANISM: Homo sapiens

<400> SEQUENCE: 103

Met Glu Lys Lys Cys Thr Leu Tyr Phe Leu Val Leu Leu Pro Phe Phe
1               5                   10                  15

Met Ile Leu Val Thr Ala
                20

<210> SEQ ID NO 104
<211> LENGTH: 17
<212> TYPE: PRT
<213> ORGANISM: Homo sapiens

<400> SEQUENCE: 104

Met Leu Leu Ser Val Pro Leu Leu Leu Gly Leu Leu Gly Leu Ala Val
1               5                   10                  15

Ala

<210> SEQ ID NO 105
<211> LENGTH: 26
<212> TYPE: PRT
<213> ORGANISM: Homo sapiens

<400> SEQUENCE: 105

Met Thr Arg Leu Thr Val Leu Ala Leu Leu Ala Gly Leu Leu Ala Ser
1               5                   10                  15

Ser Arg Ala Gly Ser Ser Pro Leu Leu Asp
                20                  25

<210> SEQ ID NO 106
<211> LENGTH: 27
<212> TYPE: PRT
<213> ORGANISM: Homo sapiens

<400> SEQUENCE: 106

Met Glu Ser Ser Arg Val Arg Leu Leu Pro Leu Leu Gly Ala Ala Leu
1               5                   10                  15
```

-continued

```
Leu Leu Met Leu Pro Leu Leu Gly Thr Arg Ala
        20                  25

<210> SEQ ID NO 107
<211> LENGTH: 15
<212> TYPE: PRT
<213> ORGANISM: Homo sapiens

<400> SEQUENCE: 107

Met Arg Leu Leu Ile Leu Thr Cys Leu Val Ala Val Ala Leu Ala
1               5                   10                  15

<210> SEQ ID NO 108
<211> LENGTH: 15
<212> TYPE: PRT
<213> ORGANISM: Homo sapiens

<400> SEQUENCE: 108

Met Lys Val Leu Ile Leu Ala Cys Leu Val Ala Leu Ala Leu Ala
1               5                   10                  15

<210> SEQ ID NO 109
<211> LENGTH: 20
<212> TYPE: PRT
<213> ORGANISM: Homo sapiens

<400> SEQUENCE: 109

Met Lys Ser Phe Leu Leu Val Val Asn Ala Leu Ala Leu Thr Leu Pro
1               5                   10                  15

Phe Leu Ala Val
        20

<210> SEQ ID NO 110
<211> LENGTH: 24
<212> TYPE: PRT
<213> ORGANISM: Homo sapiens

<400> SEQUENCE: 110

Met Gly Ala Gly Pro Ser Leu Leu Leu Ala Ala Leu Leu Leu Leu Leu
1               5                   10                  15

Ser Gly Asp Gly Ala Val Arg Cys
            20

<210> SEQ ID NO 111
<211> LENGTH: 17
<212> TYPE: PRT
<213> ORGANISM: Homo sapiens

<400> SEQUENCE: 111

Met Lys Thr Leu Leu Leu Leu Leu Val Leu Leu Glu Leu Gly Glu
1               5                   10                  15

Ala

<210> SEQ ID NO 112
<211> LENGTH: 18
<212> TYPE: PRT
<213> ORGANISM: Homo sapiens

<400> SEQUENCE: 112

Met Gln Pro Leu Leu Leu Leu Leu Ala Phe Leu Leu Pro Thr Gly Ala
1               5                   10                  15

Glu Ala
```

-continued

<210> SEQ ID NO 113
<211> LENGTH: 21
<212> TYPE: PRT
<213> ORGANISM: Homo sapiens

<400> SEQUENCE: 113

Met Ala Leu Thr Ala His Pro Ser Cys Leu Leu Ala Leu Leu Val Ala
1               5                   10                  15

Gly Leu Ala Gln Gly
            20

<210> SEQ ID NO 114
<211> LENGTH: 22
<212> TYPE: PRT
<213> ORGANISM: Homo sapiens

<400> SEQUENCE: 114

Met Pro Leu Leu Leu Tyr Thr Cys Leu Leu Trp Leu Pro Thr Ser Gly
1               5                   10                  15

Leu Trp Thr Val Gln Ala
            20

<210> SEQ ID NO 115
<211> LENGTH: 32
<212> TYPE: PRT
<213> ORGANISM: Homo sapiens

<400> SEQUENCE: 115

Met Leu Gly Ala Lys Pro His Trp Leu Pro Gly Pro Leu His Ser Pro
1               5                   10                  15

Gly Leu Pro Leu Val Leu Val Leu Leu Ala Leu Gly Ala Gly Trp Ala
            20                  25                  30

<210> SEQ ID NO 116
<211> LENGTH: 27
<212> TYPE: PRT
<213> ORGANISM: Homo sapiens

<400> SEQUENCE: 116

Met Gly Ser Gly Arg Arg Ala Leu Ser Ala Val Pro Ala Val Leu Leu
1               5                   10                  15

Val Leu Thr Leu Pro Gly Leu Pro Val Trp Ala
            20                  25

<210> SEQ ID NO 117
<211> LENGTH: 16
<212> TYPE: PRT
<213> ORGANISM: Homo sapiens

<400> SEQUENCE: 117

Met Arg Gly Leu Leu Val Leu Ser Val Leu Leu Gly Ala Val Phe Gly
1               5                   10                  15

<210> SEQ ID NO 118
<211> LENGTH: 15
<212> TYPE: PRT
<213> ORGANISM: Homo sapiens

<400> SEQUENCE: 118

Met Arg Leu Ile Leu Pro Val Gly Leu Ile Ala Thr Thr Leu Ala
1               5                   10                  15

```
<210> SEQ ID NO 119
<211> LENGTH: 15
<212> TYPE: PRT
<213> ORGANISM: Homo sapiens

<400> SEQUENCE: 119

Met Leu Ala Leu Leu Val Leu Val Thr Val Ala Leu Ala Ser Ala
1               5                   10                  15

<210> SEQ ID NO 120
<211> LENGTH: 20
<212> TYPE: PRT
<213> ORGANISM: Homo sapiens

<400> SEQUENCE: 120

Met Ser Asp Leu Leu Ser Val Phe Leu His Leu Leu Leu Phe Lys
1               5                   10                  15

Leu Val Ala Pro
            20

<210> SEQ ID NO 121
<211> LENGTH: 23
<212> TYPE: PRT
<213> ORGANISM: Homo sapiens

<400> SEQUENCE: 121

Met Lys Val Ser Ala Ala Leu Leu Trp Leu Leu Leu Ile Ala Ala Ala
1               5                   10                  15

Phe Ser Pro Gln Gly Leu Ala
            20

<210> SEQ ID NO 122
<211> LENGTH: 21
<212> TYPE: PRT
<213> ORGANISM: Homo sapiens

<400> SEQUENCE: 122

Met Lys Val Ser Val Ala Ala Leu Ser Cys Leu Met Leu Val Ala Val
1               5                   10                  15

Leu Gly Ser Gln Ala
            20

<210> SEQ ID NO 123
<211> LENGTH: 21
<212> TYPE: PRT
<213> ORGANISM: Homo sapiens

<400> SEQUENCE: 123

Met Ala Leu Leu Leu Ala Leu Ser Leu Leu Val Leu Trp Thr Ser Pro
1               5                   10                  15

Ala Pro Thr Leu Ser
            20

<210> SEQ ID NO 124
<211> LENGTH: 23
<212> TYPE: PRT
<213> ORGANISM: Homo sapiens

<400> SEQUENCE: 124

Met Gln Ile Ile Thr Thr Ala Leu Val Cys Leu Leu Leu Ala Gly Met
1               5                   10                  15

Trp Pro Glu Asp Val Asp Ser
```

<210> SEQ ID NO 125
<211> LENGTH: 24
<212> TYPE: PRT
<213> ORGANISM: Homo sapiens

<400> SEQUENCE: 125

Met Ala Arg Leu Gln Thr Ala Leu Leu Val Val Leu Val Leu Leu Ala
1               5                   10                  15

Val Ala Leu Gln Ala Thr Glu Ala
            20

<210> SEQ ID NO 126
<211> LENGTH: 26
<212> TYPE: PRT
<213> ORGANISM: Homo sapiens

<400> SEQUENCE: 126

Met Ala Gly Leu Met Thr Ile Val Thr Ser Leu Leu Phe Leu Gly Val
1               5                   10                  15

Cys Ala His His Ile Ile Pro Thr Gly Ser
            20                  25

<210> SEQ ID NO 127
<211> LENGTH: 23
<212> TYPE: PRT
<213> ORGANISM: Homo sapiens

<400> SEQUENCE: 127

Met Lys Val Ser Ala Ala Leu Leu Cys Leu Leu Leu Ile Ala Ala Thr
1               5                   10                  15

Phe Ile Pro Gln Gly Leu Ala
            20

<210> SEQ ID NO 128
<211> LENGTH: 23
<212> TYPE: PRT
<213> ORGANISM: Homo sapiens

<400> SEQUENCE: 128

Met Lys Leu Cys Val Thr Val Leu Ser Leu Leu Met Leu Val Ala Ala
1               5                   10                  15

Phe Cys Ser Pro Ala Leu Ser
            20

<210> SEQ ID NO 129
<211> LENGTH: 23
<212> TYPE: PRT
<213> ORGANISM: Homo sapiens

<400> SEQUENCE: 129

Met Lys Val Ser Ala Ala Leu Ala Val Ile Leu Ile Ala Thr Ala
1               5                   10                  15

Leu Cys Ala Pro Ala Ser Ala
            20

<210> SEQ ID NO 130
<211> LENGTH: 23
<212> TYPE: PRT
<213> ORGANISM: Homo sapiens

<400> SEQUENCE: 130

```
Met Lys Ala Ser Ala Ala Leu Leu Cys Leu Leu Leu Thr Ala Ala
1               5                   10                  15

Phe Ser Pro Gln Gly Leu Ala
            20

<210> SEQ ID NO 131
<211> LENGTH: 23
<212> TYPE: PRT
<213> ORGANISM: Homo sapiens

<400> SEQUENCE: 131

Met Ala Phe Asp Val Ser Cys Phe Phe Trp Val Val Leu Phe Ser Ala
1               5                   10                  15

Gly Cys Lys Val Ile Thr Ser
            20

<210> SEQ ID NO 132
<211> LENGTH: 16
<212> TYPE: PRT
<213> ORGANISM: Homo sapiens

<400> SEQUENCE: 132

Met Leu Phe Leu Leu Pro Leu Leu Ala Val Leu Pro Gly Asp Gly
1               5                   10                  15

<210> SEQ ID NO 133
<211> LENGTH: 21
<212> TYPE: PRT
<213> ORGANISM: Homo sapiens

<400> SEQUENCE: 133

Met Leu Gly Gln Val Val Thr Leu Ile Leu Leu Leu Leu Lys Val
1               5                   10                  15

Tyr Gln Gly Lys Gly
            20

<210> SEQ ID NO 134
<211> LENGTH: 28
<212> TYPE: PRT
<213> ORGANISM: Homo sapiens

<400> SEQUENCE: 134

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala
            20                  25

<210> SEQ ID NO 135
<211> LENGTH: 19
<212> TYPE: PRT
<213> ORGANISM: Homo sapiens

<400> SEQUENCE: 135

Met Ala Arg Pro His Pro Trp Trp Leu Cys Val Leu Gly Thr Leu Val
1               5                   10                  15

Gly Leu Ser

<210> SEQ ID NO 136
<211> LENGTH: 18
<212> TYPE: PRT
<213> ORGANISM: Homo sapiens
```

```
<400> SEQUENCE: 136

Met Leu Arg Leu Leu Leu Ala Leu Asn Leu Phe Pro Ser Ile Gln Val
1               5                   10                  15

Thr Gly

<210> SEQ ID NO 137
<211> LENGTH: 24
<212> TYPE: PRT
<213> ORGANISM: Homo sapiens

<400> SEQUENCE: 137

Met Ser Phe Pro Cys Lys Phe Val Ala Ser Phe Leu Leu Ile Phe Asn
1               5                   10                  15

Val Ser Ser Lys Gly Ala Val Ser
            20

<210> SEQ ID NO 138
<211> LENGTH: 35
<212> TYPE: PRT
<213> ORGANISM: Homo sapiens

<400> SEQUENCE: 138

Met Ser Gly Gly Trp Met Ala Gln Val Gly Ala Trp Arg Thr Gly Ala
1               5                   10                  15

Leu Gly Leu Ala Leu Leu Leu Leu Gly Leu Gly Leu Glu
            20                  25                  30

Ala Ala Ala
        35

<210> SEQ ID NO 139
<211> LENGTH: 31
<212> TYPE: PRT
<213> ORGANISM: Homo sapiens

<400> SEQUENCE: 139

Met Leu Val Arg Arg Gly Ala Arg Ala Gly Pro Arg Met Pro Arg Gly
1               5                   10                  15

Trp Thr Ala Leu Cys Leu Leu Ser Leu Leu Pro Ser Gly Phe Met
            20                  25                  30

<210> SEQ ID NO 140
<211> LENGTH: 22
<212> TYPE: PRT
<213> ORGANISM: Homo sapiens

<400> SEQUENCE: 140

Met Gln Ser Gly Thr His Trp Arg Val Leu Gly Leu Cys Leu Leu Ser
1               5                   10                  15

Val Gly Val Trp Gly Gln
            20

<210> SEQ ID NO 141
<211> LENGTH: 22
<212> TYPE: PRT
<213> ORGANISM: Homo sapiens

<400> SEQUENCE: 141

Met Glu Gln Gly Lys Gly Leu Ala Val Leu Ile Leu Ala Ile Ile Leu
1               5                   10                  15

Leu Gln Gly Thr Leu Ala
            20
```

<210> SEQ ID NO 142
<211> LENGTH: 21
<212> TYPE: PRT
<213> ORGANISM: Homo sapiens

<400> SEQUENCE: 142

Met Lys Trp Lys Ala Leu Phe Thr Ala Ala Ile Leu Gln Ala Gln Leu
1               5                   10                  15

Pro Ile Thr Glu Ala
            20

<210> SEQ ID NO 143
<211> LENGTH: 23
<212> TYPE: PRT
<213> ORGANISM: Homo sapiens

<400> SEQUENCE: 143

Met Tyr Leu Trp Leu Lys Leu Leu Ala Phe Gly Phe Ala Phe Leu Asp
1               5                   10                  15

Thr Glu Val Phe Val Thr Gly
            20

<210> SEQ ID NO 144
<211> LENGTH: 19
<212> TYPE: PRT
<213> ORGANISM: Homo sapiens

<400> SEQUENCE: 144

Met Ala Leu Leu Phe Ser Leu Ile Leu Ala Ile Cys Thr Arg Pro Gly
1               5                   10                  15

Phe Leu Ala

<210> SEQ ID NO 145
<211> LENGTH: 24
<212> TYPE: PRT
<213> ORGANISM: Homo sapiens

<400> SEQUENCE: 145

Met Pro Met Gly Ser Leu Gln Pro Leu Ala Thr Leu Tyr Leu Leu Gly
1               5                   10                  15

Met Leu Val Ala Ser Cys Leu Gly
            20

<210> SEQ ID NO 146
<211> LENGTH: 19
<212> TYPE: PRT
<213> ORGANISM: Homo sapiens

<400> SEQUENCE: 146

Met Ser Arg Gly Leu Gln Leu Leu Leu Ser Cys Ala Tyr Ser Leu
1               5                   10                  15

Ala Pro Ala

<210> SEQ ID NO 147
<211> LENGTH: 21
<212> TYPE: PRT
<213> ORGANISM: Homo sapiens

<400> SEQUENCE: 147

Met Arg Pro Arg Leu Trp Leu Leu Leu Ala Ala Gln Leu Thr Val Leu
1               5                   10                  15

His Gly Asn Ser Val
            20

<210> SEQ ID NO 148
<211> LENGTH: 22
<212> TYPE: PRT
<213> ORGANISM: Homo sapiens

<400> SEQUENCE: 148

Met Ala Arg Gly Ala Ala Leu Ala Leu Leu Phe Gly Leu Leu Gly
1               5                   10                  15

Val Leu Val Ala Ala Pro
            20

<210> SEQ ID NO 149
<211> LENGTH: 34
<212> TYPE: PRT
<213> ORGANISM: Homo sapiens

<400> SEQUENCE: 149

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala

<210> SEQ ID NO 150
<211> LENGTH: 17
<212> TYPE: PRT
<213> ORGANISM: Homo sapiens

<400> SEQUENCE: 150

Met His Leu Leu Leu Phe Gln Leu Leu Val Leu Leu Pro Leu Gly Lys
1               5                   10                  15

Thr

<210> SEQ ID NO 151
<211> LENGTH: 19
<212> TYPE: PRT
<213> ORGANISM: Homo sapiens

<400> SEQUENCE: 151

Met Lys Ile Leu Ile Leu Gly Ile Phe Leu Phe Leu Cys Ser Thr Pro
1               5                   10                  15

Ala Trp Ala

<210> SEQ ID NO 152
<211> LENGTH: 17
<212> TYPE: PRT
<213> ORGANISM: Homo sapiens

<400> SEQUENCE: 152

Met Leu Ala Ala Thr Val Leu Thr Leu Ala Leu Leu Gly Asn Ala His
1               5                   10                  15

Ala

<210> SEQ ID NO 153
<211> LENGTH: 21
<212> TYPE: PRT
<213> ORGANISM: Homo sapiens -continued

<400> SEQUENCE: 153

Met Ala Ala Ala Leu Ala Leu Val Ala Gly Val Leu Ser Gly Ala Val
1               5                   10                  15

Leu Pro Leu Trp Ser
            20

<210> SEQ ID NO 154
<211> LENGTH: 25
<212> TYPE: PRT
<213> ORGANISM: Homo sapiens

<400> SEQUENCE: 154

Met Gly Ser Asn Leu Ser Pro Gln Leu Cys Leu Met Pro Phe Ile Leu
1               5                   10                  15

Gly Leu Leu Ser Gly Gly Val Thr Thr
            20                  25

<210> SEQ ID NO 155
<211> LENGTH: 18
<212> TYPE: PRT
<213> ORGANISM: Homo sapiens

<400> SEQUENCE: 155

Met Arg Leu Leu Ala Lys Ile Ile Cys Leu Met Leu Trp Ala Ile Cys
1               5                   10                  15

Val Ala

<210> SEQ ID NO 156
<211> LENGTH: 18
<212> TYPE: PRT
<213> ORGANISM: Homo sapiens

<400> SEQUENCE: 156

Met Lys Leu Leu His Val Phe Leu Leu Phe Leu Cys Phe His Leu Arg
1               5                   10                  15

Phe Cys

<210> SEQ ID NO 157
<211> LENGTH: 21
<212> TYPE: PRT
<213> ORGANISM: Homo sapiens

<400> SEQUENCE: 157

Met Gly Val Lys Ala Ser Gln Thr Gly Phe Val Val Leu Val Leu Leu
1               5                   10                  15

Gln Cys Cys Ser Ala
            20

<210> SEQ ID NO 158
<211> LENGTH: 26
<212> TYPE: PRT
<213> ORGANISM: Homo sapiens

<400> SEQUENCE: 158

Met Gly Ala Thr Thr Met Asp Gln Lys Ser Leu Trp Ala Gly Val Val
1               5                   10                  15

Val Leu Leu Leu Leu Gln Gly Gly Ser Ala
            20                  25

<210> SEQ ID NO 159
<211> LENGTH: 21

```
<212> TYPE: PRT
<213> ORGANISM: Homo sapiens

<400> SEQUENCE: 159

Met Val Arg Ser Val Ala Trp Ala Gly Phe Met Val Leu Leu Met Ile
1               5                   10                  15

Pro Trp Gly Ser Ala
            20

<210> SEQ ID NO 160
<211> LENGTH: 23
<212> TYPE: PRT
<213> ORGANISM: Homo sapiens

<400> SEQUENCE: 160

Met Gln Val Ser Thr Ala Ala Leu Ala Val Leu Leu Cys Thr Met Ala
1               5                   10                  15

Leu Cys Asn Gln Val Leu Ser
            20

<210> SEQ ID NO 161
<211> LENGTH: 21
<212> TYPE: PRT
<213> ORGANISM: Homo sapiens

<400> SEQUENCE: 161

Met Gln Ala Ala Trp Leu Leu Gly Ala Leu Val Val Pro Gln Leu Leu
1               5                   10                  15

Gly Phe Gly His Gly
            20

<210> SEQ ID NO 162
<211> LENGTH: 21
<212> TYPE: PRT
<213> ORGANISM: Homo sapiens

<400> SEQUENCE: 162

Met Arg Pro Ala Phe Ala Leu Cys Leu Leu Trp Gln Ala Leu Trp Pro
1               5                   10                  15

Gly Pro Gly Gly Gly
            20

<210> SEQ ID NO 163
<211> LENGTH: 19
<212> TYPE: PRT
<213> ORGANISM: Homo sapiens

<400> SEQUENCE: 163

Met Pro Leu Leu Thr Leu Tyr Leu Leu Phe Trp Leu Ser Gly Tyr
1               5                   10                  15

Ser Ile Ala

<210> SEQ ID NO 164
<211> LENGTH: 18
<212> TYPE: PRT
<213> ORGANISM: Homo sapiens

<400> SEQUENCE: 164

Met Arg Leu Leu Val Leu Leu Trp Gly Cys Leu Leu Leu Pro Gly Tyr
1               5                   10                  15

Glu Ala
```

<210> SEQ ID NO 165
<211> LENGTH: 22
<212> TYPE: PRT
<213> ORGANISM: Homo sapiens

<400> SEQUENCE: 165

Met Met Lys Thr Leu Leu Leu Phe Val Gly Leu Leu Thr Trp Glu
1               5                   10                  15

Ser Gly Gln Val Leu Gly
            20

<210> SEQ ID NO 166
<211> LENGTH: 19
<212> TYPE: PRT
<213> ORGANISM: Homo sapiens

<400> SEQUENCE: 166

Met Leu Leu Leu Pro Leu Pro Leu Leu Phe Leu Leu Cys Ser Arg
1               5                   10                  15

Ala Glu Ala

<210> SEQ ID NO 167
<211> LENGTH: 18
<212> TYPE: PRT
<213> ORGANISM: Homo sapiens

<400> SEQUENCE: 167

Met Arg Ser Ala Ala Val Leu Ala Leu Leu Cys Ala Gly Gln Val
1               5                   10                  15

Thr Ala

<210> SEQ ID NO 168
<211> LENGTH: 22
<212> TYPE: PRT
<213> ORGANISM: Homo sapiens

<400> SEQUENCE: 168

Met Phe Ser Phe Val Asp Leu Arg Leu Leu Leu Leu Leu Ala Ala Thr
1               5                   10                  15

Ala Leu Leu Thr His Gly
            20

<210> SEQ ID NO 169
<211> LENGTH: 20
<212> TYPE: PRT
<213> ORGANISM: Homo sapiens

<400> SEQUENCE: 169

Met Gly Pro Leu Met Val Leu Phe Cys Leu Leu Phe Leu Tyr Pro Gly
1               5                   10                  15

Leu Ala Asp Ser
            20

<210> SEQ ID NO 170
<211> LENGTH: 22
<212> TYPE: PRT
<213> ORGANISM: Homo sapiens

<400> SEQUENCE: 170

Met Gly Pro Thr Ser Gly Pro Ser Leu Leu Leu Leu Leu Thr His
1               5                   10                  15

Leu Pro Leu Ala Leu Gly
            20

<210> SEQ ID NO 171
<211> LENGTH: 25
<212> TYPE: PRT
<213> ORGANISM: Homo sapiens

<400> SEQUENCE: 171

Met Gly Arg Asp Gln Arg Ala Val Ala Gly Pro Ala Leu Arg Arg Trp
1               5                   10                  15

Leu Leu Leu Gly Thr Val Thr Val Gly
            20                  25

<210> SEQ ID NO 172
<211> LENGTH: 26
<212> TYPE: PRT
<213> ORGANISM: Homo sapiens

<400> SEQUENCE: 172

Met Met Ala Asn Trp Ala Glu Ala Arg Pro Leu Leu Ile Leu Ile Val
1               5                   10                  15

Leu Leu Gly Gln Phe Val Ser Ile Lys Ala
            20                  25

<210> SEQ ID NO 173
<211> LENGTH: 19
<212> TYPE: PRT
<213> ORGANISM: Homo sapiens

<400> SEQUENCE: 173

Met Arg Ala Ala Arg Ala Leu Leu Pro Leu Leu Leu Gln Ala Cys Trp
1               5                   10                  15

Thr Ala Ala

<210> SEQ ID NO 174
<211> LENGTH: 21
<212> TYPE: PRT
<213> ORGANISM: Homo sapiens

<400> SEQUENCE: 174

Met Ala Arg Arg Ser Val Leu Tyr Phe Ile Leu Leu Asn Ala Leu Ile
1               5                   10                  15

Asn Lys Gly Gln Ala
            20

<210> SEQ ID NO 175
<211> LENGTH: 22
<212> TYPE: PRT
<213> ORGANISM: Homo sapiens

<400> SEQUENCE: 175

Met Lys Val Ile Ser Leu Phe Ile Leu Val Gly Phe Ile Gly Glu Phe
1               5                   10                  15

Gln Ser Phe Ser Ser Ala
            20

<210> SEQ ID NO 176
<211> LENGTH: 23
<212> TYPE: PRT
<213> ORGANISM: Homo sapiens

<400> SEQUENCE: 176

```
Met Lys Thr Cys Trp Lys Ile Pro Val Phe Phe Val Cys Ser Phe
1               5                   10                  15

Leu Glu Pro Trp Ala Ser Ala
            20

<210> SEQ ID NO 177
<211> LENGTH: 21
<212> TYPE: PRT
<213> ORGANISM: Homo sapiens

<400> SEQUENCE: 177

Met Ser Ala Cys Arg Ser Phe Ala Val Ala Ile Cys Ile Leu Glu Ile
1               5                   10                  15

Ser Ile Leu Thr Ala
            20

<210> SEQ ID NO 178
<211> LENGTH: 21
<212> TYPE: PRT
<213> ORGANISM: Homo sapiens

<400> SEQUENCE: 178

Met Trp Val Ser Trp Ala Pro Gly Leu Trp Leu Leu Gly Leu Trp Ala
1               5                   10                  15

Thr Phe Gly His Gly
            20

<210> SEQ ID NO 179
<211> LENGTH: 26
<212> TYPE: PRT
<213> ORGANISM: Homo sapiens

<400> SEQUENCE: 179

Met Pro Arg Ser Cys Cys Ser Arg Ser Gly Ala Leu Leu Leu Ala Leu
1               5                   10                  15

Leu Leu Gln Ala Ser Met Glu Val Arg Gly
            20                  25

<210> SEQ ID NO 180
<211> LENGTH: 17
<212> TYPE: PRT
<213> ORGANISM: Homo sapiens

<400> SEQUENCE: 180

Met Glu Lys Ile Leu Ile Leu Leu Val Ala Leu Ser Val Ala Tyr
1               5                   10                  15

Ala

<210> SEQ ID NO 181
<211> LENGTH: 20
<212> TYPE: PRT
<213> ORGANISM: Homo sapiens

<400> SEQUENCE: 181

Met Gly Ala Ala Gly Leu Leu Gly Val Phe Leu Ala Leu Val Ala Pro
1               5                   10                  15

Gly Val Leu Gly
            20

<210> SEQ ID NO 182
<211> LENGTH: 25
```

```
<212> TYPE: PRT
<213> ORGANISM: Homo sapiens

<400> SEQUENCE: 182

Met Val Pro Glu Val Arg Val Leu Ser Ser Leu Leu Gly Leu Ala Leu
1               5                   10                  15

Leu Trp Phe Pro Leu Asp Ser His Ala
            20                  25

<210> SEQ ID NO 183
<211> LENGTH: 31
<212> TYPE: PRT
<213> ORGANISM: Homo sapiens

<400> SEQUENCE: 183

Met Ala Gly Leu Ser Arg Gly Ser Ala Arg Ala Leu Leu Ala Ala Leu
1               5                   10                  15

Leu Ala Ser Thr Leu Leu Ala Leu Leu Val Ser Pro Ala Arg Gly
            20                  25                  30

<210> SEQ ID NO 184
<211> LENGTH: 24
<212> TYPE: PRT
<213> ORGANISM: Homo sapiens

<400> SEQUENCE: 184

Met Ser Pro Asn Phe Lys Leu Gln Cys His Phe Ile Leu Ile Phe Leu
1               5                   10                  15

Thr Ala Leu Arg Gly Glu Ser Arg
            20

<210> SEQ ID NO 185
<211> LENGTH: 34
<212> TYPE: PRT
<213> ORGANISM: Homo sapiens

<400> SEQUENCE: 185

Met Tyr Leu Val Ala Gly Asp Arg Gly Leu Ala Gly Cys Gly His Leu
1               5                   10                  15

Leu Val Ser Leu Leu Gly Leu Leu Leu Leu Ala Arg Ser Gly Thr
            20                  25                  30

Arg Ala

<210> SEQ ID NO 186
<211> LENGTH: 21
<212> TYPE: PRT
<213> ORGANISM: Homo sapiens

<400> SEQUENCE: 186

Met Glu Ile Lys His Leu Leu Phe Leu Val Ala Ala Ala Cys Leu Leu
1               5                   10                  15

Pro Met Leu Ser Met
            20

<210> SEQ ID NO 187
<211> LENGTH: 37
<212> TYPE: PRT
<213> ORGANISM: Homo sapiens

<400> SEQUENCE: 187

Met Pro Ala Gly Arg Arg Gly Pro Ala Ala Gln Ser Ala Arg Arg Pro
1               5                   10                  15
```

```
Pro Pro Leu Leu Pro Leu Leu Leu Leu Cys Val Leu Gly Ala Pro
        20                  25                  30

Arg Ala Gly Ser Gly
        35

<210> SEQ ID NO 188
<211> LENGTH: 18
<212> TYPE: PRT
<213> ORGANISM: Homo sapiens

<400> SEQUENCE: 188

Met Glu Lys Leu Leu Cys Phe Leu Val Leu Thr Ser Leu Ser His Ala
1               5                   10                  15

Phe Gly

<210> SEQ ID NO 189
<211> LENGTH: 22
<212> TYPE: PRT
<213> ORGANISM: Homo sapiens

<400> SEQUENCE: 189

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 190
<211> LENGTH: 17
<212> TYPE: PRT
<213> ORGANISM: Homo sapiens

<400> SEQUENCE: 190

Met Trp Leu Gln Ser Leu Leu Leu Gly Thr Val Ala Cys Ser Ile
1               5                   10                  15

Ser

<210> SEQ ID NO 191
<211> LENGTH: 24
<212> TYPE: PRT
<213> ORGANISM: Homo sapiens

<400> SEQUENCE: 191

Met Ala Arg Leu Gly Asn Cys Ser Leu Thr Trp Ala Ala Leu Ile Ile
1               5                   10                  15

Leu Leu Leu Pro Gly Ser Leu Glu
            20

<210> SEQ ID NO 192
<211> LENGTH: 20
<212> TYPE: PRT
<213> ORGANISM: Homo sapiens

<400> SEQUENCE: 192

Met Phe Ile Asn Ile Lys Ser Ile Leu Trp Met Cys Ser Thr Leu Ile
1               5                   10                  15

Val Thr His Ala
            20

<210> SEQ ID NO 193
<211> LENGTH: 28
<212> TYPE: PRT
```

<213> ORGANISM: Homo sapiens

<400> SEQUENCE: 193

Met Leu Gly Leu Pro Trp Lys Gly Gly Leu Ser Trp Ala Leu Leu Leu
1               5                   10                  15
Leu Leu Leu Gly Ser Gln Ile Leu Leu Ile Tyr Ala
            20                  25

<210> SEQ ID NO 194
<211> LENGTH: 28
<212> TYPE: PRT
<213> ORGANISM: Homo sapiens

<400> SEQUENCE: 194

Met Ser Ser Pro Gln Arg Arg Lys Ala Met Pro Trp Ala Leu Ser Leu
1               5                   10                  15
Leu Leu Met Gly Phe Gln Leu Leu Val Thr Tyr Ala
            20                  25

<210> SEQ ID NO 195
<211> LENGTH: 30
<212> TYPE: PRT
<213> ORGANISM: Homo sapiens

<400> SEQUENCE: 195

Met Arg Pro Gln Gly Pro Ala Ala Ser Pro Gln Arg Leu Arg Gly Leu
1               5                   10                  15
Leu Leu Leu Leu Leu Leu Gln Leu Pro Ala Pro Ser Ser Ala
            20                  25                  30

<210> SEQ ID NO 196
<211> LENGTH: 18
<212> TYPE: PRT
<213> ORGANISM: Homo sapiens

<400> SEQUENCE: 196

Met Ala Phe Leu Trp Leu Leu Ser Cys Trp Ala Leu Leu Gly Thr Thr
1               5                   10                  15
Phe Gly

<210> SEQ ID NO 197
<211> LENGTH: 34
<212> TYPE: PRT
<213> ORGANISM: Homo sapiens

<400> SEQUENCE: 197

Met Ser Leu Arg Leu Asp Thr Thr Pro Ser Cys Asn Ser Ala Arg Pro
1               5                   10                  15
Leu His Ala Leu Gln Val Leu Leu Leu Ser Leu Leu Leu Thr Ala
            20                  25                  30
Leu Ala

<210> SEQ ID NO 198
<211> LENGTH: 21
<212> TYPE: PRT
<213> ORGANISM: Homo sapiens

<400> SEQUENCE: 198

Met Asn Gln Thr Ala Ile Leu Ile Cys Cys Leu Ile Phe Leu Thr Leu
1               5                   10                  15
Ser Gly Ile Gln Gly

20

<210> SEQ ID NO 199
<211> LENGTH: 26
<212> TYPE: PRT
<213> ORGANISM: Homo sapiens

<400> SEQUENCE: 199

Met Ala Gly Pro Leu Arg Ala Pro Leu Leu Leu Ala Ile Leu Ala
1               5                   10                  15

Val Ala Leu Ala Val Ser Pro Ala Ala Gly
            20                  25

<210> SEQ ID NO 200
<211> LENGTH: 22
<212> TYPE: PRT
<213> ORGANISM: Homo sapiens

<400> SEQUENCE: 200

Met Arg Thr Pro Gly Pro Leu Pro Val Leu Leu Leu Leu Ala Gly
1               5                   10                  15

Ala Pro Ala Ala Arg Pro
            20

<210> SEQ ID NO 201
<211> LENGTH: 20
<212> TYPE: PRT
<213> ORGANISM: Homo sapiens

<400> SEQUENCE: 201

Met Ala Gln His Leu Ser Thr Leu Leu Leu Leu Ala Thr Leu Ala
1               5                   10                  15

Val Ala Leu Ala
            20

<210> SEQ ID NO 202
<211> LENGTH: 20
<212> TYPE: PRT
<213> ORGANISM: Homo sapiens

<400> SEQUENCE: 202

Met Ala Arg Pro Leu Cys Thr Leu Leu Leu Met Ala Thr Leu Ala
1               5                   10                  15

Gly Ala Leu Ala
            20

<210> SEQ ID NO 203
<211> LENGTH: 20
<212> TYPE: PRT
<213> ORGANISM: Homo sapiens

<400> SEQUENCE: 203

Met Ala Trp Pro Leu Cys Thr Leu Leu Leu Leu Ala Thr Gln Ala
1               5                   10                  15

Val Ala Leu Ala
            20

<210> SEQ ID NO 204
<211> LENGTH: 22
<212> TYPE: PRT
<213> ORGANISM: Homo sapiens

<400> SEQUENCE: 204

```
Met Arg Ile His Tyr Leu Leu Phe Ala Leu Leu Phe Leu Phe Leu Val
1               5                   10                  15

Pro Val Pro Gly His Gly
            20

<210> SEQ ID NO 205
<211> LENGTH: 20
<212> TYPE: PRT
<213> ORGANISM: Homo sapiens

<400> SEQUENCE: 205

Met Gly Leu Phe Met Ile Ile Ala Ile Leu Leu Phe Gln Lys Pro Thr
1               5                   10                  15

Val Thr Glu Gln
            20

<210> SEQ ID NO 206
<211> LENGTH: 19
<212> TYPE: PRT
<213> ORGANISM: Homo sapiens

<400> SEQUENCE: 206

Met Arg Phe Met Thr Leu Leu Phe Leu Thr Ala Leu Ala Gly Ala Leu
1               5                   10                  15

Val Cys Ala

<210> SEQ ID NO 207
<211> LENGTH: 19
<212> TYPE: PRT
<213> ORGANISM: Homo sapiens

<400> SEQUENCE: 207

Met Arg Thr Leu Ala Ile Leu Ala Ala Ile Leu Leu Val Ala Leu Gln
1               5                   10                  15

Ala Gln Ala

<210> SEQ ID NO 208
<211> LENGTH: 31
<212> TYPE: PRT
<213> ORGANISM: Homo sapiens

<400> SEQUENCE: 208

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala
            20                  25                  30

<210> SEQ ID NO 209
<211> LENGTH: 21
<212> TYPE: PRT
<213> ORGANISM: Homo sapiens

<400> SEQUENCE: 209

Met Gln Arg Leu Gly Ala Thr Leu Leu Cys Leu Leu Leu Ala Ala Ala
1               5                   10                  15

Val Pro Thr Ala Pro
            20

<210> SEQ ID NO 210
<211> LENGTH: 18
<212> TYPE: PRT
```

```
<213> ORGANISM: Homo sapiens

<400> SEQUENCE: 210

Met Val Ala Ala Val Leu Leu Gly Leu Ser Trp Leu Cys Ser Pro Leu
1               5                   10                  15

Gly Ala

<210> SEQ ID NO 211
<211> LENGTH: 23
<212> TYPE: PRT
<213> ORGANISM: Homo sapiens

<400> SEQUENCE: 211

Met Thr Ala Thr Glu Ala Leu Leu Arg Val Leu Leu Leu Leu Leu Ala
1               5                   10                  15

Phe Gly His Ser Thr Tyr Gly
            20

<210> SEQ ID NO 212
<211> LENGTH: 26
<212> TYPE: PRT
<213> ORGANISM: Homo sapiens

<400> SEQUENCE: 212

Met Ala Ala Ala Ser Arg Ser Ala Ser Gly Trp Ala Leu Leu Leu Leu
1               5                   10                  15

Val Ala Leu Trp Gln Gln Arg Ala Ala Gly
            20                  25

<210> SEQ ID NO 213
<211> LENGTH: 22
<212> TYPE: PRT
<213> ORGANISM: Homo sapiens

<400> SEQUENCE: 213

Met Arg Gly Met Lys Leu Leu Gly Ala Leu Leu Ala Leu Ala Ala Leu
1               5                   10                  15

Leu Gln Gly Ala Val Ser
            20

<210> SEQ ID NO 214
<211> LENGTH: 27
<212> TYPE: PRT
<213> ORGANISM: Homo sapiens

<400> SEQUENCE: 214

Met Val Pro Lys Leu Phe Thr Ser Gln Ile Cys Leu Leu Leu Leu
1               5                   10                  15

Gly Leu Met Gly Val Glu Gly Ser Leu His Ala
            20                  25

<210> SEQ ID NO 215
<211> LENGTH: 26
<212> TYPE: PRT
<213> ORGANISM: Homo sapiens

<400> SEQUENCE: 215

Met Ala His Val Gly Asp Cys Thr Gln Thr Pro Trp Leu Pro Val Leu
1               5                   10                  15

Val Val Ser Leu Met Cys Ser Ala Arg Ala
            20                  25
```

```
<210> SEQ ID NO 216
<211> LENGTH: 27
<212> TYPE: PRT
<213> ORGANISM: Homo sapiens

<400> SEQUENCE: 216

Met Ala Arg Pro Gly Gln Arg Trp Leu Gly Lys Trp Leu Val Ala Met
1               5                   10                  15

Val Val Trp Ala Leu Cys Arg Leu Ala Thr Pro
            20                  25

<210> SEQ ID NO 217
<211> LENGTH: 27
<212> TYPE: PRT
<213> ORGANISM: Homo sapiens

<400> SEQUENCE: 217

Met Gly Pro Pro His Ser Gly Pro Gly Gly Val Arg Val Gly Ala Leu
1               5                   10                  15

Leu Leu Leu Gly Val Leu Gly Leu Val Ser Gly
            20                  25

<210> SEQ ID NO 218
<211> LENGTH: 25
<212> TYPE: PRT
<213> ORGANISM: Homo sapiens

<400> SEQUENCE: 218

Met Gly Ser Arg Ala Glu Leu Cys Thr Leu Leu Gly Gly Phe Ser Phe
1               5                   10                  15

Leu Leu Leu Leu Ile Pro Gly Glu Gly
            20                  25

<210> SEQ ID NO 219
<211> LENGTH: 24
<212> TYPE: PRT
<213> ORGANISM: Homo sapiens

<400> SEQUENCE: 219

Met Arg Pro Ser Gly Thr Ala Gly Ala Ala Leu Leu Ala Leu Leu Ala
1               5                   10                  15

Ala Leu Cys Pro Ala Ser Arg Ala
            20

<210> SEQ ID NO 220
<211> LENGTH: 25
<212> TYPE: PRT
<213> ORGANISM: Homo sapiens

<400> SEQUENCE: 220

Met Asp Arg Gly Thr Leu Pro Leu Ala Val Ala Leu Leu Leu Ala Ser
1               5                   10                  15

Cys Ser Leu Ser Pro Thr Ser Leu Ala
            20                  25

<210> SEQ ID NO 221
<211> LENGTH: 16
<212> TYPE: PRT
<213> ORGANISM: Homo sapiens

<400> SEQUENCE: 221

Met Ile Arg Thr Leu Leu Leu Ser Thr Leu Val Ala Gly Ala Leu Ser
```

```
<210> SEQ ID NO 222
<211> LENGTH: 16
<212> TYPE: PRT
<213> ORGANISM: Homo sapiens

<400> SEQUENCE: 222

Met Ile Arg Thr Leu Leu Leu Ser Thr Leu Val Ala Gly Ala Leu Ser
1               5                   10                  15

<210> SEQ ID NO 223
<211> LENGTH: 22
<212> TYPE: PRT
<213> ORGANISM: Homo sapiens

<400> SEQUENCE: 223

Met Arg Ala Ser Ser Phe Leu Ile Val Val Phe Leu Ile Ala Gly
1               5                   10                  15

Thr Leu Val Leu Glu Ala
            20

<210> SEQ ID NO 224
<211> LENGTH: 21
<212> TYPE: PRT
<213> ORGANISM: Homo sapiens

<400> SEQUENCE: 224

Met Arg Ala Leu Trp Val Leu Gly Leu Cys Cys Val Leu Leu Thr Phe
1               5                   10                  15

Gly Ser Val Arg Ala
            20

<210> SEQ ID NO 225
<211> LENGTH: 21
<212> TYPE: PRT
<213> ORGANISM: Homo sapiens

<400> SEQUENCE: 225

Met Arg Gly Leu Ala Val Leu Leu Thr Val Ala Leu Ala Thr Leu Leu
1               5                   10                  15

Ala Pro Gly Ala Gly
            20

<210> SEQ ID NO 226
<211> LENGTH: 22
<212> TYPE: PRT
<213> ORGANISM: Homo sapiens

<400> SEQUENCE: 226

Met Ala Leu Gly Val Pro Ile Ser Val Tyr Leu Leu Phe Asn Ala Met
1               5                   10                  15

Thr Ala Leu Thr Glu Glu
            20

<210> SEQ ID NO 227
<211> LENGTH: 17
<212> TYPE: PRT
<213> ORGANISM: Homo sapiens

<400> SEQUENCE: 227

Met Ala Leu Asp Tyr Leu Leu Leu Leu Leu Ala Ser Ala Val Ala
1               5                   10                  15
```

Ala

```
<210> SEQ ID NO 228
<211> LENGTH: 16
<212> TYPE: PRT
<213> ORGANISM: Homo sapiens

<400> SEQUENCE: 228

Met Val Cys Ser Leu Trp Val Leu Leu Val Ser Ser Val Leu Ala
1               5                   10                  15

<210> SEQ ID NO 229
<211> LENGTH: 24
<212> TYPE: PRT
<213> ORGANISM: Homo sapiens

<400> SEQUENCE: 229

Met Asp His Leu Gly Ala Ser Leu Trp Pro Gln Val Gly Ser Leu Cys
1               5                   10                  15

Leu Leu Leu Ala Gly Ala Ala Trp
            20

<210> SEQ ID NO 230
<211> LENGTH: 27
<212> TYPE: PRT
<213> ORGANISM: Homo sapiens

<400> SEQUENCE: 230

Met Gly Val His Glu Cys Pro Ala Trp Leu Trp Leu Leu Leu Ser Leu
1               5                   10                  15

Leu Ser Leu Pro Leu Gly Leu Pro Val Leu Gly
            20                  25

<210> SEQ ID NO 231
<211> LENGTH: 29
<212> TYPE: PRT
<213> ORGANISM: Homo sapiens

<400> SEQUENCE: 231

Met Ile Ser Leu Pro Gly Pro Leu Val Thr Asn Leu Leu Arg Phe Leu
1               5                   10                  15

Phe Leu Gly Leu Ser Ala Leu Ala Pro Pro Ser Arg Ala
            20                  25

<210> SEQ ID NO 232
<211> LENGTH: 18
<212> TYPE: PRT
<213> ORGANISM: Homo sapiens

<400> SEQUENCE: 232

Met Trp Leu Arg Ala Phe Ile Leu Ala Thr Leu Ser Ala Ser Ala Ala
1               5                   10                  15

Trp Gly

<210> SEQ ID NO 233
<211> LENGTH: 20
<212> TYPE: PRT
<213> ORGANISM: Homo sapiens

<400> SEQUENCE: 233

Met Arg Leu Lys Asn Leu Thr Phe Ile Ile Ile Leu Ile Ile Ser Gly
1               5                   10                  15
```

Glu Leu Tyr Ala
            20

<210> SEQ ID NO 234
<211> LENGTH: 18
<212> TYPE: PRT
<213> ORGANISM: Homo sapiens

<400> SEQUENCE: 234

Met Ile Phe Leu Tyr Gln Val Val His Phe Ile Leu Phe Thr Ser Val
1               5                   10                  15

Ser Gly

<210> SEQ ID NO 235
<211> LENGTH: 28
<212> TYPE: PRT
<213> ORGANISM: Homo sapiens

<400> SEQUENCE: 235

Met Phe Pro Gly Cys Pro Arg Leu Trp Val Leu Val Leu Gly Thr
1               5                   10                  15

Ser Trp Val Gly Trp Gly Ser Gln Gly Thr Glu Ala
            20                  25

<210> SEQ ID NO 236
<211> LENGTH: 19
<212> TYPE: PRT
<213> ORGANISM: Homo sapiens

<400> SEQUENCE: 236

Met Gln Ile Glu Leu Ser Thr Cys Phe Phe Leu Cys Leu Leu Arg Phe
1               5                   10                  15

Cys Phe Ser

<210> SEQ ID NO 237
<211> LENGTH: 15
<212> TYPE: PRT
<213> ORGANISM: Homo sapiens

<400> SEQUENCE: 237

Met Trp Phe Leu Thr Thr Leu Leu Leu Trp Val Pro Val Asp Gly
1               5                   10                  15

<210> SEQ ID NO 238
<211> LENGTH: 23
<212> TYPE: PRT
<213> ORGANISM: Homo sapiens

<400> SEQUENCE: 238

Met Gly Val Pro Arg Pro Gln Pro Trp Ala Leu Gly Leu Leu Leu Phe
1               5                   10                  15

Leu Leu Pro Gly Ser Leu Gly
            20

<210> SEQ ID NO 239
<211> LENGTH: 29
<212> TYPE: PRT
<213> ORGANISM: Homo sapiens

<400> SEQUENCE: 239

Met Glu Leu Ser Gly Ala Thr Met Ala Arg Gly Leu Ala Val Leu Leu
1               5                   10                  15

Val Leu Phe Leu His Ile Lys Asn Leu Pro Ala Gln Ala
            20                  25

<210> SEQ ID NO 240
<211> LENGTH: 23
<212> TYPE: PRT
<213> ORGANISM: Homo sapiens

<400> SEQUENCE: 240

Met Asp Leu Leu Trp Ile Leu Pro Ser Leu Trp Leu Leu Leu Leu Gly
1               5                   10                  15

Gly Pro Ala Cys Leu Lys Thr
            20

<210> SEQ ID NO 241
<211> LENGTH: 19
<212> TYPE: PRT
<213> ORGANISM: Homo sapiens

<400> SEQUENCE: 241

Met Leu Leu Trp Ser Leu Leu Val Ile Phe Asp Ala Val Thr Glu Gln
1               5                   10                  15

Ala Asp Ser

<210> SEQ ID NO 242
<211> LENGTH: 27
<212> TYPE: PRT
<213> ORGANISM: Homo sapiens

<400> SEQUENCE: 242

Met Lys Leu Gly Cys Val Leu Met Ala Trp Ala Leu Tyr Leu Ser Leu
1               5                   10                  15

Gly Val Leu Trp Val Ala Gln Met Leu Leu Ala
            20                  25

<210> SEQ ID NO 243
<211> LENGTH: 18
<212> TYPE: PRT
<213> ORGANISM: Homo sapiens

<400> SEQUENCE: 243

Met Lys Ser Leu Val Leu Leu Cys Leu Ala Gln Leu Trp Gly Cys
1               5                   10                  15

His Ser

<210> SEQ ID NO 244
<211> LENGTH: 24
<212> TYPE: PRT
<213> ORGANISM: Homo sapiens

<400> SEQUENCE: 244

Met Arg Ser Gly Cys Val Val Val His Val Trp Ile Leu Ala Gly Leu
1               5                   10                  15

Trp Leu Ala Val Ala Gly Arg Pro
            20

<210> SEQ ID NO 245
<211> LENGTH: 28
<212> TYPE: PRT
<213> ORGANISM: Homo sapiens

<400> SEQUENCE: 245

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala
            20                  25

<210> SEQ ID NO 246
<211> LENGTH: 24
<212> TYPE: PRT
<213> ORGANISM: Homo sapiens

<400> SEQUENCE: 246

Met Leu Gly Ala Arg Leu Arg Leu Trp Val Cys Ala Leu Cys Ser Val
1               5                   10                  15

Cys Ser Met Ser Val Leu Arg Ala
            20

<210> SEQ ID NO 247
<211> LENGTH: 22
<212> TYPE: PRT
<213> ORGANISM: Homo sapiens

<400> SEQUENCE: 247

Met Gly Ala Pro Ala Cys Ala Leu Ala Leu Cys Val Ala Val Ala Ile
1               5                   10                  15

Val Ala Gly Ala Ser Ser
            20

<210> SEQ ID NO 248
<211> LENGTH: 21
<212> TYPE: PRT
<213> ORGANISM: Homo sapiens

<400> SEQUENCE: 248

Met Arg Leu Leu Leu Ala Leu Leu Gly Val Leu Leu Ser Val Pro Gly
1               5                   10                  15

Pro Pro Val Leu Ser
            20

<210> SEQ ID NO 249
<211> LENGTH: 24
<212> TYPE: PRT
<213> ORGANISM: Homo sapiens

<400> SEQUENCE: 249

Met Thr Pro Ser Pro Leu Leu Leu Leu Leu Pro Pro Leu Leu Leu
1               5                   10                  15

Gly Ala Phe Pro Pro Ala Ala Ala
            20

<210> SEQ ID NO 250
<211> LENGTH: 19
<212> TYPE: PRT
<213> ORGANISM: Homo sapiens

<400> SEQUENCE: 250

Met Phe Ser Met Arg Ile Val Cys Leu Val Leu Ser Val Val Gly Thr
1               5                   10                  15

Ala Trp Thr

<210> SEQ ID NO 251
<211> LENGTH: 26

```
<212> TYPE: PRT
<213> ORGANISM: Homo sapiens

<400> SEQUENCE: 251

Met Ser Trp Ser Leu His Pro Arg Asn Leu Ile Leu Tyr Phe Tyr Ala
1               5                   10                  15

Leu Leu Phe Leu Ser Ser Thr Cys Val Ala
            20                  25

<210> SEQ ID NO 252
<211> LENGTH: 19
<212> TYPE: PRT
<213> ORGANISM: Homo sapiens

<400> SEQUENCE: 252

Met Arg Leu Phe Leu Trp Asn Ala Val Leu Thr Leu Phe Val Thr Ser
1               5                   10                  15

Leu Ile Gly

<210> SEQ ID NO 253
<211> LENGTH: 21
<212> TYPE: PRT
<213> ORGANISM: Homo sapiens

<400> SEQUENCE: 253

Met Arg Leu Ser Trp Phe Arg Val Leu Thr Val Leu Ser Ile Cys Leu
1               5                   10                  15

Ser Ala Val Ala Thr
            20

<210> SEQ ID NO 254
<211> LENGTH: 35
<212> TYPE: PRT
<213> ORGANISM: Homo sapiens

<400> SEQUENCE: 254

Met Gly Leu Gln Thr Thr Lys Trp Pro Ser His Gly Ala Phe Phe Leu
1               5                   10                  15

Lys Ser Trp Leu Ile Ile Ser Leu Gly Leu Tyr Ser Gln Val Ser Lys
            20                  25                  30

Leu Leu Ala
        35

<210> SEQ ID NO 255
<211> LENGTH: 18
<212> TYPE: PRT
<213> ORGANISM: Homo sapiens

<400> SEQUENCE: 255

Met Lys Thr Leu Gln Phe Phe Phe Leu Phe Cys Cys Trp Lys Ala Ile
1               5                   10                  15

Cys Cys

<210> SEQ ID NO 256
<211> LENGTH: 20
<212> TYPE: PRT
<213> ORGANISM: Homo sapiens

<400> SEQUENCE: 256

Met Trp Lys Arg Trp Leu Ala Leu Ala Leu Ala Leu Val Ala Val Ala
1               5                   10                  15
```

Trp Val Arg Ala
            20

<210> SEQ ID NO 257
<211> LENGTH: 26
<212> TYPE: PRT
<213> ORGANISM: Homo sapiens

<400> SEQUENCE: 257

Met Arg Pro Gly Ala Pro Gly Pro Leu Trp Pro Leu Pro Trp Gly Ala
1               5                   10                  15

Leu Ala Trp Ala Val Gly Phe Val Ser Ser
            20                  25

<210> SEQ ID NO 258
<211> LENGTH: 29
<212> TYPE: PRT
<213> ORGANISM: Homo sapiens

<400> SEQUENCE: 258

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala
            20                  25

<210> SEQ ID NO 259
<211> LENGTH: 22
<212> TYPE: PRT
<213> ORGANISM: Homo sapiens

<400> SEQUENCE: 259

Met Ala Met Thr Trp Ile Val Phe Ser Leu Trp Pro Leu Thr Val Phe
1               5                   10                  15

Met Gly His Ile Gly Gly
            20

<210> SEQ ID NO 260
<211> LENGTH: 17
<212> TYPE: PRT
<213> ORGANISM: Homo sapiens

<400> SEQUENCE: 260

Met Ala Val Phe Leu Gln Leu Leu Pro Leu Leu Leu Ser Arg Ala Gln
1               5                   10                  15

Gly

<210> SEQ ID NO 261
<211> LENGTH: 26
<212> TYPE: PRT
<213> ORGANISM: Homo sapiens

<400> SEQUENCE: 261

Met Thr Ala Ala Ala Gly Ser Ala Gly Arg Ala Ala Val Pro Leu Leu
1               5                   10                  15

Leu Cys Ala Leu Leu Ala Pro Gly Gly Ala
            20                  25

<210> SEQ ID NO 262
<211> LENGTH: 19
<212> TYPE: PRT
<213> ORGANISM: Homo sapiens

<400> SEQUENCE: 262

Met Asn Trp His Leu Pro Leu Phe Leu Leu Ala Ser Val Thr Leu Pro
1               5                   10                  15

Ser Ile Cys

<210> SEQ ID NO 263
<211> LENGTH: 27
<212> TYPE: PRT
<213> ORGANISM: Homo sapiens

<400> SEQUENCE: 263

Met Ala Pro His Arg Pro Ala Pro Ala Leu Leu Cys Ala Leu Ser Leu
1               5                   10                  15

Ala Leu Cys Ala Leu Ser Leu Pro Val Arg Ala
            20                  25

<210> SEQ ID NO 264
<211> LENGTH: 32
<212> TYPE: PRT
<213> ORGANISM: Homo sapiens

<400> SEQUENCE: 264

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

<210> SEQ ID NO 265
<211> LENGTH: 24
<212> TYPE: PRT
<213> ORGANISM: Homo sapiens

<400> SEQUENCE: 265

Met Asp Tyr Tyr Arg Lys Tyr Ala Ala Ile Phe Leu Val Thr Leu Ser
1               5                   10                  15

Val Phe Leu His Val Leu His Ser
            20

<210> SEQ ID NO 266
<211> LENGTH: 19
<212> TYPE: PRT
<213> ORGANISM: Homo sapiens

<400> SEQUENCE: 266

Met Tyr Gly Lys Ile Ile Phe Val Leu Leu Leu Ser Ala Ile Val Ser
1               5                   10                  15

Ile Ser Ala

<210> SEQ ID NO 267
<211> LENGTH: 19
<212> TYPE: PRT
<213> ORGANISM: Homo sapiens

<400> SEQUENCE: 267

Met Tyr Gly Lys Ile Ile Phe Val Leu Leu Leu Ser Glu Ile Val Ser
1               5                   10                  15

Ile Ser Ala

<210> SEQ ID NO 268
<211> LENGTH: 19
<212> TYPE: PRT
<213> ORGANISM: Homo sapiens

<400> SEQUENCE: 268

Met Tyr Gly Lys Ile Ile Phe Val Leu Leu Leu Ser Gly Ile Val Ser
1               5                   10                  15

Ile Ser Ala

<210> SEQ ID NO 269
<211> LENGTH: 20
<212> TYPE: PRT
<213> ORGANISM: Homo sapiens

<400> SEQUENCE: 269

Met Lys Ser Ile Tyr Phe Val Ala Gly Leu Phe Val Met Leu Val Gln
1               5                   10                  15

Gly Ser Trp Gln
            20

<210> SEQ ID NO 270
<211> LENGTH: 36
<212> TYPE: PRT
<213> ORGANISM: Homo sapiens

<400> SEQUENCE: 270

Met Arg Leu Leu Pro Leu Ala Pro Gly Arg Leu Arg Arg Gly Ser Pro
1               5                   10                  15

Arg His Leu Pro Ser Cys Ser Pro Ala Leu Leu Leu Val Leu Gly
            20                  25                  30

Gly Cys Leu Gly
        35

<210> SEQ ID NO 271
<211> LENGTH: 16
<212> TYPE: PRT
<213> ORGANISM: Homo sapiens

<400> SEQUENCE: 271

Met Pro Leu Leu Leu Leu Leu Leu Leu Pro Ser Pro Leu His Pro
1               5                   10                  15

<210> SEQ ID NO 272
<211> LENGTH: 27
<212> TYPE: PRT
<213> ORGANISM: Homo sapiens

<400> SEQUENCE: 272

Met Ala Val Thr Asp Ser Leu Ser Arg Ala Ala Thr Val Leu Ala Thr
1               5                   10                  15

Val Leu Leu Leu Ser Phe Gly Ser Val Ala Ala
            20                  25

<210> SEQ ID NO 273
<211> LENGTH: 16
<212> TYPE: PRT
<213> ORGANISM: Homo sapiens

<400> SEQUENCE: 273

Met Pro Ala Trp Gly Ala Leu Phe Leu Leu Trp Ala Thr Ala Glu Ala
1               5                   10                  15

<210> SEQ ID NO 274
<211> LENGTH: 25
<212> TYPE: PRT

<213> ORGANISM: Homo sapiens

<400> SEQUENCE: 274

Met Thr Pro Gln Ser Leu Leu Gln Thr Thr Leu Phe Leu Leu Ser Leu
1               5                   10                  15

Leu Phe Leu Val Gln Gly Ala His Gly
            20                  25

<210> SEQ ID NO 275
<211> LENGTH: 20
<212> TYPE: PRT
<213> ORGANISM: Homo sapiens

<400> SEQUENCE: 275

Met Ala Thr Pro Arg Gly Leu Gly Ala Leu Leu Leu Leu Leu Leu Leu
1               5                   10                  15

Pro Thr Ser Gly
            20

<210> SEQ ID NO 276
<211> LENGTH: 18
<212> TYPE: PRT
<213> ORGANISM: Homo sapiens

<400> SEQUENCE: 276

Met Gln Pro Ile Leu Leu Leu Leu Ala Phe Leu Leu Leu Pro Arg Ala
1               5                   10                  15

Asp Ala

<210> SEQ ID NO 277
<211> LENGTH: 24
<212> TYPE: PRT
<213> ORGANISM: Homo sapiens

<400> SEQUENCE: 277

Met Ser Arg Thr Ala Tyr Thr Val Gly Ala Leu Leu Leu Leu Leu Gly
1               5                   10                  15

Thr Leu Leu Pro Ala Ala Glu Gly
            20

<210> SEQ ID NO 278
<211> LENGTH: 34
<212> TYPE: PRT
<213> ORGANISM: Homo sapiens

<400> SEQUENCE: 278

Met Ala Arg Ala Ala Leu Ser Ala Ala Pro Ser Asn Pro Arg Leu Leu
1               5                   10                  15

Arg Val Ala Leu Leu Leu Leu Leu Val Ala Ala Gly Arg Arg Ala
            20                  25                  30

Ala Gly

<210> SEQ ID NO 279
<211> LENGTH: 18
<212> TYPE: PRT
<213> ORGANISM: Homo sapiens

<400> SEQUENCE: 279

Met Lys Leu Ser Leu Val Ala Ala Met Leu Leu Leu Leu Ser Ala Ala
1               5                   10                  15

Arg Ala

<210> SEQ ID NO 280
<211> LENGTH: 23
<212> TYPE: PRT
<213> ORGANISM: Homo sapiens

<400> SEQUENCE: 280

Met Arg Gly Ser Glu Leu Pro Leu Val Leu Leu Ala Leu Val Leu Cys
1               5                   10                  15

Leu Ala Pro Arg Gly Arg Ala
            20

<210> SEQ ID NO 281
<211> LENGTH: 23
<212> TYPE: PRT
<213> ORGANISM: Homo sapiens

<400> SEQUENCE: 281

Met Ile Leu Asn Lys Ala Leu Met Leu Gly Ala Leu Ala Leu Thr Thr
1               5                   10                  15

Val Met Ser Pro Cys Gly Gly
            20

<210> SEQ ID NO 282
<211> LENGTH: 23
<212> TYPE: PRT
<213> ORGANISM: Homo sapiens

<400> SEQUENCE: 282

Met Ile Leu Asn Lys Ala Leu Met Leu Gly Ala Leu Ala Leu Thr Thr
1               5                   10                  15

Val Met Ser Pro Cys Gly Gly
            20

<210> SEQ ID NO 283
<211> LENGTH: 23
<212> TYPE: PRT
<213> ORGANISM: Homo sapiens

<400> SEQUENCE: 283

Met Ile Leu Asn Lys Ala Leu Leu Gly Ala Leu Ala Leu Thr Thr
1               5                   10                  15

Val Met Ser Pro Cys Gly Gly
            20

<210> SEQ ID NO 284
<211> LENGTH: 23
<212> TYPE: PRT
<213> ORGANISM: Homo sapiens

<400> SEQUENCE: 284

Met Ile Leu Asn Lys Ala Leu Met Leu Gly Ser Leu Ala Leu Thr Thr
1               5                   10                  15

Val Met Ser Pro Cys Gly Gly
            20

<210> SEQ ID NO 285
<211> LENGTH: 32
<212> TYPE: PRT
<213> ORGANISM: Homo sapiens

<400> SEQUENCE: 285

Met Ser Trp Lys Lys Ala Leu Arg Ile Pro Gly Gly Leu Arg Ala Ala
1               5                   10                  15

Thr Val Thr Leu Met Leu Ser Met Leu Ser Thr Pro Val Ala Glu Gly
            20                  25                  30

<210> SEQ ID NO 286
<211> LENGTH: 32
<212> TYPE: PRT
<213> ORGANISM: Homo sapiens

<400> SEQUENCE: 286

Met Ser Trp Lys Lys Ala Leu Arg Ile Pro Gly Gly Leu Arg Val Ala
1               5                   10                  15

Thr Val Thr Leu Met Leu Ala Met Leu Ser Thr Ser Val Ala Glu Gly
            20                  25                  30

<210> SEQ ID NO 287
<211> LENGTH: 32
<212> TYPE: PRT
<213> ORGANISM: Homo sapiens

<400> SEQUENCE: 287

Met Ser Trp Lys Lys Ala Leu Arg Ile Pro Gly Gly Leu Arg Val Ala
1               5                   10                  15

Thr Val Thr Leu Met Leu Ala Met Leu Ser Thr Pro Val Ala Glu Gly
            20                  25                  30

<210> SEQ ID NO 288
<211> LENGTH: 32
<212> TYPE: PRT
<213> ORGANISM: Homo sapiens

<400> SEQUENCE: 288

Met Ser Trp Lys Lys Ala Leu Arg Ile Pro Gly Asp Leu Arg Val Ala
1               5                   10                  15

Thr Val Thr Leu Met Leu Ala Met Leu Ser Ser Leu Leu Ala Glu Gly
            20                  25                  30

<210> SEQ ID NO 289
<211> LENGTH: 29
<212> TYPE: PRT
<213> ORGANISM: Homo sapiens

<400> SEQUENCE: 289

Met Val Cys Leu Arg Leu Pro Gly Gly Ser Cys Met Ala Val Leu Thr
1               5                   10                  15

Val Thr Leu Met Val Leu Ser Ser Pro Leu Ala Leu Ala
            20                  25

<210> SEQ ID NO 290
<211> LENGTH: 29
<212> TYPE: PRT
<213> ORGANISM: Homo sapiens

<400> SEQUENCE: 290

Met Val Cys Leu Arg Leu Pro Gly Gly Ser Cys Met Ala Val Leu Thr
1               5                   10                  15

Val Thr Leu Met Val Leu Ser Ser Pro Leu Ala Leu Ala
            20                  25

<210> SEQ ID NO 291
<211> LENGTH: 29

<212> TYPE: PRT
<213> ORGANISM: Homo sapiens

<400> SEQUENCE: 291

Met Val Cys Leu Lys Leu Pro Gly Gly Ser Cys Met Ala Ala Leu Thr
1               5                   10                  15
Val Thr Leu Thr Val Leu Ser Ser Pro Leu Ala Leu Ala
            20                  25

<210> SEQ ID NO 292
<211> LENGTH: 19
<212> TYPE: PRT
<213> ORGANISM: Homo sapiens

<400> SEQUENCE: 292

Met Lys His Ser Leu Asn Ala Leu Leu Ile Phe Leu Ile Ile Thr Ser
1               5                   10                  15
Ala Trp Gly

<210> SEQ ID NO 293
<211> LENGTH: 35
<212> TYPE: PRT
<213> ORGANISM: Homo sapiens

<400> SEQUENCE: 293

Met Gly Arg Trp Ala Trp Val Pro Ser Pro Trp Pro Pro Gly Leu
1               5                   10                  15
Gly Pro Phe Leu Leu Leu Leu Leu Leu Leu Leu Pro Arg Gly
            20                  25                  30
Phe Gln Pro
        35

<210> SEQ ID NO 294
<211> LENGTH: 19
<212> TYPE: PRT
<213> ORGANISM: Homo sapiens

<400> SEQUENCE: 294

Met Lys Phe Phe Val Phe Ala Leu Val Leu Ala Leu Met Ile Ser Met
1               5                   10                  15
Ile Ser Ala

<210> SEQ ID NO 295
<211> LENGTH: 19
<212> TYPE: PRT
<213> ORGANISM: Homo sapiens

<400> SEQUENCE: 295

Met Lys Phe Phe Val Phe Ala Leu Ile Leu Ala Leu Met Leu Ser Met
1               5                   10                  15
Thr Gly Ala

<210> SEQ ID NO 296
<211> LENGTH: 21
<212> TYPE: PRT
<213> ORGANISM: Homo sapiens

<400> SEQUENCE: 296

Met Val Asp Gly Thr Leu Leu Leu Leu Ser Glu Ala Leu Ala Leu
1               5                   10                  15
Thr Gln Thr Trp Ala

-continued

```
                    20

<210> SEQ ID NO 297
<211> LENGTH: 35
<212> TYPE: PRT
<213> ORGANISM: Homo sapiens

<400> SEQUENCE: 297

Met Leu Leu Arg Ser Lys Pro Ala Leu Pro Pro Leu Met Leu Leu
1               5                   10                  15

Leu Leu Gly Pro Leu Gly Pro Leu Ser Pro Gly Ala Leu Pro Arg Pro
            20                  25                  30

Ala Gln Ala
        35

<210> SEQ ID NO 298
<211> LENGTH: 18
<212> TYPE: PRT
<213> ORGANISM: Homo sapiens

<400> SEQUENCE: 298

Met Ser Ala Leu Gly Ala Val Ile Ala Leu Leu Leu Trp Gly Gln Leu
1               5                   10                  15

Phe Ala

<210> SEQ ID NO 299
<211> LENGTH: 19
<212> TYPE: PRT
<213> ORGANISM: Homo sapiens

<400> SEQUENCE: 299

Met Asp Trp Thr Trp Arg Ile Leu Phe Leu Val Ala Ala Ala Thr Gly
1               5                   10                  15

Ala His Ser

<210> SEQ ID NO 300
<211> LENGTH: 19
<212> TYPE: PRT
<213> ORGANISM: Homo sapiens

<400> SEQUENCE: 300

Met Glu Phe Gly Leu Ser Trp Leu Phe Leu Val Ala Ile Leu Lys Gly
1               5                   10                  15

Val Gln Cys

<210> SEQ ID NO 301
<211> LENGTH: 21
<212> TYPE: PRT
<213> ORGANISM: Homo sapiens

<400> SEQUENCE: 301

Met Leu Pro Cys Leu Val Val Leu Leu Ala Ala Leu Leu Ser Leu Arg
1               5                   10                  15

Leu Gly Ser Asp Ala
            20

<210> SEQ ID NO 302
<211> LENGTH: 19
<212> TYPE: PRT
<213> ORGANISM: Homo sapiens

<400> SEQUENCE: 302
```

Met Ala Trp Ser Leu Gly Ser Trp Leu Gly Gly Cys Leu Leu Val Ser
1               5                   10                  15

Ala Leu Gly

<210> SEQ ID NO 303
<211> LENGTH: 32
<212> TYPE: PRT
<213> ORGANISM: Homo sapiens

<400> SEQUENCE: 303

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

<210> SEQ ID NO 304
<211> LENGTH: 17
<212> TYPE: PRT
<213> ORGANISM: Homo sapiens

<400> SEQUENCE: 304

Met Ser Leu Val Leu Leu Ser Leu Ala Ala Leu Cys Arg Ser Ala Val
1               5                   10                  15

Pro

<210> SEQ ID NO 305
<211> LENGTH: 20
<212> TYPE: PRT
<213> ORGANISM: Homo sapiens

<400> SEQUENCE: 305

Met Pro Val Pro Trp Phe Leu Leu Ser Leu Ala Leu Gly Arg Ser Pro
1               5                   10                  15

Val Val Leu Ser
                20

<210> SEQ ID NO 306
<211> LENGTH: 28
<212> TYPE: PRT
<213> ORGANISM: Homo sapiens

<400> SEQUENCE: 306

Met Arg His Asn Trp Thr Pro Asp Leu Ser Pro Leu Trp Val Leu Leu
1               5                   10                  15

Leu Cys Ala His Val Val Thr Leu Leu Val Arg Ala
                20                  25

<210> SEQ ID NO 307
<211> LENGTH: 29
<212> TYPE: PRT
<213> ORGANISM: Homo sapiens

<400> SEQUENCE: 307

Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala
                20                  25

<210> SEQ ID NO 308
<211> LENGTH: 29
<212> TYPE: PRT

<213> ORGANISM: Homo sapiens

<400> SEQUENCE: 308

Met Gln Thr Phe Thr Met Val Leu Glu Glu Ile Trp Thr Ser Leu Phe
1               5                   10                  15
Met Trp Phe Phe Tyr Ala Leu Ile Pro Cys Leu Leu Thr
            20                  25

<210> SEQ ID NO 309
<211> LENGTH: 21
<212> TYPE: PRT
<213> ORGANISM: Homo sapiens

<400> SEQUENCE: 309

Met Met Pro Lys His Cys Phe Leu Gly Phe Leu Ile Ser Phe Phe Leu
1               5                   10                  15
Thr Gly Val Ala Gly
            20

<210> SEQ ID NO 310
<211> LENGTH: 25
<212> TYPE: PRT
<213> ORGANISM: Homo sapiens

<400> SEQUENCE: 310

Met Ser Glu Val Pro Val Ala Arg Val Trp Leu Val Leu Leu Leu Leu
1               5                   10                  15
Thr Val Gln Val Gly Val Thr Ala Gly
            20                  25

<210> SEQ ID NO 311
<211> LENGTH: 39
<212> TYPE: PRT
<213> ORGANISM: Homo sapiens

<400> SEQUENCE: 311

Met Leu Pro Arg Val Gly Cys Pro Ala Leu Pro Leu Pro Pro Pro Pro
1               5                   10                  15
Leu Leu Pro Leu Leu Pro Leu Leu Leu Leu Leu Gly Ala Ser Gly
            20                  25                  30
Gly Gly Gly Gly Ala Arg Ala
        35

<210> SEQ ID NO 312
<211> LENGTH: 27
<212> TYPE: PRT
<213> ORGANISM: Homo sapiens

<400> SEQUENCE: 312

Met Gln Arg Ala Arg Pro Thr Leu Trp Ala Ala Ala Leu Thr Leu Leu
1               5                   10                  15
Val Leu Leu Arg Gly Pro Pro Val Ala Arg Ala
            20                  25

<210> SEQ ID NO 313
<211> LENGTH: 26
<212> TYPE: PRT
<213> ORGANISM: Homo sapiens

<400> SEQUENCE: 313

Met Glu Arg Pro Ser Leu Arg Ala Leu Leu Leu Gly Ala Ala Gly Leu
1               5                   10                  15

Leu Leu Leu Leu Leu Pro Leu Ser Ser Ser
            20                  25

<210> SEQ ID NO 314
<211> LENGTH: 23
<212> TYPE: PRT
<213> ORGANISM: Homo sapiens

<400> SEQUENCE: 314

Met Ala Leu Ser Phe Ser Leu Leu Met Ala Val Leu Val Leu Ser Tyr
1               5                   10                  15

Lys Ser Ile Cys Ser Leu Gly
            20

<210> SEQ ID NO 315
<211> LENGTH: 23
<212> TYPE: PRT
<213> ORGANISM: Homo sapiens

<400> SEQUENCE: 315

Met Ala Leu Thr Phe Ala Leu Leu Val Ala Leu Leu Val Leu Ser Cys
1               5                   10                  15

Lys Ser Ser Cys Ser Val Gly
            20

<210> SEQ ID NO 316
<211> LENGTH: 23
<212> TYPE: PRT
<213> ORGANISM: Homo sapiens

<400> SEQUENCE: 316

Met Ala Leu Ser Phe Ser Leu Leu Met Ala Val Leu Val Leu Ser Tyr
1               5                   10                  15

Lys Ser Ile Cys Ser Leu Gly
            20

<210> SEQ ID NO 317
<211> LENGTH: 21
<212> TYPE: PRT
<213> ORGANISM: Homo sapiens

<400> SEQUENCE: 317

Met Ala Leu Pro Phe Val Leu Leu Met Ala Leu Val Val Leu Asn Cys
1               5                   10                  15

Lys Ser Ile Cys Ser
            20

<210> SEQ ID NO 318
<211> LENGTH: 20
<212> TYPE: PRT
<213> ORGANISM: Homo sapiens

<400> SEQUENCE: 318

Met Ala Leu Pro Phe Ala Leu Leu Met Ala Leu Val Val Leu Ser Cys
1               5                   10                  15

Lys Ser Ser Cys
            20

<210> SEQ ID NO 319
<211> LENGTH: 23
<212> TYPE: PRT
<213> ORGANISM: Homo sapiens

<400> SEQUENCE: 319

Met Ala Arg Ser Phe Ser Leu Leu Met Val Val Leu Val Leu Ser Tyr
1               5                   10                  15

Lys Ser Ile Cys Ser Leu Gly
            20

<210> SEQ ID NO 320
<211> LENGTH: 27
<212> TYPE: PRT
<213> ORGANISM: Homo sapiens

<400> SEQUENCE: 320

Met Ser Thr Lys Pro Asp Met Ile Gln Lys Cys Leu Trp Leu Glu Ile
1               5                   10                  15

Leu Met Gly Ile Phe Ile Ala Gly Thr Leu Ser
            20                  25

<210> SEQ ID NO 321
<211> LENGTH: 21
<212> TYPE: PRT
<213> ORGANISM: Homo sapiens

<400> SEQUENCE: 321

Met Ala Leu Leu Phe Pro Leu Leu Ala Ala Leu Val Met Thr Ser Tyr
1               5                   10                  15

Ser Pro Val Gly Ser
            20

<210> SEQ ID NO 322
<211> LENGTH: 24
<212> TYPE: PRT
<213> ORGANISM: Homo sapiens

<400> SEQUENCE: 322

Met Gly Ile Pro Met Gly Lys Ser Met Leu Val Leu Leu Thr Phe Leu
1               5                   10                  15

Ala Phe Ala Ser Cys Cys Ile Ala
            20

<210> SEQ ID NO 323
<211> LENGTH: 24
<212> TYPE: PRT
<213> ORGANISM: Homo sapiens

<400> SEQUENCE: 323

Met Ala Pro Arg Gly Cys Ile Val Ala Val Phe Ala Ile Phe Cys Ile
1               5                   10                  15

Ser Arg Leu Leu Cys Ser His Gly
            20

<210> SEQ ID NO 324
<211> LENGTH: 24
<212> TYPE: PRT
<213> ORGANISM: Homo sapiens

<400> SEQUENCE: 324

Met Arg Pro Arg Cys Cys Ile Leu Ala Leu Val Cys Trp Ile Thr Val
1               5                   10                  15

Phe Leu Leu Gln Cys Ser Lys Gly
            20

<210> SEQ ID NO 325
<211> LENGTH: 18
<212> TYPE: PRT
<213> ORGANISM: Homo sapiens

<400> SEQUENCE: 325

Met His Ser Ser Ala Leu Leu Cys Cys Leu Val Leu Leu Thr Gly Val
1               5                   10                  15

Arg Ala

<210> SEQ ID NO 326
<211> LENGTH: 22
<212> TYPE: PRT
<213> ORGANISM: Homo sapiens

<400> SEQUENCE: 326

Met Cys Pro Ala Arg Ser Leu Leu Leu Val Ala Thr Leu Val Leu Leu
1               5                   10                  15

Asp His Leu Ser Leu Ala
            20

<210> SEQ ID NO 327
<211> LENGTH: 22
<212> TYPE: PRT
<213> ORGANISM: Homo sapiens

<400> SEQUENCE: 327

Met Cys His Gln Gln Leu Val Ile Ser Trp Phe Ser Leu Val Phe Leu
1               5                   10                  15

Ala Ser Pro Leu Val Ala
            20

<210> SEQ ID NO 328
<211> LENGTH: 20
<212> TYPE: PRT
<213> ORGANISM: Homo sapiens

<400> SEQUENCE: 328

Met Val Lys Tyr Leu Leu Leu Ser Ile Leu Gly Leu Ala Phe Leu Ser
1               5                   10                  15

Glu Ala Ala Ala
            20

<210> SEQ ID NO 329
<211> LENGTH: 23
<212> TYPE: PRT
<213> ORGANISM: Homo sapiens

<400> SEQUENCE: 329

Met Thr Pro Gly Lys Thr Ser Leu Val Ser Leu Leu Leu Leu Leu Ser
1               5                   10                  15

Leu Glu Ala Ile Val Lys Ala
            20

<210> SEQ ID NO 330
<211> LENGTH: 24
<212> TYPE: PRT
<213> ORGANISM: Homo sapiens

<400> SEQUENCE: 330

Met Lys Leu Gln Cys Val Ser Leu Trp Leu Leu Gly Thr Ile Leu Ile
1               5                   10                  15

```
Leu Cys Ser Val Asp Asn His Gly
            20

<210> SEQ ID NO 331
<211> LENGTH: 17
<212> TYPE: PRT
<213> ORGANISM: Homo sapiens

<400> SEQUENCE: 331

Met Lys Val Leu Leu Arg Leu Ile Cys Phe Ile Ala Leu Leu Ile Ser
1               5                   10                  15

Ser

<210> SEQ ID NO 332
<211> LENGTH: 25
<212> TYPE: PRT
<213> ORGANISM: Homo sapiens

<400> SEQUENCE: 332

Met Glu Ile Cys Arg Gly Leu Arg Ser His Leu Ile Thr Leu Leu Leu
1               5                   10                  15

Phe Leu Phe His Ser Glu Thr Ile Cys
            20                  25

<210> SEQ ID NO 333
<211> LENGTH: 24
<212> TYPE: PRT
<213> ORGANISM: Homo sapiens

<400> SEQUENCE: 333

Met Lys Ala Ser Ser Leu Ala Phe Ser Leu Leu Ser Ala Ala Phe Tyr
1               5                   10                  15

Leu Leu Trp Thr Pro Ser Thr Gly
            20

<210> SEQ ID NO 334
<211> LENGTH: 19
<212> TYPE: PRT
<213> ORGANISM: Homo sapiens

<400> SEQUENCE: 334

Met Pro Arg Gly Trp Ala Ala Pro Leu Leu Leu Leu Leu Gln Gly
1               5                   10                  15

Gly Trp Gly

<210> SEQ ID NO 335
<211> LENGTH: 33
<212> TYPE: PRT
<213> ORGANISM: Homo sapiens

<400> SEQUENCE: 335

Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
            20                  25                  30

Ala

<210> SEQ ID NO 336
<211> LENGTH: 51
<212> TYPE: PRT
<213> ORGANISM: Homo sapiens
```

<400> SEQUENCE: 336

Met Asn Phe Gln Gln Arg Leu Gln Ser Leu Trp Thr Leu Ala Arg Pro
1               5                   10                  15

Phe Cys Pro Pro Leu Leu Ala Thr Ala Ser Gln Met Gln Met Val Val
            20                  25                  30

Leu Pro Cys Leu Gly Phe Thr Leu Leu Leu Trp Ser Gln Val Ser Gly
        35                  40                  45

Ala Gln Gly
    50

<210> SEQ ID NO 337
<211> LENGTH: 32
<212> TYPE: PRT
<213> ORGANISM: Homo sapiens

<400> SEQUENCE: 337

Met Arg Glu Arg Pro Arg Leu Gly Glu Asp Ser Ser Leu Ile Ser Leu
1               5                   10                  15

Phe Leu Gln Val Val Ala Phe Leu Ala Met Val Met Gly Thr His Thr
            20                  25                  30

<210> SEQ ID NO 338
<211> LENGTH: 21
<212> TYPE: PRT
<213> ORGANISM: Homo sapiens

<400> SEQUENCE: 338

Met Asp Ser Tyr Leu Leu Met Trp Gly Leu Leu Thr Phe Ile Met Val
1               5                   10                  15

Pro Gly Cys Gln Ala
            20

<210> SEQ ID NO 339
<211> LENGTH: 26
<212> TYPE: PRT
<213> ORGANISM: Homo sapiens

<400> SEQUENCE: 339

Met Ala Ala Pro Ala Leu Ser Trp Arg Leu Pro Leu Leu Ile Leu Leu
1               5                   10                  15

Leu Pro Leu Ala Thr Ser Trp Ala Ser Ala
            20                  25

<210> SEQ ID NO 340
<211> LENGTH: 22
<212> TYPE: PRT
<213> ORGANISM: Homo sapiens

<400> SEQUENCE: 340

Met Leu Lys Pro Ser Leu Pro Phe Thr Ser Leu Leu Phe Leu Gln Leu
1               5                   10                  15

Pro Leu Leu Gly Val Gly
            20

<210> SEQ ID NO 341
<211> LENGTH: 20
<212> TYPE: PRT
<213> ORGANISM: Homo sapiens

<400> SEQUENCE: 341

```
Met Tyr Arg Met Gln Leu Leu Ser Cys Ile Ala Leu Ser Leu Ala Leu
1               5                   10                  15

Val Thr Asn Ser
            20

<210> SEQ ID NO 342
<211> LENGTH: 19
<212> TYPE: PRT
<213> ORGANISM: Homo sapiens

<400> SEQUENCE: 342

Met Ser Arg Leu Pro Val Leu Leu Leu Gln Leu Leu Val Arg Pro
1               5                   10                  15

Gly Leu Gln

<210> SEQ ID NO 343
<211> LENGTH: 24
<212> TYPE: PRT
<213> ORGANISM: Homo sapiens

<400> SEQUENCE: 343

Met Gly Leu Thr Ser Gln Leu Leu Pro Pro Leu Phe Phe Leu Leu Ala
1               5                   10                  15

Cys Ala Gly Asn Phe Val His Gly
            20

<210> SEQ ID NO 344
<211> LENGTH: 20
<212> TYPE: PRT
<213> ORGANISM: Homo sapiens

<400> SEQUENCE: 344

Met Ile Ile Val Ala His Val Leu Leu Ile Leu Leu Gly Ala Thr Glu
1               5                   10                  15

Ile Leu Gln Ala
            20

<210> SEQ ID NO 345
<211> LENGTH: 19
<212> TYPE: PRT
<213> ORGANISM: Homo sapiens

<400> SEQUENCE: 345

Met Leu Ala Val Gly Cys Ala Leu Leu Ala Ala Leu Leu Ala Ala Pro
1               5                   10                  15

Gly Ala Ala

<210> SEQ ID NO 346
<211> LENGTH: 20
<212> TYPE: PRT
<213> ORGANISM: Homo sapiens

<400> SEQUENCE: 346

Met Thr Ile Leu Gly Thr Thr Phe Gly Met Val Phe Ser Leu Leu Gln
1               5                   10                  15

Val Val Ser Gly
            20

<210> SEQ ID NO 347
<211> LENGTH: 25
<212> TYPE: PRT
<213> ORGANISM: Homo sapiens
```

<400> SEQUENCE: 347

Met Phe His Val Ser Phe Arg Tyr Ile Phe Gly Leu Pro Pro Leu Ile
1               5                   10                  15

Leu Val Leu Leu Pro Val Ala Ser Ser
            20                  25

<210> SEQ ID NO 348
<211> LENGTH: 18
<212> TYPE: PRT
<213> ORGANISM: Homo sapiens

<400> SEQUENCE: 348

Met Leu Leu Ala Met Val Leu Thr Ser Ala Leu Leu Leu Cys Ser Val
1               5                   10                  15

Ala Gly

<210> SEQ ID NO 349
<211> LENGTH: 18
<212> TYPE: PRT
<213> ORGANISM: Homo sapiens

<400> SEQUENCE: 349

Met Gly Phe Trp Ile Leu Ala Ile Leu Thr Ile Leu Met Tyr Ser Thr
1               5                   10                  15

Ala Ala

<210> SEQ ID NO 350
<211> LENGTH: 26
<212> TYPE: PRT
<213> ORGANISM: Homo sapiens

<400> SEQUENCE: 350

Met Leu Leu Ser Gln Asn Ala Phe Ile Phe Arg Ser Leu Asn Leu Val
1               5                   10                  15

Leu Met Val Tyr Ile Ser Leu Val Phe Gly
            20                  25

<210> SEQ ID NO 351
<211> LENGTH: 18
<212> TYPE: PRT
<213> ORGANISM: Homo sapiens

<400> SEQUENCE: 351

Met Val Leu His Leu Leu Leu Phe Leu Leu Leu Thr Pro Gln Gly Gly
1               5                   10                  15

His Ser

<210> SEQ ID NO 352
<211> LENGTH: 20
<212> TYPE: PRT
<213> ORGANISM: Homo sapiens

<400> SEQUENCE: 352

Met Asp Pro Arg Leu Pro Ala Trp Ala Leu Val Leu Leu Gly Pro Ala
1               5                   10                  15

Leu Val Phe Ala
            20

<210> SEQ ID NO 353
<211> LENGTH: 25

```
<212> TYPE: PRT
<213> ORGANISM: Homo sapiens

<400> SEQUENCE: 353

Met Ala Ser Leu Phe Arg Ser Tyr Leu Pro Ala Ile Trp Leu Leu
1               5                   10                  15

Ser Gln Leu Leu Arg Glu Ser Leu Ala
            20                  25

<210> SEQ ID NO 354
<211> LENGTH: 22
<212> TYPE: PRT
<213> ORGANISM: Homo sapiens

<400> SEQUENCE: 354

Met Lys Gly Ser Ile Phe Thr Leu Phe Leu Phe Ser Val Leu Phe Ala
1               5                   10                  15

Ile Ser Glu Val Arg Ser
            20

<210> SEQ ID NO 355
<211> LENGTH: 24
<212> TYPE: PRT
<213> ORGANISM: Homo sapiens

<400> SEQUENCE: 355

Met Ala Leu Trp Met Arg Leu Leu Pro Leu Leu Ala Leu Leu Ala Leu
1               5                   10                  15

Trp Gly Pro Asp Pro Ala Ala Ala
            20

<210> SEQ ID NO 356
<211> LENGTH: 19
<212> TYPE: PRT
<213> ORGANISM: Homo sapiens

<400> SEQUENCE: 356

Met Gln Leu Phe Leu Leu Leu Cys Leu Val Leu Leu Ser Pro Gln Gly
1               5                   10                  15

Ala Ser Leu

<210> SEQ ID NO 357
<211> LENGTH: 17
<212> TYPE: PRT
<213> ORGANISM: Homo sapiens

<400> SEQUENCE: 357

Met Met Arg Glu Trp Val Leu Leu Met Ser Val Leu Leu Cys Gly Leu
1               5                   10                  15

Ala

<210> SEQ ID NO 358
<211> LENGTH: 23
<212> TYPE: PRT
<213> ORGANISM: Homo sapiens

<400> SEQUENCE: 358

Met Lys Leu Ser Gly Met Phe Leu Leu Leu Ser Leu Ala Leu Phe Cys
1               5                   10                  15

Phe Leu Thr Gly Val Phe Ser
            20
```

<210> SEQ ID NO 359
<211> LENGTH: 31
<212> TYPE: PRT
<213> ORGANISM: Homo sapiens

<400> SEQUENCE: 359

Met Ala Arg Ala Leu Cys Pro Leu Gln Ala Leu Trp Leu Leu Glu Trp
1               5                   10                  15

Val Leu Leu Leu Gly Pro Cys Ala Ala Pro Pro Ala Trp Ala
            20                  25                  30

<210> SEQ ID NO 360
<211> LENGTH: 29
<212> TYPE: PRT
<213> ORGANISM: Homo sapiens

<400> SEQUENCE: 360

Met Gly Pro Glu Arg Thr Gly Ala Ala Pro Leu Pro Leu Leu Val
1               5                   10                  15

Leu Ala Leu Ser Gln Gly Ile Leu Asn Cys Cys Leu Ala
            20                  25

<210> SEQ ID NO 361
<211> LENGTH: 32
<212> TYPE: PRT
<213> ORGANISM: Homo sapiens

<400> SEQUENCE: 361

Met Gly Pro Gly Pro Ser Arg Ala Pro Arg Ala Pro Arg Leu Met Leu
1               5                   10                  15

Cys Ala Leu Ala Leu Met Val Ala Ala Gly Gly Cys Val Val Ser Ala
            20                  25                  30

<210> SEQ ID NO 362
<211> LENGTH: 39
<212> TYPE: PRT
<213> ORGANISM: Homo sapiens

<400> SEQUENCE: 362

Met Phe Pro Thr Glu Ser Ala Trp Leu Gly Lys Arg Gly Ala Asn Pro
1               5                   10                  15

Gly Pro Glu Ala Ala Val Arg Glu Thr Val Met Leu Leu Leu Cys Leu
            20                  25                  30

Gly Val Pro Thr Gly Arg Pro
        35

<210> SEQ ID NO 363
<211> LENGTH: 23
<212> TYPE: PRT
<213> ORGANISM: Homo sapiens

<400> SEQUENCE: 363

Met Ala Ala Ala Gly Gln Leu Cys Leu Leu Tyr Leu Ser Ala Gly Leu
1               5                   10                  15

Leu Ser Arg Leu Gly Ala Ala
            20

<210> SEQ ID NO 364
<211> LENGTH: 33
<212> TYPE: PRT
<213> ORGANISM: Homo sapiens -continued

```
<400> SEQUENCE: 364

Met Ala Gly Ala Arg Ser Arg Asp Pro Trp Gly Ala Ser Gly Ile Cys
1               5                   10                  15

Tyr Leu Phe Gly Ser Leu Leu Val Glu Leu Leu Phe Ser Arg Ala Val
            20                  25                  30

Ala

<210> SEQ ID NO 365
<211> LENGTH: 18
<212> TYPE: PRT
<213> ORGANISM: Homo sapiens

<400> SEQUENCE: 365

Met Trp Leu Phe His Thr Leu Leu Cys Ile Ala Ser Leu Ala Leu Leu
1               5                   10                  15

Ala Ala

<210> SEQ ID NO 366
<211> LENGTH: 25
<212> TYPE: PRT
<213> ORGANISM: Homo sapiens

<400> SEQUENCE: 366

Met Lys Asp Ser Cys Ile Thr Val Met Ala Met Ala Leu Leu Ser Gly
1               5                   10                  15

Phe Phe Phe Phe Ala Pro Ala Ser Ser
            20                  25

<210> SEQ ID NO 367
<211> LENGTH: 30
<212> TYPE: PRT
<213> ORGANISM: Homo sapiens

<400> SEQUENCE: 367

Met Ala Phe Pro Pro Arg Arg Arg Leu Arg Leu Gly Pro Arg Gly Leu
1               5                   10                  15

Pro Leu Leu Leu Ser Gly Leu Leu Pro Leu Cys Arg Ala
            20                  25                  30

<210> SEQ ID NO 368
<211> LENGTH: 19
<212> TYPE: PRT
<213> ORGANISM: Homo sapiens

<400> SEQUENCE: 368

Met Thr Arg Thr Arg Ala Ala Leu Leu Leu Phe Thr Ala Leu Ala Thr
1               5                   10                  15

Ser Leu Gly

<210> SEQ ID NO 369
<211> LENGTH: 22
<212> TYPE: PRT
<213> ORGANISM: Homo sapiens

<400> SEQUENCE: 369

Met Leu Gly Leu Arg Pro Pro Leu Leu Ala Leu Val Gly Leu Leu Ser
1               5                   10                  15

Leu Gly Cys Val Leu Ser
            20
```

```
<210> SEQ ID NO 370
<211> LENGTH: 27
<212> TYPE: PRT
<213> ORGANISM: Homo sapiens

<400> SEQUENCE: 370

Met Ala Gly Pro Arg Pro Ser Pro Trp Ala Arg Leu Leu Ala Ala
1               5                   10                  15

Leu Ile Ser Val Ser Leu Ser Gly Thr Leu Ala
            20                  25

<210> SEQ ID NO 371
<211> LENGTH: 28
<212> TYPE: PRT
<213> ORGANISM: Homo sapiens

<400> SEQUENCE: 371

Met Lys Pro Pro Arg Pro Val Arg Thr Cys Ser Lys Val Leu Val Leu
1               5                   10                  15

Leu Ser Leu Leu Ala Ile His Gln Thr Thr Thr Ala
            20                  25

<210> SEQ ID NO 372
<211> LENGTH: 27
<212> TYPE: PRT
<213> ORGANISM: Homo sapiens

<400> SEQUENCE: 372

Met Gly Thr Lys Ala Gln Val Glu Arg Lys Leu Leu Cys Leu Phe Ile
1               5                   10                  15

Leu Ala Ile Leu Leu Cys Ser Leu Ala Leu Gly
            20                  25

<210> SEQ ID NO 373
<211> LENGTH: 28
<212> TYPE: PRT
<213> ORGANISM: Homo sapiens

<400> SEQUENCE: 373

Met Ala Arg Arg Ser Arg His Arg Leu Leu Leu Leu Leu Leu Arg Tyr
1               5                   10                  15

Leu Val Val Ala Leu Gly Tyr His Lys Ala Tyr Gly
            20                  25

<210> SEQ ID NO 374
<211> LENGTH: 31
<212> TYPE: PRT
<213> ORGANISM: Homo sapiens

<400> SEQUENCE: 374

Met Ala Leu Arg Arg Pro Pro Arg Leu Arg Leu Cys Ala Arg Leu Pro
1               5                   10                  15

Asp Phe Phe Leu Leu Leu Leu Phe Arg Gly Cys Leu Ile Gly Ala
            20                  25                  30

<210> SEQ ID NO 375
<211> LENGTH: 19
<212> TYPE: PRT
<213> ORGANISM: Homo sapiens

<400> SEQUENCE: 375

Met Phe Cys Pro Leu Lys Leu Ile Leu Leu Pro Val Leu Leu Asp Tyr
1               5                   10                  15
```

-continued

```
<210> SEQ ID NO 376
<211> LENGTH: 30
<212> TYPE: PRT
<213> ORGANISM: Homo sapiens

<400> SEQUENCE: 376

Met Leu Pro Pro Arg Pro Ala Ala Ala Leu Ala Leu Pro Val Leu
1               5                   10                  15

Leu Leu Leu Leu Val Val Leu Thr Pro Pro Thr Gly Ala
            20                  25                  30

<210> SEQ ID NO 377
<211> LENGTH: 21
<212> TYPE: PRT
<213> ORGANISM: Homo sapiens

<400> SEQUENCE: 377

Met Ser Leu Leu Val Val Ser Met Ala Cys Val Gly Phe Phe Leu Leu
1               5                   10                  15

Gln Gly Ala Trp Pro
            20

<210> SEQ ID NO 378
<211> LENGTH: 20
<212> TYPE: PRT
<213> ORGANISM: Homo sapiens

<400> SEQUENCE: 378

Met Leu Arg Met Arg Val Pro Ala Leu Leu Val Leu Leu Phe Cys Phe
1               5                   10                  15

Arg Gly Arg Ala
            20

<210> SEQ ID NO 379
<211> LENGTH: 17
<212> TYPE: PRT
<213> ORGANISM: Homo sapiens

<400> SEQUENCE: 379

Met Trp Val Pro Val Val Phe Leu Thr Leu Ser Val Thr Trp Ile Gly
1               5                   10                  15

Ala

<210> SEQ ID NO 380
<211> LENGTH: 19
<212> TYPE: PRT
<213> ORGANISM: Homo sapiens

<400> SEQUENCE: 380

Met Ile Leu Phe Lys Gln Ala Thr Tyr Phe Ile Ser Leu Phe Ala Thr
1               5                   10                  15

Val Ser Cys

<210> SEQ ID NO 381
<211> LENGTH: 18
<212> TYPE: PRT
<213> ORGANISM: Homo sapiens

<400> SEQUENCE: 381
```

```
Met Lys Leu Ile Thr Ile Leu Phe Leu Cys Ser Arg Leu Leu Leu Ser
1               5                   10                  15

Leu Thr
```

<210> SEQ ID NO 382
<211> LENGTH: 23
<212> TYPE: PRT
<213> ORGANISM: Homo sapiens

<400> SEQUENCE: 382

```
Met Glu Trp Trp Ala Ser Ser Pro Leu Arg Leu Trp Leu Leu Leu Phe
1               5                   10                  15

Leu Leu Pro Ser Ala Gln Gly
            20
```

<210> SEQ ID NO 383
<211> LENGTH: 20
<212> TYPE: PRT
<213> ORGANISM: Homo sapiens

<400> SEQUENCE: 383

```
Met Val Leu Gln Thr Gln Val Phe Ile Ser Leu Leu Leu Trp Ile Ser
1               5                   10                  15

Gly Ala Tyr Gly
            20
```

<210> SEQ ID NO 384
<211> LENGTH: 20
<212> TYPE: PRT
<213> ORGANISM: Homo sapiens

<400> SEQUENCE: 384

```
Met Val Leu Gln Thr Gln Val Phe Ile Ser Leu Leu Leu Trp Ile Ser
1               5                   10                  15

Gly Ala Tyr Gly
            20
```

<210> SEQ ID NO 385
<211> LENGTH: 19
<212> TYPE: PRT
<213> ORGANISM: Homo sapiens

<400> SEQUENCE: 385

```
Met Val Val Ala Leu Arg Tyr Val Trp Pro Leu Leu Leu Cys Ser Pro
1               5                   10                  15

Cys Leu Leu
```

<210> SEQ ID NO 386
<211> LENGTH: 19
<212> TYPE: PRT
<213> ORGANISM: Homo sapiens

<400> SEQUENCE: 386

```
Met Arg Phe Phe Val Pro Leu Phe Leu Val Gly Ile Leu Phe Pro Ala
1               5                   10                  15

Ile Leu Ala
```

<210> SEQ ID NO 387
<211> LENGTH: 21
<212> TYPE: PRT
<213> ORGANISM: Homo sapiens

```
<400> SEQUENCE: 387

Met Gly Leu Leu Gln Leu Leu Ala Phe Ser Phe Leu Ala Leu Cys Arg
1               5                   10                  15

Ala Arg Val Arg Ala
            20

<210> SEQ ID NO 388
<211> LENGTH: 33
<212> TYPE: PRT
<213> ORGANISM: Homo sapiens

<400> SEQUENCE: 388

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
            20                  25                  30

Ala

<210> SEQ ID NO 389
<211> LENGTH: 27
<212> TYPE: PRT
<213> ORGANISM: Homo sapiens

<400> SEQUENCE: 389

Met Ala Pro Arg Ser Ala Arg Arg Pro Leu Leu Leu Leu Pro Val
1               5                   10                  15

Ala Ala Ala Arg Pro His Ala Leu Ser Ser Ala
            20                  25

<210> SEQ ID NO 390
<211> LENGTH: 28
<212> TYPE: PRT
<213> ORGANISM: Homo sapiens

<400> SEQUENCE: 390

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala
            20                  25

<210> SEQ ID NO 391
<211> LENGTH: 25
<212> TYPE: PRT
<213> ORGANISM: Homo sapiens

<400> SEQUENCE: 391

Met Gly Ala Leu Ala Arg Ala Leu Pro Ser Ile Leu Leu Ala Leu Leu
1               5                   10                  15

Leu Thr Ser Thr Pro Glu Ala Leu Gly
            20                  25

<210> SEQ ID NO 392
<211> LENGTH: 24
<212> TYPE: PRT
<213> ORGANISM: Homo sapiens

<400> SEQUENCE: 392

Met Gly Pro Pro Gly Ser Pro Trp Gln Trp Val Thr Leu Leu Leu Gly
1               5                   10                  15

Leu Leu Leu Pro Pro Ala Ala Pro
            20
```

<210> SEQ ID NO 393
<211> LENGTH: 18
<212> TYPE: PRT
<213> ORGANISM: Homo sapiens

<400> SEQUENCE: 393

Met Lys Pro Leu Leu Ala Val Ser Leu Gly Leu Ile Ala Leu
1               5                   10                  15

Gln Ala

<210> SEQ ID NO 394
<211> LENGTH: 21
<212> TYPE: PRT
<213> ORGANISM: Homo sapiens

<400> SEQUENCE: 394

Met Lys Pro Val Trp Val Ala Thr Leu Leu Trp Met Leu Leu Leu Val
1               5                   10                  15

Pro Arg Leu Gly Ala
            20

<210> SEQ ID NO 395
<211> LENGTH: 19
<212> TYPE: PRT
<213> ORGANISM: Homo sapiens

<400> SEQUENCE: 395

Met Ala Thr Leu Leu Leu Leu Gly Val Leu Val Val Ser Pro Asp
1               5                   10                  15

Ala Leu Gly

<210> SEQ ID NO 396
<211> LENGTH: 18
<212> TYPE: PRT
<213> ORGANISM: Homo sapiens

<400> SEQUENCE: 396

Met Thr Pro Pro Arg Leu Phe Trp Val Trp Leu Leu Val Ala Gly Thr
1               5                   10                  15

Gln Gly

<210> SEQ ID NO 397
<211> LENGTH: 22
<212> TYPE: PRT
<213> ORGANISM: Homo sapiens

<400> SEQUENCE: 397

Met Lys Val Leu Ala Ala Gly Val Val Pro Leu Leu Leu Val Leu His
1               5                   10                  15

Trp Lys His Gly Ala Gly
            20

<210> SEQ ID NO 398
<211> LENGTH: 19
<212> TYPE: PRT
<213> ORGANISM: Homo sapiens

<400> SEQUENCE: 398

Met Trp Leu Leu Leu Thr Met Ala Ser Leu Ile Ser Val Leu Gly Thr
1               5                   10                  15

Thr His Gly

<210> SEQ ID NO 399
<211> LENGTH: 16
<212> TYPE: PRT
<213> ORGANISM: Homo sapiens

<400> SEQUENCE: 399

Met Leu Pro Leu Trp Thr Leu Ser Leu Leu Gly Ala Val Ala Gly
1               5                   10                  15

<210> SEQ ID NO 400
<211> LENGTH: 23
<212> TYPE: PRT
<213> ORGANISM: Homo sapiens

<400> SEQUENCE: 400

Met Thr Pro Ile Leu Thr Val Leu Ile Cys Leu Gly Leu Ser Leu Asp
1               5                   10                  15

Pro Arg Thr His Val Gln Ala
            20

<210> SEQ ID NO 401
<211> LENGTH: 30
<212> TYPE: PRT
<213> ORGANISM: Homo sapiens

<400> SEQUENCE: 401

Met Ala Gly Ser Arg Gln Arg Gly Leu Arg Ala Arg Val Arg Pro Leu
1               5                   10                  15

Phe Cys Ala Leu Leu Leu Ser Leu Gly Arg Phe Val Arg Gly
            20                  25                  30

<210> SEQ ID NO 402
<211> LENGTH: 19
<212> TYPE: PRT
<213> ORGANISM: Homo sapiens

<400> SEQUENCE: 402

Met Glu Leu Ser Trp His Val Val Phe Ile Ala Leu Leu Ser Phe Ser
1               5                   10                  15

Cys Trp Gly

<210> SEQ ID NO 403
<211> LENGTH: 47
<212> TYPE: PRT
<213> ORGANISM: Homo sapiens

<400> SEQUENCE: 403

Met Gly Ser Leu Gln His Cys Cys Cys Leu Leu Pro Lys Met Gly Asp
1               5                   10                  15

Thr Trp Ala Gln Leu Pro Trp Pro Gly Pro Pro His Pro Ala Met Leu
            20                  25                  30

Leu Ile Ser Leu Leu Leu Ala Ala Gly Leu Met His Ser Asp Ala
            35                  40                  45

<210> SEQ ID NO 404
<211> LENGTH: 25
<212> TYPE: PRT
<213> ORGANISM: Homo sapiens

<400> SEQUENCE: 404

```
Met Ala Arg Met Ser Phe Val Ile Ala Ala Cys Gln Leu Val Leu Gly
1               5                   10                  15

Leu Leu Met Thr Ser Leu Thr Glu Ser
            20                  25
```

<210> SEQ ID NO 405
<211> LENGTH: 20
<212> TYPE: PRT
<213> ORGANISM: Homo sapiens

<400> SEQUENCE: 405

```
Met Glu Met Leu Gln Gly Leu Leu Leu Leu Leu Ser Met Gly
1               5                   10                  15

Gly Ala Trp Ala
            20
```

<210> SEQ ID NO 406
<211> LENGTH: 18
<212> TYPE: PRT
<213> ORGANISM: Homo sapiens

<400> SEQUENCE: 406

```
Met Ser Leu Ser Ala Phe Thr Leu Phe Leu Ala Leu Ile Gly Gly Thr
1               5                   10                  15

Ser Gly
```

<210> SEQ ID NO 407
<211> LENGTH: 31
<212> TYPE: PRT
<213> ORGANISM: Homo sapiens

<400> SEQUENCE: 407

```
Met Glu Pro Pro Asp Ala Pro Ala Gln Ala Arg Gly Ala Pro Arg Leu
1               5                   10                  15

Leu Leu Leu Ala Val Leu Leu Ala Ala His Pro Asp Ala Gln Ala
            20                  25                  30
```

<210> SEQ ID NO 408
<211> LENGTH: 19
<212> TYPE: PRT
<213> ORGANISM: Homo sapiens

<400> SEQUENCE: 408

```
Met Ala Trp Ala Pro Leu Leu Leu Thr Leu Leu Ala His Cys Thr Asp
1               5                   10                  15

Cys Trp Ala
```

<210> SEQ ID NO 409
<211> LENGTH: 20
<212> TYPE: PRT
<213> ORGANISM: Homo sapiens

<400> SEQUENCE: 409

```
Met Lys Gly Phe Thr Ala Thr Leu Phe Leu Trp Thr Leu Ile Phe Pro
1               5                   10                  15

Ser Cys Ser Gly
            20
```

<210> SEQ ID NO 410
<211> LENGTH: 21
<212> TYPE: PRT
<213> ORGANISM: Homo sapiens

```
<400> SEQUENCE: 410

Met Ile Ala Ser Gln Phe Leu Ser Ala Leu Thr Leu Val Leu Leu Ile
1               5                   10                  15

Lys Glu Ser Gly Ala
            20

<210> SEQ ID NO 411
<211> LENGTH: 33
<212> TYPE: PRT
<213> ORGANISM: Homo sapiens

<400> SEQUENCE: 411

Met Gly Leu His Leu Arg Pro Tyr Arg Val Gly Leu Leu Pro Asp Gly
1               5                   10                  15

Leu Leu Phe Leu Leu Leu Leu Met Leu Leu Ala Asp Pro Ala Leu
                20                  25                  30

Pro

<210> SEQ ID NO 412
<211> LENGTH: 22
<212> TYPE: PRT
<213> ORGANISM: Homo sapiens

<400> SEQUENCE: 412

Met Glu Pro Gly Pro Ala Leu Ala Trp Leu Leu Leu Ser Leu Leu
1               5                   10                  15

Ala Asp Cys Leu Lys Ala
            20

<210> SEQ ID NO 413
<211> LENGTH: 18
<212> TYPE: PRT
<213> ORGANISM: Homo sapiens

<400> SEQUENCE: 413

Met Lys Ala Leu Ile Val Leu Gly Leu Val Leu Leu Ser Val Thr Val
1               5                   10                  15

Gln Gly

<210> SEQ ID NO 414
<211> LENGTH: 20
<212> TYPE: PRT
<213> ORGANISM: Homo sapiens

<400> SEQUENCE: 414

Met Ser Leu Phe Pro Ser Leu Pro Leu Leu Leu Leu Ser Met Val Ala
1               5                   10                  15

Ala Ser Tyr Ser
            20

<210> SEQ ID NO 415
<211> LENGTH: 34
<212> TYPE: PRT
<213> ORGANISM: Homo sapiens

<400> SEQUENCE: 415

Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
                20                  25                  30
```

Asp Ala

<210> SEQ ID NO 416
<211> LENGTH: 21
<212> TYPE: PRT
<213> ORGANISM: Homo sapiens

<400> SEQUENCE: 416

Met Lys Ala Leu Leu Ala Leu Pro Leu Leu Leu Leu Ser Thr Pro
1               5                   10                  15

Pro Cys Ala Pro Gln
            20

<210> SEQ ID NO 417
<211> LENGTH: 19
<212> TYPE: PRT
<213> ORGANISM: Homo sapiens

<400> SEQUENCE: 417

Met Lys Ser Leu Ile Leu Leu Ala Ile Leu Ala Ala Leu Ala Val Val
1               5                   10                  15

Thr Leu Cys

<210> SEQ ID NO 418
<211> LENGTH: 24
<212> TYPE: PRT
<213> ORGANISM: Homo sapiens

<400> SEQUENCE: 418

Met Ala Arg Ser Leu Val Cys Leu Gly Val Ile Ile Leu Leu Ser Ala
1               5                   10                  15

Phe Ser Gly Pro Gly Val Arg Gly
            20

<210> SEQ ID NO 419
<211> LENGTH: 20
<212> TYPE: PRT
<213> ORGANISM: Homo sapiens

<400> SEQUENCE: 419

Met Lys Thr Leu Gln Ser Thr Leu Leu Leu Leu Leu Val Pro Leu
1               5                   10                  15

Ile Lys Pro Ala
            20

<210> SEQ ID NO 420
<211> LENGTH: 34
<212> TYPE: PRT
<213> ORGANISM: Homo sapiens

<400> SEQUENCE: 420

Met Ala Arg Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
            20                  25                  30

Ala Gly

<210> SEQ ID NO 421
<211> LENGTH: 34
<212> TYPE: PRT
<213> ORGANISM: Homo sapiens

<400> SEQUENCE: 421

Met Ala His Ala Thr Leu Ser Ala Ala Pro Ser Asn Pro Arg Leu Leu
1               5                   10                  15

Arg Val Ala Leu Leu Leu Leu Leu Val Ala Ala Ser Arg Arg Ala
            20                  25                  30

Ala Gly

<210> SEQ ID NO 422
<211> LENGTH: 20
<212> TYPE: PRT
<213> ORGANISM: Homo sapiens

<400> SEQUENCE: 422

Met Gln His Arg Gly Phe Leu Leu Thr Leu Leu Ala Leu Ala
1               5                   10                  15

Leu Thr Ser Ala
            20

<210> SEQ ID NO 423
<211> LENGTH: 19
<212> TYPE: PRT
<213> ORGANISM: Homo sapiens

<400> SEQUENCE: 423

Met His Ser Phe Pro Pro Leu Leu Leu Leu Leu Phe Trp Gly Val Val
1               5                   10                  15

Ser His Ser

<210> SEQ ID NO 424
<211> LENGTH: 25
<212> TYPE: PRT
<213> ORGANISM: Homo sapiens

<400> SEQUENCE: 424

Met Val Ser Arg Lys Ala Val Ala Ala Leu Leu Val Val His Val Ala
1               5                   10                  15

Ala Met Leu Ala Ser Gln Thr Glu Ala
            20                  25

<210> SEQ ID NO 425
<211> LENGTH: 28
<212> TYPE: PRT
<213> ORGANISM: Homo sapiens

<400> SEQUENCE: 425

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys
            20                  25

<210> SEQ ID NO 426
<211> LENGTH: 26
<212> TYPE: PRT
<213> ORGANISM: Homo sapiens

<400> SEQUENCE: 426

Met Phe Pro Phe Tyr Ser Cys Trp Arg Thr Gly Leu Leu Leu Leu Leu
1               5                   10                  15

Leu Ala Val Ala Val Arg Glu Ser Trp Gln
            20                  25

<210> SEQ ID NO 427
<211> LENGTH: 40
<212> TYPE: PRT
<213> ORGANISM: Homo sapiens

<400> SEQUENCE: 427

Met Gly Ala Ala Gly Arg Ser Pro His Leu Gly Pro Ala Pro Ala
1               5                   10                  15

Arg Arg Pro Gln Arg Ser Leu Leu Leu Gln Leu Leu Leu Val
            20                  25                  30

Ala Ala Pro Gly Ser Thr Gln Ala
        35                  40

<210> SEQ ID NO 428
<211> LENGTH: 31
<212> TYPE: PRT
<213> ORGANISM: Homo sapiens

<400> SEQUENCE: 428

Met Gln Gln Arg Gly Ala Ala Gly Ser Arg Gly Cys Ala Leu Phe Pro
1               5                   10                  15

Leu Leu Gly Val Leu Phe Phe Gln Gly Val Tyr Ile Val Phe Ser
            20                  25                  30

<210> SEQ ID NO 429
<211> LENGTH: 20
<212> TYPE: PRT
<213> ORGANISM: Homo sapiens

<400> SEQUENCE: 429

Met Asn Val Leu Leu Gly Ser Val Val Ile Phe Ala Thr Phe Val Thr
1               5                   10                  15

Leu Cys Asn Ala
            20

<210> SEQ ID NO 430
<211> LENGTH: 29
<212> TYPE: PRT
<213> ORGANISM: Homo sapiens

<400> SEQUENCE: 430

Met Ala Pro Gly Ala Pro Ser Ser Ser Pro Ser Pro Ile Leu Ala Val
1               5                   10                  15

Leu Leu Phe Ser Ser Leu Val Leu Ser Pro Ala Gln Ala
            20                  25

<210> SEQ ID NO 431
<211> LENGTH: 17
<212> TYPE: PRT
<213> ORGANISM: Homo sapiens

<400> SEQUENCE: 431

Met Leu Leu Lys Thr Val Leu Leu Leu Gly His Val Ala Gln Val Leu
1               5                   10                  15

Met

<210> SEQ ID NO 432
<211> LENGTH: 21
<212> TYPE: PRT
<213> ORGANISM: Homo sapiens

```
<400> SEQUENCE: 432

Met Glu Ser Arg Val Leu Leu Arg Thr Phe Cys Leu Ile Phe Gly Leu
1               5                   10                  15

Gly Ala Val Trp Gly
            20

<210> SEQ ID NO 433
<211> LENGTH: 22
<212> TYPE: PRT
<213> ORGANISM: Homo sapiens

<400> SEQUENCE: 433

Met Ala Leu Glu Arg Leu Cys Ser Val Leu Lys Val Leu Leu Ile Thr
1               5                   10                  15

Val Leu Val Val Glu Gly
            20

<210> SEQ ID NO 434
<211> LENGTH: 19
<212> TYPE: PRT
<213> ORGANISM: Homo sapiens

<400> SEQUENCE: 434

Met Ala Gly Pro Ser Leu Ala Cys Cys Leu Leu Gly Leu Leu Ala Leu
1               5                   10                  15

Thr Ser Ala

<210> SEQ ID NO 435
<211> LENGTH: 19
<212> TYPE: PRT
<213> ORGANISM: Homo sapiens

<400> SEQUENCE: 435

Met Pro Asp Thr Met Leu Pro Ala Cys Phe Leu Gly Leu Leu Ala Phe
1               5                   10                  15

Ser Ser Ala

<210> SEQ ID NO 436
<211> LENGTH: 20
<212> TYPE: PRT
<213> ORGANISM: Homo sapiens

<400> SEQUENCE: 436

Met Pro Leu Gly Leu Leu Trp Leu Gly Leu Ala Leu Leu Gly Ala Leu
1               5                   10                  15

His Ala Gln Ala
            20

<210> SEQ ID NO 437
<211> LENGTH: 28
<212> TYPE: PRT
<213> ORGANISM: Homo sapiens

<400> SEQUENCE: 437

Met Leu Ala Ser Ser Ser Arg Ile Arg Ala Ala Trp Thr Arg Ala Leu
1               5                   10                  15

Leu Leu Pro Leu Leu Leu Ala Gly Pro Val Gly Cys
            20                  25

<210> SEQ ID NO 438
<211> LENGTH: 30
```

-continued

```
<212> TYPE: PRT
<213> ORGANISM: Homo sapiens

<400> SEQUENCE: 438

Met Glu Gly Asp Arg Val Ala Gly Arg Pro Val Leu Ser Ser Leu Pro
1               5                   10                  15

Val Leu Leu Leu Gln Leu Leu Met Leu Arg Ala Ala Ala
            20                  25                  30

<210> SEQ ID NO 439
<211> LENGTH: 41
<212> TYPE: PRT
<213> ORGANISM: Homo sapiens

<400> SEQUENCE: 439

Met Ser Arg Pro Gln Gly Leu Leu Trp Leu Pro Leu Leu Phe Thr Pro
1               5                   10                  15

Val Cys Val Met Leu Asn Ser Asn Val Leu Leu Trp Leu Thr Ala Leu
            20                  25                  30

Ala Ile Lys Phe Thr Leu Ile Asp Ser
            35                  40

<210> SEQ ID NO 440
<211> LENGTH: 24
<212> TYPE: PRT
<213> ORGANISM: Homo sapiens

<400> SEQUENCE: 440

Met Ala Arg Arg Ala Gly Gly Ala Arg Met Phe Gly Ser Leu Leu Leu
1               5                   10                  15

Phe Ala Leu Leu Ala Ala Gly Val
            20

<210> SEQ ID NO 441
<211> LENGTH: 31
<212> TYPE: PRT
<213> ORGANISM: Homo sapiens

<400> SEQUENCE: 441

Met Gln Ser Val Gln Ser Thr Ser Phe Cys Leu Arg Lys Gln Cys Leu
1               5                   10                  15

Cys Leu Thr Phe Leu Leu Leu His Leu Leu Gly Gln Val Ala Ala
            20                  25                  30

<210> SEQ ID NO 442
<211> LENGTH: 28
<212> TYPE: PRT
<213> ORGANISM: Homo sapiens

<400> SEQUENCE: 442

Met Ser Gly Ser Ser Leu Pro Ser Ala Leu Ala Leu Ser Leu Leu Leu
1               5                   10                  15

Val Ser Gly Ser Leu Leu Pro Gly Pro Gly Ala Ala
            20                  25

<210> SEQ ID NO 443
<211> LENGTH: 28
<212> TYPE: PRT
<213> ORGANISM: Homo sapiens

<400> SEQUENCE: 443

Met Leu Gly Asn Lys Arg Leu Gly Leu Ser Gly Leu Thr Leu Ala Leu
```

```
                1               5                  10                  15
Ser Leu Leu Val Cys Leu Gly Ala Leu Ala Glu Ala
            20                  25

<210> SEQ ID NO 444
<211> LENGTH: 21
<212> TYPE: PRT
<213> ORGANISM: Homo sapiens

<400> SEQUENCE: 444

Met Glu Arg Gly Leu Pro Leu Cys Ala Val Leu Ala Leu Val Leu
1               5                   10                  15

Ala Pro Ala Gly Ala
            20

<210> SEQ ID NO 445
<211> LENGTH: 31
<212> TYPE: PRT
<213> ORGANISM: Homo sapiens

<400> SEQUENCE: 445

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala
            20                  25                  30

<210> SEQ ID NO 446
<211> LENGTH: 22
<212> TYPE: PRT
<213> ORGANISM: Homo sapiens

<400> SEQUENCE: 446

Met Gln Leu Thr Arg Cys Cys Phe Val Phe Leu Val Gln Gly Ser Leu
1               5                   10                  15

Tyr Leu Val Ile Cys Gly
            20

<210> SEQ ID NO 447
<211> LENGTH: 28
<212> TYPE: PRT
<213> ORGANISM: Homo sapiens

<400> SEQUENCE: 447

Met Met Val Ala Leu Arg Gly Ala Ser Ala Leu Leu Val Leu Phe Leu
1               5                   10                  15

Ala Ala Phe Leu Pro Pro Pro Gln Cys Thr Gln Asp
            20                  25

<210> SEQ ID NO 448
<211> LENGTH: 17
<212> TYPE: PRT
<213> ORGANISM: Homo sapiens

<400> SEQUENCE: 448

Met Ala Arg Ile Leu Leu Leu Phe Leu Pro Gly Leu Val Ala Val Cys
1               5                   10                  15

Ala

<210> SEQ ID NO 449
<211> LENGTH: 21
<212> TYPE: PRT
<213> ORGANISM: Homo sapiens
```

```
<400> SEQUENCE: 449

Met Ala Pro Leu Ala Leu His Leu Leu Val Leu Val Pro Ile Leu Leu
1               5                   10                  15

Ser Leu Val Ala Ser
            20

<210> SEQ ID NO 450
<211> LENGTH: 21
<212> TYPE: PRT
<213> ORGANISM: Homo sapiens

<400> SEQUENCE: 450

Met Leu Leu Ala Trp Val Gln Ala Phe Leu Val Ser Asn Met Leu Leu
1               5                   10                  15

Ala Glu Ala Tyr Gly
            20

<210> SEQ ID NO 451
<211> LENGTH: 29
<212> TYPE: PRT
<213> ORGANISM: Homo sapiens

<400> SEQUENCE: 451

Met Ala Ala Ala Arg Leu Cys Leu Ser Leu Leu Leu Leu Ser Thr Cys
1               5                   10                  15

Val Ala Leu Leu Leu Gln Pro Leu Leu Gly Ala Gln Gly
            20                  25

<210> SEQ ID NO 452
<211> LENGTH: 20
<212> TYPE: PRT
<213> ORGANISM: Homo sapiens

<400> SEQUENCE: 452

Met Val Tyr Lys Thr Leu Phe Ala Leu Cys Ile Leu Thr Ala Gly Trp
1               5                   10                  15

Arg Val Gln Ser
            20

<210> SEQ ID NO 453
<211> LENGTH: 26
<212> TYPE: PRT
<213> ORGANISM: Homo sapiens

<400> SEQUENCE: 453

Met Ala Val Arg Glu Leu Cys Phe Pro Arg Gln Arg Gln Val Leu Phe
1               5                   10                  15

Leu Phe Leu Phe Trp Gly Val Ser Leu Ala
            20                  25

<210> SEQ ID NO 454
<211> LENGTH: 23
<212> TYPE: PRT
<213> ORGANISM: Homo sapiens

<400> SEQUENCE: 454

Met Arg Gly Ala Asn Ala Trp Ala Pro Leu Cys Leu Leu Leu Ala Ala
1               5                   10                  15

Ala Thr Gln Leu Ser Arg Gln
            20
```

<210> SEQ ID NO 455
<211> LENGTH: 22
<212> TYPE: PRT
<213> ORGANISM: Homo sapiens

<400> SEQUENCE: 455

Met Ala Arg Ala Pro Pro Leu Leu Ala Ala Leu Thr Ala Leu Leu Ala
1               5                   10                  15

Ala Ala Ala Ala Gly Gly
            20

<210> SEQ ID NO 456
<211> LENGTH: 20
<212> TYPE: PRT
<213> ORGANISM: Homo sapiens

<400> SEQUENCE: 456

Met Arg Thr Leu Ala Cys Leu Leu Leu Gly Cys Gly Tyr Leu Ala
1               5                   10                  15

His Val Leu Ala
            20

<210> SEQ ID NO 457
<211> LENGTH: 17
<212> TYPE: PRT
<213> ORGANISM: Homo sapiens

<400> SEQUENCE: 457

Met Leu Arg Arg Ala Leu Leu Cys Leu Ala Val Ala Ala Leu Val Arg
1               5                   10                  15

Ala

<210> SEQ ID NO 458
<211> LENGTH: 24
<212> TYPE: PRT
<213> ORGANISM: Homo sapiens

<400> SEQUENCE: 458

Met Arg Leu Arg Arg Leu Ala Leu Phe Pro Gly Val Ala Leu Leu Leu
1               5                   10                  15

Ala Ala Ala Arg Leu Ala Ala Ala
            20

<210> SEQ ID NO 459
<211> LENGTH: 20
<212> TYPE: PRT
<213> ORGANISM: Homo sapiens

<400> SEQUENCE: 459

Met Ala Trp Gln Gly Leu Val Leu Ala Ala Cys Leu Leu Met Phe Pro
1               5                   10                  15

Ser Thr Thr Ala
            20

<210> SEQ ID NO 460
<211> LENGTH: 22
<212> TYPE: PRT
<213> ORGANISM: Homo sapiens

<400> SEQUENCE: 460

Met Gly Trp Thr Met Arg Leu Val Thr Ala Ala Leu Leu Leu Gly Leu
1               5                   10                  15

```
Met Met Val Val Thr Gly
            20

<210> SEQ ID NO 461
<211> LENGTH: 27
<212> TYPE: PRT
<213> ORGANISM: Homo sapiens

<400> SEQUENCE: 461

Met Gln Pro Arg Trp Ala Gln Gly Ala Thr Met Trp Leu Gly Val Leu
1               5                   10                  15

Leu Thr Leu Leu Leu Cys Ser Ser Leu Glu Gly
            20                  25

<210> SEQ ID NO 462
<211> LENGTH: 19
<212> TYPE: PRT
<213> ORGANISM: Homo sapiens

<400> SEQUENCE: 462

Met Lys Leu Ala Ser Gly Phe Leu Val Leu Trp Leu Ser Leu Gly Gly
1               5                   10                  15

Gly Leu Ala

<210> SEQ ID NO 463
<211> LENGTH: 23
<212> TYPE: PRT
<213> ORGANISM: Homo sapiens

<400> SEQUENCE: 463

Met Gly Thr Ser His Pro Ala Phe Leu Val Leu Gly Cys Leu Leu Thr
1               5                   10                  15

Gly Leu Ser Leu Ile Leu Cys
            20

<210> SEQ ID NO 464
<211> LENGTH: 32
<212> TYPE: PRT
<213> ORGANISM: Homo sapiens

<400> SEQUENCE: 464

Met Arg Leu Pro Gly Ala Met Pro Ala Leu Ala Leu Lys Gly Glu Leu
1               5                   10                  15

Leu Leu Leu Ser Leu Leu Leu Leu Leu Glu Pro Gln Ile Ser Gln Gly
            20                  25                  30

<210> SEQ ID NO 465
<211> LENGTH: 23
<212> TYPE: PRT
<213> ORGANISM: Homo sapiens

<400> SEQUENCE: 465

Met Ser Arg Ser Leu Leu Leu Arg Phe Leu Leu Phe Leu Leu Leu Leu
1               5                   10                  15

Pro Pro Leu Pro Val Leu Leu
            20

<210> SEQ ID NO 466
<211> LENGTH: 21
<212> TYPE: PRT
<213> ORGANISM: Homo sapiens
```

-continued

```
<400> SEQUENCE: 466

Met Ala Gln Gly Val Leu Trp Ile Leu Leu Gly Leu Leu Trp Ser
1               5                   10                  15

Asp Pro Gly Thr Ala
            20

<210> SEQ ID NO 467
<211> LENGTH: 21
<212> TYPE: PRT
<213> ORGANISM: Homo sapiens

<400> SEQUENCE: 467

Met Ala Ala Ala Met Pro Leu Ala Leu Val Leu Leu Leu Leu Gly
1               5                   10                  15

Pro Gly Gly Trp Cys
            20

<210> SEQ ID NO 468
<211> LENGTH: 28
<212> TYPE: PRT
<213> ORGANISM: Homo sapiens

<400> SEQUENCE: 468

Met Arg Leu Leu Gln Leu Leu Phe Arg Ala Ser Pro Ala Thr Leu Leu
1               5                   10                  15

Leu Val Leu Cys Leu Gln Leu Gly Ala Asn Lys Ala
            20                  25

<210> SEQ ID NO 469
<211> LENGTH: 41
<212> TYPE: PRT
<213> ORGANISM: Homo sapiens

<400> SEQUENCE: 469

Met Val Gly Gln Met Tyr Cys Tyr Pro Gly Ser His Leu Ala Arg Ala
1               5                   10                  15

Leu Thr Arg Ala Leu Ala Leu Ala Leu Val Leu Ala Leu Leu Val Gly
            20                  25                  30

Pro Phe Leu Ser Gly Leu Ala Gly Ala
            35                  40

<210> SEQ ID NO 470
<211> LENGTH: 31
<212> TYPE: PRT
<213> ORGANISM: Homo sapiens

<400> SEQUENCE: 470

Met Ser Ser Ala Ala Gly Phe Cys Ala Ser Arg Pro Gly Leu Leu Phe
1               5                   10                  15

Leu Gly Leu Leu Leu Leu Pro Leu Val Val Ala Phe Ala Ser Ala
            20                  25                  30

<210> SEQ ID NO 471
<211> LENGTH: 18
<212> TYPE: PRT
<213> ORGANISM: Homo sapiens

<400> SEQUENCE: 471

Met Arg Pro Leu Leu Leu Leu Ala Leu Leu Gly Trp Leu Leu Leu Ala
1               5                   10                  15

Glu Ala
```

<210> SEQ ID NO 472
<211> LENGTH: 26
<212> TYPE: PRT
<213> ORGANISM: Homo sapiens

<400> SEQUENCE: 472

Met Gly Leu Gly Ala Arg Gly Ala Trp Ala Ala Leu Leu Gly Thr
1               5                   10                  15

Leu Gln Val Leu Ala Leu Leu Gly Ala Ala
            20                  25

<210> SEQ ID NO 473
<211> LENGTH: 32
<212> TYPE: PRT
<213> ORGANISM: Homo sapiens

<400> SEQUENCE: 473

Met Ile Thr Gly Val Phe Ser Met Arg Leu Trp Thr Pro Val Gly Val
1               5                   10                  15

Leu Thr Ser Leu Ala Tyr Cys Leu His Gln Arg Arg Val Ala Leu Ala
                20                  25                  30

<210> SEQ ID NO 474
<211> LENGTH: 32
<212> TYPE: PRT
<213> ORGANISM: Homo sapiens

<400> SEQUENCE: 474

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
                20                  25                  30

<210> SEQ ID NO 475
<211> LENGTH: 28
<212> TYPE: PRT
<213> ORGANISM: Homo sapiens

<400> SEQUENCE: 475

Met Ile Arg Ala Ala Pro Pro Pro Leu Phe Leu Leu Leu Leu Leu
1               5                   10                  15

Leu Leu Leu Val Ser Trp Ala Ser Arg Gly Glu Ala
            20                  25

<210> SEQ ID NO 476
<211> LENGTH: 25
<212> TYPE: PRT
<213> ORGANISM: Homo sapiens

<400> SEQUENCE: 476

Met Lys Val Leu Leu Ala Ala Ala Leu Ile Ala Gly Ser Val Phe Phe
1               5                   10                  15

Leu Leu Leu Pro Gly Pro Ser Ala Ala
            20                  25

<210> SEQ ID NO 477
<211> LENGTH: 16
<212> TYPE: PRT
<213> ORGANISM: Homo sapiens

<400> SEQUENCE: 477

Met Leu Leu Ile Leu Leu Ser Val Ala Leu Ala Leu Ser Ser Ala
1               5                   10                  15

<210> SEQ ID NO 478
<211> LENGTH: 24
<212> TYPE: PRT
<213> ORGANISM: Homo sapiens

<400> SEQUENCE: 478

Met Lys Glu Asn Val Ala Ser Ala Thr Val Phe Thr Leu Leu Leu Phe
1               5                   10                  15

Leu Asn Thr Cys Leu Leu Asn Gly
            20

<210> SEQ ID NO 479
<211> LENGTH: 28
<212> TYPE: PRT
<213> ORGANISM: Homo sapiens

<400> SEQUENCE: 479

Met Asn Ile Lys Gly Ser Pro Trp Lys Gly Ser Leu Leu Leu Leu Leu
1               5                   10                  15

Val Ser Asn Leu Leu Leu Cys Gln Ser Val Ala Pro
            20                  25

<210> SEQ ID NO 480
<211> LENGTH: 19
<212> TYPE: PRT
<213> ORGANISM: Homo sapiens

<400> SEQUENCE: 480

Met Arg Gly Ala Thr Arg Val Ser Ile Met Leu Leu Leu Val Thr Val
1               5                   10                  15

Ser Asp Cys

<210> SEQ ID NO 481
<211> LENGTH: 27
<212> TYPE: PRT
<213> ORGANISM: Homo sapiens

<400> SEQUENCE: 481

Met Arg Ser Leu Cys Cys Ala Pro Leu Leu Leu Leu Leu Leu Leu Pro
1               5                   10                  15

Pro Leu Leu Leu Thr Pro Arg Ala Gly Asp Ala
            20                  25

<210> SEQ ID NO 482
<211> LENGTH: 27
<212> TYPE: PRT
<213> ORGANISM: Homo sapiens

<400> SEQUENCE: 482

Met Ile Thr Glu Gly Ala Gln Ala Pro Arg Leu Leu Pro Pro Leu
1               5                   10                  15

Leu Leu Leu Leu Thr Leu Pro Ala Thr Gly Ser
            20                  25

<210> SEQ ID NO 483
<211> LENGTH: 23
<212> TYPE: PRT
<213> ORGANISM: Homo sapiens

<400> SEQUENCE: 483

```
Met Ala Gly Cys Val Pro Leu Leu Gln Gly Leu Val Leu Val Leu Ala
1               5                   10                  15

Leu His Arg Val Glu Pro Ser
                20
```

<210> SEQ ID NO 484
<211> LENGTH: 16
<212> TYPE: PRT
<213> ORGANISM: Homo sapiens

<400> SEQUENCE: 484

```
Met Leu Leu Ile Leu Leu Ser Val Ala Leu Leu Ala Leu Ser Ser Ala
1               5                   10                  15
```

<210> SEQ ID NO 485
<211> LENGTH: 16
<212> TYPE: PRT
<213> ORGANISM: Homo sapiens

<400> SEQUENCE: 485

```
Met Leu Leu Ile Leu Leu Ser Val Ala Leu Leu Ala Phe Ser Ser Ala
1               5                   10                  15
```

<210> SEQ ID NO 486
<211> LENGTH: 27
<212> TYPE: PRT
<213> ORGANISM: Homo sapiens

<400> SEQUENCE: 486

```
Met Ala Ser Ser Pro Trp Gly Cys Val Cys Gly Leu Leu Leu Leu Leu
1               5                   10                  15

Leu Pro Leu Leu Gly Thr Gly Pro Ala Leu Gly
                20                  25
```

<210> SEQ ID NO 487
<211> LENGTH: 22
<212> TYPE: PRT
<213> ORGANISM: Homo sapiens

<400> SEQUENCE: 487

```
Met Ala Thr His His Thr Leu Trp Met Gly Leu Ala Leu Leu Gly Val
1               5                   10                  15

Leu Gly Asp Leu Gln Ala
                20
```

<210> SEQ ID NO 488
<211> LENGTH: 25
<212> TYPE: PRT
<213> ORGANISM: Homo sapiens

<400> SEQUENCE: 488

```
Met Ile Pro Ala Lys Asp Met Ala Lys Val Met Ile Val Met Leu Ala
1               5                   10                  15

Ile Cys Phe Leu Thr Lys Ser Asp Gly
                20                  25
```

<210> SEQ ID NO 489
<211> LENGTH: 19
<212> TYPE: PRT
<213> ORGANISM: Homo sapiens

<400> SEQUENCE: 489

-continued

Met Arg Arg Leu Leu Glu Pro Cys Trp Trp Ile Leu Phe Leu Lys Ile
1               5                   10                  15

Thr Ser Ser

<210> SEQ ID NO 490
<211> LENGTH: 28
<212> TYPE: PRT
<213> ORGANISM: Homo sapiens

<400> SEQUENCE: 490

Met Val Phe Val Arg Arg Pro Trp Pro Ala Leu Thr Thr Val Leu Leu
1               5                   10                  15

Ala Leu Leu Val Cys Leu Gly Ala Leu Val Asp Ala
            20                  25

<210> SEQ ID NO 491
<211> LENGTH: 25
<212> TYPE: PRT
<213> ORGANISM: Homo sapiens

<400> SEQUENCE: 491

Met Arg Lys Asp Arg Leu Leu His Leu Cys Leu Val Leu Leu Leu Ile
1               5                   10                  15

Leu Leu Ser Ala Ser Asp Ser Asn Ser
            20                  25

<210> SEQ ID NO 492
<211> LENGTH: 22
<212> TYPE: PRT
<213> ORGANISM: Homo sapiens

<400> SEQUENCE: 492

Met Ala Gln Thr Ser Ser Tyr Phe Met Leu Ile Ser Cys Leu Met Phe
1               5                   10                  15

Leu Ser Gln Ser Gln Gly
            20

<210> SEQ ID NO 493
<211> LENGTH: 26
<212> TYPE: PRT
<213> ORGANISM: Homo sapiens

<400> SEQUENCE: 493

Met Leu Pro Pro Met Ala Leu Pro Ser Val Ser Trp Met Leu Leu Ser
1               5                   10                  15

Cys Leu Ile Leu Leu Cys Gln Val Gln Gly
            20                  25

<210> SEQ ID NO 494
<211> LENGTH: 23
<212> TYPE: PRT
<213> ORGANISM: Homo sapiens

<400> SEQUENCE: 494

Met Glu Ala Pro Ala Ala Gly Leu Phe Leu Leu Leu Leu Gly Thr
1               5                   10                  15

Trp Ala Pro Ala Pro Gly Ser
            20

<210> SEQ ID NO 495
<211> LENGTH: 22
<212> TYPE: PRT

<213> ORGANISM: Homo sapiens

<400> SEQUENCE: 495

Met Ala Pro Pro Gly Ser Ser Thr Val Phe Leu Leu Ala Leu Thr Ile
1               5                   10                  15

Ile Ala Ser Thr Trp Ala
            20

<210> SEQ ID NO 496
<211> LENGTH: 26
<212> TYPE: PRT
<213> ORGANISM: Homo sapiens

<400> SEQUENCE: 496

Met Glu Leu Ala Leu Arg Arg Ser Pro Val Pro Arg Trp Leu Leu Leu
1               5                   10                  15

Leu Pro Leu Leu Leu Gly Leu Asn Ala Gly
            20                  25

<210> SEQ ID NO 497
<211> LENGTH: 28
<212> TYPE: PRT
<213> ORGANISM: Homo sapiens

<400> SEQUENCE: 497

Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly
            20                  25

<210> SEQ ID NO 498
<211> LENGTH: 28
<212> TYPE: PRT
<213> ORGANISM: Homo sapiens

<400> SEQUENCE: 498

Met Ala Leu Gln Arg Thr His Ser Leu Leu Leu Leu Leu Leu Leu Thr
1               5                   10                  15

Leu Leu Gly Leu Gly Leu Val Gln Pro Ser Tyr Gly
            20                  25

<210> SEQ ID NO 499
<211> LENGTH: 28
<212> TYPE: PRT
<213> ORGANISM: Homo sapiens

<400> SEQUENCE: 499

Met Ala Arg Lys Leu Ser Val Ile Leu Ile Leu Thr Phe Ala Leu Ser
1               5                   10                  15

Val Thr Asn Pro Leu His Glu Leu Lys Ala Ala Ala
            20                  25

<210> SEQ ID NO 500
<211> LENGTH: 18
<212> TYPE: PRT
<213> ORGANISM: Homo sapiens

<400> SEQUENCE: 500

Met Arg Leu Phe Thr Gly Ile Val Phe Cys Ser Leu Val Met Gly Val
1               5                   10                  15

Thr Ser

<210> SEQ ID NO 501
<211> LENGTH: 18
<212> TYPE: PRT
<213> ORGANISM: Homo sapiens

<400> SEQUENCE: 501

Met Lys Leu Leu Thr Gly Leu Val Phe Cys Ser Leu Val Leu Gly Val
1               5                   10                  15

Ser Ser

<210> SEQ ID NO 502
<211> LENGTH: 19
<212> TYPE: PRT
<213> ORGANISM: Homo sapiens

<400> SEQUENCE: 502

Met Asn Lys Pro Leu Leu Trp Ile Ser Val Leu Thr Ser Leu Leu Glu
1               5                   10                  15

Ala Phe Ala

<210> SEQ ID NO 503
<211> LENGTH: 20
<212> TYPE: PRT
<213> ORGANISM: Homo sapiens

<400> SEQUENCE: 503

Met Gln Pro Thr Leu Leu Ser Leu Leu Gly Ala Val Gly Leu Ala
1               5                   10                  15

Ala Val Asn Ser
        20

<210> SEQ ID NO 504
<211> LENGTH: 20
<212> TYPE: PRT
<213> ORGANISM: Homo sapiens

<400> SEQUENCE: 504

Met Lys Leu Met Val Leu Val Phe Thr Ile Gly Leu Thr Leu Leu
1               5                   10                  15

Gly Val Gln Ala
        20

<210> SEQ ID NO 505
<211> LENGTH: 38
<212> TYPE: PRT
<213> ORGANISM: Homo sapiens

<400> SEQUENCE: 505

Met Gly Leu Arg Ser Trp Leu Ala Ala Pro Trp Gly Ala Leu Pro Pro
1               5                   10                  15

Arg Pro Pro Leu Leu Leu Leu Leu Leu Leu Leu Leu Leu Gln Pro
            20                  25                  30

Pro Pro Pro Thr Trp Ala
            35

<210> SEQ ID NO 506
<211> LENGTH: 25
<212> TYPE: PRT
<213> ORGANISM: Homo sapiens

<400> SEQUENCE: 506

```
Met Gln Thr Pro Arg Ala Ser Pro Pro Arg Pro Ala Leu Leu Leu Leu
1               5                   10                  15

Leu Leu Leu Leu Gly Gly Ala His Gly
            20                  25
```

<210> SEQ ID NO 507
<211> LENGTH: 23
<212> TYPE: PRT
<213> ORGANISM: Homo sapiens

<400> SEQUENCE: 507

```
Met Lys Pro Asn Ile Ile Phe Val Leu Ser Leu Leu Leu Ile Leu Glu
1               5                   10                  15

Lys Gln Ala Ala Val Met Gly
            20
```

<210> SEQ ID NO 508
<211> LENGTH: 23
<212> TYPE: PRT
<213> ORGANISM: Homo sapiens

<400> SEQUENCE: 508

```
Met Lys Ser Ile Ile Leu Phe Val Leu Ser Leu Leu Leu Ile Leu Glu
1               5                   10                  15

Lys Gln Ala Ala Val Met Gly
            20
```

<210> SEQ ID NO 509
<211> LENGTH: 19
<212> TYPE: PRT
<213> ORGANISM: Homo sapiens

<400> SEQUENCE: 509

```
Met Trp Arg Ser Leu Gly Leu Ala Leu Ala Leu Cys Leu Leu Pro Ser
1               5                   10                  15

Gly Gly Thr
```

<210> SEQ ID NO 510
<211> LENGTH: 24
<212> TYPE: PRT
<213> ORGANISM: Homo sapiens

<400> SEQUENCE: 510

```
Met Leu Gln Gly Pro Gly Ser Leu Leu Leu Leu Phe Leu Ala Ser His
1               5                   10                  15

Cys Cys Leu Gly Ser Ala Arg Gly
            20
```

<210> SEQ ID NO 511
<211> LENGTH: 32
<212> TYPE: PRT
<213> ORGANISM: Homo sapiens

<400> SEQUENCE: 511

```
Met Val Cys Gly Ser Pro Gly Gly Met Leu Leu Leu Arg Ala Gly Leu
1               5                   10                  15

Leu Ala Leu Ala Ala Leu Cys Leu Leu Arg Val Pro Gly Ala Arg Ala
            20                  25                  30
```

<210> SEQ ID NO 512
<211> LENGTH: 19
<212> TYPE: PRT

<213> ORGANISM: Homo sapiens

<400> SEQUENCE: 512

Met Gly Ser Gly Leu Pro Leu Val Leu Leu Thr Leu Leu Gly Ser
1               5                   10                  15

Ser His Gly

<210> SEQ ID NO 513
<211> LENGTH: 21
<212> TYPE: PRT
<213> ORGANISM: Homo sapiens

<400> SEQUENCE: 513

Met Arg Leu Ser Val Cys Leu Leu Met Val Ser Leu Ala Leu Cys Cys
1               5                   10                  15

Tyr Gln Ala His Ala
            20

<210> SEQ ID NO 514
<211> LENGTH: 20
<212> TYPE: PRT
<213> ORGANISM: Homo sapiens

<400> SEQUENCE: 514

Met Lys Leu Ala Ala Leu Leu Gly Leu Cys Val Ala Leu Ser Cys Ser
1               5                   10                  15

Ser Ala Ala Ala
            20

<210> SEQ ID NO 515
<211> LENGTH: 29
<212> TYPE: PRT
<213> ORGANISM: Homo sapiens

<400> SEQUENCE: 515

Met Glu Ser Arg Gly Pro Leu Ala Thr Ser Arg Leu Leu Leu Leu Leu
1               5                   10                  15

Leu Leu Leu Leu Leu Arg His Thr Arg Gln Gly Trp Ala
            20                  25

<210> SEQ ID NO 516
<211> LENGTH: 16
<212> TYPE: PRT
<213> ORGANISM: Homo sapiens

<400> SEQUENCE: 516

Met Lys Thr Ala Leu Ile Leu Leu Ser Ile Leu Gly Met Ala Cys Ala
1               5                   10                  15

<210> SEQ ID NO 517
<211> LENGTH: 18
<212> TYPE: PRT
<213> ORGANISM: Homo sapiens

<400> SEQUENCE: 517

Met Phe Ala Leu Gly Leu Pro Phe Leu Val Leu Leu Val Ala Ser Val
1               5                   10                  15

Glu Ser

<210> SEQ ID NO 518
<211> LENGTH: 21
<212> TYPE: PRT

-continued

<213> ORGANISM: Homo sapiens

<400> SEQUENCE: 518

Met Leu Trp Leu Phe Gln Ser Leu Leu Phe Val Phe Cys Phe Gly Pro
1               5                   10                  15

Gly Asn Val Val Ser
            20

<210> SEQ ID NO 519
<211> LENGTH: 22
<212> TYPE: PRT
<213> ORGANISM: Homo sapiens

<400> SEQUENCE: 519

Met Ala Gly Ser Pro Thr Cys Leu Thr Leu Ile Tyr Ile Leu Trp Gln
1               5                   10                  15

Leu Thr Gly Ser Ala Ala
            20

<210> SEQ ID NO 520
<211> LENGTH: 22
<212> TYPE: PRT
<213> ORGANISM: Homo sapiens

<400> SEQUENCE: 520

Met Val Met Arg Pro Leu Trp Ser Leu Leu Leu Trp Glu Ala Leu Leu
1               5                   10                  15

Pro Ile Thr Val Thr Gly
            20

<210> SEQ ID NO 521
<211> LENGTH: 25
<212> TYPE: PRT
<213> ORGANISM: Homo sapiens

<400> SEQUENCE: 521

Met Lys Ser Ser Gly Leu Phe Pro Phe Leu Val Leu Leu Ala Leu Gly
1               5                   10                  15

Thr Leu Ala Pro Trp Ala Val Glu Gly
            20                  25

<210> SEQ ID NO 522
<211> LENGTH: 22
<212> TYPE: PRT
<213> ORGANISM: Homo sapiens

<400> SEQUENCE: 522

Met Lys Ser Leu Thr Trp Ile Leu Gly Leu Trp Ala Leu Ala Ala Cys
1               5                   10                  15

Phe Thr Pro Gly Glu Ser
            20

<210> SEQ ID NO 523
<211> LENGTH: 24
<212> TYPE: PRT
<213> ORGANISM: Homo sapiens

<400> SEQUENCE: 523

Met Leu Ser Cys Arg Leu Gln Cys Ala Leu Ala Ala Leu Ser Ile Val
1               5                   10                  15

Leu Ala Leu Gly Cys Val Thr Gly
            20

<210> SEQ ID NO 524
<211> LENGTH: 18
<212> TYPE: PRT
<213> ORGANISM: Homo sapiens

<400> SEQUENCE: 524

Met Leu Ala Leu Leu Cys Ser Cys Leu Leu Ala Ala Gly Ala Ser
1               5                   10                  15

Asp Ala

<210> SEQ ID NO 525
<211> LENGTH: 23
<212> TYPE: PRT
<213> ORGANISM: Homo sapiens

<400> SEQUENCE: 525

Met Leu Pro Pro Ala Ile His Phe Tyr Leu Leu Pro Leu Ala Cys Ile
1               5                   10                  15

Leu Met Lys Ser Cys Leu Ala
            20

<210> SEQ ID NO 526
<211> LENGTH: 23
<212> TYPE: PRT
<213> ORGANISM: Homo sapiens

<400> SEQUENCE: 526

Met Gln Leu Pro Leu Ala Leu Cys Leu Val Cys Leu Val His Thr
1               5                   10                  15

Ala Phe Arg Val Val Glu Gly
            20

<210> SEQ ID NO 527
<211> LENGTH: 35
<212> TYPE: PRT
<213> ORGANISM: Homo sapiens

<400> SEQUENCE: 527

Met Ala Pro Ala Arg Thr Met Ala Arg Ala Arg Leu Ala Pro Ala Gly
1               5                   10                  15

Ile Pro Ala Val Ala Leu Trp Leu Leu Cys Thr Leu Gly Leu Gln Gly
            20                  25                  30

Thr Gln Ala
        35

<210> SEQ ID NO 528
<211> LENGTH: 27
<212> TYPE: PRT
<213> ORGANISM: Homo sapiens

<400> SEQUENCE: 528

Met Ala Gln Leu Cys Gly Leu Arg Arg Ser Arg Ala Phe Leu Ala Leu
1               5                   10                  15

Leu Gly Ser Leu Leu Leu Ser Gly Val Leu Ala
            20                  25

<210> SEQ ID NO 529
<211> LENGTH: 28
<212> TYPE: PRT
<213> ORGANISM: Homo sapiens

```
<400> SEQUENCE: 529

Met Gly His His Arg Pro Trp Leu His Ala Ser Val Leu Trp Ala Gly
1               5                   10                  15

Val Ala Ser Leu Leu Pro Pro Ala Met Thr Gln
            20                  25

<210> SEQ ID NO 530
<211> LENGTH: 27
<212> TYPE: PRT
<213> ORGANISM: Homo sapiens

<400> SEQUENCE: 530

Met Met Gln Lys Leu Leu Lys Cys Ser Arg Leu Val Leu Ala Leu Ala
1               5                   10                  15

Leu Ile Leu Val Leu Glu Ser Ser Val Gln Gly
            20                  25

<210> SEQ ID NO 531
<211> LENGTH: 19
<212> TYPE: PRT
<213> ORGANISM: Homo sapiens

<400> SEQUENCE: 531

Met Lys Phe Leu Val Phe Ala Phe Ile Leu Ala Leu Met Val Ser Met
1               5                   10                  15

Ile Gly Ala

<210> SEQ ID NO 532
<211> LENGTH: 17
<212> TYPE: PRT
<213> ORGANISM: Homo sapiens

<400> SEQUENCE: 532

Met Leu Gln Asn Ser Ala Val Leu Leu Val Leu Val Ile Ser Ala Ser
1               5                   10                  15

Ala

<210> SEQ ID NO 533
<211> LENGTH: 23
<212> TYPE: PRT
<213> ORGANISM: Homo sapiens

<400> SEQUENCE: 533

Met Arg Gln Ser His Gln Leu Pro Leu Val Gly Leu Leu Leu Phe Ser
1               5                   10                  15

Phe Ile Pro Ser Gln Leu Cys
            20

<210> SEQ ID NO 534
<211> LENGTH: 18
<212> TYPE: PRT
<213> ORGANISM: Homo sapiens

<400> SEQUENCE: 534

Met Arg His Leu Gly Ala Phe Leu Phe Leu Leu Gly Val Leu Gly Ala
1               5                   10                  15

Leu Thr

<210> SEQ ID NO 535
<211> LENGTH: 22
<212> TYPE: PRT
```

```
<213> ORGANISM: Homo sapiens

<400> SEQUENCE: 535

Met Gly Ala Met Thr Gln Leu Leu Ala Gly Val Phe Leu Ala Phe Leu
1               5                   10                  15

Ala Leu Ala Thr Glu Gly
            20

<210> SEQ ID NO 536
<211> LENGTH: 21
<212> TYPE: PRT
<213> ORGANISM: Homo sapiens

<400> SEQUENCE: 536

Met Glu Leu Trp Gly Ala Tyr Leu Leu Cys Leu Phe Ser Leu Leu
1               5                   10                  15

Thr Gln Val Thr Thr
            20

<210> SEQ ID NO 537
<211> LENGTH: 24
<212> TYPE: PRT
<213> ORGANISM: Homo sapiens

<400> SEQUENCE: 537

Met Ala Thr Met Glu Asn Lys Val Ile Cys Ala Leu Val Leu Val Ser
1               5                   10                  15

Met Leu Ala Leu Gly Thr Leu Ala
            20

<210> SEQ ID NO 538
<211> LENGTH: 21
<212> TYPE: PRT
<213> ORGANISM: Homo sapiens

<400> SEQUENCE: 538

Met Ala Ala Arg Ala Leu Cys Met Leu Gly Leu Val Leu Ala Leu Leu
1               5                   10                  15

Ser Ser Ser Ser Ala
            20

<210> SEQ ID NO 539
<211> LENGTH: 28
<212> TYPE: PRT
<213> ORGANISM: Homo sapiens

<400> SEQUENCE: 539

Met Ile Tyr Thr Met Lys Lys Val His Ala Leu Trp Ala Ser Val Cys
1               5                   10                  15

Leu Leu Leu Asn Leu Ala Pro Ala Pro Leu Asn Ala
            20                  25

<210> SEQ ID NO 540
<211> LENGTH: 22
<212> TYPE: PRT
<213> ORGANISM: Homo sapiens

<400> SEQUENCE: 540

Met Gly Arg Gly Leu Leu Arg Gly Leu Trp Pro Leu His Ile Val Leu
1               5                   10                  15

Trp Thr Arg Ile Ala Ser
            20
```

-continued

```
<210> SEQ ID NO 541
<211> LENGTH: 20
<212> TYPE: PRT
<213> ORGANISM: Homo sapiens

<400> SEQUENCE: 541

Met Ser Pro Phe Leu Tyr Leu Val Leu Leu Val Leu Gly Leu His Ala
1               5                   10                  15

Thr Ile His Cys
            20

<210> SEQ ID NO 542
<211> LENGTH: 19
<212> TYPE: PRT
<213> ORGANISM: Homo sapiens

<400> SEQUENCE: 542

Met Ala Leu Val Leu Glu Ile Phe Thr Leu Leu Ala Ser Ile Cys Trp
1               5                   10                  15

Val Ser Ala

<210> SEQ ID NO 543
<211> LENGTH: 22
<212> TYPE: PRT
<213> ORGANISM: Homo sapiens

<400> SEQUENCE: 543

Met Arg Ala Pro Gly Cys Gly Arg Leu Val Leu Pro Leu Leu Leu Leu
1               5                   10                  15

Ala Ala Ala Ala Leu Ala
            20

<210> SEQ ID NO 544
<211> LENGTH: 21
<212> TYPE: PRT
<213> ORGANISM: Homo sapiens

<400> SEQUENCE: 544

Met Val Trp Arg Val Pro Pro Phe Leu Leu Pro Ile Leu Phe Leu Ala
1               5                   10                  15

Ser His Val Gly Ala
            20

<210> SEQ ID NO 545
<211> LENGTH: 22
<212> TYPE: PRT
<213> ORGANISM: Homo sapiens

<400> SEQUENCE: 545

Met Asp Ser Leu Ala Ser Leu Val Leu Cys Gly Val Ser Leu Leu Leu
1               5                   10                  15

Ser Gly Thr Val Glu Gly
            20

<210> SEQ ID NO 546
<211> LENGTH: 23
<212> TYPE: PRT
<213> ORGANISM: Homo sapiens

<400> SEQUENCE: 546

Met Ala Pro Phe Glu Pro Leu Ala Ser Gly Ile Leu Leu Leu Leu Trp
```

```
1               5                  10                  15
Leu Ile Ala Pro Ser Arg Ala
            20

<210> SEQ ID NO 547
<211> LENGTH: 26
<212> TYPE: PRT
<213> ORGANISM: Homo sapiens

<400> SEQUENCE: 547

Met Gly Ala Ala Ala Arg Thr Leu Arg Leu Ala Leu Gly Leu Leu Leu
1               5                  10                  15

Leu Ala Thr Leu Leu Arg Pro Ala Asp Ala
            20                  25

<210> SEQ ID NO 548
<211> LENGTH: 23
<212> TYPE: PRT
<213> ORGANISM: Homo sapiens

<400> SEQUENCE: 548

Met Thr Pro Trp Leu Gly Leu Ile Val Leu Leu Gly Ser Trp Ser Leu
1               5                  10                  15

Gly Asp Trp Gly Ala Glu Ala
            20

<210> SEQ ID NO 549
<211> LENGTH: 21
<212> TYPE: PRT
<213> ORGANISM: Homo sapiens

<400> SEQUENCE: 549

Met Trp Arg Cys Pro Leu Gly Leu Leu Leu Leu Pro Leu Ala Gly
1               5                  10                  15

His Leu Ala Leu Gly
            20

<210> SEQ ID NO 550
<211> LENGTH: 24
<212> TYPE: PRT
<213> ORGANISM: Homo sapiens

<400> SEQUENCE: 550

Met Thr Ser Ile Phe His Phe Ala Ile Ile Phe Met Leu Ile Leu Gln
1               5                  10                  15

Ile Arg Ile Gln Leu Ser Glu Glu
            20

<210> SEQ ID NO 551
<211> LENGTH: 23
<212> TYPE: PRT
<213> ORGANISM: Homo sapiens

<400> SEQUENCE: 551

Met Arg Gln Thr Leu Pro Cys Ile Tyr Phe Trp Gly Gly Leu Leu Pro
1               5                  10                  15

Phe Gly Met Leu Cys Ala Ser
            20

<210> SEQ ID NO 552
<211> LENGTH: 23
<212> TYPE: PRT
```

<213> ORGANISM: Homo sapiens

<400> SEQUENCE: 552

Met Met Ser Ala Ser Arg Leu Ala Gly Thr Leu Ile Pro Ala Met Ala
1               5                   10                  15

Phe Leu Ser Cys Val Arg Pro
            20

<210> SEQ ID NO 553
<211> LENGTH: 20
<212> TYPE: PRT
<213> ORGANISM: Homo sapiens

<400> SEQUENCE: 553

Met Gly Asp His Leu Asp Leu Leu Gly Val Val Leu Met Ala Gly
1               5                   10                  15

Pro Val Phe Gly
            20

<210> SEQ ID NO 554
<211> LENGTH: 37
<212> TYPE: PRT
<213> ORGANISM: Homo sapiens

<400> SEQUENCE: 554

Met Ala Ala Ala Trp Pro Ser Gly Pro Ser Pro Glu Ala Val Thr
1               5                   10                  15

Ala Arg Leu Val Gly Val Leu Trp Phe Val Ser Val Thr Thr Gly Pro
                20                  25                  30

Trp Gly Ala Val Ala
            35

<210> SEQ ID NO 555
<211> LENGTH: 22
<212> TYPE: PRT
<213> ORGANISM: Homo sapiens

<400> SEQUENCE: 555

Met Gly Ser Pro Gly Met Val Leu Gly Leu Leu Val Gln Ile Trp Ala
1               5                   10                  15

Leu Gln Glu Ala Ser Ser
            20

<210> SEQ ID NO 556
<211> LENGTH: 26
<212> TYPE: PRT
<213> ORGANISM: Homo sapiens

<400> SEQUENCE: 556

Met Ala Leu Pro Pro Gly Pro Ala Ala Leu Arg His Thr Leu Leu Leu
1               5                   10                  15

Leu Pro Ala Leu Leu Ser Ser Gly Trp Gly
            20                  25

<210> SEQ ID NO 557
<211> LENGTH: 33
<212> TYPE: PRT
<213> ORGANISM: Homo sapiens

<400> SEQUENCE: 557

Met Trp Gly Ala Arg Arg Ser Ser Val Ser Ser Ser Trp Asn Ala Ala
1               5                   10                  15

```
Ser Leu Leu Gln Leu Leu Leu Ala Ala Leu Leu Ala Ala Gly Ala Arg
            20                  25                  30

Ala

<210> SEQ ID NO 558
<211> LENGTH: 30
<212> TYPE: PRT
<213> ORGANISM: Homo sapiens

<400> SEQUENCE: 558

Met Ala Ala Ala Cys Gly Pro Gly Ala Ala Gly Tyr Cys Leu Leu Leu
1               5                   10                  15

Gly Leu His Leu Phe Leu Leu Thr Ala Gly Pro Ala Leu Gly
            20                  25                  30

<210> SEQ ID NO 559
<211> LENGTH: 33
<212> TYPE: PRT
<213> ORGANISM: Homo sapiens

<400> SEQUENCE: 559

Met Ala Thr Leu Trp Gly Gly Leu Leu Arg Leu Gly Ser Leu Leu Ser
1               5                   10                  15

Leu Ser Cys Leu Ala Leu Ser Val Leu Leu Ala Gln Leu Ser Asp
            20                  25                  30

Ala

<210> SEQ ID NO 560
<211> LENGTH: 34
<212> TYPE: PRT
<213> ORGANISM: Homo sapiens

<400> SEQUENCE: 560

Met Thr Pro Pro Glu Arg Leu Phe Leu Pro Arg Val Cys Gly Thr Thr
1               5                   10                  15

Leu His Leu Leu Leu Leu Gly Leu Leu Leu Val Leu Leu Pro Gly Ala
            20                  25                  30

Gln Gly

<210> SEQ ID NO 561
<211> LENGTH: 38
<212> TYPE: PRT
<213> ORGANISM: Homo sapiens

<400> SEQUENCE: 561

Met Glu Pro Pro Gly Asp Trp Gly Pro Pro Pro Trp Arg Ser Thr Pro
1               5                   10                  15

Lys Thr Asp Val Leu Arg Leu Val Leu Tyr Leu Thr Phe Leu Gly Ala
            20                  25                  30

Pro Cys Tyr Ala Pro Ala
            35

<210> SEQ ID NO 562
<211> LENGTH: 28
<212> TYPE: PRT
<213> ORGANISM: Homo sapiens

<400> SEQUENCE: 562

Met Gly Ala Gly Ala Thr Gly Arg Ala Met Asp Gly Pro Arg Leu Leu
1               5                   10                  15
```

```
Leu Leu Leu Leu Leu Gly Val Ser Leu Gly Gly Ala
            20                  25

<210> SEQ ID NO 563
<211> LENGTH: 25
<212> TYPE: PRT
<213> ORGANISM: Homo sapiens

<400> SEQUENCE: 563

Met Ala Gln His Gly Ala Met Gly Ala Phe Arg Ala Leu Cys Gly Leu
1               5                   10                  15

Ala Leu Leu Cys Ala Leu Ser Leu Gly
            20                  25

<210> SEQ ID NO 564
<211> LENGTH: 29
<212> TYPE: PRT
<213> ORGANISM: Homo sapiens

<400> SEQUENCE: 564

Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys
            20                  25

<210> SEQ ID NO 565
<211> LENGTH: 22
<212> TYPE: PRT
<213> ORGANISM: Homo sapiens

<400> SEQUENCE: 565

Met Ala Pro Val Ala Val Trp Ala Ala Leu Ala Val Gly Leu Glu Leu
1               5                   10                  15

Trp Ala Ala Ala His Ala
            20

<210> SEQ ID NO 566
<211> LENGTH: 20
<212> TYPE: PRT
<213> ORGANISM: Homo sapiens

<400> SEQUENCE: 566

Met Val Arg Leu Pro Leu Gln Cys Val Leu Trp Gly Cys Leu Leu Thr
1               5                   10                  15

Ala Val His Pro
            20

<210> SEQ ID NO 567
<211> LENGTH: 29
<212> TYPE: PRT
<213> ORGANISM: Homo sapiens

<400> SEQUENCE: 567

Met Arg Ala Leu Glu Gly Pro Gly Leu Ser Leu Leu Cys Leu Val Leu
1               5                   10                  15

Ala Leu Pro Ala Leu Leu Pro Val Pro Ala Val Arg Gly
            20                  25

<210> SEQ ID NO 568
<211> LENGTH: 18
<212> TYPE: PRT
<213> ORGANISM: Homo sapiens
```

```
<400> SEQUENCE: 568

Met Arg Val Leu Leu Ala Ala Leu Gly Leu Phe Leu Gly Ala Leu
1               5                   10                  15

Arg Ala

<210> SEQ ID NO 569
<211> LENGTH: 23
<212> TYPE: PRT
<213> ORGANISM: Homo sapiens

<400> SEQUENCE: 569

Met Gly Asn Ser Cys Tyr Asn Ile Val Ala Thr Leu Leu Leu Val Leu
1               5                   10                  15

Asn Phe Glu Arg Thr Arg Ser
            20

<210> SEQ ID NO 570
<211> LENGTH: 21
<212> TYPE: PRT
<213> ORGANISM: Homo sapiens

<400> SEQUENCE: 570

Met Glu Leu Thr Glu Leu Leu Leu Val Val Met Leu Leu Leu Thr Ala
1               5                   10                  15

Arg Leu Thr Leu Ser
            20

<210> SEQ ID NO 571
<211> LENGTH: 18
<212> TYPE: PRT
<213> ORGANISM: Homo sapiens

<400> SEQUENCE: 571

Met Gly Thr Gln Glu Gly Trp Cys Leu Leu Leu Cys Leu Ala Leu Ser
1               5                   10                  15

Gly Ala

<210> SEQ ID NO 572
<211> LENGTH: 20
<212> TYPE: PRT
<213> ORGANISM: Homo sapiens

<400> SEQUENCE: 572

Met Lys Ser Leu Ser Leu Leu Leu Ala Val Ala Leu Gly Leu Ala Thr
1               5                   10                  15

Ala Val Ser Ala
            20

<210> SEQ ID NO 573
<211> LENGTH: 55
<212> TYPE: PRT
<213> ORGANISM: Homo sapiens

<400> SEQUENCE: 573

Met Gly Leu Trp Gly Gln Ser Val Pro Thr Ala Ser Ser Ala Arg Ala
1               5                   10                  15

Gly Arg Tyr Pro Gly Ala Arg Thr Ala Ser Gly Thr Arg Pro Trp Leu
                20                  25                  30

Leu Asp Pro Lys Ile Leu Lys Phe Val Val Phe Ile Val Ala Val Leu
                35                  40                  45
```

-continued

Leu Pro Val Arg Val Asp Ser
    50              55

<210> SEQ ID NO 574
<211> LENGTH: 21
<212> TYPE: PRT
<213> ORGANISM: Homo sapiens

<400> SEQUENCE: 574

Met Asn Lys Leu Leu Cys Cys Ala Leu Val Phe Leu Asp Ile Ser Ile
1               5                   10                  15

Lys Trp Thr Thr Gln
            20

<210> SEQ ID NO 575
<211> LENGTH: 25
<212> TYPE: PRT
<213> ORGANISM: Homo sapiens

<400> SEQUENCE: 575

Met Lys Pro Ser Leu Leu Cys Arg Pro Leu Ser Cys Phe Leu Met Leu
1               5                   10                  15

Leu Pro Trp Pro Leu Ala Thr Leu Thr
            20                  25

<210> SEQ ID NO 576
<211> LENGTH: 18
<212> TYPE: PRT
<213> ORGANISM: Homo sapiens

<400> SEQUENCE: 576

Met Leu Gly Val Leu Val Leu Gly Ala Leu Ala Leu Ala Gly Leu Gly
1               5                   10                  15

Phe Pro

<210> SEQ ID NO 577
<211> LENGTH: 19
<212> TYPE: PRT
<213> ORGANISM: Homo sapiens

<400> SEQUENCE: 577

Met Arg Leu Ala Val Gly Ala Leu Leu Val Cys Ala Val Leu Gly Leu
1               5                   10                  15

Cys Leu Ala

<210> SEQ ID NO 578
<211> LENGTH: 19
<212> TYPE: PRT
<213> ORGANISM: Homo sapiens

<400> SEQUENCE: 578

Met Lys Leu Val Phe Leu Val Leu Leu Phe Leu Gly Ala Leu Gly Leu
1               5                   10                  15

Cys Leu Ala

<210> SEQ ID NO 579
<211> LENGTH: 15
<212> TYPE: PRT
<213> ORGANISM: Homo sapiens

<400> SEQUENCE: 579

Met Asn Pro Leu Leu Ile Leu Thr Phe Val Ala Ala Leu Ala
1               5                   10                  15

<210> SEQ ID NO 580
<211> LENGTH: 15
<212> TYPE: PRT
<213> ORGANISM: Homo sapiens

<400> SEQUENCE: 580

Met Asn Leu Leu Leu Ile Leu Thr Phe Val Ala Ala Val Ala
1               5                   10                  15

<210> SEQ ID NO 581
<211> LENGTH: 20
<212> TYPE: PRT
<213> ORGANISM: Homo sapiens

<400> SEQUENCE: 581

Met Thr Ala Leu Phe Leu Met Ser Met Leu Phe Gly Leu Ala Cys Gly
1               5                   10                  15

Gln Ala Met Ser
            20

<210> SEQ ID NO 582
<211> LENGTH: 18
<212> TYPE: PRT
<213> ORGANISM: Homo sapiens

<400> SEQUENCE: 582

Met Gly Leu Ala Trp Gly Leu Gly Val Leu Phe Leu Met His Val Cys
1               5                   10                  15

Gly Thr

<210> SEQ ID NO 583
<211> LENGTH: 27
<212> TYPE: PRT
<213> ORGANISM: Homo sapiens

<400> SEQUENCE: 583

Met Ala Met Leu Leu Gly Ala Ser Val Leu Ile Leu Trp Leu Gln Pro
1               5                   10                  15

Asp Trp Val Asn Ser Gln Gln Lys Asn Asp Asp
            20                  25

<210> SEQ ID NO 584
<211> LENGTH: 21
<212> TYPE: PRT
<213> ORGANISM: Homo sapiens

<400> SEQUENCE: 584

Met Gly Thr Ser Leu Leu Cys Trp Met Ala Leu Cys Leu Leu Gly Ala
1               5                   10                  15

Asp His Ala Asp Thr
            20

<210> SEQ ID NO 585
<211> LENGTH: 26
<212> TYPE: PRT
<213> ORGANISM: Homo sapiens

<400> SEQUENCE: 585

Met Glu Thr Arg Pro Arg Leu Gly Ala Thr Cys Leu Leu Gly Phe Ser
1               5                   10                  15

```
Phe Leu Leu Leu Val Ile Ser Ser Asp Gly
            20                  25
```

```
<210> SEQ ID NO 586
<211> LENGTH: 29
<212> TYPE: PRT
<213> ORGANISM: Homo sapiens

<400> SEQUENCE: 586

Met His Pro Ala Val Phe Leu Ser Leu Pro Asp Leu Arg Cys Ser Leu
1               5                   10                  15

Leu Leu Leu Val Thr Trp Val Phe Thr Pro Val Thr Thr
            20                  25
```

```
<210> SEQ ID NO 587
<211> LENGTH: 24
<212> TYPE: PRT
<213> ORGANISM: Homo sapiens

<400> SEQUENCE: 587

Met Ser Ala Pro Lys Leu Leu Ser Leu Gly Cys Ile Phe Phe Pro Leu
1               5                   10                  15

Leu Leu Phe Gln Gln Ala Arg Ala
            20
```

```
<210> SEQ ID NO 588
<211> LENGTH: 20
<212> TYPE: PRT
<213> ORGANISM: Homo sapiens

<400> SEQUENCE: 588

Met Arg Ala Leu Leu Ala Arg Leu Leu Leu Cys Val Leu Val Val Ser
1               5                   10                  15

Asp Ser Lys Gly
            20
```

```
<210> SEQ ID NO 589
<211> LENGTH: 21
<212> TYPE: PRT
<213> ORGANISM: Homo sapiens

<400> SEQUENCE: 589

Met Lys Leu Ala Val Thr Leu Thr Leu Val Thr Leu Ala Leu Cys Cys
1               5                   10                  15

Ser Ser Ala Ser Ala
            20
```

```
<210> SEQ ID NO 590
<211> LENGTH: 20
<212> TYPE: PRT
<213> ORGANISM: Homo sapiens

<400> SEQUENCE: 590

Met Tyr Lys Leu Ala Ser Cys Cys Leu Leu Phe Ile Gly Phe Leu Asn
1               5                   10                  15

Pro Leu Leu Ser
            20
```

```
<210> SEQ ID NO 591
<211> LENGTH: 24
<212> TYPE: PRT
<213> ORGANISM: Homo sapiens
```

```
<400> SEQUENCE: 591

Met Pro Gly Lys Met Val Val Ile Leu Gly Ala Ser Asn Ile Leu Trp
1               5                   10                  15

Ile Met Phe Ala Ala Ser Gln Ala
            20

<210> SEQ ID NO 592
<211> LENGTH: 26
<212> TYPE: PRT
<213> ORGANISM: Homo sapiens

<400> SEQUENCE: 592

Met Asn Phe Leu Leu Ser Trp Val His Trp Ser Leu Ala Leu Leu Leu
1               5                   10                  15

Tyr Leu His His Ala Lys Trp Ser Gln Ala
            20                  25

<210> SEQ ID NO 593
<211> LENGTH: 31
<212> TYPE: PRT
<213> ORGANISM: Homo sapiens

<400> SEQUENCE: 593

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala
            20                  25                  30

<210> SEQ ID NO 594
<211> LENGTH: 24
<212> TYPE: PRT
<213> ORGANISM: Homo sapiens

<400> SEQUENCE: 594

Met Gln Arg Gly Ala Ala Leu Cys Leu Arg Leu Trp Leu Cys Leu Gly
1               5                   10                  15

Leu Leu Asp Gly Leu Val Ser Gly
            20

<210> SEQ ID NO 595
<211> LENGTH: 24
<212> TYPE: PRT
<213> ORGANISM: Homo sapiens

<400> SEQUENCE: 595

Met Glu Arg Gly Ala Gly Ala Lys Leu Leu Pro Leu Leu Leu Leu Leu
1               5                   10                  15

Arg Ala Thr Gly Phe Thr Cys Ala
            20

<210> SEQ ID NO 596
<211> LENGTH: 23
<212> TYPE: PRT
<213> ORGANISM: Homo sapiens

<400> SEQUENCE: 596

Met Ala Glu Leu Pro Gly Pro Phe Leu Cys Gly Ala Leu Leu Gly Phe
1               5                   10                  15

Leu Cys Leu Ser Gly Leu Ala
            20
```

<210> SEQ ID NO 597
<211> LENGTH: 19
<212> TYPE: PRT
<213> ORGANISM: Homo sapiens

<400> SEQUENCE: 597

Met Gly Ile Leu Leu Gly Leu Leu Leu Gly His Leu Thr Val Asp
1               5                   10                  15

Thr Tyr Gly

<210> SEQ ID NO 598
<211> LENGTH: 16
<212> TYPE: PRT
<213> ORGANISM: Homo sapiens

<400> SEQUENCE: 598

Met Thr Ala Glu Phe Leu Ser Leu Leu Cys Leu Gly Leu Cys Leu Gly
1               5                   10                  15

<210> SEQ ID NO 599
<211> LENGTH: 19
<212> TYPE: PRT
<213> ORGANISM: Homo sapiens

<400> SEQUENCE: 599

Met Ala Pro Leu Arg Pro Leu Leu Ile Leu Ala Leu Leu Ala Trp Val
1               5                   10                  15

Ala Leu Ala

<210> SEQ ID NO 600
<211> LENGTH: 22
<212> TYPE: PRT
<213> ORGANISM: Homo sapiens

<400> SEQUENCE: 600

Met Ile Pro Ala Arg Phe Ala Gly Val Leu Leu Ala Leu Ala Leu Ile
1               5                   10                  15

Leu Pro Gly Thr Leu Cys
            20

<210> SEQ ID NO 601
<211> LENGTH: 23
<212> TYPE: PRT
<213> ORGANISM: Homo sapiens

<400> SEQUENCE: 601

Met Arg Gly Thr Pro Lys Thr His Leu Leu Ala Phe Ser Leu Leu Cys
1               5                   10                  15

Leu Leu Ser Lys Val Arg Thr
            20

<210> SEQ ID NO 602
<211> LENGTH: 24
<212> TYPE: PRT
<213> ORGANISM: Homo sapiens

<400> SEQUENCE: 602

Met Ala Pro Ile Ser Leu Ser Trp Leu Leu Arg Leu Ala Thr Phe Cys
1               5                   10                  15

His Leu Thr Val Leu Leu Ala Gly
            20

<210> SEQ ID NO 603
<211> LENGTH: 21
<212> TYPE: PRT
<213> ORGANISM: Homo sapiens

<400> SEQUENCE: 603

Met Arg Leu Leu Ile Leu Ala Leu Leu Gly Ile Cys Ser Leu Thr Ala
1               5                   10                  15

Tyr Ile Val Glu Gly
            20

<210> SEQ ID NO 604
<211> LENGTH: 23
<212> TYPE: PRT
<213> ORGANISM: Homo sapiens

<400> SEQUENCE: 604

Met Asp Ser Leu Arg Lys Met Leu Ile Ser Val Ala Met Leu Gly Ala
1               5                   10                  15

Gly Ala Gly Val Gly Tyr Ala
            20

<210> SEQ ID NO 605
<211> LENGTH: 20
<212> TYPE: PRT
<213> ORGANISM: Homo sapiens

<400> SEQUENCE: 605

Met Gly Leu Pro Gly Leu Phe Cys Leu Ala Val Leu Ala Ala Ser Ser
1               5                   10                  15

Phe Ser Lys Ala
            20

<210> SEQ ID NO 606
<211> LENGTH: 17
<212> TYPE: PRT
<213> ORGANISM: Homo sapiens

<400> SEQUENCE: 606

Met Val Pro Val Leu Leu Ser Leu Leu Leu Leu Gly Pro Ala Val
1               5                   10                  15

Pro

<210> SEQ ID NO 607
<211> LENGTH: 16
<212> TYPE: PRT
<213> ORGANISM: Homo sapiens

<400> SEQUENCE: 607

Met Leu Thr Val Ala Leu Leu Ala Leu Leu Cys Ala Ser Ala Ser Gly
1               5                   10                  15

<210> SEQ ID NO 608
<211> LENGTH: 38
<212> TYPE: PRT
<213> ORGANISM: Homo sapiens

<400> SEQUENCE: 608

Met Ala Cys Arg Gln Arg Gly Gly Ser Trp Ser Pro Ser Gly Trp Phe
1               5                   10                  15

Asn Ala Gly Trp Ser Thr Tyr Arg Ser Ile Ser Leu Phe Phe Ala Leu
            20                  25                  30

Val Thr Ser Gly Asn Ser
        35

<210> SEQ ID NO 609
<211> LENGTH: 2520
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(2493)
<220> FEATURE:
<221> NAME/KEY: CDS
<222> LOCATION: (2497)..(2520)

<400> SEQUENCE: 609

```
atg aaa ttc tta gtc aac gtt gca cta gtt ttt atg gtc gtg tac att      48
Met Lys Phe Leu Val Asn Val Ala Leu Val Phe Met Val Val Tyr Ile
1               5                   10                  15 tct tac atc tat gcg atg ccg atg gat gtg att tta gtt ttg tgg ttc      96
Ser Tyr Ile Tyr Ala Met Pro Met Asp Val Ile Leu Val Leu Trp Phe
            20                  25                  30 tgt gta tgc acc gcc agg aca gtg ttg ggc ttt ggg atg gac cct gac     144
Cys Val Cys Thr Ala Arg Thr Val Leu Gly Phe Gly Met Asp Pro Asp
        35                  40                  45 ctt cag ctg gac atc atc tca gag ctc gac ctg gtg aac acc acc ctg     192
Leu Gln Leu Asp Ile Ile Ser Glu Leu Asp Leu Val Asn Thr Thr Leu
    50                  55                  60 gga gtc acg cag gtg gct gga ctg cac aac gcc agt aaa gca ttt cta     240
Gly Val Thr Gln Val Ala Gly Leu His Asn Ala Ser Lys Ala Phe Leu
65                  70                  75                  80 ttt caa gat gta cag aga gag atc cat tcg gcc cct cac gtg agt gag     288
Phe Gln Asp Val Gln Arg Glu Ile His Ser Ala Pro His Val Ser Glu
                85                  90                  95 aag ctg atc cag cta ttc cgg aat aag agc gag ttc acc ttt ttg gct     336
Lys Leu Ile Gln Leu Phe Arg Asn Lys Ser Glu Phe Thr Phe Leu Ala
            100                 105                 110 aca gtg cag cag aaa cca tcc acc tca ggg gtg ata ctg tcc atc cgg     384
Thr Val Gln Gln Lys Pro Ser Thr Ser Gly Val Ile Leu Ser Ile Arg
        115                 120                 125 gag ctg gag cac agc tat ttt gaa ctg gag agc agt ggc cca aga gaa     432
Glu Leu Glu His Ser Tyr Phe Glu Leu Glu Ser Ser Gly Pro Arg Glu
    130                 135                 140 gag ata cgc tac cat tac ata cat ggt gga aag ccc agg act gag gcc     480
Glu Ile Arg Tyr His Tyr Ile His Gly Gly Lys Pro Arg Thr Glu Ala
145                 150                 155                 160 ctt ccc tac cgc atg gca gac gga caa tgg cac aag gtc gcg ctg tca     528
Leu Pro Tyr Arg Met Ala Asp Gly Gln Trp His Lys Val Ala Leu Ser
                165                 170                 175 gtg agc gcc tct cac ctc ctg ctc cac atc gac tgc aat agg att tac     576
Val Ser Ala Ser His Leu Leu Leu His Ile Asp Cys Asn Arg Ile Tyr
            180                 185                 190 gag cgt gtg ata gac cct ccg gag acc aac ctt cct cca gga agc aat     624
Glu Arg Val Ile Asp Pro Pro Glu Thr Asn Leu Pro Pro Gly Ser Asn
        195                 200                 205 ctg tgg ctt ggg caa cgt aac caa aag cat ggc ttt tca aaa gga atc     672
Leu Trp Leu Gly Gln Arg Asn Gln Lys His Gly Phe Ser Lys Gly Ile
    210                 215                 220 atc caa gat ggt aag atc atc ttc atg ccg aat ggt ttc atc aca cag     720
Ile Gln Asp Gly Lys Ile Ile Phe Met Pro Asn Gly Phe Ile Thr Gln
225                 230                 235                 240
```

```
tgt ccc aac ctc aat cgc act tgc cca aca tgc agt gac ttc ctg agc      768
Cys Pro Asn Leu Asn Arg Thr Cys Pro Thr Cys Ser Asp Phe Leu Ser
            245                 250                 255 ctg gtt caa gga ata atg gat ttg caa gag ctt ttg gcc aag atg act      816
Leu Val Gln Gly Ile Met Asp Leu Gln Glu Leu Leu Ala Lys Met Thr
            260                 265                 270 gca aaa ctg aat tat gca gag acg aga ctt ggt caa ctg gaa aat tgc      864
Ala Lys Leu Asn Tyr Ala Glu Thr Arg Leu Gly Gln Leu Glu Asn Cys
            275                 280                 285 cac tgt gag aag acc tgc caa gtg agt ggg ctg ctc tac agg gac caa      912
His Cys Glu Lys Thr Cys Gln Val Ser Gly Leu Leu Tyr Arg Asp Gln
            290                 295                 300 gac tcc tgg gtg gat ggt gac aac tgt ggg aac tgc acg tgc aaa agt      960
Asp Ser Trp Val Asp Gly Asp Asn Cys Gly Asn Cys Thr Cys Lys Ser
305                 310                 315                 320 ggt gcc gtg gag tgc cgc agg atg tcc tgt ccc ccg ctc aac tgt tcc     1008
Gly Ala Val Glu Cys Arg Arg Met Ser Cys Pro Pro Leu Asn Cys Ser
                325                 330                 335 ccg gac tca ctt cct gtg cac att tcc ggc cag tgt tgt aaa gtt tgc     1056
Pro Asp Ser Leu Pro Val His Ile Ser Gly Gln Cys Cys Lys Val Cys
            340                 345                 350 aga cca aaa tgt atc tat gga gga aaa gtt ctt gct gag ggc cag cgg     1104
Arg Pro Lys Cys Ile Tyr Gly Gly Lys Val Leu Ala Glu Gly Gln Arg
            355                 360                 365 att tta acc aag acc tgc cgg gaa tgt cga ggt gga gtc ttg gta aaa     1152
Ile Leu Thr Lys Thr Cys Arg Glu Cys Arg Gly Gly Val Leu Val Lys
            370                 375                 380 atc aca gaa gct tgc cct cct ttg aac tgc tca gca aag gat cat att     1200
Ile Thr Glu Ala Cys Pro Pro Leu Asn Cys Ser Ala Lys Asp His Ile
385                 390                 395                 400 ctt cca gag aat cag tgc tgc agg gtc tgc cca ggt cat aac ttc tgt     1248
Leu Pro Glu Asn Gln Cys Cys Arg Val Cys Pro Gly His Asn Phe Cys
                405                 410                 415 gca gaa gca cct aag tgc gga gaa aac tcg gaa tgc aaa aat tgg aat     1296
Ala Glu Ala Pro Lys Cys Gly Glu Asn Ser Glu Cys Lys Asn Trp Asn
            420                 425                 430 aca aaa gca acc tgt gag tgc aag aat gga tac atc tct gtc cag ggc     1344
Thr Lys Ala Thr Cys Glu Cys Lys Asn Gly Tyr Ile Ser Val Gln Gly
            435                 440                 445 aac tct gca tac tgt gaa gat att gat gag tgt gca gct aaa atg cac     1392
Asn Ser Ala Tyr Cys Glu Asp Ile Asp Glu Cys Ala Ala Lys Met His
450                 455                 460 tat tgt cat gcc aac acc gtg tgt gtc aac ttg ccg ggg ttg tat cgc     1440
Tyr Cys His Ala Asn Thr Val Cys Val Asn Leu Pro Gly Leu Tyr Arg
465                 470                 475                 480 tgt gac tgc gtc cca ggg tac atc cgt gtg gat gac ttc tct tgt acg     1488
Cys Asp Cys Val Pro Gly Tyr Ile Arg Val Asp Asp Phe Ser Cys Thr
                485                 490                 495 gag cat gat gat tgt ggc agc gga caa cac aac tgc gac aaa aat gcc     1536
Glu His Asp Asp Cys Gly Ser Gly Gln His Asn Cys Asp Lys Asn Ala
            500                 505                 510 atc tgt acc aac aca gtc cag gga cac agc tgc acc tgc cag ccg ggt     1584
Ile Cys Thr Asn Thr Val Gln Gly His Ser Cys Thr Cys Gln Pro Gly
            515                 520                 525 tac gtg gga aat ggc acc atc tgc aaa gca ttc tgt gaa gag ggt tgc     1632
Tyr Val Gly Asn Gly Thr Ile Cys Lys Ala Phe Cys Glu Glu Gly Cys
            530                 535                 540 aga tac gga ggt acc tgt gtg gct cct aac aag tgt gtc tgt cct tct     1680
Arg Tyr Gly Gly Thr Cys Val Ala Pro Asn Lys Cys Val Cys Pro Ser
```

```
                545                 550                 555                 560 gga ttc acg gga agc cac tgt gag aaa gat att gat gaa tgc gca gag                       1728
Gly Phe Thr Gly Ser His Cys Glu Lys Asp Ile Asp Glu Cys Ala Glu
                565                 570                 575 gga ttc gtt gaa tgc cac aac tac tcc cgc tgt gtt aac ctg cca ggg                       1776
Gly Phe Val Glu Cys His Asn Tyr Ser Arg Cys Val Asn Leu Pro Gly
            580                 585                 590 tgg tac cac tgt gag tgc aga agc ggt ttc cat gac gat ggg acc tac                       1824
Trp Tyr His Cys Glu Cys Arg Ser Gly Phe His Asp Asp Gly Thr Tyr
        595                 600                 605 tca ctg tcc ggg gag tcc tgc att gat atc gat gaa tgt gcc tta aga                       1872
Ser Leu Ser Gly Glu Ser Cys Ile Asp Ile Asp Glu Cys Ala Leu Arg
    610                 615                 620 act cac act tgt tgg aat gac tct gcc tgc atc aac tta gca gga gga                       1920
Thr His Thr Cys Trp Asn Asp Ser Ala Cys Ile Asn Leu Ala Gly Gly
625                 630                 635                 640 ttt gac tgc ctg tgt ccc tct ggg ccc tcc tgc tct ggt gac tgt ccc                       1968
Phe Asp Cys Leu Cys Pro Ser Gly Pro Ser Cys Ser Gly Asp Cys Pro
                645                 650                 655 cac gaa gga ggg ctg aag cat aat ggg cag gtg tgg att ctg aga gaa                       2016
His Glu Gly Gly Leu Lys His Asn Gly Gln Val Trp Ile Leu Arg Glu
            660                 665                 670 gac agg tgt tca gtc tgt tcc tgc aag gat ggg aag ata ttc tgc cgg                       2064
Asp Arg Cys Ser Val Cys Ser Cys Lys Asp Gly Lys Ile Phe Cys Arg
        675                 680                 685 cgg aca gct tgt gat tgc cag aat cca aat gtt gac ctt ttt tgc tgc                       2112
Arg Thr Ala Cys Asp Cys Gln Asn Pro Asn Val Asp Leu Phe Cys Cys
    690                 695                 700 cca gag tgc gat acc agg gtc acc agc caa tgt tta gat caa agt gga                       2160
Pro Glu Cys Asp Thr Arg Val Thr Ser Gln Cys Leu Asp Gln Ser Gly
705                 710                 715                 720 cag aag ctc tat cga agt gga gac aac tgg acc cac agc tgc cag cag                       2208
Gln Lys Leu Tyr Arg Ser Gly Asp Asn Trp Thr His Ser Cys Gln Gln
                725                 730                 735 tgc cga tgt ctg gaa gga gag gca gac tgc tgg cct ctg gct tgc cct                       2256
Cys Arg Cys Leu Glu Gly Glu Ala Asp Cys Trp Pro Leu Ala Cys Pro
            740                 745                 750 agt ttg ggc tgt gaa tac aca gcc atg ttt gaa ggg gag tgt tgt ccc                       2304
Ser Leu Gly Cys Glu Tyr Thr Ala Met Phe Glu Gly Glu Cys Cys Pro
        755                 760                 765 cga tgt gtc agt gac ccc tgc ctg gct ggt aat att gcc tat gac atc                       2352
Arg Cys Val Ser Asp Pro Cys Leu Ala Gly Asn Ile Ala Tyr Asp Ile
    770                 775                 780 aga aaa act tgc ctg gac agc ttt ggt gtt tcg agg ctg agc gga gcc                       2400
Arg Lys Thr Cys Leu Asp Ser Phe Gly Val Ser Arg Leu Ser Gly Ala
785                 790                 795                 800 gtg tgg aca atg gct gga tct cct tgt aca acc tgc aaa tgc aag aat                       2448
Val Trp Thr Met Ala Gly Ser Pro Cys Thr Thr Cys Lys Cys Lys Asn
                805                 810                 815 ggg aga gtc tgc tgc tct gtg gat ctg gag tgt att gag aat aac tga                       2496
Gly Arg Val Cys Cys Ser Val Asp Leu Glu Cys Ile Glu Asn Asn
            820                 825                 830 gac tac aag gac gac gat gac aag                                                       2520
Asp Tyr Lys Asp Asp Asp Asp Lys
            835

<210> SEQ ID NO 610
<211> LENGTH: 839
<212> TYPE: PRT
<213> ORGANISM: Artificial Sequence
```

<220> FEATURE:
<223> OTHER INFORMATION: Synthetic Construct

<400> SEQUENCE: 610

```
Met Lys Phe Leu Val Asn Val Ala Leu Val Phe Met Val Val Tyr Ile
1               5                   10                  15

Ser Tyr Ile Tyr Ala Met Pro Met Asp Val Ile Leu Val Leu Trp Phe
            20                  25                  30

Cys Val Cys Thr Ala Arg Thr Val Leu Gly Phe Gly Met Asp Pro Asp
        35                  40                  45

Leu Gln Leu Asp Ile Ile Ser Glu Leu Asp Leu Val Asn Thr Thr Leu
    50                  55                  60

Gly Val Thr Gln Val Ala Gly Leu His Asn Ala Ser Lys Ala Phe Leu
65                  70                  75                  80

Phe Gln Asp Val Gln Arg Glu Ile His Ser Ala Pro His Val Ser Glu
                85                  90                  95

Lys Leu Ile Gln Leu Phe Arg Asn Lys Ser Glu Phe Thr Phe Leu Ala
            100                 105                 110

Thr Val Gln Gln Lys Pro Ser Thr Ser Gly Val Ile Leu Ser Ile Arg
        115                 120                 125

Glu Leu Glu His Ser Tyr Phe Glu Leu Glu Ser Ser Gly Pro Arg Glu
    130                 135                 140

Glu Ile Arg Tyr His Tyr Ile His Gly Gly Lys Pro Arg Thr Glu Ala
145                 150                 155                 160

Leu Pro Tyr Arg Met Ala Asp Gly Gln Trp His Lys Val Ala Leu Ser
                165                 170                 175

Val Ser Ala Ser His Leu Leu Leu His Ile Asp Cys Asn Arg Ile Tyr
            180                 185                 190

Glu Arg Val Ile Asp Pro Pro Glu Thr Asn Leu Pro Pro Gly Ser Asn
        195                 200                 205

Leu Trp Leu Gly Gln Arg Asn Gln Lys His Gly Phe Phe Lys Gly Ile
    210                 215                 220

Ile Gln Asp Gly Lys Ile Ile Phe Met Pro Asn Gly Phe Ile Thr Gln
225                 230                 235                 240

Cys Pro Asn Leu Asn Arg Thr Cys Pro Thr Cys Ser Asp Phe Leu Ser
                245                 250                 255

Leu Val Gln Gly Ile Met Asp Leu Gln Glu Leu Leu Ala Lys Met Thr
            260                 265                 270

Ala Lys Leu Asn Tyr Ala Glu Thr Arg Leu Gly Gln Leu Glu Asn Cys
        275                 280                 285

His Cys Glu Lys Thr Cys Gln Val Ser Gly Leu Leu Tyr Arg Asp Gln
    290                 295                 300

Asp Ser Trp Val Asp Gly Asp Asn Cys Gly Asn Cys Thr Cys Lys Ser
305                 310                 315                 320

Gly Ala Val Glu Cys Arg Arg Met Ser Cys Pro Pro Leu Asn Cys Ser
                325                 330                 335

Pro Asp Ser Leu Pro Val His Ile Ser Gly Gln Cys Cys Lys Val Cys
            340                 345                 350

Arg Pro Lys Cys Ile Tyr Gly Gly Lys Val Leu Ala Glu Gly Gln Arg
        355                 360                 365

Ile Leu Thr Lys Thr Cys Arg Glu Cys Arg Gly Gly Val Leu Val Lys
    370                 375                 380

Ile Thr Glu Ala Cys Pro Pro Leu Asn Cys Ser Ala Lys Asp His Ile
385                 390                 395                 400
```

```
Leu Pro Glu Asn Gln Cys Cys Arg Val Cys Pro Gly His Asn Phe Cys
            405                 410                 415

Ala Glu Ala Pro Lys Cys Gly Glu Asn Ser Glu Cys Lys Asn Trp Asn
        420                 425                 430

Thr Lys Ala Thr Cys Glu Cys Lys Asn Gly Tyr Ile Ser Val Gln Gly
        435                 440                 445

Asn Ser Ala Tyr Cys Glu Asp Ile Asp Glu Cys Ala Ala Lys Met His
    450                 455                 460

Tyr Cys His Ala Asn Thr Val Cys Val Asn Leu Pro Gly Leu Tyr Arg
465                 470                 475                 480

Cys Asp Cys Val Pro Gly Tyr Ile Arg Val Asp Phe Ser Cys Thr
                485                 490                 495

Glu His Asp Asp Cys Gly Ser Gly Gln His Asn Cys Asp Lys Asn Ala
            500                 505                 510

Ile Cys Thr Asn Thr Val Gln Gly His Ser Cys Thr Cys Gln Pro Gly
        515                 520                 525

Tyr Val Gly Asn Gly Thr Ile Cys Lys Ala Phe Cys Glu Glu Gly Cys
    530                 535                 540

Arg Tyr Gly Gly Thr Cys Val Ala Pro Asn Lys Cys Val Cys Pro Ser
545                 550                 555                 560

Gly Phe Thr Gly Ser His Cys Glu Lys Asp Ile Asp Glu Cys Ala Glu
                565                 570                 575

Gly Phe Val Glu Cys His Asn Tyr Ser Arg Cys Val Asn Leu Pro Gly
            580                 585                 590

Trp Tyr His Cys Glu Cys Arg Ser Gly Phe His Asp Asp Gly Thr Tyr
        595                 600                 605

Ser Leu Ser Gly Glu Ser Cys Ile Asp Ile Asp Glu Cys Ala Leu Arg
    610                 615                 620

Thr His Thr Cys Trp Asn Asp Ser Ala Cys Ile Asn Leu Ala Gly Gly
625                 630                 635                 640

Phe Asp Cys Leu Cys Pro Ser Gly Pro Ser Cys Ser Gly Asp Cys Pro
                645                 650                 655

His Glu Gly Gly Leu Lys His Asn Gly Gln Val Trp Ile Leu Arg Glu
            660                 665                 670

Asp Arg Cys Ser Val Cys Ser Cys Lys Asp Gly Lys Ile Phe Cys Arg
        675                 680                 685

Arg Thr Ala Cys Asp Cys Gln Asn Pro Asn Val Asp Leu Phe Cys Cys
    690                 695                 700

Pro Glu Cys Asp Thr Arg Val Thr Ser Gln Cys Leu Asp Gln Ser Gly
705                 710                 715                 720

Gln Lys Leu Tyr Arg Ser Gly Asp Asn Trp Thr His Ser Cys Gln Gln
                725                 730                 735

Cys Arg Cys Leu Glu Gly Glu Ala Asp Cys Trp Pro Leu Ala Cys Pro
            740                 745                 750

Ser Leu Gly Cys Glu Tyr Thr Ala Met Phe Glu Gly Glu Cys Cys Pro
        755                 760                 765

Arg Cys Val Ser Asp Pro Cys Leu Ala Gly Asn Ile Ala Tyr Asp Ile
    770                 775                 780

Arg Lys Thr Cys Leu Asp Ser Phe Gly Val Ser Arg Leu Ser Gly Ala
785                 790                 795                 800

Val Trp Thr Met Ala Gly Ser Pro Cys Thr Thr Cys Lys Cys Lys Asn
                805                 810                 815
```

-continued

```
Gly Arg Val Cys Cys Ser Val Asp Leu Glu Cys Ile Glu Asn Asn Asp
            820                 825                 830

Tyr Lys Asp Asp Asp Asp Lys
        835

<210> SEQ ID NO 611
<211> LENGTH: 16
<212> TYPE: PRT
<213> ORGANISM: Homo sapiens

<400> SEQUENCE: 611

Met Pro Met Asp Leu Ile Leu Val Val Trp Phe Cys Val Cys Thr Ala
1               5                   10                  15

<210> SEQ ID NO 612
<211> LENGTH: 21
<212> TYPE: PRT
<213> ORGANISM: Homo sapiens

<400> SEQUENCE: 612

Met Glu Ser Arg Val Leu Leu Arg Thr Phe Cys Leu Ile Phe Gly Leu
1               5                   10                  15

Gly Ala Val Trp Gly
            20

<210> SEQ ID NO 613
<211> LENGTH: 20
<212> TYPE: PRT
<213> ORGANISM: Artificial Sequence
<220> FEATURE:
<223> OTHER INFORMATION: Synthetic peptide

<400> SEQUENCE: 613

Met Tyr Arg Met Gln Leu Leu Ser Cys Ile Ala Leu Ser Leu Ala Leu
1               5                   10                  15

Val Thr Asn Ser
            20

<210> SEQ ID NO 614
<211> LENGTH: 19
<212> TYPE: PRT
<213> ORGANISM: Artificial Sequence
<220> FEATURE:
<223> OTHER INFORMATION: Synthetic peptide

<400> SEQUENCE: 614

Met Pro His His His His His His Gly Gly Gly Asp Asp Asp Asp Lys
1               5                   10                  15

Asp Pro Met
```